(12) United States Patent
Paliyath et al.

(10) Patent No.: US 12,409,148 B2
(45) Date of Patent: Sep. 9, 2025

(54) PLANT TISSUE-DERIVED NANOPARTICLES AND FOOD POWDERS

(71) Applicant: PSIGRYPH INC., Waterloo (CA)

(72) Inventors: Gopinadhan Paliyath, Waterloo (CA); Krishnaraj Tiwari, Mont Royal (CA); Julieta Correa-Betanzo, Toronto (CA); Priya Padmanabhan, Waterloo (CA); Nagisa Nosrati, Guelph (CA); Marica Bakovic, Guelph (CA)

(73) Assignee: PSIGRYPH INC., Waterloo (CA)

( * ) Notice: Subject to any disclaimer, the term of this patent is extended or adjusted under 35 U.S.C. 154(b) by 944 days.

(21) Appl. No.: 17/294,099

(22) PCT Filed: Nov. 15, 2019

(86) PCT No.: PCT/CA2019/051634
§ 371 (c)(1),
(2) Date: May 14, 2021

(87) PCT Pub. No.: WO2020/097739
PCT Pub. Date: May 22, 2020

(65) Prior Publication Data
US 2022/0008349 A1    Jan. 13, 2022

Related U.S. Application Data

(60) Provisional application No. 62/767,915, filed on Nov. 15, 2018.

(51) Int. Cl.
| | | |
|---|---|---|
| A61K 9/51 | (2006.01) | |
| A23L 33/00 | (2016.01) | |
| A23L 33/105 | (2016.01) | |
| A23P 10/40 | (2016.01) | |
| A61G 17/04 | (2006.01) | |
| A61K 8/11 | (2006.01) | |
| A61K 8/49 | (2006.01) | |
| A61K 8/9789 | (2017.01) | |
| A61K 31/12 | (2006.01) | |
| A61K 31/337 | (2006.01) | |
| A61K 31/353 | (2006.01) | |
| A61K 31/733 | (2006.01) | |
| A61K 33/04 | (2006.01) | |
| A61K 33/06 | (2006.01) | |
| A61K 33/26 | (2006.01) | |
| A61K 33/30 | (2006.01) | |
| A61K 36/28 | (2006.01) | |
| A61K 36/31 | (2006.01) | |
| A61K 36/324 | (2006.01) | |
| A61K 36/48 | (2006.01) | |
| A61K 36/67 | (2006.01) | |
| A61K 36/736 | (2006.01) | |
| A61K 36/81 | (2006.01) | |
| A61K 36/906 | (2006.01) | |
| A61K 36/9066 | (2006.01) | |
| A61K 47/46 | (2006.01) | |
| A61P 3/04 | (2006.01) | |

(Continued)

(52) U.S. Cl.
CPC .......... *A61K 9/5161* (2013.01); *A23L 33/105* (2016.08); *A23L 33/30* (2016.08); *A23P 10/40* (2016.08); *A61G 17/04* (2013.01); *A61K 8/11* (2013.01); *A61K 8/498* (2013.01); *A61K 8/9789* (2017.08); *A61K 9/5192* (2013.01); *A61K 31/12* (2013.01); *A61K 31/337* (2013.01); *A61K 31/353* (2013.01); *A61K 31/733* (2013.01); *A61K 33/04* (2013.01); *A61K 33/06* (2013.01); *A61K 33/26* (2013.01); *A61K 33/30* (2013.01); *A61K 36/28* (2013.01); *A61K 36/31* (2013.01); *A61K 36/324* (2013.01); *A61K 36/48* (2013.01); *A61K 36/67* (2013.01); *A61K 36/736* (2013.01); *A61K 36/81* (2013.01); *A61K 36/906* (2013.01); *A61K 36/9066* (2013.01); *A61K 47/46* (2013.01); *A61P 3/04* (2018.01); *A61P 3/06* (2018.01); *A61P 3/10* (2018.01); *A61P 29/00* (2018.01); *A61P 35/00* (2018.01); *A23V 2002/00* (2013.01)

(58) Field of Classification Search
None
See application file for complete search history.

(56) References Cited

U.S. PATENT DOCUMENTS

2008/0146701 A1    6/2008  Sain et al.

FOREIGN PATENT DOCUMENTS

| CN | 104177508 B | 12/2014 |
|---|---|---|
| CN | 104983841 | * 10/2015 |

(Continued)

OTHER PUBLICATIONS

Chen et al. (Core-Shell Soy Protein-Soy Polysaccharide Complex (Nano)particles as carriers for Improved Stability and Sustained Release of Curcumin, Journal of Agricultural and Food Chemistry, 2016, 64, 5053-5059). (Year: 2016).*

(Continued)

*Primary Examiner* — Melissa S Mercier
(74) *Attorney, Agent, or Firm* — NIXON PEABODY LLP; David S. Resnick; Nicole D. Kling

(57) ABSTRACT

Provided herein are nanoparticles including self-assembled cellular components derived from a homogenized plant tissue. Also provided are food powders and other related compositions. Methods for preparing such nanoparticles and food powders, as well as uses thereof in the treatment or prevention of diseases or disorders in a subject and/or as delivery vehicles are also described.

19 Claims, 63 Drawing Sheets

Specification includes a Sequence Listing.

(51) Int. Cl.
*A61P 3/06* (2006.01)
*A61P 3/10* (2006.01)
*A61P 29/00* (2006.01)
*A61P 35/00* (2006.01)

(56) References Cited

FOREIGN PATENT DOCUMENTS

| | | |
|---|---|---|
| CN | 104983841 A | 10/2015 |
| CN | 106243237 A | 12/2016 |
| CN | 106805254 A | 6/2017 |
| EP | 3305303 A1 | 4/2018 |
| WO | 2010102802 A1 | 9/2010 |
| WO | 2012078798 A1 | 6/2012 |
| WO | 2015/074120 A1 | 5/2015 |
| WO | 2015/087329 A1 | 6/2015 |
| WO | 2016191895 A1 | 12/2016 |
| WO | WO-2018048489 A1 * 3/2018 ............. A23L 19/00 |
| WO | 2018/062343 A1 | 4/2018 |

OTHER PUBLICATIONS

Beconini et al. (Chitosan-based nanoparticles containing cherry extract from *Prunus avium* L. to improve the resistance to endothelial cells to oxidative stress, Nutrients 10/11:1598, Nov. 1, 2018). (Year: 2018).*
Hiasa et al., "Prevention of Aggregation of Pectin—Containing Cellulose Nanofibers Prepared from Mandarin Peel" Journal of Feber Science and Technology 72:17-26 (Aug. 8, 2023).
Varanasi et al, Producing nanofibres from carrots with a chemical-free process. Carbohydrate Polymers (2018), vol. 184, pp. 307-314 (Year: 2018).
Fang "Guide Book of Dietary Health Care for Cancer Patients", 1st edition, p. 120, Tianjin Science and Technology Press [English Translaton Provided].
Guangtan "Diabetic Diet for Symptomatic Adjustment", 1st edition, p. 79, Science and Technology Literature Press [English Translation Provided].
Jinping "Isolation and structural identification of antioxidant and immunomodulatory active substances in cherry pulp", China Outstanding Master/Doctor's Dissertation Database (Ph.D.)—Agricultural Science and Technology Series, vol. 03, D048-12 [English Translation Provided].
Jinzhi "Hypertension Diet and Regulation", 1st edition, p. 157, Hebei Science and Technology Press [English Translation Provided].
Shunyang "Functional Foods and Health Care", 1st edition,, p. 294, Science and Technology Literature Press [English Translation Provided].
Yanli "The Complete Book of Nine Body Types for Health Care", 1st editioni, pp. 136-137, Knowledge Press [English Translation Provided].
Hiasa et al. "Research on production of cellulose nanofibers from resources not utilizing citrus, and material utilization technology." Academic Dissertation 1-88 (2016). English Summary Provided.
Han et al., "Effect of cherry lyophilized powder on metabolic syndrome caused by high-fat diet" Journal of Binzhou Medical College, 36(3), pp. 166-168 (Jun. 30, 2013) [Only Abstract in English].
Beconcini et al. "Chitosan-based nanoparticles containing cherry extract from *Prunus avium* L. to improve the resistance of endothelial cells to oxidative stress." Nutrients 10(11): 1598 pp. 1-13 (2018).
Chen et al. "Core-shell soy protein-soy polysaccharide complex (nano) particles as carriers for improved stability and sustained release of curcumin." Journal of Agricultural and Food Chemistry 64(24): 5053-5059 (2016).
Chen et al. "Micronization and nanosizing of particles for an enhanced quality of food: A review." Critical Reviews in Food Science and Nutrition 58(6): 993-1001 (2018).
Davidov-Pardo et al. "Chapter Nine: Food-grade protein-based nanoparticles and microparticles for bioactive delivery: fabrication, characterization, and utilization." In Advances in Protein Chemistry and Structural Biology, Protein and Peptide Nanoparticles for Drug Delivery, Ed. R. Donev (98): 293-325 (2015).
Defrates et al. "Protein polymer-based nanoparticles: fabrication and medical applications." International Journal of Molecular Sciences 19(6): 1717 pp. 1-20 (2018).
Han et al. "Self-assembling behavior of cellulose nanoparticles during freeze-drying: effect of suspension concentration, particle size, crystal structure, and surface charge." Biomacromolecules 14(5): 1529-1540 (2013).
Isik. "The uniaxial and coaxial encapsulations of sour cherry (*Prunus cerasus* L.) concentrate by electrospinning and their in vitro bioaccessibility." Food Chemistry 265: 260-273 (2018).
Jacob et al. "Physico-chemical characteristics of nanovesicle—carbohydrate complexes in grape juice concentrate." Journal of Agricultural and Food Chemistry 56(4): 1305-1315 (2008).
Zhang et al. "Soy peptide nanoparticles by ultrasound-induced self-assembly of large peptide aggregates and their role on emulsion stability." Food Hydrocolloids 74: 62-71 (2018).

* cited by examiner

PLANT TISSUE-DERIVED NANOPARTICLES AND FOOD POWDERS

CROSS-REFERENCE TO RELATED APPLICATIONS

This Application is a 35 U.S.C. § 371 National Phase Entry Application of International Application No. PCT/CA2019/051634 filed Nov. 15, 2019, which designates the U.S. and claims benefit under 35 U.S.C. § 119 (e) of the U.S. Provisional Application No. 62/767,915 filed Nov. 15, 2018, the contents of which are incorporated herein by reference in their entirety.

SEQUENCE LISTING

The instant application contains a Sequence Listing which has been submitted electronically in TXT format and is hereby incorporated by reference in its entirety. Said TXT copy, created on May 14, 2025, is named 08939660US1.txt and is 8,937 bytes in size.

FIELD OF INVENTION

The present invention relates generally to nanoparticles and food powders, and uses thereof. More specifically, the present invention relates to plant tissue-derived nanoparticles and food powders, and uses thereof.

BACKGROUND

Fruits are rich sources of dietary components ranging from simple molecules such as sugars that provide energy to complex macromolecules such as cellulose and pectin which serve as dietary fibres, vitamins, minerals, and nutraceuticals that have varied disease-preventive and health regulatory functions (Paliyath et al., 2011). Polyphenols, especially flavonoids and derivatives, have recently gained increasing interest because of their numerous biological effects such as free-radical scavenging, modulation of enzyme activities, inhibition of cell proliferation, as well as their potential utility as antibiotic, anti-allergic and anti-inflammatory agents (Clifford and Brown, 2006). Polyphenols have been shown to have potential roles in the prevention of cardiovascular diseases, cancers and other degenerative diseases (Scalbert et al., 2005, Paliyath et al., 2011). Because of their wide distribution in foods and beverages of plant origin (including juices, tea, coffee, and wine), polyphenols may be considered as common micronutrients in the human diet. Consumption of polyphenol-rich foods has been promoted as a means to prevent the development of chronic diseases, as well as to reduce the mortality rates caused by chronic diseases.

The biological activity of polyphenols in vivo is dependent on the absorption and metabolism thereof, as well as their distribution in the body after ingestion (Clifford and Brown, 2006). In the case of the gastrointestinal tract (GIT), the epithelial cells are in contact with these components or their metabolites. The level of polyphenols in foods can range from 100-5000 mg/kg (Manach et al., 2004), however, the extent of absorption of dietary polyphenols in the intestine is relatively small (Spencer and Rice Evans, 2003). Plasma- and tissue-levels of free phenolic components in general are in the low micromolar range. As well, it has been proposed that not all of the phenolic components consumed are bio-available because of food matrix interactions (Saura-Calixto and Diaz-Rubio, 2007; Saura-Calixto et al., 2007; Del Rio et al., 2010). Understanding the nature and role of diet-derived structures is important, since their study impacts understanding of the influence of food-derived nanomaterials on human health.

The influence of nanomaterials on human health is increasingly being scrutinized, as the use of engineered nanomaterials is increasing worldwide (Maynard, 2006). Engineered nanomaterials can escape into the environment as airborne nanostructured agglomerates (eg. silver nanoparticles, $TiO_2$) or SWNT (single walled Carbon nanotubes), and get inside the body through inhalation, ingestion and penetration through skin, and subsequently get mobilized into other organs. Nanoparticles of Titanium and Zinc are increasingly being used in the cosmetic industry. Engineered nanomaterials from biological components are also being explored in drug delivery, cosmetics, food ingredients, coatings, food packaging, etc. (Azeredo et al., 2009; Ramasamy et al., 2009; Zhao et.al., 2011; Sessa et al., 2011; Zhang et al., 2012). Nanomaterials can also enter the body through the food chain, especially through the consumption of plant derived food that has accumulated such materials from soil, water and air (Rico et al., 2011). The presence of macromolecules in food with potential to self-assemble into nanostructures would be especially significant (IOM, 2009). Potential formation of amorphous carbon nanoparticles has been observed to exist in caramalized food, for example (Palashuddin et al., 2012).

Alternative, additional, and/or improved nanomaterials and/or methods for the production thereof are desirable.

SUMMARY OF INVENTION

It is an object of the present disclosure to provide nanoparticles and food powders, derivable from natural sources (i.e. plant tissue), for use as a food supplement, in the treatment and/or prevention of certain diseases or disorders, and/or in the delivery of a bioactive agent to a subject in need thereof. Methods for the production thereof are also provided.

In an embodiment, there is provided herein a nanoparticle comprising self-assembled cellular components derived from a homogenized plant tissue, the cellular components comprising one or more structural carbohydrates or cleavage products thereof, wherein lipids are not a structural component of the nanoparticle.

In another embodiment of the above nanoparticle, the nanoparticle may be substantially lipid-free.

In still another embodiment of any of the above nanoparticle or nanoparticles, the nanoparticle may comprise pectin, hemicellulose, peptide and/or protein, an organic acid, at least one polyphenol, cleavage products thereof, or any combination thereof.

In still another embodiment of any of the above nanoparticle or nanoparticles, the nanoparticle may comprise:
  a pectin-based inner core;
  an intermediate layer surrounding the inner core, the intermediate layer comprising macromolecules of pectin and hemicellulose and/or cleavage products thereof, polyphenol, and organic acid; and
  a fibrillated outer layer comprising macromolecular carbohydrate and protein, optionally formed from catabolism during ripening and/or during homogenization of the plant tissue.

In another embodiment of any of the above nanoparticle or nanoparticles, the organic acid may comprise malic acid, ascorbic acid, or both.

In still another embodiment of any of the above nanoparticle or nanoparticles, the polyphenol may comprise an anthocyanin.

In yet another embodiment of any of the above nanoparticle or nanoparticles, the cellular components may comprise those liberated from the plant tissue during ripening or during homogenization of ripened fruit, which are capable of self-assembling into the nanoparticle.

In still another embodiment of any of the above nanoparticle or nanoparticles, the one or more structural carbohydrates may comprise one or more of pectin, pectic acid, methyl ester of pectin, a pectin derivative, polygalacturonic acid, rhamnogalacturonans, xylogucans, hemicelluloses, xyloglucans possessing β-(1→4)-linked backbones of glucose, mannose, or xylose, and/or arabinogalactans, and/or cleavage products thereof.

In still another embodiment of any of the above nanoparticle or nanoparticles, the nanoparticle may have a substantially spherical structure with a diameter of about 50-250 nm.

In another embodiment of any of the above nanoparticle or nanoparticles, the nanoparticle may comprise:
  a pectin-based inner core;
  an intermediate layer surrounding the inner core, the intermediate layer comprising one or more spiral fibril structures comprising pectin or a derivative thereof, and one or more hemicellulose-derived molecules or a derivative thereof; and
  a fibrillated outer layer comprising hemicellulose or a cleavage product thereof, and one
  or more peptides derived from cellular proteins.

In still another embodiment of any of the above nanoparticle or nanoparticles, the nanoparticle may be stabilized by hydrogen-bonding interactions present at a pH ranging from about 3 to about 7 and formed between macromolecules derived from catabolism of cellular components of the plant tissue and possessing hydroxyl groups and/or amino groups and/or organic acid groups.

In yet another embodiment of any of the above nanoparticle or nanoparticles, the nanoparticle may be non-crystalline.

In still another embodiment of any of the above nanoparticle or nanoparticles, the nanoparticle may further comprise a biologically active agent.

In another embodiment of any of the above nanoparticle or nanoparticles, the biologically active agent may be a pharmaceutically active drug, protein, enzyme, nutraceutical, or nutrient.

In still another embodiment of any of the above nanoparticle or nanoparticles, the nanoparticle may be in aqueous solution.

In yet another embodiment of any of the above nanoparticle or nanoparticles, the nanoparticle may be in powder form.

In still another embodiment of any of the above nanoparticle or nanoparticles, the nanoparticle may be in dehydrated, lyophilized, freeze-dried, spray-dried, or nanospray-dried form.

In still another embodiment of any of the above nanoparticle or nanoparticles, the plant tissue may comprise a fruit or vegetable plant tissue.

In another embodiment of any of the above nanoparticle or nanoparticles, the plant tissue may comprise a senescing fruit, a ripening vegetable, or any combination thereof; preferably, wherein the plant tissue comprises cherry, blueberry, grape, peach, nectarine, plum, apricot, *papaya*, tomato, or any combination thereof.

In still another embodiment of any of the above nanoparticle or nanoparticles, the plant tissue may comprise a sour cherry fruit tissue.

In another embodiment, there is provided herein a method for preparing nanoparticles from homogenized plant tissue, said method comprising:
  preparing a homogenized plant tissue in solution, comprising cellular components liberated from the plant tissue;
  removing debris from the homogenized plant tissue, if present; and
  optionally, dialyzing the homogenized plant tissue to remove non-complexed compounds, or removing the non-complexed compounds by size exclusion,
thereby providing a solution comprising the nanoparticles which are formed by self-assembly of the cellular components.

In another embodiment of the above method, the method may further comprise a step of dehydrating, lyophilizing, freeze-drying, spray-drying, or nanospray-drying the solution comprising the nanoparticle.

In another embodiment of any of the above method or methods, the nanoparticles may be formed by self-assembly in a substantially aqueous medium.

In still another embodiment of any of the above method or methods, the step of preparing the homogenized plant tissue in solution may comprise homogenizing a plant tissue in an aqueous, organic, or a mixed aqueous-organic medium.

In yet another embodiment of any of the above method or methods, the step of preparing the homogenized plant tissue in solution may comprise subjecting a plant tissue to high shear homogenization and/or sonolation in an aqueous, organic, or a mixed aqueous-organic medium comprising any one or more of water, ethanol, methanol, or acetone.

In still another embodiment of any of the above method or methods, the step of removing debris may comprise dialysis, filtering the homogenized plant tissue, centrifuging the homogenized plant tissue, or performing tangential flow filtration or continuous flow filtration on the homogenized plant tissue, or any combination thereof.

In another embodiment of any of the above method or methods, the method may be for preparing a nanoparticle as described herein.

In another embodiment, there is provided herein a method for preparing a nanoparticle from homogenized plant tissue, said method comprising:
  preparing a homogenized plant tissue in solution, comprising cellular components liberated from the plant tissue;
  allowing the nanoparticle to form by self-assembly of the cellular components;
  removing debris from the homogenized plant tissue, if present; and
  freeze-drying, spray-drying, or nanospray drying to form a powder comprising the nanoparticle.

In another embodiment of the above method, the self-assembly may occur in a substantially aqueous medium.

In still another embodiment of any of the above method or methods, the step of preparing the homogenized plant tissue in solution may comprise subjecting a plant tissue to high shear homogenization in an aqueous, organic, or a mixed aqueous-organic medium.

In another embodiment of any of the above method or methods, the step of removing debris may comprise filtering the homogenized plant tissue, or centrifuging the homogenized plant tissue, or both.

In yet another embodiment of any of the above method or methods, the method may be for preparing a nanoparticle as described herein.

In another embodiment, there is provided herein a nanoparticle prepared by any of the above method or methods.

In another embodiment, there is provided herein a food powder prepared from any of the above nanoparticle or nanoparticles, optionally wherein the food powder is provided in a micro-scale fine powder form.

In another embodiment, there is provided herein a method of delivering a biologically active agent to a subject, a cell, or an organism in need thereof, said method comprising:
    administering any of the above nanoparticle or nanoparticles, which is complexed with, or conjugated with, the biologically active agent using a chemical or physical process, to the subject, cell, or organism.

In another embodiment of the above method, the biologically active agent may be an element such as Selenium, Zinc, Iron, or Magnesium.

In another embodiment of any of the above method or methods, the biologically active agent may be an anticancer drug, and the subject may be a subject with cancer.

In another embodiment of any of the above method or methods, the anticancer drug may be paclitaxel, vincristine, or any natural or synthetic compound used in treatment of cancer.

In another embodiment of any of the above method or methods, the biologically active agent may be introduced into the nanoparticle during formation nanoparticle, or the biologically active agent may be complexed with or conjugated with already formed nanoparticles in an aqueous-based medium optionally comprising an alcohol or other organic component.

In another embodiment of any of the above method or methods, the aqueous-based medium may comprise DMSO, or a buffer, or both.

In another embodiment, there is provided herein a method of treating a disease or disorder associated with increased levels of reactive oxygen species leading to inflammation in a subject in need thereof, comprising:
    administering any of the above nanoparticle or nanoparticles to the subject.

In another embodiment, there is provided herein a method for treating or reducing inflammation in a subject in need thereof, said method comprising:
    administering any of the above nanoparticle or nanoparticles to the subject.

In another embodiment of the above method, the nanoparticle may comprise, or be co-administered with, an anti-inflammatory agent.

In yet another embodiment of the above method or methods, the anti-inflammatory agent may comprise curcumin.

In another embodiment, there is provided herein a method for treating or reducing obesity in a subject in need thereof, said method comprising:
    administering any of the above nanoparticle or nanoparticles to the subject.

In another embodiment of the above method, the nanoparticle may comprise components derived at least in part from nut, legume, herb, spice, vegetable, or fungal plant tissue, traditionally used for food or medical purposes.

In another embodiment, there is provided herein a method for treating or preventing cancer in a subject in need thereof, said method comprising:
    administering any of the above nanoparticle or nanoparticles to the subject.

In another embodiment of the above method, the nanoparticle may be simultaneously or sequentially co-administered with an anticancer drug.

In still another embodiment of the above method or methods, the nanoparticle may be complexed with, or conjugated with, an anticancer drug.

In yet another embodiment of the above method or methods, the anticancer drug may be paclitaxel or vincristine.

In another embodiment, there is provided herein a method for providing a subject with soluble dietary fibre, said method comprising:
    administering any of the above nanoparticle or nanoparticles to the subject.

In another embodiment, there is provided herein a viscosity enhancing food additive comprising any of the above nanoparticle or nanoparticles.

In another embodiment, there is provided herein a method for attenuating post-prandial sugar levels in the blood of a subject in need thereof, said method comprising:
    administering any of the above nanoparticle or nanoparticles to the subject.

In another embodiment, there is provided herein a cosmetic product comprising any of the above nanoparticle or nanoparticles.

In yet another embodiment, there is provided herein a composition for topical administration to a subject in need thereof, the composition comprising any of the above nanoparticle or nanoparticles, and optionally a biologically active agent.

In still another embodiment, there is provided herein a method for preventing sun burn in a subject in need thereof, said method comprising:
    applying any of the above nanoparticle or nanoparticles to the skin of the subject.

In another embodiment of the above method, the nanoparticle may comprise, or may be applied with, additional anthocyanin or another UV-protective agent.

In another embodiment, there is provided herein a method for reducing cell proliferation, said method comprising:
    treatment of a cell or tissue or organ with any of the above nanoparticle or nanoparticles.

In another embodiment of the above method, the nanoparticle may be simultaneously or sequentially used with an anticancer drug.

In still another embodiment of the above method or methods, the nanoparticle may be complexed with, or conjugated with, an anticancer drug.

In yet another embodiment of the above method or methods, the anticancer drug may be paclitaxel or vincristine.

In another embodiment, there is provided herein a method for reducing triglyceride accumulation in the liver of a subject in need thereof, said method comprising:
    administering any of the above nanoparticle or nanoparticles to the subject.

In another embodiment, there is provided herein a use of any of the above nanoparticle or nanoparticles for delivering a biologically active agent to a subject or cell in need thereof.

In another embodiment of the above use, the biologically active agent may be an element such as Selenium, Zinc, Magnesium or Iron.

In another embodiment of the above use or uses, the biologically active agent may be an anticancer drug, and the subject may be a subject with cancer.

In yet another embodiment of the above use or uses, the anticancer drug may be paclitaxel or vincristine.

In still another embodiment of any of the above use or uses, the biologically active agent may be introduced into the nanoparticle during formation of the nanoparticle, or the biologically active agent may be complexed with or conjugated with already formed nanoparticles in an aqueous-based medium.

In another embodiment of the above use or uses, the aqueous-based medium may comprise DMSO, or a buffer, or both.

In another embodiment, there is provided herein a use of any of the above nanoparticle or nanoparticles for treating a disease or disorder associated with reactive oxygen species in a subject in need thereof.

In another embodiment, there is provided herein a use of any of the above nanoparticle or nanoparticles for treating or reducing inflammation in a subject in need thereof.

In yet another embodiment of the above use or uses, the nanoparticle may comprise or may be for administration with an anti-inflammatory agent.

In still another embodiment of the above use or uses, the anti-inflammatory agent may comprise curcumin.

In another embodiment, there is provided herein a use of any of the above nanoparticle or nanoparticles for treating or reducing obesity in a subject in need thereof.

In yet another embodiment of the above use or uses, the nanoparticle may be derived at least in part from nut, legume, herb, spice, vegetable, or fungal plant tissue.

In another embodiment, there is provided herein a use of any of the above nanoparticle or nanoparticles for treating or preventing cancer in a subject in need thereof.

In yet embodiment of the above use or uses, the nanoparticle may be for simultaneous or sequential co-administration with an anticancer drug.

In still another embodiment of the above use or uses, the nanoparticle may be complexed with, or conjugated with, an anticancer drug.

In yet another embodiment of the above use or uses, the anticancer drug may be paclitaxel or vincristine.

In another embodiment, there is provided herein a use of any of the above nanoparticle or nanoparticles for providing a subject with soluble dietary fibre.

In yet another embodiment, there is provided herein a use of any of the above nanoparticle or nanoparticles as a viscosity enhancing food additive or fibre substitute.

In still another embodiment, there is provided herein a use of any of the above nanoparticle or nanoparticles for attenuating post-prandial sugar levels in the blood of a subject in need thereof.

In another embodiment, there is provided herein a use of any of the above nanoparticle or nanoparticles in a cosmetic product.

In yet another embodiment, there is provided herein a use of any of the above nanoparticle or nanoparticles for administration topically to a subject in need thereof.

In another embodiment, there is provided herein a use of any of the above nanoparticle or nanoparticles as a drug delivery vehicle for topical administration.

In another embodiment, there is provided herein a use of any of the above nanoparticle or nanoparticles for preventing sun burn in a subject in need thereof, wherein the nanoparticle is for application to the skin of the subject.

In yet another embodiment of the above use, the nanoparticle may comprise, or may be applied with, additional anthocyanin or another UV-protective agent.

In another embodiment, there is provided herein a use of any of the above nanoparticle or nanoparticles for reducing cell proliferation.

In another embodiment of the above use, the nanoparticle may be for use simultaneously or sequentially with an anticancer drug.

In still another embodiment of the above use or uses, the nanoparticle may be complexed with, or conjugated with, an anticancer drug.

In still another embodiment of the above use or uses, the anticancer drug may be paclitaxel or vincristine.

In another embodiment, there is provided herein a use of any of the above nanoparticle or nanoparticles for reducing triglyceride accumulation in the liver of a subject in need thereof.

In another embodiment, there is provided herein a targeted nanoparticle comprising any of the above nanoparticle or nanoparticles, conjugated with a targeting antibody specific for a cancer marker.

In another embodiment of the above targeted nanoparticle, the targeting antibody may comprise PD-L1 antibody, or an antigen binding fragment thereof, for targeting of the targeted nanoparticle to cancer cells.

In still another embodiment of the above targeted nanoparticle or targeted nanoparticles, the targeted nanoparticle may be complexed with, or conjugated with, at least one cytotoxic or anti-cancer drug.

In yet another embodiment of the above targeted nanoparticle or targeted nanoparticles, the targeted nanoparticle may be complexed with, or conjugated with, paclitaxel, doxorubicin, or both.

In another embodiment, there is provided herein an antibacterial nanoparticle, comprising any of the above nanoparticle or nanoparticles, complexed with or conjugated with an antibacterial agent.

In another embodiment of the above antibacterial nanoparticle, the antibacterial agent may comprise lysozyme, a tetracycline, or Nisin, or any combination thereof.

In still another embodiment of the above antibacterial nanoparticle or antibacterial nanoparticles, the antibacterial nanoparticle may be for use in treating or preventing MDR bacterial infection.

In another embodiment, there is provided herein a food powder comprising self-assembled cellular components derived from a homogenized plant tissue, the cellular components comprising one or more structural carbohydrates or cleavage products thereof, and further comprising at least one nutritional agent, wherein lipids are not a structural component of the food powder.

In another embodiment of the above food powder, the food powder may comprise:
fibrous structures winding about, or around, themselves to form a nanosphere-like structure.

In still another embodiment of any of the above food powder or food powders, the food powder may further comprise a hydrophobic component.

In still another embodiment of any of the above food powder or food powders, the hydrophobic component may comprise or may be provided in almond milk, coconut milk, and/or milk derived from an edible nut.

In still another embodiment of any of the above food powder or food powders, the nutritional agent may comprise a naturally occurring active ingredient having a health benefit.

In yet another embodiment of any of the above food powder or food powders, the nutritional agent may comprise one or more carotenoids, annonacins, Boswelia, Ashwagandha, Ginger family members, cannabinodiols, fructo-oligosaccharides, galacto-oligosaccharides, inulin, Jerusalem artichoke, Piperaceae family members, *Piper nigrum* or a wild relative containing piperine and/or derivatives thereof, or any active ingredient thereof having a health benefit, or any extract, derivative, or product isolated therefrom, or any combinations thereof.

In still another embodiment of any of the above food powder or food powders, the food powder may comprise:
  sour cherry, or an aqueous extract thereof;
  almond milk or another homogenate of almonds;
  soymilk, or another homogenate of soybean;
  broccoli, or an aqueous extract thereof; and
  turmeric, or a powder thereof.

In yet another embodiment of any of the above food powder or food powders, the food powder may comprise:
  about 25-30 v/v % sour cherry extract (at least about 0.1 mg/ml of polyphenol equivalent);
  about 25-30 v/v % almond milk or other homogenate of almonds;
  about 10-18 v/v % soymilk or other homogenate of soybean;
  about 25-30 v/v % broccoli extract; and
  about 0.5-2.5 w/v % turmeric or powder thereof.

In another embodiment of any of the above food powder or food powders, the sour cherry extract may be about 1-2 mg/ml polyphenol equivalent.

In another embodiment, there is provided herein a method for preparing food powder from homogenized plant tissue, said method comprising:
  preparing a homogenized plant tissue in solution, comprising cellular components liberated from the plant tissue, the cellular components comprising one or more structural carbohydrates or cleavage products thereof, and the homogenized plant tissue in solution further comprising at least one nutritional agent;
  optionally, removing debris from the homogenized plant tissue in solution, if present; and
  freeze-drying, lyophilizing, spray-drying, or nanospray drying the homogenized plant tissue in solution to form the food powder.

In another embodiment of the above method, the plant tissue may comprise a fruit, vegetable, or other plant tissue.

In still another embodiment of any of the above method or methods, the plant tissue may comprise a senescing fruit, a ripening vegetable, or any combination thereof; preferably, wherein the plant tissue comprises cherry, blueberry, grape, peach, nectarine, plum, apricot, *papaya*, tomato, fruits and/or berries of wild origin, or any combination thereof.

In yet another embodiment of any of the above method or methods, the homogenized plant tissue in solution may further comprise a hydrophobic component.

In another embodiment of any of the above method or methods, the hydrophobic component may comprise or may be provided in almond milk, coconut milk, and/or milk derived from an edible nut.

In still another embodiment of any of the above method or methods, the nutritional agent may comprise a naturally occurring active ingredient having a health benefit.

In still another embodiment of any of the above method or methods, the nutritional agent may comprise one or more carotenoids, annonacins, Boswelia, Ashwagandha, Ginger family members, cannabinodiols, fructo-oligosaccharides, galacto-oligosaccharides, inulin, Jerusalem artichoke, Piperaceae family members, *Piper nigrum* or a wild relative containing piperine and/or derivatives thereof, or any active ingredient thereof having a health benefit, or any extract, derivative, or product isolated therefrom, or any combinations thereof.

In yet another embodiment of any of the above method or methods, the homogenized plant tissue in solution may comprise:
  sour cherry, or an aqueous extract thereof;
  almond milk or another homogenate of almonds;
  soymilk, or another homogenate of soybean;
  broccoli, or an aqueous extract thereof; and
  turmeric, or a powder thereof.

In another embodiment of any of the above method or methods, the homogenized plant tissue in solution may comprise:
  about 25-30 v/v % sour cherry extract (at least about 0.1 mg/ml of polyphenol equivalent);
  about 25-30 v/v % almond milk or other homogenate of almonds;
  about 10-18 v/v % soymilk or other homogenate of soybean;
  about 25-30 v/v % broccoli extract; and
  about 0.5-2.5 w/v % turmeric or powder thereof.

In yet another embodiment of any of the above method or methods, the sour cherry extract may be about 1-2 mg/ml polyphenol equivalent.

In still another embodiment of any of the above method or methods, the step of preparing the homogenized plant tissue may comprise homogenizing the plant tissue in an aqueous medium, an organic medium, or a mixed aqueous-organic medium.

In still another embodiment of any of the above method or methods, the plant tissue may comprise one or more nutrient-containing materials, which may be fresh, pre-processed, or concentrated materials, or any combination thereof.

In yet another embodiment of any of the above method or methods, the step of preparing the homogenized plant tissue may comprise homogenizing the plant tissue with a blender, preferably operating at high rpm and generating high shear forces, a sonolator, or another high performance mixing device.

In still another embodiment of any of the above method or methods, the step of removing debris may comprise removing debris with a centrifugal device, with a filtration device, by membrane filtration, by tangential flow filtration, or any combination thereof.

In yet another embodiment of any of the above method or methods, the plant tissue may comprise a plant tissue obtained from or comprising sour cherry, almond or almond milk, soybean or soymilk, broccoli, turmeric, or any combination thereof.

In still another embodiment of any of the above method or methods, the homogenized plant tissue may comprise sour cherry extract, almond milk, soymilk, broccoli extract, and turmeric powder.

In another embodiment, there is provided herein a food powder produced by any of the above method or methods.

In still another embodiment, there is provided herein a method of delivering a biologically active agent to a subject, a cell, or an organism in need thereof, said method comprising:
  administering any of the above food powder or food powders, which is complexed with, or conjugated with, the biologically active agent using a chemical or physical process, to the subject or cell or organism.

In another embodiment of the above method, the biologically active agent may be an element such as Selenium, Zinc, Iron, or magnesium.

In still another embodiment of the above method or methods, the biologically active agent may be an anticancer drug, and the subject may be a subject with cancer.

In yet another embodiment of any of the above method or methods, the anticancer drug may be paclitaxel, vincristine, or any natural or synthetic compound used for treatment of cancer.

In another embodiment of any of the above method or methods, the biologically active agent may be introduced into the food powder during formation of the food powder, or the biologically active agent may be complexed with or conjugated with already formed food powder in an aqueous-based medium optionally comprising an alcohol or other organic component.

In another embodiment of any of the above method or methods, the aqueous-based medium may comprise DMSO, or a buffer, or both.

In still another embodiment, there is provided herein a method of treating a disease or disorder associated with increased levels of reactive oxygen species leading to inflammation in a subject in need thereof, comprising:
    administering any of the above food powder or food powders to the subject.

In still another embodiment, there is provided herein a method for treating or reducing inflammation in a subject in need thereof, said method comprising:
    administering any of the above food powder or food powders to the subject.

In another embodiment of the above method, the food powder may comprise, or may be co-administered with, an anti-inflammatory agent.

In still another embodiment of any of the above method or methods, the anti-inflammatory agent may comprise curcumin.

In still another embodiment, there is provided herein a method for treating or reducing obesity in a subject in need thereof, said method comprising:
    administering any of the above food powder or food powders to the subject.

In another embodiment of the above method, the food powder may contain or comprise components derived at least in part from nut, legume, herb, spice, vegetable, or fungal plant tissue, used for food or medical purposes.

In yet another embodiment, there is provided herein a method for treating or preventing cancer in a subject in need thereof, said method comprising:
    administering any of the above food powder or food powders to the subject.

In still another embodiment of the above method, the food powder may be simultaneously or sequentially co-administered with an anticancer drug.

In yet another embodiment of any of the above method or methods, the food powder may be complexed with, or conjugated with, an anticancer drug.

In still another embodiment of any of the above method or methods, the anticancer drug may be paclitaxel or vincristine.

In still another embodiment, there is provided herein a method for providing a subject with soluble dietary fibre, said method comprising:
    administering any of the above food powder or food powders to the subject.

In still another embodiment, there is provided herein a viscosity enhancing food additive comprising any of the above food powder or food powders.

In still another embodiment, there is provided herein a method for attenuating post-prandial sugar levels in the blood of a subject in need thereof, said method comprising:
    administering any of the above food powder or food powders to the subject.

In yet another embodiment, there is provided herein a method for reducing cell proliferation, said method comprising:
    treatment of a cell or tissue or organ with any of the above food powder or food powders.

In another embodiment of the above method, the food powder may be simultaneously or sequentially used with an anticancer drug.

In yet another embodiment of the above method, the food powder may be complexed with, or conjugated with, an anticancer drug.

In still another embodiment of the above method or methods, the anticancer drug may be paclitaxel or vincristine.

In still another embodiment, there is provided herein a method for reducing triglyceride accumulation in the liver of a subject in need thereof, said method comprising:
    administering any of the above food powder or food powders to the subject.

In still another embodiment, there is provided herein a use of any of the above food powder or food powders for delivering a biologically active agent to a subject or cell in need thereof. In another embodiment of the above use, the biologically active agent may be an element such as Selenium, Zinc, Magnesium or Iron.

In still another embodiment of the above use or uses, the biologically active agent may be an anticancer drug, and the subject is a subject with cancer.

In yet another embodiment of the above use or uses, the anticancer drug may be paclitaxel or vincristine.

In still another embodiment of any of the above use or uses, the biologically active agent may be introduced into the food powder during formation of the food powder, or the biologically active agent may be complexed with or conjugated with already formed food powder in an aqueous-based medium optionally comprising an alcohol or other organic component.

In still another embodiment of any of the above use or uses, the aqueous-based medium may comprise DMSO, or a buffer, or both.

In still another embodiment, there is provided herein a use of any of the above food powder or food powders for treating a disease or disorder associated with reactive oxygen species in a subject in need thereof.

In yet another embodiment, there is provided herein a use of any of the above food powder or food powders for treating or reducing inflammation in a subject in need thereof.

In another embodiment of the above use, the food powder may comprise or may be for administration with an anti-inflammatory agent.

In still another embodiment of the above use or uses, the anti-inflammatory agent may comprise curcumin.

In still another embodiment, there is provided herein a use of any of the above food powder or food powders for treating or reducing obesity in a subject in need thereof.

In yet another embodiment of any of the above use or uses, the food powder may be derived at least in part from nut, legume, herb, spice, vegetable, or fungal plant tissue.

In another embodiment, there is provided herein a use of any of the above food powder or food powders for treating or preventing cancer in a subject in need thereof.

In yet another embodiment of any of the above use or uses, the food powder may be for simultaneous or sequential co-administration with an anticancer drug.

In still another embodiment of any of the above use or uses, the food powder may be complexed with, or conjugated with, an anticancer drug.

In yet another embodiment of any of the above use or uses, the anticancer drug may be paclitaxel or vincristine.

In still another embodiment, there is provided herein a use of any of the above food powder or food powders for providing a subject with soluble dietary fibre.

In still another embodiment, there is provided herein a use of any of the above food powder or food powders as a viscosity enhancing food additive or fibre substitute.

In still another embodiment, there is provided herein a use of any of the above food powder or food powders for attenuating post-prandial sugar levels in the blood of a subject in need thereof.

In still another embodiment, there is provided herein a use of any of the above food powder or food powders for reducing cell proliferation.

In another embodiment of the above use, the food powder may be for use simultaneously or sequentially with an anticancer drug.

In still another embodiment of the above use or uses, the food powder may be complexed with, or conjugated with, an anticancer drug.

In still nother embodiment of any of the above use or uses, the anticancer drug may be paclitaxel or vincristine.

In still another embodiment, there is provided herein a use of any of the above food powder or food powders for reducing triglyceride accumulation in the liver of a subject in need thereof.

In still another embodiment, there is provided herein an antibacterial food powder, comprising any of the above food powder or food powders, complexed with or conjugated with an antibacterial agent.

In another embodiment of the above antibacterial food powder, the antibacterial agent may comprise lysozyme, a tetracycline, or Nisin, or any combination thereof.

In still another embodiment of any of the above antibacterial food powder or antibacterial food powders, the antibacterial food powder may be for use in treating or preventing MDR bacterial infection.

In yet another embodiment, there is provided herein a method for loading any of the above nanoparticle or nanoparticles with a biologically active agent or cargo, said method comprising:
providing a dehydrated, lyophilized, or freeze-dried sample of the nanoparticles;
mixing the biologically active agent or cargo with the sample of the nanoparticles to provide a mixture; and
adding water or aqueous-based solution to the mixture so as to shrink the nanoparticles, trapping the biologically active agent or cargo therein.

In yet another embodiment, there is provided herein a nanofibre comprising self-assembled cellular components derived from a homogenized plant tissue, the cellular components comprising one or more structural carbohydrates or cleavage products thereof, wherein lipids and polyphenols are not a structural components of the nanofibre.

In another embodiment of the above nanofibre, the nanofibre may be substantially lipid-free, may be substantially polyphenol-free, or both.

In still another embodiment of any of the above nanofibre or nanofibres, the nanofibre may comprise:
an elongated fibre comprising one or more strands comprising or made from at least one structural carbohydrate.

In yet another embodiment of any of the above nanofibre or nanofibres, the nanofibre may comprise pectin, hemicellulose, peptide and/or protein, an organic acid, cleavage products thereof, or any combination thereof.

In yet another embodiment of any of the above nanofibre or nanofibres, the organic acid may comprise malic acid, ascorbic acid, or both.

In still another embodiment of any of the above nanofibre or nanofibres, the cellular components may comprise those liberated from the plant tissue during ripening or during homogenization of ripened fruit, which are capable of self-assembling into the nanofibre.

In yet another embodiment of any of the above nanofibre or nanofibres, the one or more structural carbohydrates may comprise one or more of pectin, pectic acid, methyl ester of pectin, a pectin derivative, polygalacturonic acid, rhamnogalacturonans, xylogucans, hemicelluloses, xyloglucans possessing $\beta$-(1→4)-linked backbones of glucose, mannose, or xylose, and/or arabinogalactans, and/or cleavage products thereof.

In another embodiment of any of the above nanofibre or nanofibres, the nanofibre may have a fibre shape with a diameter of about 5-10 nm.

In yet another embodiment of any of the above nanofibre or nanofibres, the nanofibre may be stabilized by hydrogen-bonding interactions and formed between macromolecules derived from catabolism of cellular components of the plant tissue and possessing hydroxyl groups and/or amino groups and/or organic acid groups.

In yet another embodiment of any of the above nanofibre or nanofibres, the nanofibre may be non-crystalline.

In still another embodiment of any of the above nanofibre or nanofibres, the nanofibre may further comprise a biologically active agent.

In yet another embodiment of any of the above nanofibre or nanofibres, the biologically active agent may be a pharmaceutically active drug, protein, enzyme, nutraceutical, or nutrient.

In yet another embodiment of any of the above nanofibre or nanofibres, the nanofibre may be in aqueous solution.

In yet another embodiment of any of the above nanofibre or nanofibres, the nanofibre may be in powder form.

In yet another embodiment of any of the above nanofibre or nanofibres, the nanofibre may be in dehydrated, lyophilized, freeze-dried, spray-dried, or nanospray-dried form.

In yet another embodiment of any of the above nanofibre or nanofibres, the plant tissue may comprise a fruit or vegetable plant tissue and/or polyphenols may have been removed from the plant tissue prior to homogenization.

In yet another embodiment of any of the above nanofibre or nanofibres, the plant tissue may comprise a senescing fruit, a ripening vegetable, or any combination thereof; preferably, wherein the plant tissue comprises cherry, blueberry, grape, peach, nectarine, plum, apricot, *papaya*, tomato, or any combination thereof.

In yet another embodiment of any of the above nanofibre or nanofibres, the plant tissue may comprise a sour cherry fruit tissue.

In still another embodiment, there is provided herein a method for preparing nanofibres from homogenized plant tissue, said method comprising:

preparing a homogenized plant tissue in solution having low polyphenol content, comprising cellular components liberated from the plant tissue;

removing debris from the homogenized plant tissue, if present; and optionally, dialyzing the homogenized plant tissue to remove non-complexed compounds, or removing the non-complexed compounds by size exclusion, thereby providing a solution comprising the nanofibres which are formed by self-assembly of the cellular components.

In another embodiment of the above method, the method may further comprise a step of dehydrating, lyophilizing, freeze-drying, spray-drying, or nanospray-drying the solution comprising the nanofibre.

In yet another embodiment of any of the above method or methods, the nanofibres may be formed by self-assembly in a substantially aqueous medium.

In yet another embodiment of any of the above method or methods, the step of preparing the homogenized plant tissue in solution may comprise homogenizing a plant tissue in an aqueous, organic, or mixed aqueous-organic medium.

In yet another embodiment of any of the above method or methods, the step of preparing the homogenized plant tissue in solution may comprise subjecting a plant tissue to high shear homogenization and/or sonolation in an aqueous, organic, or mixed aqueous-organic medium comprising any one or more of water, ethanol, methanol, or acetone.

In still another embodiment of any of the above method or methods, the step of preparing the homogenized plant tissue in solution may comprise a step of bleaching the plant tissue to remove polyphenols therefrom prior to homogenization of the plant tissue.

In another embodiment of any of the above method or methods, the bleaching may comprise performing an extraction of polyphenols from the plant tissue with an extraction solvent.

In yet another embodiment of any of the above method or methods, the extraction solvent may comprise ethanol.

In yet another embodiment of any of the above method or methods, the step of removing debris may comprise dialysis, filtering the homogenized plant tissue, centrifuging the homogenized plant tissue, or performing tangential flow filtration or continuous flow filtration on the homogenized plant tissue, or any combination thereof.

In still another embodiment of any of the above method or methods, the method may be for preparing any of the above nanofibre or nanofibres.

In another embodiment, there is provided herein a method for preparing a nanofibre from homogenized plant tissue, said method comprising:

preparing a homogenized plant tissue in solution having low polyphenol content, comprising cellular components liberated from the plant tissue;

removing debris from the homogenized plant tissue, if present;

allowing the nanofibre to form by self-assembly of the cellular components; and freeze-drying, spray-drying, or nanospray drying to form a powder comprising the nanofibre.

In another embodiment of the above method, the self-assembly may occur in a substantially aqueous medium.

In still another embodiment of any of the above method or methods, the step of preparing the homogenized plant tissue in solution may comprise homogenizing a plant tissue in an aqueous, organic, or mixed aqueous-organic medium.

In yet another embodiment of any of the above method or methods, the step of preparing the homogenized plant tissue in solution may comprise subjecting a plant tissue to high shear homogenization and/or sonolation in an aqueous, organic, or mixed aqueous-organic medium comprising any one or more of water, ethanol, methanol, or acetone.

In yet another embodiment of any of the above method or methods, the step of preparing the homogenized plant tissue in solution may comprise a step of bleaching the plant tissue to remove polyphenols therefrom prior to homogenization of the plant tissue.

In yet another embodiment of any of the above method or methods, the bleaching may comprise performing an extraction of polyphenols from the plant tissue with an extraction solvent.

In still another embodiment of any of the above method or methods, the extraction solvent may comprise ethanol.

In another embodiment of any of the above method or methods, the step of removing debris may comprise dialysis, filtering the homogenized plant tissue, centrifuging the homogenized plant tissue, or performing tangential flow filtration or continuous flow filtration on the homogenized plant tissue, or any combination thereof.

In yet another embodiment of any of the above method or methods, the plant tissue may comprise plant tissue extracted with an extraction solvent to remove polyphenols therefrom.

In another embodiment of any of the above method or methods, the extraction solvent may comprise ethanol.

In still another embodiment of any of the above method or methods, the method may be for preparing any of the above nanofibre or nanofibres.

In another embodiment, there is provided heirne a nanofibre prepared by any of the above method or methods.

In another embodiment, there is provided herein a food powder prepared from any of the above nanofibre or nanofibres, optionally wherein the food powder is provided in a micro-scale fine powder form.

In another embodiment, there is provided herein a method of delivering a biologically active agent to a subject or cell in need thereof, said method comprising:

administering any of the above nanofibre or nanofibres, which is complexed with or conjugated with the biologically active agent, to the subject.

In another embodiment of the above method, the biologically active agent may be an element such as Selenium, Zinc, Iron, or Magnesium.

In still another embodiment of any of the above method or methods, the biologically active agent may be an anti-cancer drug, and the subject may be a subject with cancer.

In still another embodiment of any of the above method or methods, the anticancer drug may be paclitaxel, vincristine, or any natural or synthetic compound used for treatment of cancer.

In yet another embodiment of any of the above method or methods, the biologically active agent may be introduced into the nanofibre during formation of the nanofibre, or the biologically active agent may be complexed with or conjugated with already formed nanofibres in an aqueous-based medium optionally comprising an alcohol or other organic component.

In another embodiment of any of the above method or methods, the aqueous-based medium may comprise DMSO, or a buffer, or both.

In still another embodiment, there is provided herein a method for treating or preventing cancer in a subject in need thereof, said method comprising:

administering any of the above nanofibre or nanofibres to the subject.

In another embodiment of the above method, the nanofibre may be simultaneously or sequentially co-administered with an anticancer drug.

In still another embodiment of any of the above method or methods, the nanofibre may be complexed with, or conjugated with, an anticancer drug.

In yet another embodiment of any of the above method or methods, the anticancer drug may be paclitaxel or vincristine.

In still another embodiment, there is provided herein a method for providing a subject with soluble dietary fibre, said method comprising:
administering any of the above nanofibre or nanofibres to the subject.

In still another embodiment, there is provided herein a viscosity enhancing food additive comprising any of the above nanofibre or nanofibres.

In another embodiment, there is provided herein a method for attenuating post-prandial sugar levels in the blood of a subject in need thereof, said method comprising:
administering any of the above nanofibre or nanofibres to the subject.

In still another embodiment, there is provided herein a cosmetic product comprising any of the above nanofibre or nanofibres.

In yet another embodiment, there is provided herein a composition for topical administration to a subject in need thereof, the composition comprising any of the above nanofibre or nanofibres, and optionally a biologically active agent.

In still another embodiment, there is provided herein a method for preventing sun burn in a subject in need thereof, said method comprising:
applying any of the above nanofibre or nanofibres to the skin of the subject.

In yet another embodiment of the above method, the nanofibre may comprise, or may be applied with, anthocyanin or another UV-protective agent.

In yet another embodiment, there is provided herein a method for reducing cell proliferation, said method comprising:
treatment of a cell or tissue or organ with any of the above nanofibre or nanofibres.

In still another embodiment of the above method, the nanofibre may be simultaneously or sequentially used with an anticancer drug.

In yet another embodiment of any of the above method or methods, the nanofibre may be complexed with, or conjugated with, an anticancer drug.

In still another embodiment of any of the above method or methods, the anticancer drug may be paclitaxel or vincristine.

In still another embodiment, there is provided herein a method for reducing triglyceride accumulation in the liver of a subject in need thereof, said method comprising:
administering any of the above nanofibre or nanofibres to the subject.

In yet another embodiment, there is provided herein a use of any of the above nanofibre or nanofibres for delivering a biologically active agent to a subject or cell in need thereof.

In another embodiment of the above use, the biologically active agent may be an element such as Selenium, Zinc, Magnesium or Iron.

In yet another embodiment of any of the above use or uses, the biologically active agent may be an anticancer drug, and the subject may be a subject with cancer.

In still another embodiment of any of the above use or uses, the anticancer drug may be paclitaxel or vincristine.

In yet another embodiment of any of the above use or uses, the biologically active agent may be introduced into the nanofibre during formation of the nanofibre, or the biologically active agent may be complexed with or conjugated with already formed nanofibres in an aqueous-based medium.

In still another embodiment of any of the above use or uses, the aqueous-based medium may comprise DMSO, or a buffer, or both.

In yet another embodiment, there is provided herein a use of any of the above nanofibre or nanofibres for treating or preventing cancer in a subject in need thereof.

In still another embodiment of any of the above use or uses, the nanofibre may be for simultaneous or sequential co-administration with an anticancer drug.

In yet another embodiment of any of the above use or uses, the nanofibre may be complexed with, or conjugated with, an anticancer drug.

In another embodiment of any of the above use or uses, the anticancer drug may be paclitaxel or vincristine.

In another embodiment, there is provided herein a use of any of the above nanofibre or nanofibres for providing a subject with soluble dietary fibre.

In still another embodiment, there is provided herein a use of any of the above nanofibre or nanofibres as a viscosity enhancing food additive or fibre substitute.

In yet another embodiment, there is provided herein a use of any of the above nanofibre or nanofibres for attenuating post-prandial sugar levels in the blood of a subject in need thereof.

In another embodiment, there is provided herein a use of any of the above nanofibre or nanofibres in a cosmetic product.

In still another embodiment, there is provided herein a use of any of the above nanofibre or nanofibres for administration topically to a subject in need thereof, wherein the nanofibre is optionally complexed with or conjugated with a biologically active agent.

In yet another embodiment, there is provided herein a use of any of the above nanofibre or nanofibres as a drug delivery vehicle for topical administration.

In still another embodiment, there is provided herein a use of any of the above nanofibre or nanofibres for preventing sun burn in a subject in need thereof, wherein the nanofibre is for application to the skin of the subject.

In another embodiment of the above use, the nanofibre may comprise, or may be applied with, anthocyanin or another UV-protective agent.

In yet another embodiment, there is provided herein a use of any of the above nanofibre or nanofibres for reducing cell proliferation.

In another embodiment of the above use, the nanofibre may be for use simultaneously or sequentially with an anticancer drug.

In still another embodiment of the above use or uses, the nanofibre may be complexed with, or conjugated with, an anticancer drug.

In yet another embodiment of the above use or uses, the anticancer drug may be paclitaxel or vincristine.

In another embodiment, there is provided herein a use of any of the above nanofibre or nanofibres for reducing triglyceride accumulation in the liver of a subject in need thereof.

In another embodiment, there is provided herein a targeted nanofibre comprising any of the above nanofibre or nanofibres, conjugated with a targeting antibody specific for a cancer marker.

In another embodiment of the above targeted nanofibre, the targeting antibody may comprise PD-L1 antibody, or an antigen-binding fragment thereof, for targeting of the targeted nanofibre to cancer cells.

In still another embodiment of the above targeted nanofibre or targeted nanofibres, the targeted nanofibre may be complexed with, or conjugated with, at least one cytotoxic or anti-cancer drug.

In yet another embodiment of any of the above targeted nanofibre or targeted nanofibres, the targeted nanofibre may be complexed with, or conjugated with, paclitaxel, doxorubicin, or both.

In another embodiment, there is provided herein an antibacterial nanofibre, comprising any of the above nanofibre or nanofibres, complexed with or conjugated with an antibacterial agent.

In another embodiment of the above antibacterial nanofibre, the antibacterial agent may comprise lysozyme, a tetracycline, or Nisin, or any combination thereof.

In still another embodiment of any of the above antibacterial nanofibre or antibacterial nanofibres, the antibacterial nanofibre may be for use in treating or preventing MDR bacterial infection.

In certain embodiments, there is provided herein a composition comprising any of the above nanoparticle or nanoparticles, any of the above food powder or food powders, any of the above nanofibre or nanofibres, or any combinations thereof. In certain embodiments, the composition may further comprise a pharmaceutically acceptable excipient, carrier, or diluent. In certain embodiments, it is contemplated that mixtures of any two, or any three, of the nanoparticles, nanofibres, and/or food powders as described herein may be used for uses and/or methods as described herein. In certain embodiments, for example, a mixture of nanoparticles and nanofibres may be used; a mixture of nanoparticles and food powder may be used; a mixture of nanofibres with food powder may be used; or a mixture of nanoparticles, nanofibres, and food powder may be used.

DETAILED DESCRIPTION

Figure 1:
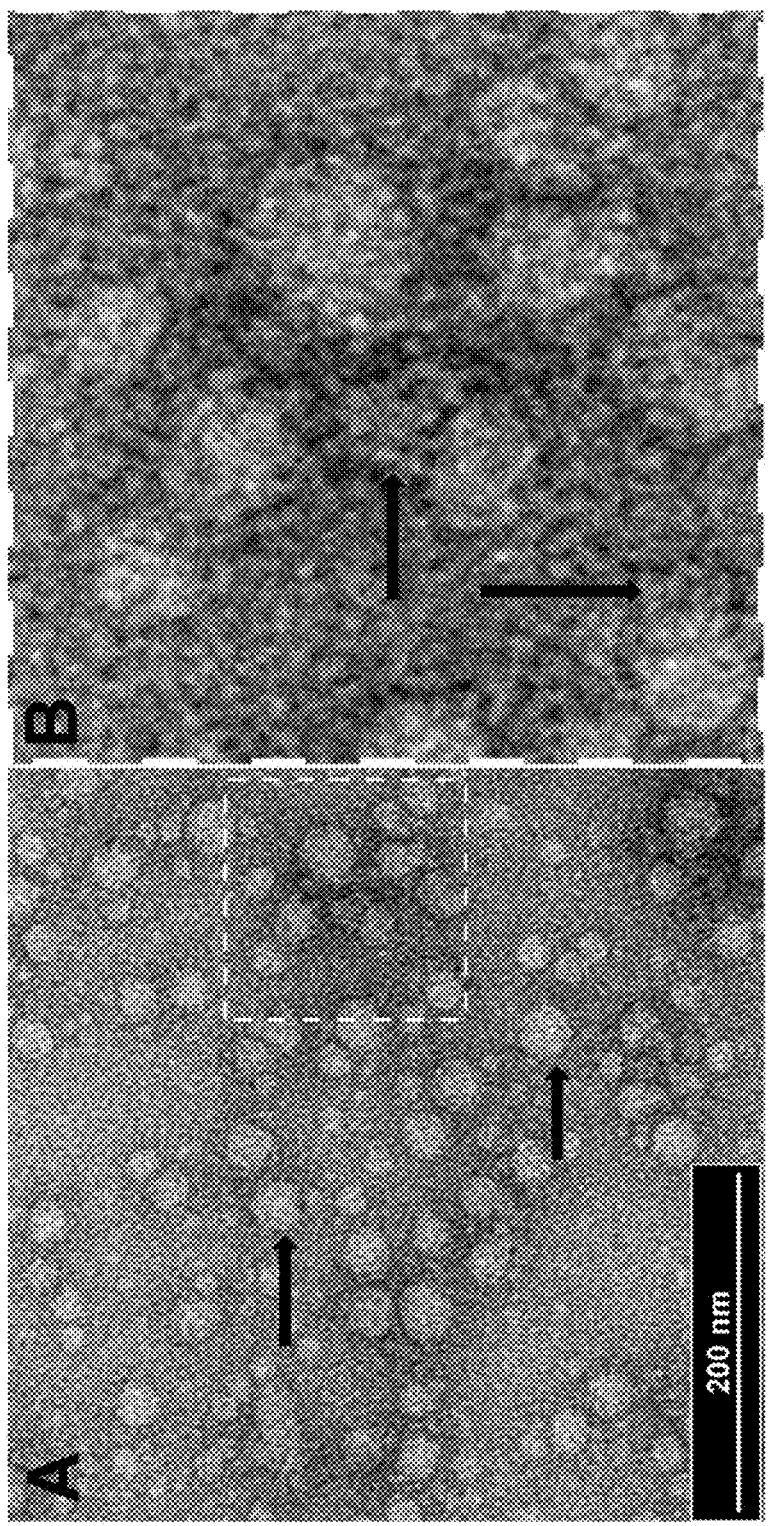
FIG. 1 shows transmission electron microscopy images of nanoparticles prepared from sour cherry (A). Nanoparticles were allowed to adsorb to a carbon-coated nickel grid for 1 min by floating the grids on a 50 µl drop of the extract. The grid was removed, blotted dry at the edge and floated on to a drop of 1% uranyl acetate. After 30 seconds, the grid was removed, blotted dry at the edge and directly examined using a Leo Electron microscope. In a liquid medium, the nanoparticles vary in size between 50-100 nm in diameter. Panel B shows a magnified view of the nanoparticles. The arrows indicate fibril-like structures emanating from the nanoparticles.

Described herein are plant tissue-derived nanoparticles and food powders, methods for the production thereof, and uses thereof. For comparison, nanofibres and methods for the production thereof are also described. It will be appreciated that embodiments and examples are provided for illustrative purposes intended for those skilled in the art, and are not meant to be limiting in any way.

As described in detail hereinbelow, nanoparticles, food powders, and nanofibers have now been developed which may feature several interesting properties. Although nanoparticles and nanofibers may both be prepared from plant tissue, these two nanostructures have been prepared herein using notably different methods, and these two nanostructures have been found herein to adopt notably different structures, to feature significant differences in terms of composition, and to feature interesting differences (and similarities) in terms of function and/or biological effects.

By way of example, nanoparticles including self-assembled cellular components derived from a homogenized plant tissue, the cellular components including one or more cell wall and/or other cellular components, are described herein. Also described, in comparison, are nanofibres including self-assembled cellular components derived from a homogenized plant tissue from which polyphenols have been extracted, the cellular components including one or more cell wall and/or other cellular components. Methods and protocols for preparing such nanoparticles and nanofibres (indicating differences therebetween), as well as uses of such nanoparticles and nanofibres in, for example, the treatment or prevention of diseases or disorders in a subject and/or as delivery vehicles are also described. Food powders related to (but distinct from) the presently described nanoparticles and nanofibers, and particularly the present nanoparticles, are also described in detail herein.

Nanoparticles and Methods for the Production Thereof

Nanoparticles:

In an embodiment, there is provided herein a nanoparticle comprising self-assembled cellular components derived from a homogenized plant tissue, the cellular components comprising one or more cell wall and/or other cellular components. In certain embodiments, the cellular components may include components liberated from the plant tissue by homogenization, which self-assemble into the nanoparticle, for example. In certain embodiments, the one or more cell wall components may include pectin and/or derivatives thereof.

In certain embodiments, there is provided herein a nanoparticle comprising self-assembled cellular components derived from a homogenized plant tissue, the cellular components comprising one or more structural carbohydrates or cleavage products thereof, wherein lipids are not a structural component of the nanoparticle.

In certain embodiments, the nanoparticles may be substantially or fully lipid free, or may contain only minimal, residual, or trace amounts of lipids. In certain embodiments, lipids, such as phospholipids, diacylglycerols, triacylglycerols, free fatty acids or aldehydes and alkanes, are not structural components of the nanoparticle (i.e. lipids, and the nanoparticles as a whole, do not form uni- or multi-lamellar vesicles of a membranous nature). In certain embodiments, if some amount of lipid is present, the lipid amount is below a critical micellar concentration (CMC) level and does not form micelles or vesicles. In certain embodiments, lipid does not substantially contribute to nanoparticle tertiary or quaternary structure, and/or does not contribute to nanoparticle self-assembly. In certain embodiments, plant tissue may be selected so as to provide little or no lipid, and/or lipids may be removed prior to nanoparticle self-assembly.

In certain embodiments, the cellular components may comprise those liberated from the plant tissue during ripening or during homogenization of ripened fruit, which are capable of self-assembling into the nanoparticle.

In certain embodiments, the plant tissue may comprise, for example, a plant tissue or plant material of a fruit, vegetable, leaf, flower, seed (at generally any stage of development), or any combination thereof. In certain embodiments, mixtures of two or more tissues may be used. In certain embodiments, a plurality of tissues may be used, each enriched in one or more components of the nanoparticles, such that homogenization of the mixture provides the components for self-assembly to form the nanoparticles. In certain embodiments, the plant tissue or plant material may comprise sour cherry, blueberry, portions thereof or mixtures thereof, for example. In certain embodiments, the plant material or plant tissue may comprise a ripe fruit. In certain embodiments, developing fruits (before ripening) may not contain sufficient nanoparticle components, but may still be used by mixing with other plant materials or tissues and/or particular nanoparticle components to compensate, and/or where the immature fruit is treated with enzymes to generate sufficient nanoparticle components to allow for nanoparticle assembly following homogenization. In certain embodiments, homogenization of the plant tissue may be performed in a manner so as to increase ripening by increasing exposure of cellular components to ripening enzymes under conditions in which the ripening enzymes will be active. In certain embodiments, the plant tissue may provide pectin, one or more hemicelluloses, protein/peptide, one or more carbohydrates, malic acid (or another organic acid able to form hydrogen bonds), at least one anthocyanin, and/or ascorbic acid, or any combination thereof. In certain embodiments, the plant tissue may provide, at least, pectin, one or more hemicelluloses, protein/peptide, one or more carbohydrates, malic acid (or another organic acid able to form hydrogen bonds), at least one anthocyanin, and ascorbic acid. In certain embodiments, the nanoparticle may comprise pectin, hemicellulose, peptide and/or protein, an organic acid, at least one polyphenol, cleavage products thereof, or any combination thereof. In certain embodiments, the organic acid may comprise malic acid, ascorbic acid, or both. In certain embodiments, the polyphenol may comprise an anthocyanin. In certain embodiments, the cellular components comprise those liberated from the plant tissue during ripening and/or during homogenization of ripened fruit, which are capable of self-assembling into the nanoparticle. In certain embodiments, homogenization may increase exposure of cellular components to ripening enzyme(s) forming cleavage products which may contribute to the nanoparticle.

In certain embodiments, nanoparticles as described herein may be free, or substantially free, of starch (such as Alpha- and Beta-amylose). Starch tends to form dendromer-type structures, and therefore presence of higher levels of starch in the plant tissue used to generate the nanoparticles may interfere with nanoparticle generation. In certain embodiments, if plant tissues containing starch are to be used, they may be used sparingly to keep starch content low. For example, if a banana is to be used as part of the plant tissue, the proportion of the plant tissue represented by the banana may be comparatively low relative to other components of the plant tissue being used. In certain embodiments, similar considerations may also apply to food powders and/or nanofibres as also described in detail herein.

In certain embodiments, the plant tissue may be in a partially degraded state (e.g. ripened) with partially degraded cell wall, or may be generated from plant tissues with the addition of carbohydrate and/or protein catabolizing enzymes to a tissue during homogenization that catabolize cell wall components. In certain embodiments, the beginning plant tissue may be partially processed, such as by fixing in a preservation agent such as alcohol or acetic acid (vinegar), and rehydrated before being subjected to homogenization. In certain embodiments, plant tissue may be blended with ascorbic acid and malic acid to facilitate structural integrity and/or yield of nanoparticles, for example.

In certain embodiments, the plant tissue may comprise a fruit or vegetable plant tissue. In certain embodiments, the plant tissue may comprise a senescing fruit, a ripening vegetable, or any combination thereof. In certain preferred embodiments, the plant tissue may comprise cherry (such as sour cherry, for example), blueberry, grape, peach, nectarine, plum, apricot, *papaya*, tomato, or any combinations thereof. By way of example, in certain preferred embodiments, the plant tissue may comprise a sour cherry fruit tissue. In certain embodiments, the plant tissue may comprise fruit skins and/or outer tissue of fruits, such as in cocoa for example.

In certain embodiments, the nanoparticle may comprise pectin, hemicellulose, peptide and/or protein, an organic acid, at least one polyphenol, cleavage products thereof, or any combinations thereof. In certain embodiments, the organic acid may comprise malic acid, ascorbic acid, or both. In certain embodiments, the polyphenol may comprise an anthocyanin.

In certain embodiments, the one or more structural carbohydrates of the nanoparticle may comprise one or more of pectin, pectic acid, methyl ester of pectin, a pectin derivative, polygalacturonic acid, rhamnogalacturonans, hemicelluloses such as xyloglucans (which may in certain embodiments be neither cellulose nor pectin) and possessing β-(1-→4)-linked backbones of glucose, mannose, or xylose, and/or arabinogalactans, and/or cleavage products thereof.

In certain embodiments, the nanoparticle may have a substantially spherical structure with a diameter of about 50 to about 250 nm, for example. In certain embodiments, the nanoparticle may be non-crystalline. In certain embodiments, the nanoparticle may be provided in aqueous solution, in dried powder form, or in dehydrated, lyophilized, freeze-dried, spray-dried, or nanospray-dried form.

Figure 17:
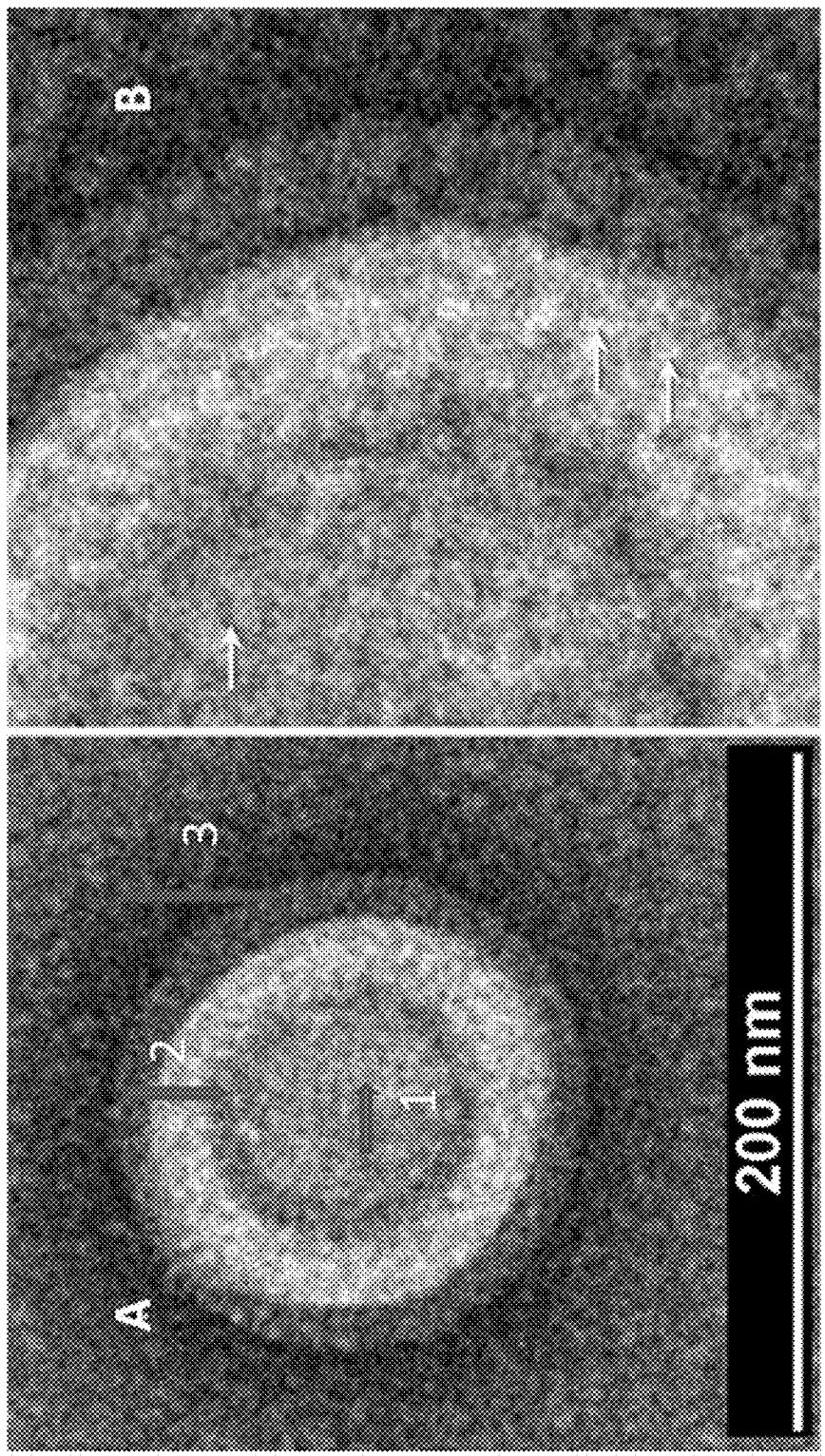
FIG. 17 shows results suggesting a proposed structural model for the nanoparticle. A magnified view of a nanoparticle as observed by TEM in sour cherry homogenate is provided in Panel A and a magnified region is shown in B. The aqueous homogenate of sour cherry was centrifuged (15000×g) for 15 minutes at 4° C. to sediment the debris and gel-like pectinaceous material. The homogenate was passed through a PD 10 size exclusion column packed with Sephadex G 25 (exclusion limit 5 kD, 7.5 ml bed volume, Amersham Biosciences), and the void volume fractions collected. The fraction containing nanoparticles was subjected to transmission electron microscopy. The figure shows a collapsed region around the inner core showing a ring shaped structure (Panel A, arrow 1), surrounded by a less electron dense region comprised of helical filamentous structures potentially containing pectin and protein (Panel A, arrow 2), sometimes in the spiral organization (arrow 2) as seen earlier. Surrounding this layer, there is a slightly more electron dense fibre-like region forming the outer part of the nanoparticle (Panel A, arrow 3) potentially comprising arabinogalactan-protein containing filaments and may contain polyphenols (i.e. anthocyanins). An enlarged magnified view of the nanoparticle is shown in Panel B. The helical elements are indicated by arrows.

In certain embodiments, the nanoparticle may comprise: a pectin-based inner core; an intermediate layer surrounding the inner core, the intermediate layer comprising macromolecules of pectin and hemicellulose and/or cleavage products thereof, polyphenols, and organic acids; and a fibrillated outer layer comprising macromolecular structural carbohydrate and protein (peptides), optionally formed from catabolism products formed during ripening and/or during homogenization of the plant tissue. FIG. 17, described in further detail hereinbelow, depicts an example of such a structural organization. In certain embodiments, the pectin-based inner core may be a generally hollow, or solid, sphere-shaped structure, and treatment of the nanoparticle with a pectin degrading enzyme such as polygalacturonase/pectinase may result in the inner core breaking down into smaller globules (indicating that the inner core may be pectin-based). In certain embodiments, the intermediate layer may comprise a layer formed by macromolecules of pectin and hemicellulose origin, hydrogen bonded through anthocyanins, ascorbic and malic acids, and peptides originating from various cellular proteins, for example. In certain embodiments, the fibrillated outer layer may comprise macromolecular structural carbohydrates and/or protein originating from catabolism occurring during ripening of the plant tissue, for example.

In certain embodiments, the nanoparticles may comprise one or more peptides originating from protein degradation occurring in the plant tissue during ripening and/or during homogenization. In certain embodiments, the nanoparticles may comprise one or more catabolites of structural carbohydrates, occurring in the plant tissue during ripening and/or during homogenization.

In certain embodiments, the nanoparticle may comprise: a pectin-based inner core; an intermediate layer surrounding the inner core, the intermediate layer comprising one or more spiral fibril structures comprising pectin or a derivative thereof, and one or more hemicellulose-derived molecules or a derivative thereof; and a fibrillated outer layer comprising hemicellulose or a cleavage product thereof, and one or more peptides derived from cellular proteins.

In certain embodiments, the nanoparticle may be stabilized by hydrogen-bonding interactions present at a pH ranging from about 3 to about 7 and formed between macromolecules derived from catabolism of cellular components of the plant tissue and possessing hydroxyl groups (as found in sugars, for example) and/or amino groups (as found in peptides, for example) and/or organic acid groups (as found in ascorbic acid and/or malic acid, for example). In certain embodiments, the hydrogen-bonding interactions may also involve hydroxyl groups of small molecules such as polyphenols (such as anthocyanins, for example Cyanidin-3-glucoside, and/or Cyanidin-3-rutinoside). In certain embodiments, nanoparticles may be formed/self-assembled under somewhat neutral-acidic conditions (such as at a pH of about 3 to about 7), and in a solution which is not a buffer or another solution having a high ionic strength which might interfere with hydrogen bonding. In certain embodiments, calcium ions may act as bridges between the polygalacturonic acid chains enabling stabilization of nanoparticles. As will be understood, salts such as potassium, sodium, and/or calcium might be present in the solution, having originated from the plant tissue, for example.

As will be understood, the conditions under which cellular components liberated from the plant tissue by homogenization may self-assemble into the nanoparticle may vary depending on the particular application and materials used. In certain embodiments, the conditions may be at a temperature ranging between about 4° C. to about 40° C., preferably from about 15° C. to about 35° C. In certain embodiments the conditions may be in water, or in a mixture of water with a water miscible organic solvent such as (but not limited to) methanol or ethanol. In certain embodiments, the conditions under which cellular components liberated from the plant tissue by homogenization may self-assemble into the nanoparticle may be in solution which is about 15 to 100% v/v water, more preferably about 30 to about 100% v/v water, and most preferably about 100% v/v water. Where self assembly occurs in an aqueous or substantially aqueous solution, it is contemplated that in certain embodiments enzymes normally present in a ripening environment, such as polygalactouronase, may be added to the mix, especially to aid self-assembly when using unripened fruit as, or as part of, the plant tissue. In certain embodiments, the conditions under which self-assembly may occur may be in a substantially aqueous medium, for example. In certain embodiments, the production of nanoparticles may be achieved by procedures as described herein using a suitable medium. Typically, the medium may be water or an aqueous medium, but may in certain embodiments be or comprise water and a miscible organic solvent such as, but not limited to, one or more alcohols which may include ethanol and/or methanol, one or more ketones such as acetone, one or more solvents which may include dimethyl sulfoxide, either separately or in any suitable combinations thereof. In certain embodiments, the self-assembly of the nanoparticles may occur in one of the media described hereinabove. The conditions for self-assembly may comprise any thermodynamically feasible conditions. In certain embodiments, the conditions for self-assembly may, for example, comprise temperature from about 4° C. to about 30° C., ion concentrations that are generally in accordance with those found physiologically (i.e. micromolar to millimolar levels), sugar concentration in a range of about 5-10 percent w/v, and natural organic acids present in the millimolar range, for example.

In certain embodiments, a preferred method may include a method in which fruit tissue is homogenized in an aqueous or alcoholic medium (or a combination of both), at about 4° C., using a blender, polytron or any other device that can disrupt cellular organization. After making a smooth homogenate of the strating material, is the homogenate may be filtered to remove the debris, and centrifuged a about 10000×g to sediment fine debris. The resulting homogenate may be dialyzed using about a 100 kD cutoff dialysis bag for about 15 hours at about 4° C. The solution from the dialysis bag may be collected and subjected to a form of water removal and/or freeze drying/spray drying, nanospray drying etc. to provide the nanoparticles. These may be stored dry at about −20° C. in the dark where long term storage is desired, for example.

In certain embodiments, homogenization may include any suitable method of maceration of plant tissue such as grinding, blending, high shear homogenizing, or homogenizing using a device such as a polytron, of plant tissues.

In certain embodiments, plant tissues may include one or more fruits and/or vegetables, which may or may not be in combination with other plant tissues. In examples where a nutraceutical product is desired, a carrier (such as a fruit) and a nutraceutical-containing plant (such as, for example, Turmeric rhizomes) may be used as plant tissue. In certain embodiments, a plant tissue (such as a fruit) along with a purified, or partially purified, product (such as turmeric powder, or curcumin, for example) may be used.

Some examples of nutraceutical compounds and plant families may include:

a. Carotenoids (beta-carotene, lycopene, lutein and/or other xanthophylls, astaxanthin, etc);
b. Annonacins (Polyketides derived from Annona fruits with anticancer properties);
c. Boswellia (which may act in conjunction with curcumin providing added anti-inflammatory function, for example);
d. Ashwagandha (a herbal component containing withanoliides with antistress, and cancer preventive properties), primarily with a steroid structure;
e. Ginger family members that include edible ginger (*Zingiber officinalis*), mango ginger (*Curcuma amada*) and others containing several bioactive ingredients including gingerols and shogaols;
f. *Curcuma longa* (turmeric, containing curcumin);
g. Cannabinodiols which are the medicinally active ingredients of *Cannabis* sp. without hallucinogenic activity;
h. Fructo-oligosaccharides and galacto-oligosaccharides as well as inulin from Jerusalem artichoke, to enhance prebiotic content;
i. Piperaceae members such as *Piper nigrum* and its wild relatives containing piperine and several derivatives; and/or
j. Any other suitable ingredients from plants not listed above.

In further embodiments, the nanoparticles may comprise at least one polyphenol. In certain embodiments, the polyphenol may be, or comprise, an anthocyanin, or several anthocyanins. In still further embodiments, the nanoparticles may further comprise an organic acid, such as malic acid, ascorbic acid, or both. In certain embodiments, the nanoparticles may comprise more than one polyphenol. As will be understood, the polyphenol composition of the nanoparticle May reflect the polyphenol composition of the plant tissue (for example, the fruit) being used, and any additional polyphenol being supplied (if external polyphenol is being added). Where sour cherry is being used, for example, polyphenols may include Cyanidin 3 rutinoside or glucoside. Where blueberry is used, polyphenols may include multiple phenolics and anthocyanins found in blueberry. Examples of polyphenols (both anthocyanin and phenolic) are indicated in the following Table:

| Anthocyanin Component | Phenolic Component |
|---|---|
| Delpinidin 3-galactoside | Caffeic acid |
| Delphinidin 3-glucoside | Ferulic acid |
| Delphinidin 3-arabinoside | Gallic acid |

-continued

| Anthocyanin Component | Phenolic Component |
|---|---|
| Cyanidin 3-glucoside | Cinnamic acid |
| Petunidin 3-galactoside | Phenyl acetic acid |
| Peonidin 3-galactoside | Catechins/Epicatechins |
| Petunidin 3-arabinoside | Isorhamnetin |
| Malvinidin 3-galactoside | Myricetin |
| Peonidin 3-arabinoside | Chlorogenic acid |
| Malvidin 3-glucoside | 4-O-feruloyl quinic acid |
| Malvidin 3-arabinoside | Quercetin 3-arabinoside |
| Delpinidin 6-acetyl-3-glucoside | Syringetin 3-O-galactoside |
| Malvidin 6-acetyl 3-glucoside | |

In certain embodiments, the nanoparticles may have a substantially spherical structure with a diameter of about 50-250 nm. In certain embodiments, the nanoparticles may comprise a pectin-based core, surrounded by one or more spiral fibril structures comprising pectin components (for example, Rhamnogalacturonans), one or more hemicellulose-derived molecules (for example, Xyloglucans), and one or more peptides derived from cell wall proteins such as hydroxyproline rich glycoproteins (HRGPs).

In certain embodiments, the nanoparticle may further comprise one or more biologically active agents. The biologically active agents may be complexed with, conjugated with, or mixed with the nanoparticles in certain embodiments. By way of example, the biologically active agent may be a pharmaceutically active drug, a nutraceutical, or a nutrient. The person of skill in the art having regard to the teachings herein will be aware of a variety of suitable pharmaceutical drugs, nutraceuticals, and/or nutrients which may be used depending on the particular application. In certain embodiments, a pharmaceutically active drug may include any suitable drug developed to control chronic diseases, such as those used in cancer therapy (for example, vincristine, vinblastine, paclitaxel, doxorubicin, polyketides, cannabinodiols etc.). In certain embodiments, a nutraceutical may comprise carotenoids (for example, lycopene, zeaxanthin, astaxanthin, which may have potential for use in eye drops for example), anti-inflammatoirech as Turmeric/curcumin, Boswellia, Ashwagandha and/or other bioactive herbals), nutrients (such as $Fe^{2+}$, Zn, Se, Cobalamins (Vit B12)), and/or antioxidant enzymes such as superoxide dismutase, catalase to targeted areas, Ischemia/reperfusion, etc.

In certain embodiments, the nanoparticle may be provided in aqueous solution, in powder form, or in dehydrated, lyophilized, freeze-dried, spray-dried, or nanospray-dried form, for example. In certain embodiments, the nanoparticles may be formulated for oral administration. In certain embodiments, the nanoparticles may be provided in a form suitable for ingestion with food. In certain embodiments, the nanoparticles may be provided in capsules, in injectable form, in spray form for mucosal areas, and/or in a form for topical administration (such as an ointment) for cutaneous application.

In certain embodiments, there is provided herein a composition comprising a nanoparticle as described herein. In certain embodiments, the nanoparticles or composition may further comprise a pharmaceutically acceptable carrier, excipient, or diluent added during or after the preparation of nanoparticle. In certain embodiments, the composition may further comprise a biologically active agent, such as a drug, biomolecule, protein, enzyme, antibody or any other pharmaceutical agent.

In still further embodiments, the plant tissue from which the nanoparticles are prepared may comprise a fruit or vegetable plant tissue. In certain embodiments, the plant tissue may comprise a fruit such as cherry, blueberry, grape, either independently or in combinations, and may in certain embodiments additionally include other products of nutritional importance such as broccoli, almond, soybean or turmeric, either as tissue or as a processed product, or any combination thereof. By way of example, the plant tissue may comprise a sour cherry fruit. In certain embodiments, the plant tissue may further comprise a nutrient or nutraceutical carrier of plant origin. In certain embodiments, the plant tissue may comprise, for example, a sour cherry fruit in combination with vegetable tissue (for example, broccoli, mushrooms, nuts or nut products (i.e. almond, hazelnut), roots (i.e. Ashwagandha, *ginseng, cyperus*, etc. . . . )).

Extensive studies have been performed, indicating that the organizational structure of nanoparticles described herein is complex. Based on experimental evidence obtained (see the Examples section set out below), and without wishing to be bound by theory in any way, the following structural model of certain embodiments of nanoparticles described herein is proposed:

- From EM data, the nanoparticle may comprise of a distinct inner core, surrounded by a distinct intermediate layer, over which a more fibrillated outer layer with protruding fibre-like structures may be provided. The three distinct regions (inner core, intermediate layer, and outer layer) are distinguishable on the basis of their capacity to bind to heavy metal (e.g. Uranium acetate). Uranium ions can bind to negatively charged moieties such as that of sugar acids (glucuronic, galacturonic acids) of polymeric chains making that region electron dense. Thus, the distinction between the three layers may reflect differences in the composition of the polymers in these layers.
- Enzyme treatment of nanoparticles resulted in fragmentation of the structure, revealing intermediary structures. Pectinase (polygalacturonase) treatment resulted in the disruption of the entire nanoparticle into vesicular structures, suggesting that polygalacturonic acid moieties may be dispersed throughout the nanoparticle.
- Treatment with beta-1,4-glucanase resulted in the dissolution of the outer structures of the nanoparticle, leaving an inner core. Since there were no appreciable levels of long chain cellulose molecules present in the structure (x-ray-diffraction), it appears that this activity may be directed to hemicellulose moieties with beta-1,4-glucan structure. Therefore, it is contemplated that hemicelluloses may form a major part of the constituents that are arranged in the middle/intermediate and outer layers of the nanoparticles.
- The core structure was observed after treating with trypsin. Trypsin treatment also resulted in the dissolution of the outer and intermediate layers, leaving the spherical pectin-based inner core. Therefore, both the outer and intermediate layers may also contain proteins/peptides.
- Antibodies raised against homogalacturonan showed a strong reaction to the nanofibers during SDS-PAGE. SDS-PAGE reveals the presence of anthocyanins, peptides, and pectin in the nanoparticles, while the nanofiber is devoid of anthocyanins. It is speculated that the antibodies may have been unable to reach the interior of the nanoparticle, and therefore gave a weak reaction. This also shows that homogalacturonans may be exposed in the nanofibers, and resulted in strong cross-reactivity with the antibodies (dot blots, FIG. 12).
- Cross reactivity with antibodies raised against extensin was very low in both nanoparticles and nanofibers (dot blots, FIG. 12), suggesting that extensin-originated peptides are not present in appreciable levels in either of nanoparticles and nanofibers.
- By contrast, strong reactivity was observed against antibodies raised against hemicellulose-protein (arabinogalactan-protein) suggesting that this may be a major component of the outer layers of the nanoparticles, and as a constituent of nanofibers.

In certain embodiments, nanoparticles as described herein may further comprise one or more biologically active agents, such as a drug, nutrient, biomolecule (i.e. protein, enzyme, nucleic acid), nutraceutical, or other pharmaceutical agent. In certain embodiments, the biologically active agent may be complexed with, or chemically conjugated with, the nanoparticle. In certain embodiments, the biologically active agent may be introduced to (and complexed or conjugated with) the nanoparticle during, or after, nanoparticle formation.

In another embodiment, there is provided herein a targeted nanoparticle comprising a nanoparticle as described herein, conjugated with a targeting antibody specific for a cancer marker. In certain embodiments, the targeting antibody may comprise PD-L1 antibody for targeting of the targeted nanoparticle to cancer cells. In certain embodiments, the targeted nanoparticle may be complexed with, or conjugated with, at least one cytotoxic or anti-cancer drug. In certain embodiments, the targeted nanoparticle may be complexed with, or conjugated with, paclitaxel, doxorubicin, or both.

In another embodiment, there is provided herein an antibacterial nanoparticle, comprising a nanoparticle as described herein, complexed with or conjugated with an antibacterial agent. In certain embodiments, the antibacterial agent may comprise lysozyme, a tetracycline, or Nisin, or any combination thereof. In certain embodiments, the antibacterial nanoparticle may be for use in treating or preventing MDR bacterial infection.

Methods for Preparing Nanoparticles:

In an embodiment, there is provided herein a method for preparing a nanoparticle (such as those described herein, for example) from homogenized plant tissue, said method comprising:

- providing a homogenized plant tissue in solution, comprising cellular components liberated from the plant tissue;
- removing debris from the homogenized plant tissue, if present; and
- optionally, dialyzing the homogenized plant tissue to remove non-complexed compounds, or removing the non-complexed compounds by size exclusion, thereby providing a solution comprising the nanoparticle which is formed by self-assembly of the cellular components.

In certain embodiments, the solution may comprise any suitable medium. Typically, the solution may comprise water or an aqueous medium, but may in certain embodiments be or comprise water and a miscible organic solvent such as, but not limited to, one or more alcohols which may include ethanol and/or methanol, one or more ketones such as acetone, one or more solvents which may include dimethyl sulfoxide, either separately or in any suitable combinations thereof.

In certain embodiments, the debris may be removed by dialysis, filtering the homogenized plant tissue, centrifuging the homogenized plant tissue, or performing tangential flow filtration or continuous flow filtration on the homogenized plant tissue, or any combination thereof. In certain embodiments, the step of removing debris may comprise filtering the homogenized plant tissue, or centrifuging the homogenized plant tissue, or both. In certain embodiments, the debris may be removed by one or combinations of techniques, which may include centrifugation (for example, simple or continuous flow centrifugation) and/or membrane filtration (for example, dialysis, centrifugal separation using membranes of appropriate cut off, for example 1-100 μm), tangential flow filtration, column separation for size exclusion, etc. . . . , either individually or involving a combination of such techniques. In certain embodiments, centrifugation at ~9000-12000 g may sediment most debris, or filtration through a 100 micron filter may provide for suitable removal of debris.

In certain embodiments, the step of dialyzing (if performed) may be performed using a simple dialysis against water (or another aqueous solution, although water is preferable), although this may be more readily used for lab-scale rather than commercial large scale product. Thus, in certain embodiments, dialysis/separation may be performed using continuous centrifugal separation, a tangential flow filtration, or may be omitted by making the particles sufficiently fine so that the dialysis separation may be omitted (using equipment such as a high shear homogenizer (eg. Sonolator) or a microfluidizer, for example).

In certain embodiments, the clarified homogenate removed of debris may further be purified using a membrane filtration technique where smaller molecules that are not incorporated into the nanoparticles may be removed. This may include, for example, a simple dialysis using (for example) a 100,000 MW cut-off dialysis bag against water, or subjecting the homogenate to tangential filtration (cross-flow filtration) through a suitable membrane of similar cut-off size, or a filtration across a membrane using a stirred cell (eg. Amicon, or similar set up) by means of which the nanoparticles may be concentrated. Alternatively, size exclusion columns of similar exclusion limits (100,000 MW) may be used, where the nanoparticles are eluted in the void volume using a solvent (water or a buffer of low molarity (e.g. 1 mM, for example) at pH of about 4-5). Such operations may preferably be conducted at about 4° C.

In certain embodiments, the method may further comprise a step of subjecting the solution comprising the nanoparticle to dehydrating, lyophilizing, freeze-drying, spray-drying, or nanospray-drying the solution comprising the nanoparticle.

In certain embodiments, the method may involve forming the nanoparticles by self-assembly under suitable conditions. In certain embodiments, for example, the conditions may be at a temperature ranging between about 4° C. to about 40° C., preferably from about 15° C. to about 35° C. In certain embodiments the conditions may be in water, or in a mixture of water with a water miscible organic solvent such as (but not limited to) methanol or ethanol. In certain embodiments, the conditions under which cellular components liberated from the plant tissue by homogenization may self-assemble into the nanoparticle may be in solution which is about 15 to 100% v/v water, more preferably about 30 to about 100% v/v water, and most preferably about 100% v/v water. Where self-assembly occurs in an aqueous or substantially aqueous solution, it is contemplated that in certain embodiments enzymes normally present in a ripening environment, such as polygalacturonase, may be added to the mix, especially to aid self-assembly when using unripened fruit as, or as part of, the plant tissue. In certain embodiments, the conditions under which self-assembly may occur may be in a substantially aqueous medium, for example. In certain embodiments, the production of nanoparticles may be achieved by procedures as described herein using a suitable medium. Typically, the medium may be water or an aqueous medium, but may in certain embodiments be or comprise water and a miscible organic solvent such as, but not limited to, one or more alcohols which may include ethanol and/or methanol, one or more ketones such as acetone, one or more solvents which may include dimethyl sulfoxide, either separately or in any suitable combinations thereof. In certain embodiments, the self-assembly of the nanoparticles may occur in one of the media described hereinabove. The conditions for self-assembly may comprise any thermodynamically feasible conditions. In certain embodiments, the conditions for self-assemble may, for example, comprise temperature from about 4° C. to about 30° C., ion concentrations that are generally in accordance with those found physiologically (i.e. micromolar to milli molar levels), and sugar concentration in a range of about 5-10 percent (w/v) and natural organic acids present in the millimolar range, for example.

In certain embodiments, the method may involve forming the nanoparticle by self-assembly n a substantially aqueous medium. Typically, in the method described above the dialysis may be performed at about 4° C. overnight to facilitate nanoparticle assembly. If the dialysis is conducted at room temperature, the risk of contamination from atmospheric contaminants may increase. In certain embodiments, nanoparticles may be prepared under GMP conditions to provide pure nanoparticles, particularly in pharmaceutical applications such as applications where pharmaceutical drug(s) are to be added to the nanoparticles. In certain embodiments, homogenized plant tissue (i.e. homogenates) may be prepared in a ratio of about 1 g tissue to 1 or 2 ml water. The tissue is typically already 80-90% water. These conditions may vary based on the properties of the starting material. Nanoparticles may, in certain embodiments, be formed, or begin forming, during the process of homogenization, and may also for subsequently, for example during dialysis (if performed). In certain embodiments, a nanoparticle solution containing about 80% nanoparticle, or more, may be obtained. In certain embodiments, temperatures may be generally kept low, for example at about 4° C., to prevent undesirable degradation.

In another embodiment of the above method, the step of providing the homogenized plant tissue in solution may comprise homogenizing a plant tissue in an aqueous or organic medium (such as, but not limited to, an aqueous or organic medium (or mixture thereof) comprising water, ethanol, methanol, or acetone, or a mixture thereof, for example). In certain embodiments, homogenized plant tissue may be prepared by a polytron or sonication using, for example, a sonolator. In still another embodiment, the step of providing the homogenized plant tissue in solution may comprise subjecting a plant tissue to high shear homogenization and/or sonication in an aqueous or organic medium comprising, for example, any one or more of water, ethanol, methanol, or acetone. In certain embodiments, high shear homogenization may comprise homogenization at about 3000-5000 rpm, with a blade having a diameter of about 20 cm, at about 80 kN, for example (the person of skill in the art having regard to the teachings herein will be aware of suitable high shear homogenization conditions to suit the particular application). If, for example, sonication and/or cavitation may be used, shear forces may be selected such that nanoparticles are not pulled apart by the conditions used. In certain embodiments, the size range to be achieved for the homogenized plant tissue in solution may be about 50 to about 250 nm, for example. In certain embodiments, a polytron set to a rate of about 6-7, using 30 second pulses, for about 3 cycles may be used, for example.

By way of example, the homogenized plant tissue may, in certain illustrative embodiments, comprise a plant tissue such as a cherry fruit, which has been homogenized with a blender at about 4500 rpm for about 5 minutes, and then further subjected to fine homogenization with a polytron for about 5 minutes. The resultant slurry may then be filtered through about 4 layers of cheese cloth and centrifuged at about 10,000×g to remove debris, and the supernatant may be collected. The supernatant may be dialyzed in about a 10,000 D cut off dialysis bag against water to remove small molecular mass components. Following dialysis, the solution may be freeze-dried, or spray dried, to obtain nanoparticles in powder form.

In certain embodiments, a Sonolator may be used, which employs accelerated fluid flow, ultrasonic cavitation, and turbulence for making dispersions. In the case of nanoparticles, it is contemplated that a relatively low pressure system may be preferred, so pump selection may be performed accordingly. Sonolator is a product of Sonic Corporation, Stratford, Connecticut (www.sonicmixing.com).

In still another embodiment, there is provided herein a method for preparing a nanoparticle as described herein from homogenized plant tissue, said method comprising:
preparing a homogenized plant tissue in solution, comprising cellular components liberated from the plant tissue;
allowing the nanoparticle to form by self-assembly of the cellular components;
removing debris from the homogenized plant tissue, if present; and
freeze-drying, spray-drying, or nanospray drying to form a powder comprising the nanoparticle.

By way of example, in certain embodiments the spray drying step may employ, for example, a Fujisaki 4 nozzle spray drying system, which can evaporate water at differing capacities (DAIICHI JITSUGYO (AMERICA), Inc. (DJA) 939 A.E.C. Drive, Wood Dale, IL 60191, USA). One such pilot scale model (MDL 150) can evaporate ~10 kg water per hour, with a projected capacity of spray drying ~200 litres of homogenate per day with a recovery of ~40 kg of NP or food powder per day, for example.

In certain embodiments, the above method may be used where the plant tissue comprises, for example, sour cherry. It has been discovered that sour cherry works particularly well with the above-described method, which does not require performance of a dialysis step prior to forming the powder comprising the nanoparticle.

In certain embodiments of the above method, the self-assembly may occur in a substantially aqueous medium. In certain embodiments, the step of preparing the homogenized plant tissue in solution may comprise subjecting a plant tissue to high shear homogenization in an aqueous or organic medium. In certain embodiments, the step of removing debris may comprise filtering the homogenized plant tissue, or centrifuging the homogenized plant tissue, or both.

In certain embodiments, it is contemplated that nanoparticles as described herein may be used for delivering a cargo, such as a bioactive agent or another agent of interest. It has been observed that nanoparticles as described herein may expand in size when freeze or spray-dried, for example, and may then shrink in size when placed in aqueous solution or water. Accordingly, in certain embodiments, it is contemplated that dry or substantially dry powders or other preparations of nanoparticles may be mixed with a particular cargo, and then water or aqueous solution added to shrink the nanoparticles, thereby trapping the cargo in the nanoparticles for delivery thereof. In experimental studies, a nanoparticle solution gave 50-250 nm diameter structures, and when observed under SEM (Vacuum drying effect) these were observed to have a shell-shaped structure ~4-5 times larger in diameter according to data from TEM and SEM, providing an example of such size expansion upon drying.

In certain embodiments, where it is desirable for the nanoparticle to be complexed with, or conjugated with, another moiety such as a biologically active agent, any of the methods described herein may further comprise an additional step of introducing the moiety (i.e. the biologically active agent) to the homogenized plant tissue in solution, or to the already formed nanoparticle under conditions suitable for the moiety to complex with, or be chemically coupled or conjugated with, the nanoparticle.

In certain embodiments, for example, chemical conjugation may be achieved using procedures adapted to the functional groups which are present in the nanoparticles (i.e. —$NH_2$, —COOH, —OH) and in the conjugating agent. For example, while using Dylight in Example 3 below, the dye was activated using N-hydroxysuccinimide (NHS) esters, which is a reactive group used for labelling —$NH_2$ moieties of proteins. NHS esters of compounds react with primary amines of an acceptor (i.e. nanoparticle, nanofiber containing peptides) forming stable covalent amide bonds and releasing the NHS groups. As will be understood, other coupling or cross-linking agents for bonding at the same or different functional groups are also available (for example, from Thermofisher Scientific).

In a preferred embodiment, nanoparticles and/or nanofibres may be dissolved in phosphate buffered saline and mixed with Borate buffer, 0.67 M as recommended (Thermofisher scientific) to provide a concentration level of 2 mg/ml. After mixing thoroughly with the activated labelling agent (NHS ester), the mixture may be incubated at 25° C. for an hour. The mixture containing the conjugated product (NP/NF) may be separated using a size exclusion column or a spin column supplied by the manufacturer. The conjugated NP/NF may be eluted in the void volume. The conjugated product may be lyophilized and stored as a dry powder at −20° C., for example (see, for example, Nour Karra and Simon Benita* (2012) The Ligand Nanoparticle Conjugation Approach for Targeted Cancer Therapy; Current Drug Metabolism, 2012, 13, 22-41, herein incorporated by reference).

Nanofibres and Methods for the Production Thereof

Nanofibres

Nanofibres have also been developed, and are described herein. Although nanoparticles and nanofibers may both be prepared from plant tissue, these two nanostructures have been prepared herein using notably different methods, and these two nanostructures have been found herein to adopt notably different structures, to feature significant differences in terms of composition, and to feature interesting differences (and similarities) in terms of function and/or biological effects.

Accordingly, there is also described herein a nanofibre comprising self-assembled cellular components derived from a homogenized plant tissue. In comparison to the nanoparticles as described above, the nanofibers differ in a number of ways, particularly in that the nanofibers are derived from a homogenized plant tissue from which polyphenols have been extracted or which is already naturally low in polyphenol content. In certain examples, the cellular components may include components liberated from the plant tissue by homogenization, which self-assemble into the nanofibre. In certain examples, the one or more cellular components may include pectin. In certain examples, the nanofibres may comprise one or more hemicellulose-derived molecules, one or more peptides derived from cell wall protein, or both.

In an embodiment, there is provided herein a nanofibre comprising self-assembled cellular components derived from a homogenized plant tissue, the cellular components comprising one or more structural carbohydrates or cleavage products thereof, wherein lipids and polyphenols are not structural components of the nanofibre.

As described herein, the presently described nanofibres may be prepared with generally any suitable plant tissue such as that which may be used for preparing nanoparticles as described in detail herein (see above, for example), providing that the polyphenols have first been extracted or are otherwise found at low or reduced levels in the plant tissue. In certain embodiments, the self-assembly, cellular components, structural carbohydrates or cleavage products thereof, and lipid content of the nanofibres may be substantially similar to that of the nanoparticles as described in detail here, with the exception that polyphenols do not play a structural role in the nanofibres, resulting in the nanofibres adopting significantly different structure and organization versus the nanoparticles.

In certain embodiments, the nanofibre may be substantially lipid-free, may be substantially polyphenol-free, or both.

Figure 4:
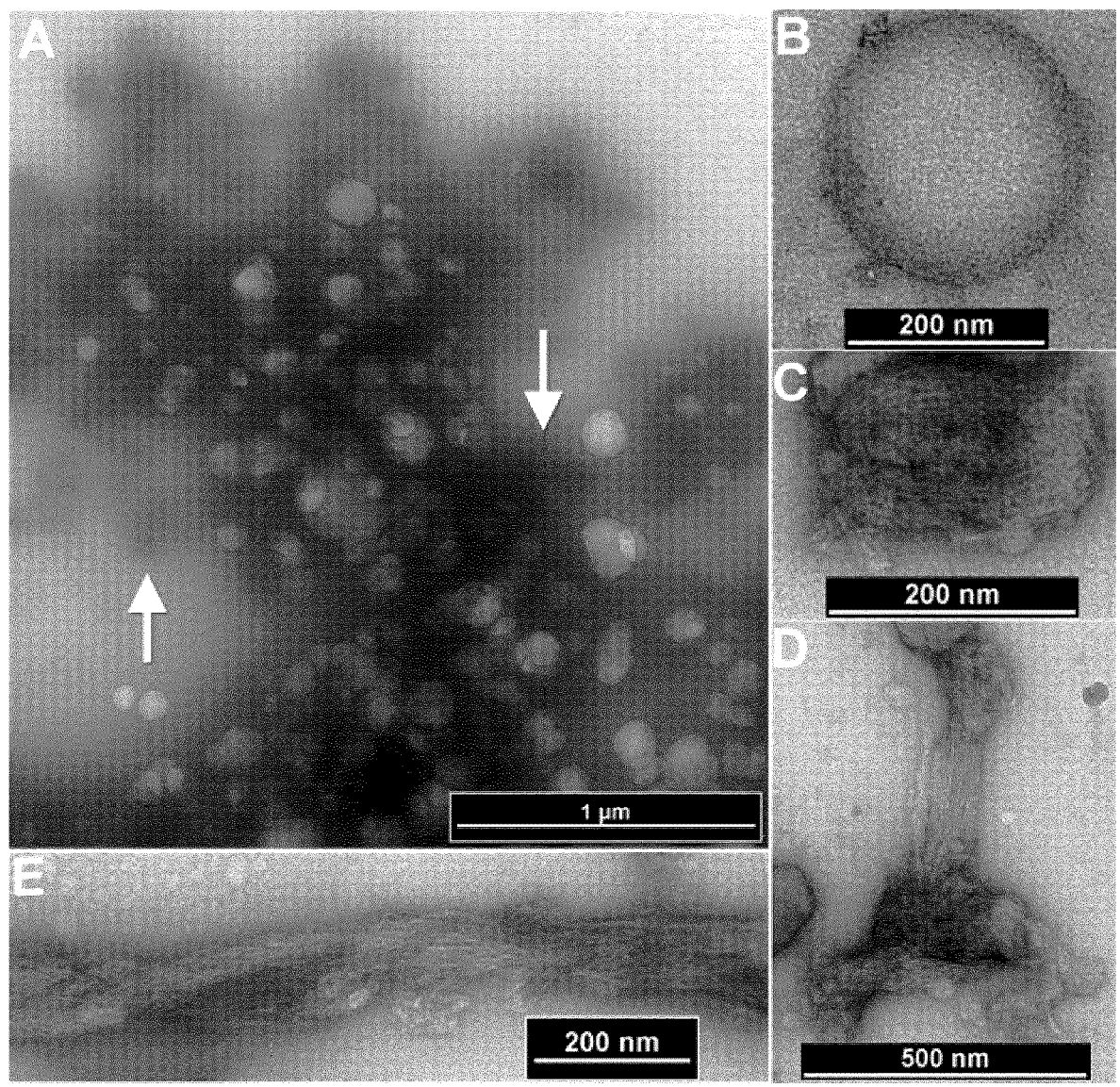
FIG. 4 shows effect of trypsin treatment on the structure of nanoparticles prepared from sour cherry. Dialyzed extract (1 ml) was treated with 1 unit of trypsin for 15 min, and the nanoparticles were examined as described above. Trypsin treatment results in the dissolution of the outer filamentous structure (Panel A, stained with Ruthenium Red) seen as dark stained areas around the globular interior pectin shell of the nanoparticles. The shell-like structures tend to fuse together as also observed after cellulase treatment (see FIG. 3). Dissolution of outer shell by trypsin suggests that the outer filamentous coat is also made up of protein (i.e. glycoproteins of the extension type found in cell wall), and potentially peptides derived from their degradation that occur during ripening and senescenece. Panel B shows a magnified view of a shell like structure. Panel C shows a partially digested nanoparticle showing the filamentous coating dispersing into fibrils/fibrillary structures. Panel D shows a nanoparticle that has been stripped off the fibrillary structures. The arrow shows the globular shell left after dissolution of the fibrillary structures. Panel E shows a magnified view of the fibrils/fibrillary structures showing an intertwined assembly that potentially form the fibrils/fibrillary structures. The fibrils/fibrillary structures are not filamentous and appear to lack bilateral symmetry, and appear as spirally arranged molecules would around its own axis to form fibrillary structures with formed primary, secondary, and tertiary rope-like forms.
Figure 7:
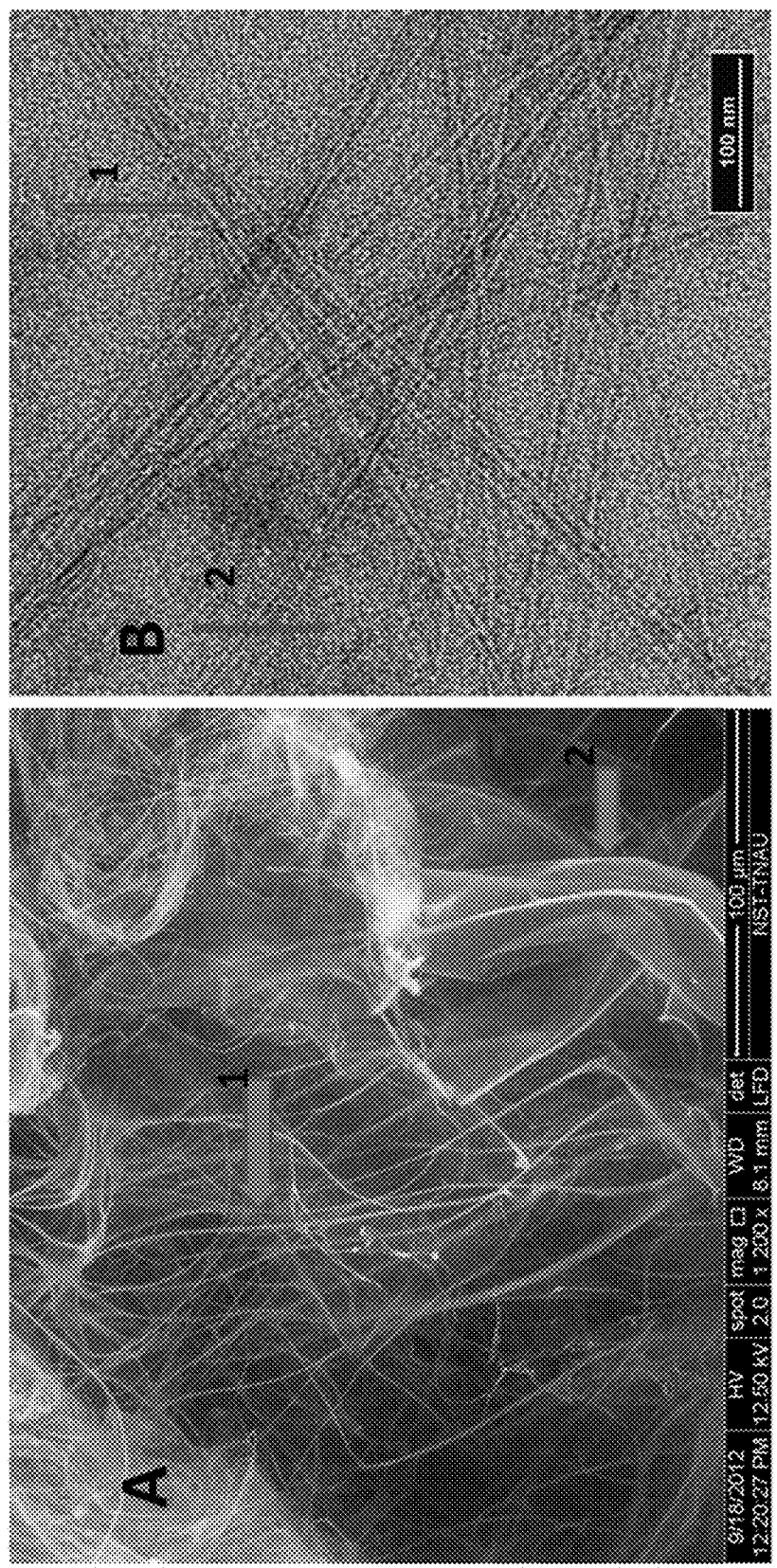
FIG. 7 shows scanning electron micrograph (Panel A) and Transmission Electron Micrograph of nanofibres isolated from ethanol bleached sour cherry. Sour cherry fruit were incubated in 50% ethanol to remove polyphenols (anthocyanins) (3×), washed and homogenized in water. The homogenate was dialyzed against water after removal of debris and the dialyzed extract was freeze dried for SEM, and used directly for TEM. Panel A shows nanofibrous and nanofilm structure of the nanofibres (arrow 1, 2). After staining with uranyl acetate, the nanofibres appear as long (micrometer or more) structures (arrow 1) which are 5 to 10 nm in diameter (Panel B). These fibres still retain the ability to form spiral structures (arrow 2) in solution. As shown, in comparison, nanofibres and nanoparticles have different structures.

In certain embodiments, the nanofibre may comprise an elongated fibre comprising one or more strands comprising or made of at least one structural carbohydrate. In certain embodiments, a basic nanofiber may comprise of elongated fibres that are micrometers in length and having a diameter of about 5 to about 10 nm (see FIG. 37, left and Right Panels). These fibres appear to be homologous to the fibres that are released from the nanoparticles after Trypsin treatment (see FIG. 4, panels, D, E). Such fibre-like structures are also observed when dry nanofibers are examined with a scanning electron microscope (see FIG. 7, Panel A). In certain embodiments, the nanofibre may be considered as a product of ethanol bleaching of a nanoparticle. The nanofiber is also observed as a spirally wound structure (see FIG. 2, Panel C), indicating its potential origin from the macromolecules that surround the pectin core of the nanoparticles.

In certain embodiments, the nanofibre may comprise pectin, hemicellulose, peptide and/or protein, an organic acid, cleavage products thereof, or any combination thereof. In certain embodiments, the organic acid may comprise malic acid, ascorbic acid, or both.

In certain embodiments, the cellular components may comprise those liberated from the plant tissue during ripening or during homogenization of ripened fruit, which are capable of self-assembling into the nanofibre.

In certain embodiments, the one or more structural carbohydrates comprise one or more of pectin, pectic acid, methyl ester of pectin, a pectin derivative, polygalacturonic acid, rhamnogalacturonans, xylogucans, hemicelluloses, xyloglucans possessing β-(1→4)-linked backbones of glucose, mannose, or xylose, and/or arabinogalactans, and/or cleavage products thereof.

In certain embodiments, the nanofibre may have a fibre shape with a diameter of about 5 to about 10 nm, for example. In certain embodiments, the nanofibre may be non-crystalline.

In certain embodiments, the nanofibre may be stabilized by hydrogen-bonding interactions and formed between macromolecules derived from catabolism of cellular components of the plant tissue and possessing hydroxyl groups and/or amino groups and/or organic acid groups.

In certain embodiments, the nanofibre may further comprise a biologically active agent. By way of example, in certain embodiments, nanofibres as described herein may further comprise one or more biologically active agents, such as a drug, nutrient, biomolecule (i.e. protein, enzyme, nucleic acid), nutraceutical, or other pharmaceutical agent. In certain embodiments, the biologically active agent may be complexed with, or chemically conjugated with, the nanofibre. In certain embodiments, the biologically active agent may be introduced to (and complexed or conjugated with) the nanofibre during, or after, nanofibre formation. In certain embodiments, the biologically active agent may be or comprise a pharmaceutically active drug, protein, enzyme, nutraceutical, or nutrient.

In certain embodiments, the nanofibre may be provided in generally any suitable form, such as those described with reference to the nanoparticles above. In certain embodiments, the nanofibres may be provided in aqueous solution, in powder form, or in dehydrated, lyophilized, freeze-dried, spray-dried, or nanospray-dried form, for example.

In certain embodiments, the plant tissue used for preparing the nanofibres may comprise a fruit or vegetable plant tissue low in polyphenols, or from which polyphenols have been extracted or removed. In certain embodiments, the plant tissue may comprise a senescing fruit, a ripening vegetable, or any combination thereof; preferably, wherein the plant tissue comprises cherry (for example, sour cherry), blueberry, grape, peach, nectarine, plum, apricot, *papaya*, tomato, or any combination thereof, low in polyphenol content and/or from which polyphenols have been removed or reduced. In certain embodiments, the plant tissue may comprise fruit skins and/or outer tissue of fruits, such as in cocoa for example, low in polyphenol content and/or from which polyphenols have been removed or reduced.

In certain examples, the nanofibre may have a filamentous or fibrous structure with a diameter of about 5 to about 10 nm and a length in the micrometer range. In certain examples, the nanofibre may further comprise one or more biologically active agents. The biologically active agents may be complexed with, conjugated with, or mixed with the nanofibres in certain examples. By way of illustrative example, the biologically active agent may be a pharmaceutically active drug, a nutraceutical, or a nutrient. In certain embodiments, the biologically active agent may comprise one or more cancer drug, such as paclitaxel, docetaxel, doxorubicin, vincristine, and/or vinblastine; one or more metals such as iron, magnesium, selenium, and/or zinc; one or more nutraceuticals such as Boswellia, Withanolides, Annonacins, tetracyclines such as vancomycin, and other antibacterial agents such as nicin, lysozyme, and other molecules with similar properties used for controlling diseases and bacterial food contamination.

In certain examples, the nanofibre may be provided in aqueous solution, in powder form, or in dehydrated, lyophilized, freeze-dried, spray-dried, or nanospray-dried form, for example.

In certain embodiments, nanofibres may be provided as capsules to be ingested with food, or as nanofibre-nutraceutical complexes (e.g. Boswellia, Curcumin, Ashwagandha, etc., see examples provided herein in connection with the nanoparticles and/or food powders for additional examples), for example.

By way of example, the homogenized plant tissue may, in certain illustrative embodiments, comprise a plant tissue such as a cherry fruit, which has been subjected to substantial removal or depletion of small molecular mass components (including polyphenols) by immersing in about 95% ethanol (1:1 w/v) for about 24-48 hours, after which the solution may be decanted and the fruit further incubated in ethanol for another 48 hours so that the majority, or substantially all, of the color components (i.e. anthocyanins) are removed. The fruit tissue may then be thoroughly washed with water for about 24 hours (2×-3× in an equivalent volume of water). The fruit tissue may then be homogenized with a blender at about 4500 rpm for about 5 minutes, and then further subjected to fine homogenization with a polytron for about 5 minutes. The resultant slurry may then be filtered through about 4 layers of cheese cloth and centrifuged at about 10,000×g to remove debris, and the supernatant may be collected. The supernatant may be dialyzed in about a 10,000 D cut off dialysis bag against water to remove small molecular mass components. Following dialysis, the solution may be freeze-dried, or spray dried, to obtain nanofibers in powder form.

Alternatively, in certain embodiments, the fruit tissue may be subjected to cold pressing to separate the juice. The pomace thus obtained may be subjected to removal of color components, and then subjected to incubation in ethanol in order to remove the color components (e.g. Anthocyanins, and other polyphenols that may hydrogen bond with the carbohydrates and peptides of nanoparticles). After hydrating, the tissue may be homogenized and processed as described above.

In still further examples, the plant tissue from which the nanofibres are prepared may comprise a fruit or vegetable plant tissue. In certain examples, the plant tissue may comprise a cherry, blueberry, grape, or any combinations of fruits thereof. By way of a preferred example, the plant tissue may comprise a sour cherry fruit tissue.

Methods for the Production of Nanofibres

In another embodiment, a method for preparing nanofibres (such as those described herein) from homogenized plant tissue may comprise:
preparing a homogenized plant tissue in solution having low polyphenol content, comprising cellular components liberated from the plant tissue;
removing debris from the homogenized plant tissue, if present; and
optionally, dialyzing the homogenized plant tissue to remove non-complexed compounds, or removing non-complexed compounds by size exclusion,
thereby providing a solution comprising the nanofibres which are formed by self-assembly of the cellular components.

In certain embodiments, bleached plant tissue may be generally considered as a tissue from which simple, free, soluble molecules are removed by extracting them out of the tissue using an organic solvent which is highly miscible with water. This may include solvents such as ethanol, methanol, acetone, etc. These solvents may break the cellular compartmentalization and enable leaching of mostly free molecules such as anthocyanins, sugars, organic acids etc. into the dehydrating medium. An osmotic dehydration using sucrose solution by contrast pulls out mostly water, leaving the components in the fruit. Bleaching as recited herein refers to the loss in colour of the tissue, and is not an oxidation process.

In another embodiment, there is provided herein a method for preparing a nanofibre from homogenized plant tissue, said method comprising:
preparing a homogenized plant tissue in solution having low polyphenol content, comprising cellular components liberated from the plant tissue;
removing debris from the homogenized plant tissue, if present;
allowing the nanofibre to form by self-assembly of the cellular components; and
freeze-drying, spray-drying, or nanospray drying to form a powder comprising the nanofibre.

In certain embodiments, methods of preparing nanofibres and steps thereof as described herein may be substantially similar to those described herein for producing nanoparticles, with the distinction that the plant tissue may be low in polyphenol content, or the plant tissue may be a plant tissue from which polyphenols have been extracted so as to favour nanofibre formation.

In certain examples of the above methods, the nanofibre may form by self-assembly in a substantially aqueous medium. In certain embodiments, a low temperature (i.e. about 4° C.) may be used during homogenization, and it is contemplated that a wide range of water-miscible solvents may be used to isolate the nanofibres.

In certain examples of the above methods, the method may comprise a step of dehydrating, lyophilizing, freeze-drying, spray-drying, or nanospray-drying the solution comprising the nanofibre.

In certain embodiments, the step of preparing the homogenized plant tissue in solution may comprise homogenizing a plant tissue in an aqueous or organic medium, or a mixed aqueous/organic medium. In certain embodiments, the step of preparing the homogenized plant tissue in solution may comprise subjecting a plant tissue to high shear homogenization and/or sonolation in an aqueous or organic medium comprising any one or more of water, ethanol, methanol, or acetone.

In still further examples, the step of preparing the homogenized plant tissue in solution may comprise a step of bleaching the plant tissue to remove polyphenols therefrom prior to homogenization of the plant tissue. In another embodiment, the bleaching of the plant tissue may comprise performing an extraction of polyphenols from the plant tissue with an extraction solution. In certain embodiments, the extraction solution may comprise ethanol.

In another example, the step of providing the homogenized bleached plant tissue in solution may comprise subjecting a plant tissue to high shear homogenization in an aqueous or organic medium. In another example, the step of providing the homogenized bleached plant tissue in solution may comprise homogenizing the bleached plant tissue in an aqueous or organic medium.

In certain embodiments, the step of removing debris may comprise dialysis, filtering the homogenized plant tissue, centrifuging the homogenized plant tissue, or performing tangential flow filtration or continuous flow filtration on the homogenized plant tissue, or any combination thereof.

Food Powders and Additives, and Methods for the Production Thereof

Food Powders and Additives

In another embodiment, there is provided herein a food powder or food additive comprising the nanoparticles and/or nanofibres described herein, or portions or components thereof, or structures related thereto. In certain embodiments, the food powder may comprise the basic structural components of nanoparticle and/or nanofibre forming a micron-scale fine powder form, for example.

In another embodiment, there is provided herein a food powder comprising self-assembled cellular components derived from a homogenized plant tissue, the cellular components comprising one or more structural carbohydrates or cleavage products thereof, and further comprising at least one nutritional agent.

In certain embodiments, the food powder may comprise fibrous structures winding about themselves to form a nanosphere-like structure.

In certain embodiments, food powders as described herein may comprise a substantially spherical or oblong shaped structure ranging in size from about 1 µm to about 10 µm under the conditions of preparation. In certain embodiments, this large structure may dissipate as smaller spherical structures in the range of about 50 to 100 nm when dissolved in water. In certain embodiments, the food powder structure may comprise of randomly wound and assembled fibre or fibres homologous to those observed in nanoparticles and nanofibres. In certain embodiments, the whole structure of the food powder may be similar or analogous to that of a nanosphere, where there is no precise organization of fibres, and the fibres may be capable of adsorbing several ingredients present in the homogenate of tissue extracts, for example.

In certain embodiments, the one or more nutritional agents of the food powder may be complexed with the above-described fibrous nanosphere structures of the food powder, and may contribute to food powder formation and/or resultant structure thereof.

In certain embodiments, the food powder may further comprise a hydrophobic component. In certain embodiments, the hydrophobic component may comprise or be provided in almond milk, coconut milk, and/or milk derived from an edible nut.

In certain embodiments, the nutritional agent may comprise a naturally occurring active ingredient having a health benefit. In certain embodiments, the nutritional agent may comprise one or more components such as carotenoids, annonacins, Boswelia, withanolides of Ashwagandha, gingerols and shaogaols of Ginger family members, cannabinodiols, fructo-oligosaccharides, galacto-oligosaccharides, inulin, Piperine and derivatives of Piperaceae family members, *Piper nigrum* and *Piper longum* or other wild relatives containing these ingredients and/or derivatives thereof, or any active ingredient thereof having a health benefit, or any extract, derivative, or product isolated therefrom, or any combinations thereof.

In a preferred embodiment, the food powder may comprise:
  sour cherry, or an aqueous extract thereof;
  almond milk or another homogenate of almonds;
  soymilk, or another homogenate of soybean;
  broccoli, or an aqueous extract thereof; and
  turmeric, or a powder thereof.

In certain further preferred embodiments, the food powder may comprise:
  about 25-30 v/v % sour cherry extract (at least about 0.1 mg/ml of polyphenol equivalent);
  about 25-30 v/v % almond milk or other homogenate of almonds;
  about 10-18 v/v % soymilk or other homogenate of soybean;
  about 25-30 v/v % broccoli extract; and
  about 0.5-2.5 w/v % turmeric or powder thereof.

The above food powder example was designed to provide a good aesthetic product which doesn't smell of broccoli or soybean. It will be understood that various other components, combinations of components, and relative percentages of components, are also contemplated herein.

In certain further embodiments, the sour cherry extract may be about 1-2 mg/ml polyphenol equivalent.

In certain embodiments, the sour cherry extract may be combined with, or replaced by, one or more fruit powders commercially produced from dried whole fruits, fruit pomace, or powders produced from fruit juices by spray drying, or another commercially available fruit powder of interest. In certain embodiments, fruits that are dried and powdered to micron size may be used to rehydrate and homogenize, rather than fresh fruits, for example.

As described herein, the presently described food powders may be prepared with generally any suitable plant tissue which may be used for preparing nanoparticles and/or nanofibres as described in detail herein. In certain embodiments, food powder may be prepared from a fruit, vegetable or another plant tissue or product capable of forming carbohydrate-based nanoparticles or nanofibers as described herein, but as will be understood the food powder may have a different organization such as a structure which is more nanosphere-like. Food powders may be prepared in any suitable medium comprising aqueous, organic, or a combination thereof. The food powders may, in certain embodiments, further comprise a nutritional agent or nutrient-containing material (or a nutrient) that is desired to be included in the food powder product (which will typically be tailored for the intended application of the food powder), and may include fresh, processed, or concentrated powders, either alone or in any desired combinations by weight or volume.

In certain embodiments, the food powders described herein may be prepared from a plant tissue which is suitable for preparing a nanoparticle and/or a nanofibre as already described in detail herein, in combination with a nutritional agent or nutrient-containing material. As will be understood, the nutritional agent or nutrient-containing material will typically be tailored for the intended application of the food powder, and may include fresh, processed, or concentrated powders, either alone or in any desired combinations by weight or volume. In certain embodiments, the food powder may be developed with nutritional agents or nutrient-containing components or with components targeted to address a particular physiological condition (such as a chronic condition, for example), and such nutritional agent or nutrient-containing material may have preventive and/or curative properties, for example. As will be understood, the term nutritional agent or nutrient as used herein may include any suitable active agent or compound appropriate for the particular indication (or material comprising said active agent or compound), and is not limited to those entities typically considered as nutrients such as those found in food. By way of example, in certain embodiments, a nutrient may include any suitable natural (or unnatural) ingredient having a health benefit. In certain embodiments, the plant tissue may comprise fruit skins and/or outer tissue of fruits, such as in cocoa for example.

In certain embodiments, the food powder may comprise:
  1. Sour cherry (or sour cherry extract), or an another fruit or vegetable (or extract thereof) which is capable of forming carbohydrate-based nanoparticles or nanofibers as described herein;
  2. A hydrophobic component (such as, but not limited to, almond milk) which can incorporate hydrophobic molecules from the added substances (other examples being coconut milk, or milk derived from edible nuts, for example); and 3. A nutrient-containing material (such as a functional food extract, for example) that contains one or more bioactive ingredient/ingredients tailored for the desired application of the food powder, for example.

Some non-limiting examples of nutrient-containing materials may include one or more of the following active compounds and/or plant families:

Carotenoids (i.e. beta-carotene, lycopene, lutein and other xanthophylls, astaxanthin, etc.);

Annonacins (i.e. polyketides derived from Annona fruits with anticancer properties);

Boswellia (which may act in conjunction with curcumin providing added anti-inflammatory function);

Ashwagandha (a herbal component containing withanoliides with anti-stress, and cancer preventive properties, primarily with a steroid structure);

Ginger family members that may include, for example, edible ginger (*Zingiber officinalis*), mango ginger (*Curcuma amada*), or others containing any of several bioactive ingredients including gingerols and shogaols; *Curcuma longa* (i.e. turmeric, containing curcumin);

Cannabinodiols (which are the medicinally active ingredients of *Cannabis* sp. without hallucinogenic activity);

Fructo-oligosaccharides and galacto-oligosaccharides, as well as inulin from Jerusalem artichoke, to enhance prebiotic content;

Piperaceae members such as *Piper nigrum* and its wild relatives containing piperine and several derivatives; and/or any other suitable ingredient(s) (such as, but not limited to, those derived from plants) not already listed above;

and/or any extract, derivative, product isolated therefrom, or material or plant tissue containing such component.

Methods for the Production of Food Powders and Additives

In another embodiment, there is provided herein a method for preparing food powder from homogenized plant tissue, said method comprising:

preparing a homogenized plant tissue in solution, comprising cellular components liberated from the plant tissue, the cellular components comprising one or more structural carbohydrates or cleavage products thereof, and the homogenized plant tissue in solution further comprising at least one nutritional agent;

optionally, removing debris from the homogenized plant tissue in solution, if present; and freeze-drying, lyophilizing, spray-drying, or nanospray drying the homogenized plant tissue in solution to form the food powder.

Examples of suitable plant tissue, and nutritional agents, have already been described in detail hereinabove.

In yet another embodiment of the above method, the step of preparing the homogenized plant tissue may comprise homogenizing the plant tissue in an aqueous medium, an organic medium, or a mixed aqueous-organic medium. In certain embodiments, food powder may be prepared by homogenization of the food powder starting materials in solution. For example, homogenization may be achieved using a blender, preferably operating at a high rpm and capable of generating high shear forces, or any other suitable machine capable of high performance mixing such as a sonolator.

In certain embodiments, the homogenized plant tissue in solution may be filtered to remove debris, or debris may be otherwise removed from the homogenized mixture. By way of example, a centrifugal device or filtration device (for example, a membrane filtration device, or tangential flow filtration device) capable of filtering the debris (i.e. particulate matter that has not gone into the homogenate and settles under gravity) may be used to remove debris.

In certain embodiments, the food powder may then be dehydrated, lyophilized, spray-dried, nano-spray-dried, or otherwise dehydrated or dried. By way of example, equipment that is capable of removing water (or another solvent being used) may be used, which may include a nanospray drier, or a lyophilizer for aqueous samples, or more preferably a high efficiency spray drier capable of spray drying large volumes may be used, for example. In certain embodiments, the drier may operate under reduced pressure.

In another embodiment, the plant tissue may comprise a fruit, vegetable, or plant tissue. In still another embodiment, the plant tissue may comprise a senescing fruit, a ripening vegetable, or any combination thereof; preferably, wherein the plant tissue comprises cherry, blueberry, grape, peach, nectarine, plum, apricot, *papaya*, tomato, or any combination thereof. In certain embodiments, the plant tissue may comprise a plant tissue obtained from or comprising sour cherry, almond or almond milk, soybean or soymilk, broccoli, turmeric, or any combination thereof. In certain embodiments, the homogenized plant tissue may comprise sour cherry extract, almond milk, soymilk, broccoli extract, and turmeric powder. Suitable plant tissues have already been described in detail above.

In certain embodiments, the homogenized plant tissue in solution may further comprise a hydrophobic component as already described hereinabove.

In still another embodiment, the plant tissue may comprise one or more nutrient-containing materials, which may be fresh, pre-processed, or concentrated materials, or any combination thereof.

In certain embodiments of the above methods, the step of preparing the homogenized plant tissue may comprise homogenizing the plant tissue with a blender, preferably operating at high rpm and generating high shear forces, a sonolator, or another high performance mixing device.

In certain embodiments of the above methods, the step of removing debris may comprise removing debris with a centrifugal device, with a filtration device, by membrane filtration, by tangential flow filtration, or any combination thereof.

In certain embodiments, the plant tissue may comprise a plant tissue obtained from or comprising sour cherry, almond or almond milk, soybean or soymilk, broccoli, turmeric, or any combination thereof.

In a preferred embodiment, the starting materials for the method may comprise:

sour cherry, or an aqueous extract thereof;
almond milk or another homogenate of almonds;
soymilk, or another homogenate of soybean;
broccoli, or an aqueous extract thereof; and
turmeric, or a powder thereof.

In certain further preferred embodiments, the starting materials for the method may comprise:

about 25-30 v/v % sour cherry extract (at least about 0.1 mg/ml of polyphenol equivalent);
about 25-30 v/v % almond milk or other homogenate of almonds;
about 10-18 v/v % soymilk or other homogenate of soybean;
about 25-30 v/v % broccoli extract; and
about 0.5-2.5 w/v % turmeric or powder thereof.

In certain embodiments, the sour cherry extract may be about 1-2 mg/ml polyphenol equivalent, for example.

The above food powder example was designed to provide a good aesthetic product which doesn't smell of broccoli or soybean. It will be understood that various other components, combinations of components, and relative percentages of components, are also contemplated herein.

In certain embodiments, methods of preparing food powders and steps thereof as described herein may be substantially similar to those described herein for producing nanoparticles and/or nanofibres, with the distinction that the presence of the at least one nutritional agent favours production of the food powder nanosphere structure, rather than nanoparticle and/or nanofibre structures.

Uses of Nanoparticles, Nanofibres, and Food Powders

Examples of contemplated uses of nanoparticles, nanofibres, and food powders as described herein are set out below. These examples are not intended to be limiting, but instead provide illustrative examples intended for the person of skill in the art. Experimental studies set out in the Examples section below provide further details concerning exemplary methods and uses.

In certain embodiments, references herein to a subject or cell may include an animal subject or an animal cell. In certain embodiments, the animal may be a mammal. In certain embodiments, the animal may be human.

Nanoparticles:

In one embodiment, there is provided herein a method of delivering a biologically active agent to a subject in need thereof, said method comprising:
  administering a nanoparticle as described herein, which is complexed with, or conjugated with, the biologically active agent, to the subject.

By way of example, in certain embodiments, the biologically active agent may be Selenium, Zinc, Magnesium, and/or Iron. In certain embodiments, the biologically active agent may comprise an anticancer drug, and the subject may be a subject with cancer. In certain embodiments, the anticancer drug may be paclitaxel or vincristine or another natural or synthetic compound used in treatment of cancer. In certain embodiments, the biologically active agent may be introduced into the nanoparticle during formation of the nanoparticle, or the biologically active agent may be complexed with already formed nanoparticles in an aqueous-based medium optionally comprising an alcohol or other organic compound. In certain embodiments, the aqueous-based medium may comprise DMSO, or a buffer, or both.

In another embodiment, there is provided herein a method of treating a disease or disorder associated with reactive oxygen species in a subject in need thereof, said method comprising:
  administering a nanoparticle as described herein to the subject.

In certain embodiments, the nanoparticle may act as an antioxidant.

In still another embodiment, there is provided herein a method for treating or reducing inflammation in a subject in need thereof, said method comprising:
  administering a nanoparticle as described herein to the subject.

In certain embodiments, the nanoparticle may comprise, or be sequentially, simultaneously, or co-administered with an anti-inflammatory agent. In certain embodiments, the anti-inflammatory agent may comprise curcumin.

In still another embodiment, there is provided herein a method for treating or reducing obesity in a subject in need thereof, said method comprising:
  administering a nanoparticle as described herein to the subject.

In certain embodiments, the nanoparticle may comprise components derived at least in part from nut, legume, herb, spice, vegetable, or fungal plant tissue, traditionally used for food or medical purposes In yet another embodiment, there is provided herein a method for treating or preventing cancer in a subject in need thereof, said method comprising:
  administering a nanoparticle as described herein to the subject.

In certain embodiments, the nanoparticle may be simultaneously or sequentially or co-administered with an anticancer drug. In certain embodiments, the nanoparticle may be complexed with, or conjugated with, an anticancer drug. In still further embodiments, the anticancer drug may be paclitaxel or vincristine.

In yet another embodiment, there is provided herein a method for providing a subject with soluble dietary fibre, said method comprising:
  administering a nanoparticle as described herein to the subject.

In still another embodiment, there is provided herein a viscosity enhancing food additive comprising a nanoparticle as described herein.

In yet another embodiment, there is provided herein a method for attenuating post-prandial sugar levels in the blood of a subject in need thereof, said method comprising:
  administering a nanoparticle as described herein to the subject.

In yet another embodiment, there is provided herein a cosmetic product comprising a nanoparticle as described herein.

In still another embodiment, there is provided herein a composition for topical administration to a subject in need thereof, the composition comprising a nanoparticle as described herein, and optionally a biologically active agent.

In yet another embodiment, there is provided herein a method for preventing sun burn in a subject in need thereof, said method comprising:
  applying a nanoparticle as described herein to the skin of the subject.

In certain embodiments, the nanoparticle may comprise, or be applied with, additional anthocyanin or another UV-protective agent.

In another embodiment, there is provided herein a method for reducing cell proliferation, said method comprising:
  contacting a cell or tissue or organ with a nanoparticle as described herein.

In certain embodiments, the nanoparticle may be simultaneously or sequentially used with an anticancer drug. In yet another embodiment, the nanoparticle may be complexed with, or conjugated with, an anticancer drug. In still another embodiment, the anticancer drug may be paclitaxel or vincristine.

In yet another embodiment, there is provided herein a method for reducing triglyceride accumulation in the liver of a subject in need thereof, said method comprising:
  administering a nanoparticle as described herein to the subject.

In still another embodiment, there is provided herein a method for reducing a cholesterol level in a subject in need thereof, said method comprising:
  administering a nanoparticle as described herein.

In yet another embodiment, there is provided herein a method for improving lipid metabolism in a subject in need thereof, said method comprising:

administering a nanoparticle as described herein.

In another embodiment, there is provided herein a targeted nanoparticle comprising a nanoparticle as described herein, conjugated with a targeting antibody specific for a cancer marker. In certain embodiments, the targeting antibody may comprise PD-L1 antibody for targeting of the nanoparticle to cancer cells. In certain embodiments, the targeted nanoparticle may be complexed with, or conjugated with, at least one cytotoxic or anti-cancer drug. In certain embodiments, the targeted nanoparticle may be complexed with, or conjugated with, paclitaxel, doxorubicin, or both, and/or another anticancer agent such as, for example, one or more pathway-directed antibodies (i.e. PI3K (Phosphatidylinositon-3-kinase).

In another embodiment, there is provided herein an antibacterial nanoparticle, comprising a nanoparticle as described herein, complexed with or conjugated with an antibacterial agent. In certain embodiments, the antibacterial agent may comprise lysozyme, a tetracycline, or Nisin, or any combination thereof. In certain embodiments, the antibacterial nanoparticle may be for use in treating or preventing MDR bacterial infection, and/or in sterilization of surfaces such as in the food industry and/or in hospitals, for example.

Nanofibres:

In an embodiment, there is provided herein a method of delivering a biologically active agent to a subject in need thereof, said method comprising:

administering a nanofibre as described herein, which is complexed with, or conjugated with, the biologically active agent, to the subject.

In certain embodiments, the biologically active agent may comprise Zinc or Iron or Selenium or Magnesium, or any combination thereof. In certain embodiments, the biologically active agent may comprise an anticancer drug, and the subject may be a subject with cancer. In certain embodiments, the anticancer drug may be paclitaxel or vincristine.

In certain embodiments, the biologically active agent may be introduced into the nanofibre during formation of the nanofibre, or the biologically active agent may complexed with already formed nanofibres in an aqueous-based medium optionally comprising an alcohol or other organic compound. In certain embodiments, the aqueous-based medium may comprise DMSO, or a buffer, or both.

In another embodiment, there is provided herein a method for treating or preventing cancer in a subject in need thereof, said method comprising:

administering a nanofibre as described herein to the subject.

In certain embodiments, the nanofibre may be simultaneously or sequentially or co-administered with an anticancer drug. In certain embodiments, the nanofibre may be complexed with, or conjugated with, an anticancer drug. In certain embodiments, the anticancer drug may be paclitaxel or vincristine.

In another embodiment, there is provided herein a method for providing a subject with soluble dietary fibre, said method comprising:

administering a nanofibre as described herein to the subject.

In certain embodiments, there is provided herein a viscosity enhancing food additive comprising a nanofibre as described herein.

In another embodiment, there is provided herein a method for attenuating post-prandial sugar levels in the blood of a subject in need thereof, said method comprising:

administering a nanofibre as described herein to the subject.

In another embodiment, there is provided herein a cosmetic product comprising a nanofibre as described herein.

In another embodiment, there is provided herein a composition for topical administration to a subject in need thereof, the composition comprising a nanofibre as described herein, and optionally a biologically active agent.

In another embodiment, there is provided herein a method for preventing sun burn in a subject in need thereof, said method comprising:

applying a nanofibre as described herein to the skin of the subject.

In certain embodiments, the nanofibre may comprise, or be applied with, anthocyanin or another UV-protective agent.

In yet another embodiment, there is provided herein a method for reducing cell proliferation, said method comprising:

introducing a nanofiber, optionally complexed or conjugated with a cytotoxic agent, to a cell or tissue or organ.

In certain embodiments, the nanofibre may be complexed or conjugated with a targeting antibody specific for the cell or tissue or organ.

In certain embodiments, the nanofibre may be simultaneously or sequentially or co-administered or used with an anticancer drug. In certain embodiments, the nanofibre may be complexed with, or conjugated with, an anticancer drug. In certain embodiments, the anticancer drug may be paclitaxel or vincristine.

In another embodiment, there is provided herein a method for reducing triglyceride accumulation in the liver of a subject in need thereof, said method comprising:

administering a nanofibre as described herein to the subject.

In another embodiment, there is provided herein a targeted nanofibre comprising a nanofibre as described herein, conjugated with a targeting antibody specific for a cancer marker. In certain embodiments, the targeting antibody may comprise PD-L1 antibody for targeting of the targeted nanofibre to cancer cells. In certain embodiments, the targeted nanofibre may be complexed with, or conjugated with, at least one cytotoxic or anti-cancer drug. In certain embodiments, the targeted nanofibre may be complexed with, or conjugated with, paclitaxel, doxorubicin, or both.

In another embodiment, there is provided herein an antibacterial nanofibre, comprising a nanofibre as described herein, complexed with or conjugated with an antibacterial agent. In certain embodiments, the antibacterial agent may comprise lysozyme, a tetracycline, or Nisin, or any combination thereof. In certain embodiments, the antibacterial nanofibre may be for use in treating or preventing MDR bacterial infection.

Food Powder:

In an embodiment, there is provided herein a method of delivering a biologically active agent to a subject or an organism in need thereof, said method comprising:

administering a food powder as described herein, which is complexed with, or conjugated with, the biologically active agent using a chemical or physical process, to the subject.

In another embodiment, the biologically active agent may be an element such as Selenium, Zinc, Iron, or magnesium. In another embodiment, the biologically active agent may be an anticancer drug, and the subject may be a subject with cancer. In certain embodiments, the anticancer drug may be paclitaxel, vincristine, or any natural or synthetic compound used in treatment of cancer.

In another embodiment, the biologically active agent may be introduced into the food powder during formation of the food powder, or the biologically active agent may complexed with already formed food powder in an aqueous-based medium optionally comprising an alcohol or other organic compound. In certain embodiments, the aqueous-based medium may comprise DMSO, or a buffer, or both.

In yet another embodiment, there is provided herein a method of treating a disease or disorder associated with increased levels of reactive oxygen species leading to inflammation in a subject in need thereof, comprising:
administering a food powder as described herein to the subject.

In another embodiment, there is provided herein a method for treating or reducing inflammation in a subject in need thereof, said method comprising:
administering a food powder as described herein to the subject.

In certain embodiments, the food powder may comprise, or be co-administered with, an anti-inflammatory agent. In certain embodiments, the anti-inflammatory agent may comprise curcumin.

In another embodiment, there is provided herein a method for treating or reducing obesity in a subject in need thereof, said method comprising:
administering a food powder as described herein to the subject.

In yet another embodiment, the food powder may comprise components derived at least in part from nut, legume, herb, spice, vegetable, or fungal plant tissue, traditionally used for food or medical purposes.

In another embodiment, there is provided herein a method for treating or preventing cancer in a subject in need thereof, said method comprising:
administering a food powder as described herein to the subject.

In another embodiment, the food powder may be simultaneously or sequentially co-administered with an anticancer drug. In yet another embodiment, the food powder may be complexed with, or conjugated with, an anticancer drug. In still another embodiment, the anticancer drug may be paclitaxel or vincristine.

In another embodiment, there is provided herein a method for providing a subject with soluble dietary fibre, said method comprising:
administering a food powder as described herein to the subject.

In another embodiment, there is provided herein a viscosity enhancing food additive comprising a food powder as described herein.

In another embodiment, there is provided herein a method for attenuating post-prandial sugar levels in the blood of a subject in need thereof, said method comprising:
administering a food powder as described herein to the subject.

In another embodiment, there is provided herein a method for reducing cell proliferation, said method comprising:
treatment of a cell or tissue or organ with a food powder as described herein.

In another embodiment, the food powder may be simultaneously or sequentially used with an anticancer drug. In yet another embodiment, the food powder may be complexed with, or conjugated with, an anticancer drug. In still another embodiment, the anticancer drug may be paclitaxel or vincristine.

In another embodiment, there is provided herein a method for reducing triglyceride accumulation in the liver of a subject in need thereof, said method comprising:
administering a food powder as described herein to the subject.

In another embodiment, there is provided herein an antibacterial food powder, comprising a food powder as described herein, complexed with or conjugated with an antibacterial agent. In certain embodiments, the antibacterial agent may comprise lysozyme, a tetracycline, or Nisin, or any combination thereof. In certain embodiments, the antibacterial food powder may be for use in treating or preventing MDR bacterial infection.

In another embodiment, there is provided herein an antibacterial food powder, comprising a food powder as described herein, complexed with or conjugated with an antibacterial agent. In another embodiment, the antibacterial agent may comprise a lysozyme, a tetracycline, or Nisin, or any combination thereof. In certain embodiments, the antibacterial food powder may be for use in treating or preventing MDR bacterial infection.

Example 1—Preparation and Characterization of Nanoparticles and Nanofibres

Spontaneous Assembly of Macromolecules in Sour Cherry (*Prunus cerasus* L.) Fruit into Nanoparticles and Nanofibres Under Cell Disrupting Conditions, and Comparisons Therebetween It was hypothesized by the present inventors that nanostructures could be generated by particular fruit processing methods where cell disruption occurs, providing an environment where molecular interactions could occur, and potentially resulting in the formation of well-defined nanostructures. The present Example describes the preparation, isolation, physico-chemical properties, and structural characteristics of nanoparticles and nanofibres derived from biological sources (sour cherry fruit in this example) using different methods, that may have beneficial roles in, for example, food function, chronic disease prevention, and/or improving drug and/or bioactive delivery into cells.

In this Example, homogenization of sour cherry fruits in an aqueous medium (or an alcoholic medium containing both alcohol and water), and spontaneous assembly of cellular components (for example, pectin, glucans, oligosaccharide linked to proteins, and/or degradation products thereof), polyphenols, and organic acids (for example, malic acid) to form nanoparticles (and nanofibres, where polyphenols have been extracted from the fruit being homogenized) was performed and studied. Nanoparticles formed in these studies were detergent stable, uniformly spherical structures ranging in size from about 25 to about 50 nm in solution, and much larger in size when dehydrated after lyophilization into a powder. A morphologically different type of nanostructure, referred to herein as nanofibre, was also prepared, which was distinct from the spherical structures and in the form of nanofibres, about 5 about 10 nm in width, and micrometers in length, which were generated from ethanol-bleached cherry devoid of polyphenols as the plant tissue used for homogenization. The complexes could be completely disrupted by treating with pectinase, indicating the pectin nature of the constituent structures. As well, treatment with cellulase and trypsin resulted in the removal of the outer fibrillar structures of the nanoparticles, exposing an inner core. SDS-PAGE of nanoparticles revealed polypeptides of varying masses, co-migrating with pectin and polyphenols as a smear, while the nanofibres showed primarily polypeptides. Both nanoparticles and nanofibres showed a strong affinity to antibodies raised against arabinogalactan-protein complexes, and a far lower affinity to anti-extensin. The nanoparticles did not react with anti-homogalacturonan, and anti-xyloglucan, while the nanofibres showed very strong reaction. Nanoparticles were enriched in hexose sugars such as glucose, galactose/galacturonic acid, and mannose, while the nanofibres were enriched in pentoses such as arabinose. FT-IR spectra of the nanoparticles and the nanofibres showed similarities to those of proteins and pectin. A 38 kD polypeptide, that was visible as a distinct band after SDS-PAGE showed sequence similarities to glucan endo-1,3-beta-glucosidase, while a 20 kD polypeptide showed similarities to thaumatin-like protein. The present Example describes structural characteristics of self-assembled nanoparticles from sour cherry fruits, in comparison with nanofibres also derived from sour cherry fruits in a different manner.

Materials and Methods

Sour cherry: The sour cherry fruits used in this Example came from the Vineland Research Station, Vineland, Ontario, where these are maintained as germplasm. All the varieties are high polyphenol containing varieties, ranging in polyphenol content in the range of 300-500 mg/100 g fresh weight. The major variety used for the present studies was V 70151, others such as V 71261, Hymann Conserva and Hymann Rubisn also showed high levels of nanoparticle formation. The sour cherry used in this example was *Prunus cerasus* L.

Chemicals were obtained from Sigma Chemical Co., St Louis, USA; Fisher Chemicals; In Vitrogen; Molecular Probes; among others.

Preparation and Isolation of Nanoparticles, and Preparation and Isolation of Nanofibres:

For nanoparticles, the extraction method involved homogenizing the sour cherry fruit using a polytron homogenizer with PTA 10 probe in a medium (preferably water as used in this Example, but may alternatively use absolute or diluted methanol or ethanol, for example), in 1:1 w/w proportion (1 g tissue to 1 ml water or alcohol), at an intermediate (4-5) setting until the fruit tissue was completely homogenized. The homogenate was filtered through 4 layers of cheese cloth to remove debris. The resulting homogenate was centrifuged (18,000×g) in a Sorvall RC 6 Plus centrifuge for 20 minutes. The supernatant was decanted. Five ml of the supernatant was dialyzed (spectra-Por, 6-8 kD cut off) against water (1 litre) for 12 hours at 4° C. The dialyzed extract within the dialysis bag was stored frozen at −20° C., just as the supernatant (termed crude extract). Since the extract may contain enzymes which might degrade the nanoparticles when in aqueous solution, the dialyzed extract was maintained at low temperature. In embodiments where an alcoholic or substantially alcoholic medium is used, such enzymes would likely be denatured and/or having reduced activity, although low temperature is still generally preferred. As described herein, once lyophilized or spray dried (for example), the nanoparticles are stable.

Polyphenols that leached into water were diluted considerably, so, for experimental purposes, this was concentrated by hydrophobic interaction chromatography by passing through a sep-pak C18 cartridge, and eluting with methanol.

For lyophilisation, the dialyzed homogenate was taken in a flask having 1 litre volume (~250 ml), and made into a shell by cooling in liquid $N_2$. The flask was attached to a lyophilizer (operating at −60C, and a vacuum of 3-4 Toricelli, used for this purpose). Alcoholic solutions were dialyzed against water to remove alcohol before conducting lyophilisation. In the case of nanoparticles, complete removal of water was not achieved by this method, potentially because of the water bound to nanoparticles, but this may provide a concentrated solution. Nanofibre solutions may be dialyzed into a fine powder using such method.

For nanofibres, pitted sour cherry fruits were immersed in 50% ethanol for 48 h with 3 solvent changes, and this resulted in removal of polyphenols leaving cherry fruits with an off white colour (referred to as bleaching herein). Pitting of the sour cherry fruits creates contact surface with the solvent, and it is contemplated that in certain embodiments fruits may even be sliced into smaller size pieces to further enhance the removal of polyphenols. The bleached fruits/slices were immersed in water and thoroughly washed 3 times in water to remove ethanol (3 h total). These fruits were homogenized in water or methanol (1:1 w/w) using polytron as used for unbleached cherry extraction described above. After removal of debris with centrifugation (18000× g) for 15 minutes, the homogenate was dialyzed against water. The dialyzed extract containing the nanofibres was substantially free of polyphenols and could be lyophilized into a fluffy white powder.

For nanospray drying, the nanoparticle/nanofiber solution was diluted to a consistency with water, such that it will form a fine spray (thick solutions tend to clog the nozzle of the sprayer used). Nanospray drying was conducted using a Buchi minispray drier (B290) (pump speed-35-50% providing 10-15 ml flow, Inlet temperature at 180° C., outlet temperature at 100° C., with an airflow maintained at 400litre/hour). The resulting powder was stored in sealed tubes at −20° C.

Electron Microscopy: About 500 to 1000 µg of processed nano-sized cherry powder nanoparticle or nanofibre powders were dusted uniformly on one side of a double sided adhesive carbon conducting tape. The tape was then mounted on a 12 mm diameter aluminum stub. Sample surfaces were observed at different magnification and the images were recorded using the Scanning Electron Microscope (Model QUANTA 250, FEI, The Netherlands).

Transmission electron microscopy of nanoparticles was conducted using the dialyzed extract or powders dissolved in water (~100-200 µg per ml) as described earlier (Jacob and Paliyath, 2008). Carbon coated nickel grids were floated on a 50 µl drop of the solution, and the nanoparticles were allowed to adsorb to the grid for 30 s. The grid was blotted dry and floated on a drop of 1% Uranyl acetate for 30 s. The grid was blotted dry and examined under a Leo 912 B transmission electron microscope.

Analysis of proteins: To evaluate the protein degradation during processing, protein was extracted from each step using TRIzol® as suggested by the manufacturer (Invitrogen). In brief, 100 µg protein equivalent of sample (as determined by Bradford reagent) was homogenized or mixed well in TRIzol reagent (1 ml) and incubated at room temperature for 5 min. The homogenate was centrifuged at 12000×g for 15 min at 4° C. For phase separation, 200 ul of chloroform was added and vortexed to mix well and centrifuged at 12000×g for 15 min at 4° C.

The aqueous and organic phases were separated. The aqueous phase was dried by lyophilisation. The dried residue was redissolved by heating (90° C.) in sample loading buffer for SDS-PAGE. To precipitate the protein from the organic fraction, 1.5 ml of isopropanol was added, and incubated for 10 min at room temperature followed by centrifugation at 12000×g for 10 min at 4° C. The pellet obtained after centrifugation was washed three times using 0.3M guanidine hydrochloride in 95% ethanol followed by a final wash using 2 ml of 100% ethanol. Pellet was redissolved by heating in sample loading buffer. Protein samples were separated on 10% polyacrylamide gels under denaturing and reducing conditions. The gel was fixed in 10% acetic acid and stained with Coomassie brilliant blue.

Association of polyphenols and peptides in nanoparticles: Nanoparticle formation during homogenization of sour cherry in water was a spontaneous process. The resultant homogenate was highly acidic with pH typically around 3.0. To test whether homogenization in near neutral pH has an effect on nanoparticle formation and on association of proteins and polyphenols, sour cherry was also homogenized in 300 mM sodium citrate buffer at pH 6.0. In TRIzol™ protein extraction method, free proteins transit into the organic phase, whereas tightly associated proteins with hydrophilic molecules such as carbohydrates may partition into the aqueous phase. To evaluate the association of polyphenols and proteins in the nanoparticles, proteins from aqueous and organic phases obtained after TRIzol™ extraction were analyzed using SDS-PAGE. The diluted aqueous phase was concentrated by lyophilisation, whereas proteins from the organic phase were precipitated using isopropanol as described earlier. The precipitated interphase was directly solubilized in protein sample loading buffer. Proteins were separated on 10% polyacrylamide gels under denaturing and reducing conditions. After electrophoresis, the gel was incubated in 10% acetic acid for 5 min and a picture was taken highlighting the distribution of colored polyphenols. Thereafter, the gel was stained with coomassie brilliant blue for detection of proteins.

Figure 12:
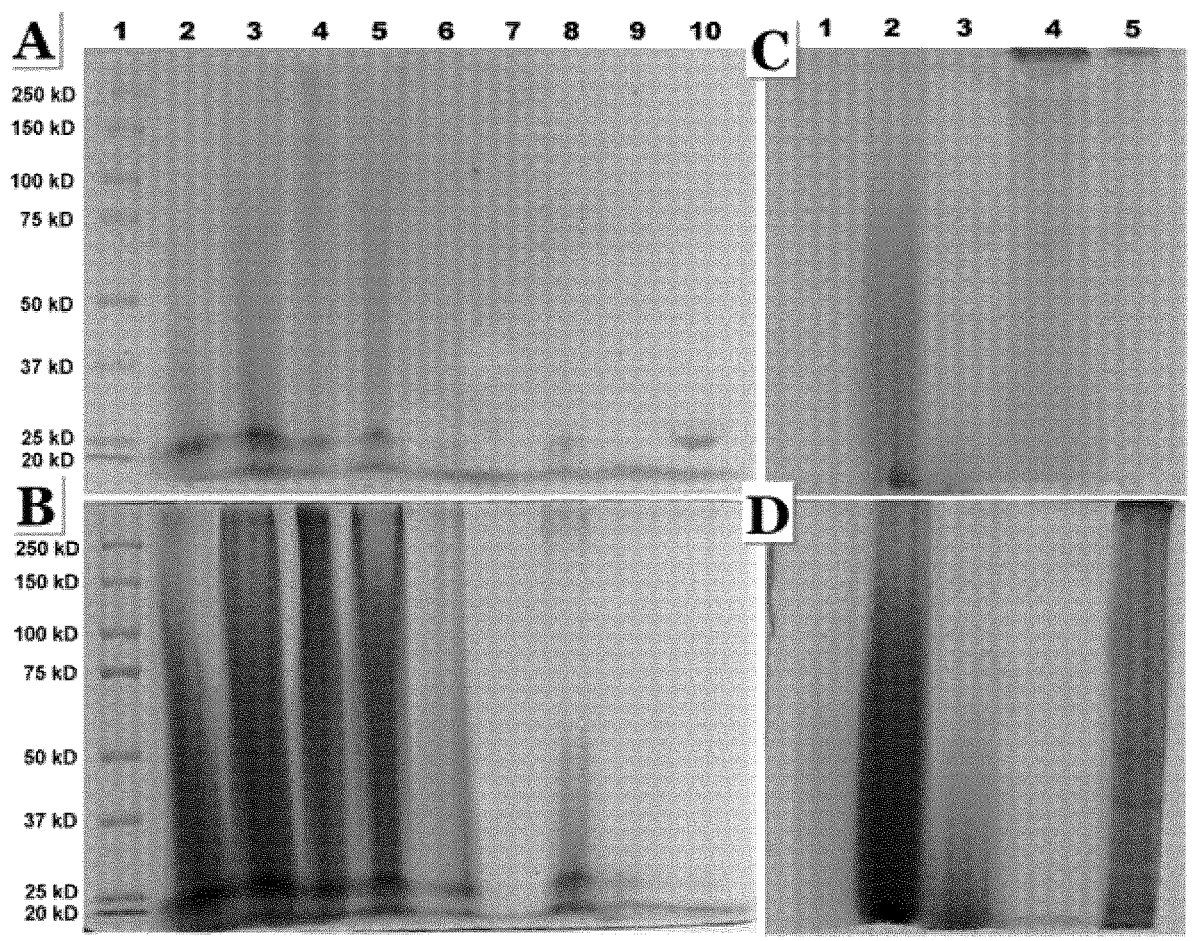
FIG. 12 shows SDS-PAGE analysis of peptides in nanoparticles. The extraction and dialysis was conducted in water as well as a buffer (potassium citrate, 300 mM, pH, 6, final pH after homogenization was pH 5) to enhance the stability of polyphenols (anthocyanins). The panel A shows the gel before staining to reveal the pink colour due to polyphenols (anthocyanins) when the gel is incubated in 10% acetic acid in water (v/v). The panel B shows the same gel that has been stained with coomassie brilliant blue to reveal peptides. Lane 1-Molecular markers; Lane 2 shows the association of polyphenols (anthocyanins) and polypeptides in nanoparticles from lyophilized powder of dialyzed water extract loaded in sample buffer. After Trizol extraction, supernatant (aqueous phase, Lane 3) shows the presence of peptides and their association with polyphenols (anthocyanins). Lane 4-Buffered dialyzed extract powder loaded in sample buffer. Lanes 5, 6 and 7 correspond to the supernatant, interphase and organic phase of the dialyzed extract powder obtained after trizol extraction. Note that the bulk of peptides and polyphenols (anthocyanins) are in the aqueous (hydrophilic) phase of trizol extract (lane 5). Lane 7 corresponding to the organic phase does not show anthocyanin or peptide staining. Lanes 8, 9 and 10 correspond to the supernatant, interphase and the organic phase obtained after trizol extraction of dialyzed extract powder from ethanol bleached cherries where most of the polyphenols (anthocyanins) have been removed. Lane 8, panel B shows staining with Coomassie blue. The interphase and the organic phase of bleached cherry dialyzed extract showed minimal staining for peptides (lanes 9, 10; panel B). Association of pectin and polypeptides in the nanoparticles as revealed by the similarity in staining with propidium iodide and coomassie brilliant blue after SDS-PAGE of dialyzed extract powder (Panels C and D). Panel C shows the staining pattern with propidium iodide (10 µg in water, 0.2% in water). Lane 1 corresponds to a standard sample of commercially available pectin. Lane 2 represents dialyzed powder of dialyzed extract; Lane 3 corresponds to the dialyzate, and this fraction shows relatively more intense staining for polypeptides. Lane 4 corresponds to a standard of polygalacturonic acid which show staining with propidium iodide, and not for polypeptides. The jelly like pellet of sour cherry homogenate also shows the presence of pectin and polypeptides (lane 5)

In these tests, nanoparticle formation was favoured at a low pH, ranging from 3-6. The association of polyphenols with peptides may be understood by the comigration of peptides and anthocyanins as observed in the unstained gel (FIG. 12A) and the same gel stained with Coomassie brillian blue (FIG. 12 B).

Association of pectic acids in nanoparticles: Apple pectin and polygalauronic acid were dissolved in 0.1N NaOH and used as standards. The nanoparticle and free polyphenols along with these pectic samples were resolved on 10% polyacrylamide gels under denaturing/reducing condition. After electrophoresis, the gel was stained with propidium iodide (10 µg/ml in water) for one hour and photographed. The same gel was again stained with coomassie brilliant blue.

Western and spot blot analysis of structural components in nanoparticles: To identify the nature of major carbohydrate structural components of the nanoparticle, spot blot and western blot were performed using three monoclonal antibodies (www.Plantprobes.net) raised against homogalacturonan (LM20), extensin (LM1) and arabinogalactan-protein (LM14). Lyophilized powder of nanoparticles and nanofibres from unbleached and bleached sour cherry, respectively, was heated in boiling water for 5 min in sample loading buffer and resolved using 10% SDS-PAGE under reducing condition. The resolved polypeptides from the gel were electrotransferred on to nitrocellulose membrane overnight. For the dot blot analysis, 2 ul of the boiled sample was directly applied onto nitrocellulose membrane. These nitrocellulose membranes were blocked with 5% non-fat milk powder solution in PBS (phosphate buffered saline) buffer for 1 hr at room temperature. After washing three times with PBS-T (PBS with 0.1% Tween-20) and a final wash with PBS, membranes were incubated in primary antibody solution (20× diluted) in PBS for 2 h at room temperature. After incubation, membranes were washed three times with PBS-T and a final wash in PBS before incubation in the anti-rat-AP conjugated secondary antibody for 1 hr in room temperature. After incubation in secondary antibody, membranes were washed three times in PBS-T and a final wash in PBS. Color development was achieved using Bio-Rad Alkaline phosphatise conjugate substrate kit as recommended by the manufacturer.

Analysis was done on Varian Saturn 2000 system equipped with ion-trap. GC was programmed at constant flow rate of 1 ml/min on Sil-CB8 (0.25 mm×30 m) column. Injector temperature was kept constant at 250° C. on split mode (20:1). Oven temperature was held constant at 100° C. for 4 min during injection then ramped to 250° C. at the rate of 8° C./min and maintained at 250° C. for additional 3 min. Ion-trap was programmed to analyze mass between 40-650 m/z with initial delay segment of 3 min.

Derivatization of sugars: Trimethylsilyl (TMS) derivatives of various pentose and hexose sugars were prepared to determine their respective retention time in the given GC-MS parameters. Various sugar standards (2 mg) were dissolved in 100 µl of anhydrous pyridine and 100 µl of BSTFA: TMCS (N,O-bis(trimethylsilyl) trifluoroacetamide: trimethylchlorosilane; 99:1) was added to the solution in a glass vial. Derivatization was conducted using procedures described by the supplier (Sigma). The reaction mixture was incubated at 80° C. for 2 hours. 1 µl of derivatized sugar was injected in GC-MS for analysis.

Derivatization of nanoparticle: Nanoparticles were prepared fresh by homogenization of 10 gm sour cherry fruit in 10 ml distilled water generally as described above. The homogenate was centrifuged at 15000 g for 20 min. The clarified juice from supernatant was passed through 10 ml PD-10 desalting column and further dialyzed against distilled water with 6-8 kDa cut-off membrane. 100 µl of purified nanoparticle was mixed with 200 µl of concentrated TFA to a final concentration of 8.6M and incubated at 90° C. for 2 hrs. The hydrolyzed sample was dried under stream of nitrogen. The dried sample was resuspended in 100 µl of pyridine and 100 µl of BSTFA: TMCS (99:1) was added to the solution. Derivatization was done by incubating at 80° C. for 1 hr. For GC-MS analysis 1 µl of sample was injected.

Derivatization of nanofibre: Nanofibre solution was prepared by dissolving 4 mg of lyophilized nanofibre in 1 ml water. 100 µl of nanofibre was hydrolyzed in 8.6M TFA at 90° C. for 2 hrs. Hydrolyzed sample was filtered through glass fiber filter and dried under stream of nitrogen. The dried sample was resuspended in 100 µl of pyridine and 100 µl of BSTFA: TMCS (99:1) was added to the solution. Derivatization was done by incubating at 80° C. for 1 hr. For GC-MS analysis 1 µl of sample was injected.

FT-IR analysis of nanoparticles: FT-IR analysis of nanoparticles and nanofibres was conducted using a Bruker Tensor 27 InfraRed spectrometer. Equal amounts of powders (1%) were mixed with KBr and made into a transparent disc which was scanned for acquiring the spectra.

X-Ray Diffraction of nanoparticles: Small Angle X-ray Diffraction of the nanoparticles was conducted using a Bruker Nanostar SAXS diffractometer. Lyophilized powders of nanoparticles from dialyzed extract of unbleached cherry and the dialysate were used for the diffraction analysis.

Statistical analysis: Statistical analyses were conducted using GraphPad Prism version 4. Results having two means were compared using a Student's t test. Results with multiple means were compared using one way ANOVA followed by "Tukey's test" to evaluate the level of significance. Significantly different means ($p<0.05$) are denoted by different superscripts.

Results and Discussion

Characterization of Nanoparticles: In these studies, homogenization of fruits in an aqueous medium disrupted the natural organization of cellular macromolecules and simple molecules, resulting in their random, but structured assembly leading to the generation of structures with distinct physicochemical and structural characteristics. Differences in size between polyphenols and nanostructures complexed with polyphenols were used to separate these structures through dialysis, using a low molecular mass cut off membrane or a PD-10 column that enabled size exclusion separation. Polyphenol contents of the crude sour cherry extract, dialyzed extract containing nanoparticles, and the dialyzate (containing molecules excluded by the membrane with molecular masses of ~6 kD and lower) are shown in Table 1. Nearly 80% of the polyphenols in the extract was retained within the dialysis membrane, suggesting that the polyphenols exist in a complexed state. By comparison to other fruits such as grape and blueberry, complex formation was much higher in sour cherry (although nanoparticles also formed in grape and blueberry). HPLC-MS separation of polyphenolic components revealed the presence of cyanidin-3 rutinoside as the major anthocyanin with peonidin 3-rutinoside in lesser abundance. Phenolic acids such as chlorogenic acid, and para-coumaroyl quinic acid were present at much smaller levels (see Table 2). Antioxidant activities of the crude extract, dialyzed extract (nanoparticle; NP) and the dialysate from both aqueous and methanol extracts are given in Table 3. All extracts showed high levels of superoxide-, hydroxyl-, and DPPH radical scavenging activities. The crude extract showed the highest antioxidant capacity under both extraction conditions. Dialyzate possessed the lowest antioxidant activity. A significant portion of antioxidant capacity was associated with the nanoparticles (i.e. the dialyzed extract).

Extraction in methanol (~50% v/v final) also resulted in the formation of nanoparticles.

Dialyzed extract could be lyophilyzed into a fluffy powder containing protein (10-12%), polyphenols (12-14%), pectin (10%-15%) and other carbohydrates (eg. hemicellulose components such as xyloglucan, pectin components such as arabinogalactans). Once formed, the polyphenols in the nanoparticles could not be extracted with ethanol (50-100%). The complexes were generally acid stable (pH<3). Addition of 10% trichloroacetic acid resulted in the precipitation of complexes as a reddish residue, however, alkaline conditions (>pH 7) resulted in the ring cleavage of polyphenols, potentially destabilizing the macromolecular organization. In comparison, the nanofibres from ethanol-bleached cherry did not contain detectable amounts of polyphenols, but contained protein (~15%), pectin (15-20%) and other carbohydrates (hemicelluloses such as xyloglucans, pectic components such as arabinoxylans and complexed pectins (60-70%). Since complex formation is a random event, a strict proportionality between types of components is difficult to achieve, and so a general proportion of various components is provided.

TABLE 1

Total Polyphenol Content in Sour Cherry Extract
Total Polyphenol Content (mg gallic acid/g fresh weight equivalent)

| Sample | Water Extract | Methanol Extract |
|---|---|---|
| Crude Extract | $0.88 \pm 0.1^{b,c}$-$0.94 \pm 0.1^{b,c}$ | $1.04 \pm 0.1^{b,c}$-$1.13 \pm 0.1^{b,c}$ |
| Dialyzed Extract (Nanoparticles) | $0.65 \pm 0.1^{a,c}$-$0.63 \pm 0.1^{a,c}$ | $0.70 \pm 0.1^{a,c}$-$0.80 \pm 0.1^{a,c}$ |
| Dialyzate | $0.03 \pm 0.1^{a,b}$-$0.06 \pm 0.1^{a,b}$ | $0.03 \pm 0.1^{a,b}$-$0.05 \pm 0.1^{a,b}$ |

Superscript "a" denotes statistical significance at $p < 0.05$ from CE (Water and Methanol); "b" denotes statistical significance at $p < 0.05$ from DE (Water and Methanol); and "c" denotes statistical significance at $p < 0.05$ from DZ (Water and Methanol) respectively. The values from each set are Mean ± Standard Error from three independent estimations.

TABLE 2

Polyphenol Composition of the Dialyzed Extracts of Sour Cherry (mg gallic acid equivalent/g fresh weight)

| Polyphenols | Dialyzed Water Extract | Dialyzed Methanol Extract |
|---|---|---|
| Cyanidin-3-Sophoroside | $0.07 \pm 0.1$ | $0.07 \pm 0.0$ |
| Cyanidin-3-Rutinoside | $0.71 \pm 0.1^b$ | $0.55 \pm 0.1^a$ |
| Peonidin-3-Rutinoside | $0.17 \pm 0.1$ | $0.16 \pm 0.0$ |
| Pelargonidin-3-Rutinoside | $0.06 \pm 0.1^b$ | $0.1 \pm 0.1^a$ |
| p-Coumaroyl quinic Acid | $0.02 \pm 0.0$ | $0.01 \pm 0.0$ |
| Chlorogenic Acid | $0.04 \pm 0.1$ | $0.04 \pm 0.1$ |

Superscript "a" and "b" denote the statistical significance at $p < 0.05$ between components in dialyzed water extract and dialyzed methanol extract, respectively for each Phenolic component.
ND: Not Detected. Quantification was conducted by HPLC-MS analysis and peak area comparison.

TABLE 3

Antioxidant Capacity of Crude Extract, Dialyzed Extract, and the Dialysate from Sour Cherry
Antioxidant Activity (% Quench rate/μg polyphenol)

| | Water Extract | | | Methanol Extract | | |
|---|---|---|---|---|---|---|
| | | Dialyzed | | | Dialyzed | |
| Antioxidant Assay | Crude Extract | Extract (Nanoparticles) | Dialyzate | Crude Extract | Dialyzed Extract | Dialyzate |
| Superoxide Scavenging | $2.6 \pm 0.2^{b,c}$ | $1.8 \pm 0.1^a$ | $1.4 \pm 0.1^a$ | $3.6 \pm 0.1^{b,c}$ | $2.5 \pm 0.1^{a,c}$ | $1.6 \pm 0.2^{a,b}$ |
| Hydroxyl Radical Scavenging | $4.9 \pm 0.2^{b,c}$ | $2.1 \pm 0.2^{a,c}$ | $1.5 \pm 0.1^{a,b}$ | $6.5 \pm 0.3^{b,c}$ | $3.9 \pm 0.3^{a,c}$ | $1.8 \pm 0.1^{a,b}$ |
| DPPH Radical Scavenging | $8.2 \pm 0.3^{b,c}$ | $4.4 \pm 0.5^a$ | $4.7 \pm 0.1^a$ | $8.8 \pm 0.2^{b,c}$ | $6.2 \pm 0.2^{a,c}$ | $3.3 \pm 0.4^{a,b}$ |

DPPH, Hydroxyl and Superoxide radical scavenging capacity (RSC) of sour cherry extracts. Superscript "a" denotes statistical significance at $p < 0.05$ from crude extract (CE) (Water and Methanol); "b" denotes statistical significance at $p < 0.05$ from dialyzed extract (DE) (Water and Methanol); and "c" denotes statistical significance at $p < 0.05$ from dialyzate (DL) (Water and Methanol) respectively.

Figure 2:
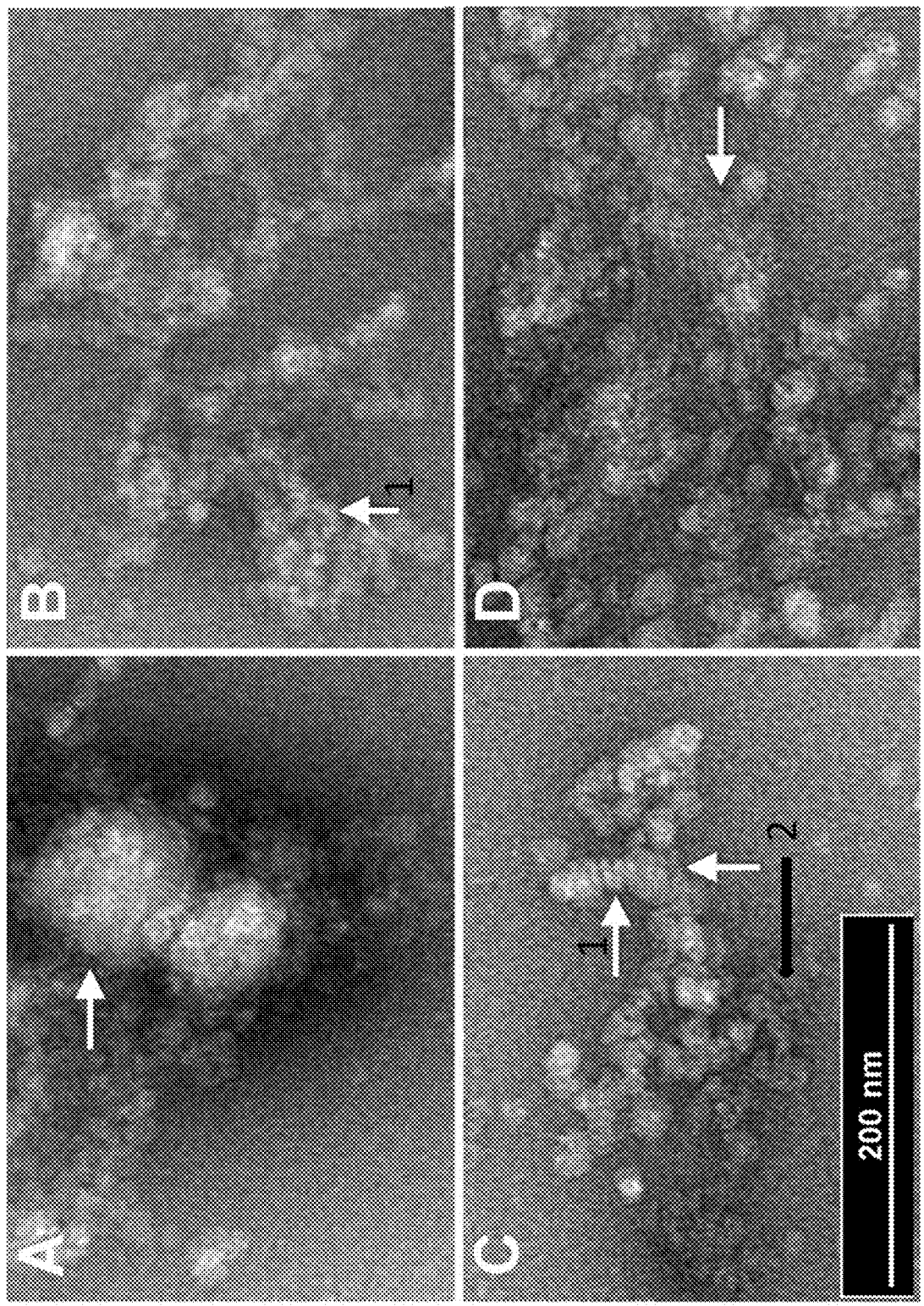
FIG. 2 shows magnified views of nanoparticles as observed under the EM. Panel A-Two nanoparticles that have been stripped of the outer structures (arrow 2) exposing a much smoother interior shell (arrow 1). Panels B, C-Panels showing detailed morphology of the outer coating comprising of fibrils. The arrow 1 shows regions of the fibrils having a spiral filamentous structure. The spiral filamentous structures are coated with fibrils (arrow 2). Panel C shows a region with simple fibril structure stripped off the spiral filaments. Panel D shows a mat of fibrils (arrow), formed during potential natural disassociation of the complexes when stored as a solution.

Morphology of Nanoparticles: Transmission Electron Microscopy (TEM) of the dialyzed extract revealed nanoparticles with diameters in the range of about 25 to about 50 nm (FIG. 1A, arrows). The sizes varied considerably suggesting that the complexes may be potentially transformed through loss of structural components. The nanoparticles possessed linear filamentous components winding around a central structure These structures can be seen stretching between two nanoparticles in the magnified view of the complexes (FIG. 1 B, arrow. The variation in the sizes of nanoparticles may arise from multiple fibres winding around the central core several times. The fibres appear to be unwound (FIG. 1B, arrow) in several nanoparticles suggesting that these may be held together by non-covalent bonds, and changes in the external environment may dissociate the nanoparticles into their building units. TEM of the structural components of the nanoparticles are shown in FIG. 2. FIG. 2A shows the core structure of the nanoparticle as a spherical structure which is stripped of the winding filaments (arrow. The fibre-like structures can be observed in the background emanating from the central spherical structure. The substructure of the filaments revealing a spiral fibril structure can be seen in FIG. 2B and C (arrows 1, 2). FIG. 2D shows extended fibre structures (arrow) composed of the fibrils. Thus, the nanoparticles appeared to possess multiple levels of organization to form substructures with distinct characteristics, the central core, the fibres surrounding the core, fibre structures assembled as spirals that can be extended into fibrils which may be held together through non-covalent bonds.

Structural components of Nanoparticles: In the present example, ripe sour cherry was used as the plant tissue for preparing the nanoparticles and nanofibres. Macromolecules that are present in ripe fruits are primarily carbohydrates such as cellulose, hemicelluloses, pectin, and glycoproteins associated with the cell wall (Negi and Handa, 2008). There is very little soluble protein in ripe fruits. In fruits such as cherry, organic acids are the principal storage molecules, which get converted to sugars during ripening. Starch, which is a major storage component, exists as high molecular mass structures, and is absent in ripe fruits. Polyphenol biosynthesis increases during the ripening process with the accumulation of polyphenols in vacuoles imparting red colour to the fruits.

Figure 3:
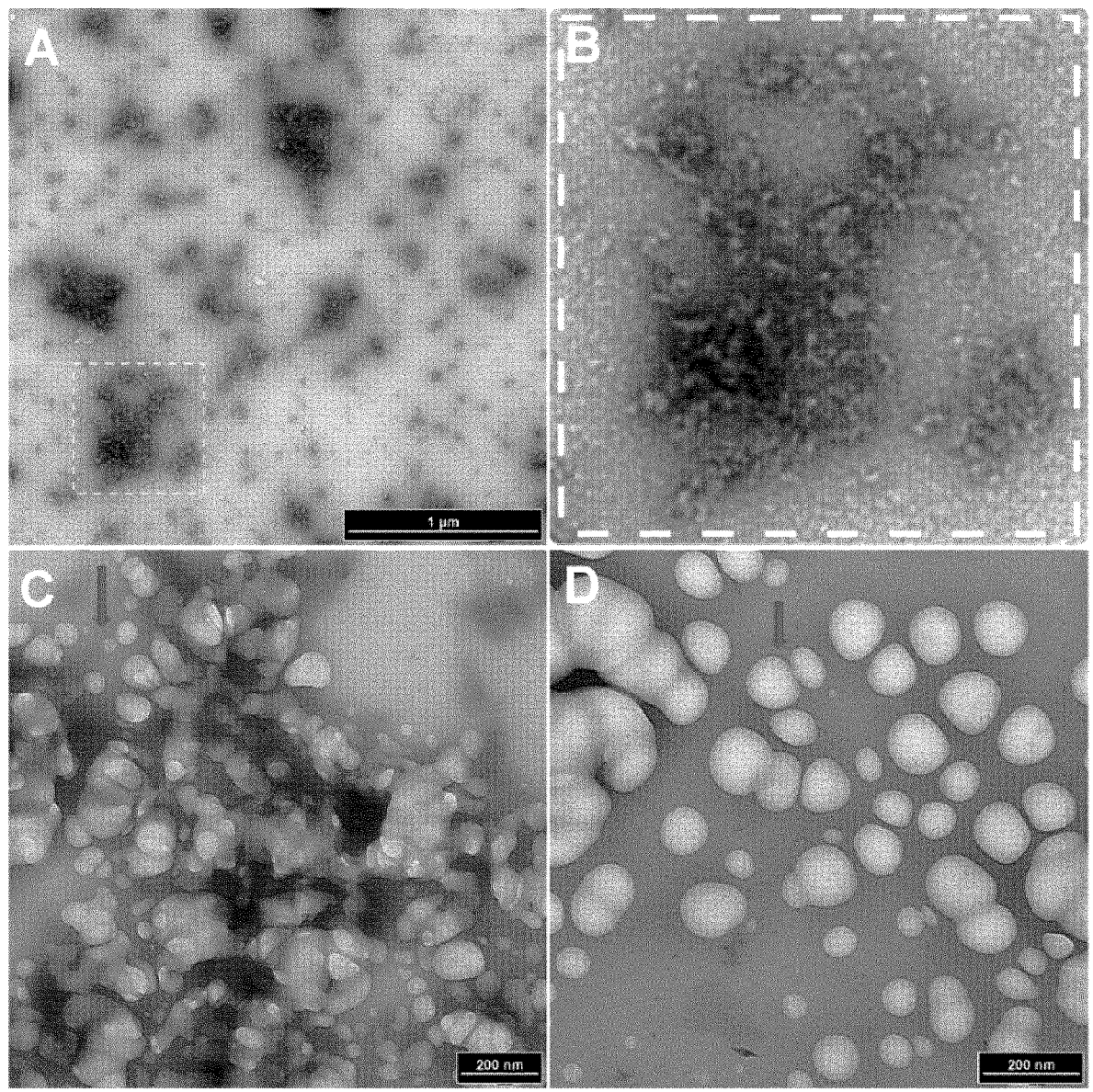
FIG. 3 shows effect of pectinase (polygalacturonase) treatment on the stability of nanoparticles. One ml of dialyzed extract containing nanoparticles (0.8-1 mg polyphenol equivalent/ml) was treated with pectinase (1 unit/ml of extract) for 15 min. The nanoparticles were allowed to adsorb to carbon coated nickel grids and visualized after staining with uranyl acetate as described earlier. Panel A-Dissolution of spherical complexes into smaller vesicular and filamentous structures can be seen (boxed region) after subjecting the extract to polygalacturonase treatment indicating the presence of macromolecular structures containing α-1,4-glycosidic linkage of polygalacturonic acid. Panel B shows a magnified version of the boxed region. Panels C and D shows the effect of treating the nanoparticles with cellulase (β-1,4-glucanase) that strips of the complexes of the filamentous coat leaving an inner core indicating the presence of β-1,4-glucan type components in the filaments.

Therefore, the nanoparticles from sour cherry may be constituted by cell wall carbohydrates (structural carbohydrates) and proteins as major structural components. If so, it was hypothesized that the nanoparticles may be subjected to enzymatic digestion using pectinolytic and cellulolytic enzymes as well as proteases, and the stability assessed through structural examination to learn more about structural organization. The effect of pectinase (polygalacturonase, a 1-4-glycosidase) treatment on the stability of nanoparticles is shown in FIG. 3A and a magnified region is shown in 3B. After subjecting to pectinase digestion (1unit/ml) the nanoparticles were totally disassembled into small tubular/vesicular structures interspersed within an electron dense matrix potentially formed by the binding of Uranium ions to negatively charged molecules of galacturonic acid in pectin (Negi and Handa, 2008). It is interesting to note that these digested structures resembled the nanovesicles observed in commercial Concord grape juice (Jacob and Paliyath, 2008). Fruit homogenates are typically treated with pectinase to obtain a higher juice yield during industrial processing. This observation suggests that the nanoparticles contain a high level of carbohydrate oligomers derived from pectin. The nanoparticles were also treated with cellulase ($\beta$-1,4-glucanase, 1 unit/ml) and the resulting structural modifications studied. By contrast to pectinase digestion, treatment with cellulase resulted in the formation of much larger vesicles and vesicular aggregates (FIGS. 3C and 3D, arrows). Since cellulase cannot digest pectin, the structures left over after digestion may be made of pectin, potentially, the core of the nanoparticles. Therefore, the cellulose moieties may form the part of the filamentous structure surrounding the pectin core of the nanoparticles. The nanoparticles were also subjected to incubation in the presence of trypsin (1 unit/ml), which again digested the outer filamentous structure of the nanoparticles leaving a core made of pectin (FIG. 4A). These structures also resembled the empty shell structure observed after cellulase treatment, indicating that the outer filamentous structure of the nanoparticles contained both cellulose moieties and polypeptides (i.e. proteinaceous material). A magnified view of the shell structure after stripping the outer fibre structures by trypsin treatment is shown in FIG. 4B. Intermediary structures formed during trypsin digestion are shown in FIGS. 4C, 4D and 4E. FIG. 4C shows a nanoparticle surrounded by concentric rings of fibre-like structures (i.e. organization of fibres around pectin core) that are becoming released as a result of trypsin treatment. FIG. 4D shows a shell of the nanoparticle along with the fibres that are stripped off the complex. FIG. 4E shows the substructure of the fibre materials constituted by long fibrillar structures that are intermingled and woven around into a structure resembling a rope, showing the potential of fibres to form large woven entities. These fibre-like structures are long, reaching micrometers in length, but with a diameter of about 2 to about 3 nm. The resilience of the nanoparticles to chemical treatments may come from this structural complexity that stabilizes the structure through interactions by different types of macromolecules.

Figure 5:
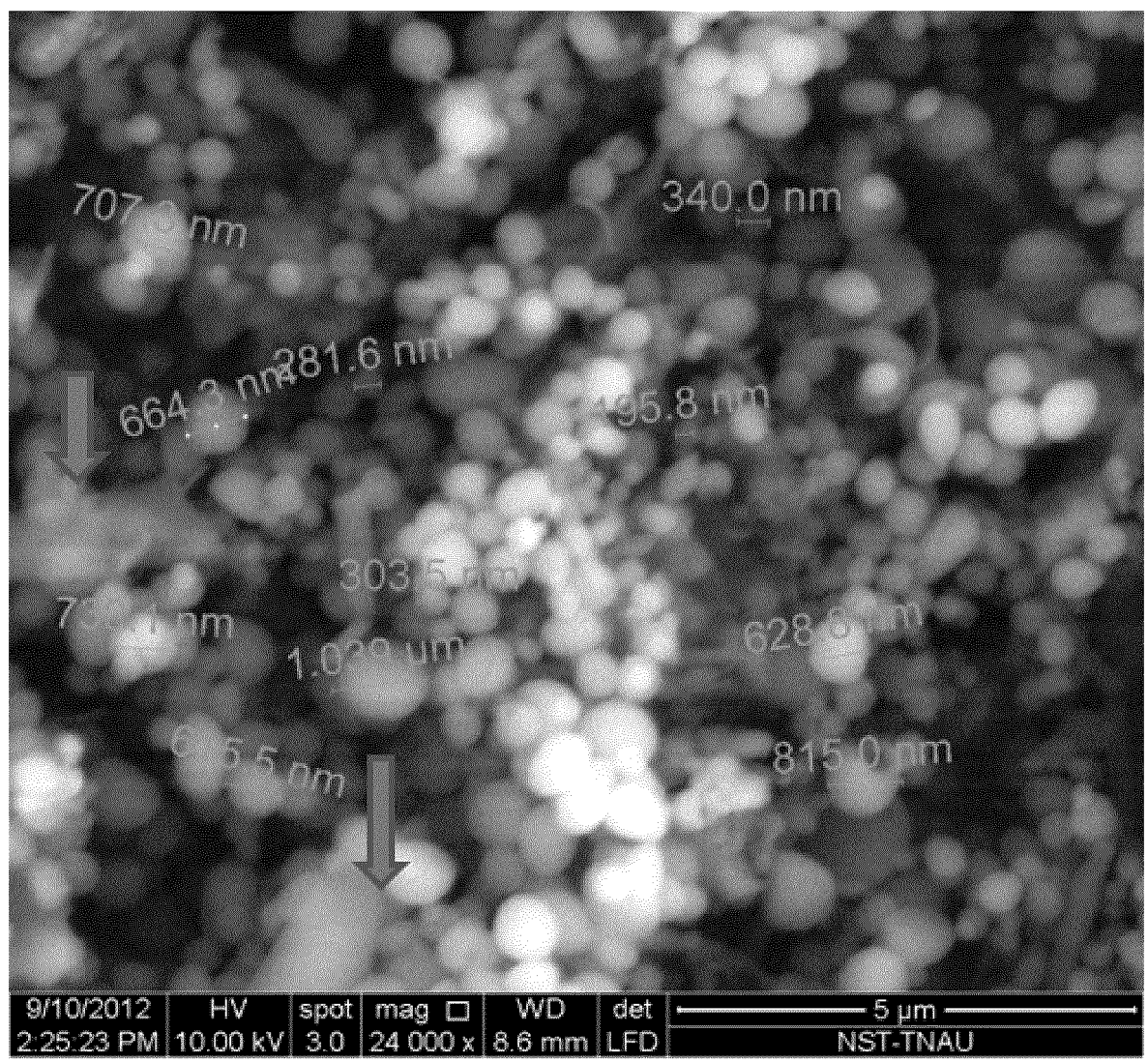
FIG. 5 shows a scanning electron micrograph of freeze-dried dialyzed sour cherry extract showing the nanoparticles. Removal of water appears to enhance the size of nanoparticles, with potentially collapsed external fibrillary moieties. Without wishing to be bound by theory, in an aqueous environment, the outer moieties of nanoparticles appear to be free and extended, the structures may be held together at least in part through hydrogen bonding. When water is removed, the fibrillary structures may tend to fuse with the pectin core of the nanoparticles, also expanding since there are no water molecules to facilitate hydrogen bonding. While in solution, the nanoparticles in general show a size distribution ranging from 25 to 50 nm in diameter, after freeze drying the size 200-800 nm, some reaching over a micrometer in diameter.
Figure 6:
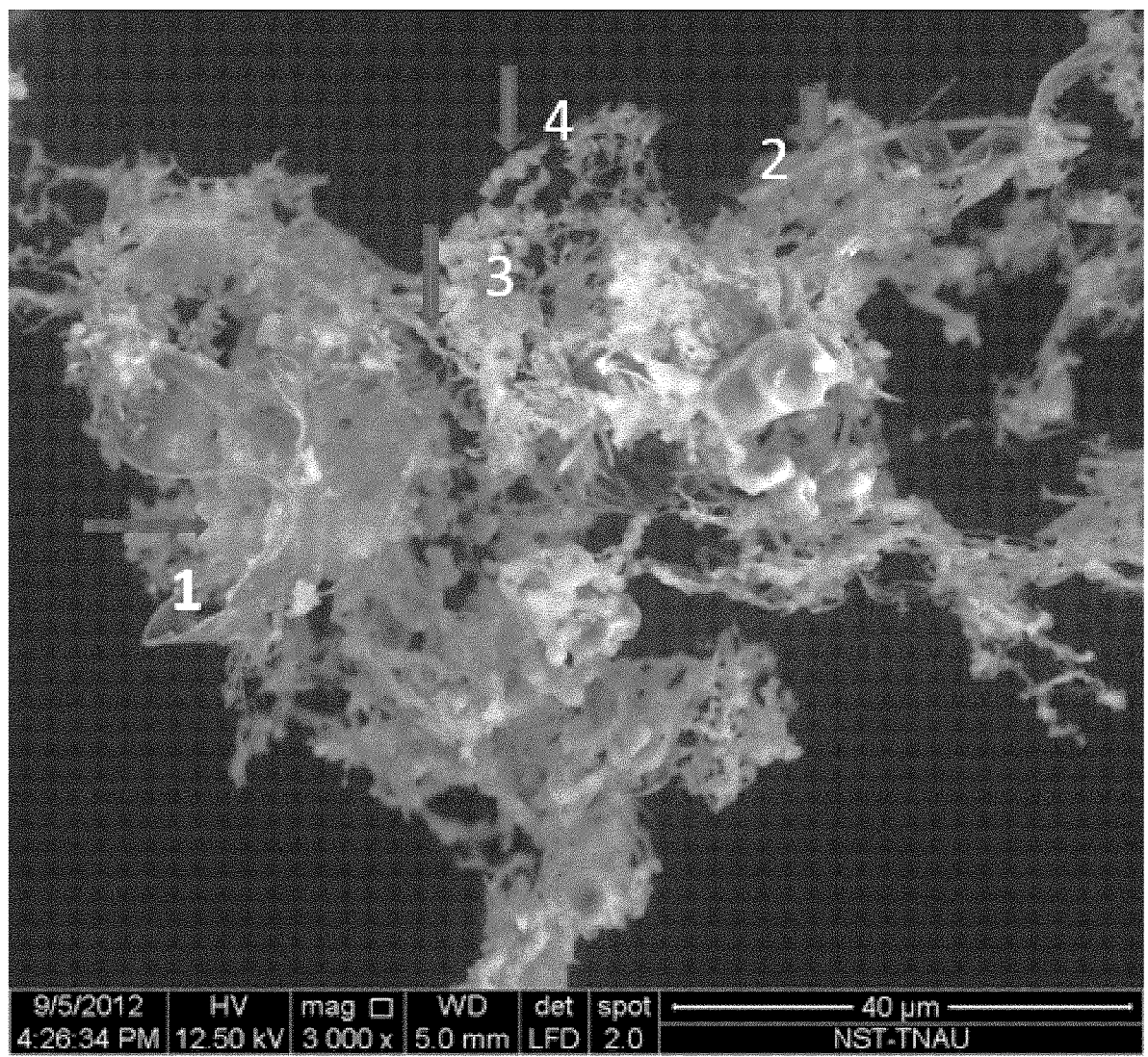
FIG. 6 shows a scanning electron micrograph of the dialyzed extract from sour cherry showing the formation of multiple structures comprising sheets (arrow 1), tubular regions (arrow 2), and fibrils (arrow 3). Budding of nanoparticles can be seen in some regions (arrow 4). These structures represent intermediate stages in the formation of nanoparticles.

Scanning Electron Microscopy (SEM) of dry nanoparticle powder: Nanoparticles were lyophilized, and upon removal of water, an amorphous powder was obtained. Examination of this powder by SEM revealed structural aspects potentially indicative of transitory stages resulting in the formation of nanoparticles. The size distribution of nanoparticles is shown in FIG. 5. In the dry form, the diameters of these complexes ranged from <200 nm to over a micrometer in diameter. This is nearly ten-fold higher than what was observed in the hydrated nanoparticles in suspension (FIG. 1A), where the size variation was from about 25 nm to about 50 nm. This suggests that during slow dehydration, water bound to the nanoparticles are removed leading to an expansion of the complex. Rehydration of the powder by suspending in water resulted in their reversal to small nanoparticles (data not shown). In addition to spherical structures, tubular structures were also observed in the lyophilized powder (FIG. 5, arrow). Structural variations in lyophilized powder can further be seen in FIG. 6 which shows the heterogeneity of transitory structures in the form of sheets (arrow 1), filaments (arrow 2), tubes (arrow 3) and vesicles, all of which can be seen in an intermingled state. A region showing the budding of vesicles from tubular structures is shown by arrow 4. Thus, in terms of their origin, it appears that the sheets tend to form tubular structures, which may bud off vesicular structures, that get coated with pectic/cellulosic oligomers-polypeptides, and other small molecules such as polyphenols and malic acid during the formation of nanoparticles.

Nanofibres from Bleached cherry: As the polyphenols were tightly bound to the nanoparticles and were difficult to remove by solvent extraction (alcohol, DMSO, acids), attempts were made to remove the polyphenols from the fruits by ethanol before generation of nanoparticles. Fruits were immersed in 50% ethanol for 48 h with 3 solvent changes, and this resulted in removal of polyphenols leaving cherry fruits with an off-white colour. Generally the same procedure for preparing the nanoparticles was then performed. Removal of polyphenols resulted in a total structural change from what was observed for the nanoparticles. Examination of the lyophilized powder showed extended strands or filamentous structures (nanofibres) interspersed with films that were nanometers (2-3 nm) in diameter that extended into micrometers in length (FIG. 7A). In an aqueous state, the (nanofibres retained their morphology with micrometers in length and about 5 to about 10 nm in diameter (FIG. 7B, arrow 1). These filaments also showed regions with a helical structure (FIG. 7B, arrow 2) suggesting that these may potentially have been originated from the spiral fibre-like structures coating the nanoparticles, that appear as stretched fibresafter treatment (FIG. 4E) with trypsin. Thus, it appears that polyphenols have a major role in determining the structural organization of the nanoparticles, and these interactions may also involve association with polypeptides.

Polyphenols have been known to interact with proteins (Dangles and Dufour, 2006). Functionally, apple pectin has been known to interact with polyphenols and enhance the beneficial effects in colonic fermentation and lipid removal from the body (Aprikian et al., 2003). Structurally, polyphenols are known to interact with both pectin and cellulose through ionic, and hydrogen bonding (Padayachee et al., 2012). Polyphenols interacted with both cellulose and pectin components in a biphasic process with binding as high as 18%. Cellulose pectin composites showed the highest binding. Thus, a combination of polypeptides, pectic/cellulosic oligomers may thus provide a highly favorable environment for polyphenol binding, which even after removal of polyphenols still retained the polypeptide-pectin-cellulose backbone, assembled into nanofibres.

Figure 8:
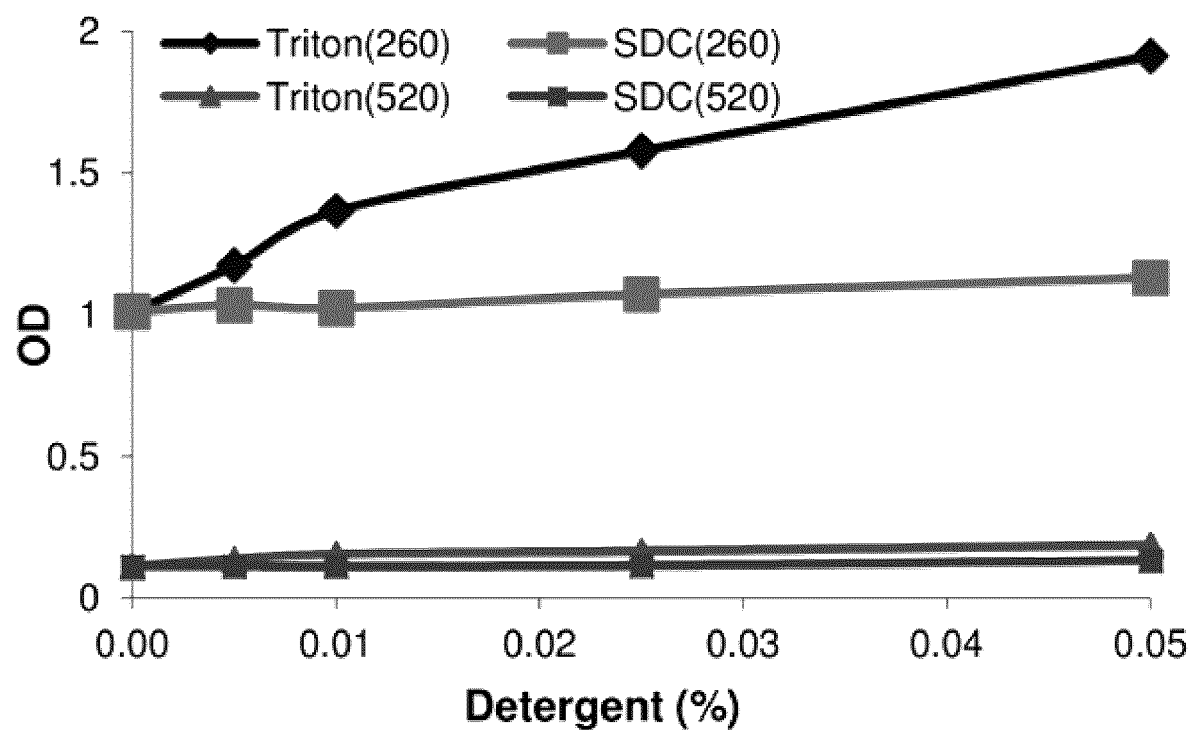
FIG. 8 shows effect of detergents on the stability of nanoparticles. Dialyzed extract from sour cherry was incubated in the presence of increasing concentrations of lipid-destabilizing detergents such as Triton-X 100 and sodium deoxycholate in 6-8 kDa cut off dialysis bags and dialyzed against water adjusted to a pH of 4, for 12 h. The absorbance of polyphenols inside the dialysis bag was measured at 520 nm (benzopyran) and 260 nm (phenolic ring). The detergent treatments did not result in the disruption of complexes, as no losses in polyphenol content could be observed after extensive dialysis. If the nanoparticles contained lipids as structural entities/components, detergent treatment would have resulted in a leakage of polyphenols from the dialysis bag into the dialyzate, with a corresponding decrease in absorbance in the extract within the dialysis bag. The increase in absorbance with Triton-X 100 at 260 nm may originate due to the absorption of the phenyl moiety of Triton-X 100 at 260 nm as its concentration increases in the solution.

Stability of nanoparticles to detergents: The stability of nanoparticles was further examined by treating the dialyzed extract with detergents such as Trition X-100 and sodium deoxycholate, which can disrupt macromolecular structures. When the dialyzed extract containing nanoparticles were incubated with increasing concentrations of these detergents, the polyphenol levels associated with the nanoparticles remained nearly constant when measured at 520 nm, the absorption maximum characteristic to benzopyran moiety of anthocyanins (FIG. 8). Similar results were also obtained with sodium deoxycholate. When measured at 260 nm showing an increase, potentially indicating micelle formation above the critical micellar concentration of Triton X-100 entrapping polyphenols within. These results also suggest the absence of lipids among the structural components of nanoparticles.

Figure 9:
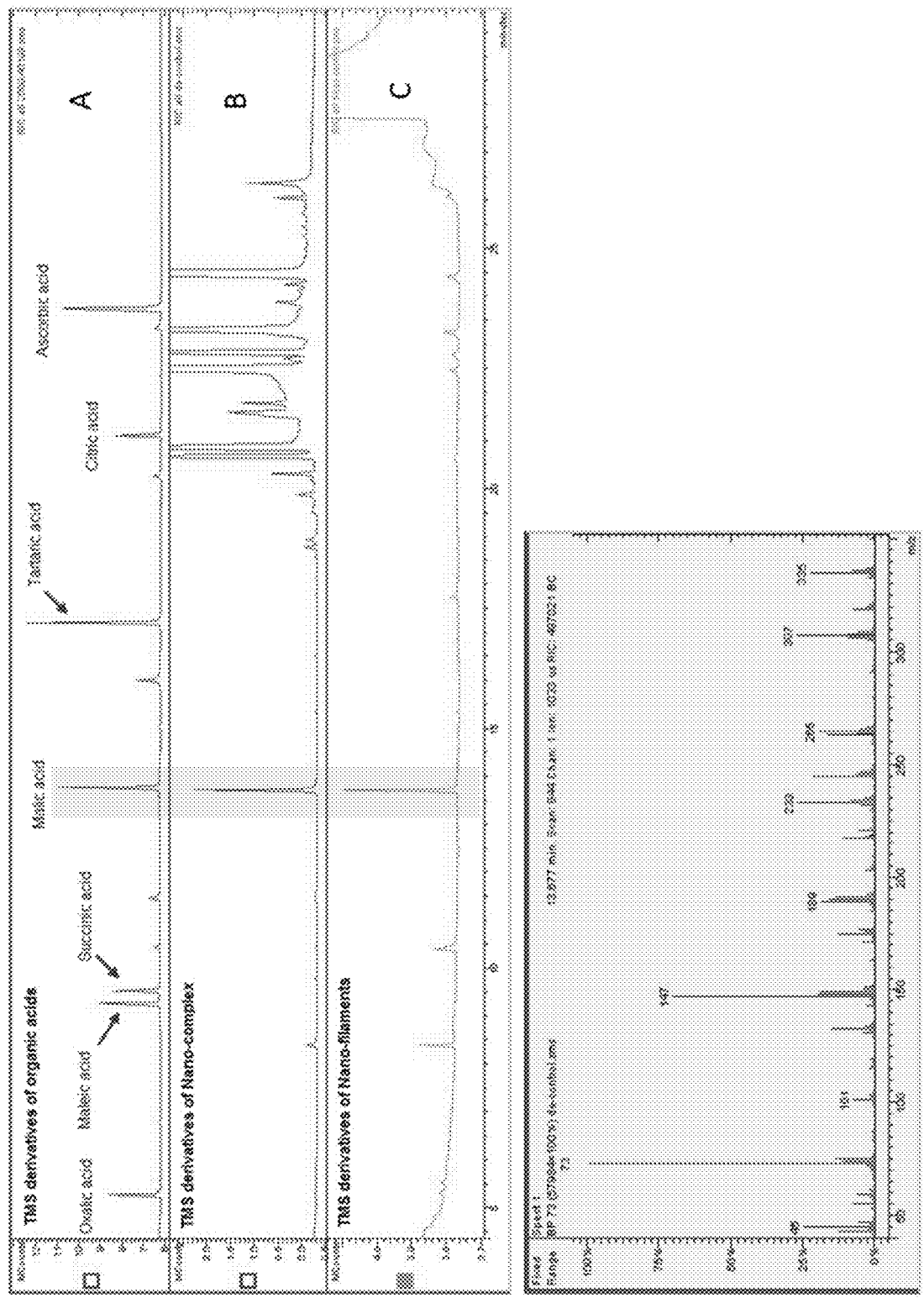
FIG. 9 shows organic composition of nanoparticles which were obtained after filtering the homogenate through a size exclusion column (PD 10). Both nanoparticles and nanofibres were isolated and lyophilized into a powder. Powder (400 ug) was dissolved in 100 ul pyridine, and 100 ul of BSTFA: TMCS mixture (99:1) was added. The solution was incubated at 80 C for 1 h. One ul was directly injected for GC-MS analysis. Non-hydrolyzing trimethylsilylation (TMS) of organic acid standards (A), nanoparticle (B), and nanofibres (C) and their separation using GC-MS, indicating presence of malic acid, is shown. As shown, in comparison, nanofibres and nanoparticles are different types of structures having different compositions, while malic acid is a common component. The lower panel shows the mass spectrum of reference malic acid trimethyl silyl derivative.

Chemical Composition of Nanoparticles and Comparison with Nanofibres:

Acidic nature of nanoparticles: Nanoparticles were highly stable in both aqueous solution and as a dry powder. During size exclusion chromatography of nanoparticles, polyphenols bound to the nanoparticles were eluted in the void volume, showing a maximum absorption at 520 nm that is characteristic of polyphenols, and a pH of 3. Elution of free polyphenols present in the solution was delayed, and the eluate appeared blue grey, and showed a pH close to 7, at which, the benzopyran ring cleavage of anthocyanins occurred with an associated loss of red colour. After extensive dialysis of sour cherry extract that would have removed free organic acids in the juice molecules, the dialyzed extract still showed a pH close to 3, which suggested that there may be acidic components (organic acids) bound to the nanoparticles as structural components, apart from the oligogalcturonic moieties of homogalacturonans (pH 3). To identify such components, nanoparticles and nanofibres were dried and trimethylsilyl derivatives prepared and the derivatives subjected to GC-MS analysis. The results are shown in FIG. 9. The top panel at (A) shows the elution pattern of standard organic acids. (B) and (C) show the elution profiles of compounds from the nanoparticles and nanofibres, respectively. Both nanoparticles and nanofibres showed the clear presence of malic acid that was eluted at 13.7 minutes (Mass spectrum, trimethylsilyl derivative). Malic acid is the major organic acid present in sour cherry fruits. Being a hydroxyl-acid, malic acid may form hydrogen bonds to stabilize molecular associations between components of the nanoparticles and nanofibres. The peaks eluting between 20-25 minutes are from derivatized sugars or oligosaccharides. The lower panel of FIG. 9 shows the mass spectrum of reference malic acid trimethyl silyl derivative.

Figure 11:
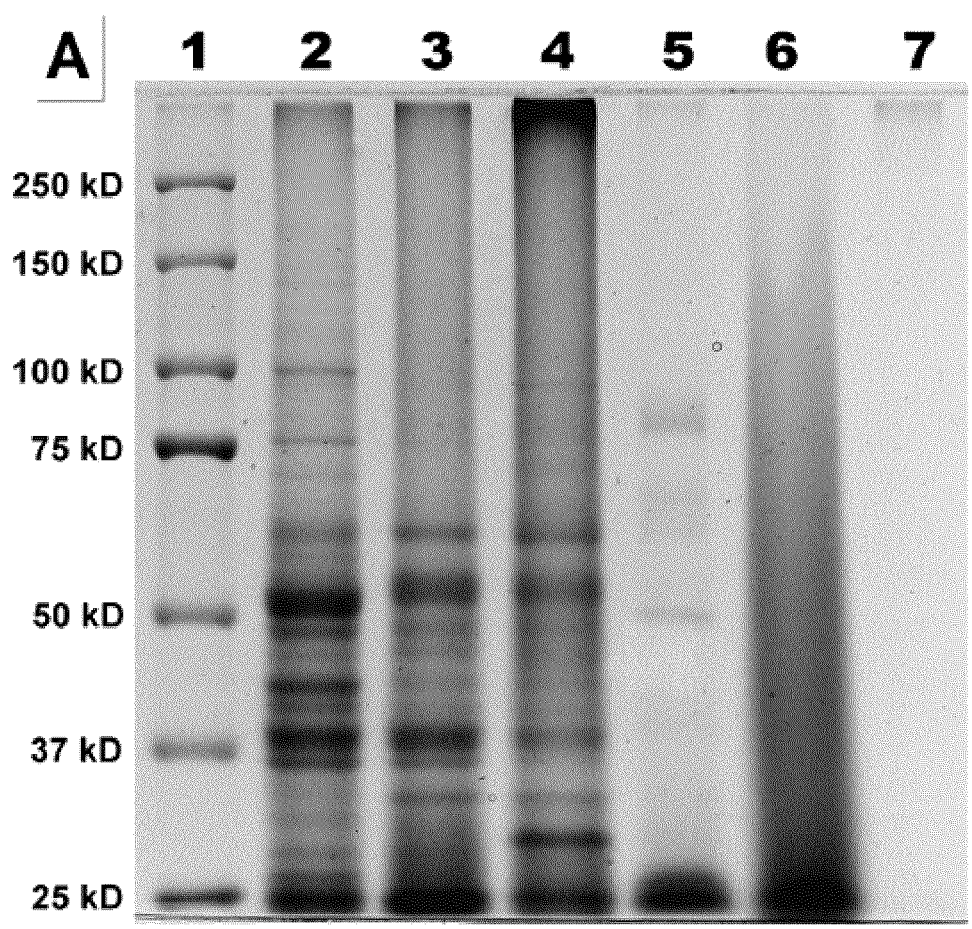
FIG. 11 shows SDS-PAGE analysis of proteins isolated from sour cherry fractions and stained with Coomassie blue. Protein from the whole fruit was isolated by trizol extraction. Under conditions where protease activity is inhibited (as in the presence of phenol, guanidinium isothiocyanate), protein degradation is minimal and the proteins exist in the organic phase (phenol: chloroform) after the addition of water and phase separation. Lane 1-Molecular mass markers; Lane 2-Protein isolated from the whole fruit; Lane 3-Protein from the fruit homogenate in water; Lane 4-Protein from cell debris juice obtained after centrifugation at 15000×g; Lane 5-Protein in clear juice obtained after centrifugation at 15000×g; Lane 6-Lyophilized powder of dialyzed extract dissolved and loaded in sample buffer; Lane 7-Protein extracted from lyophilized powder using trizol reagent, organic phase. After water extraction of the fruit, the juice primarily contains low molecular mass peptides (25 kD) which are still in the organic phase. Lyophilized powder of dialyzed extract (lane 6) does not show discrete bands of proteins but show a smear (lane 6) of peptides when visualized after SDS-PAGE and coomassie-blue staining. Trizol extraction and phase separation of the extract with water should theoretically lead to the migration of protein into the organic rich phase (phenol: chloroform phase). No staining could be observed with coomassie brilliant blue (lane 7), suggesting that peptides may have migrated to the aqueous phase because of enhanced hydrophilicity (association with carbohydrates, polyphenols) (lane 7). Equivalent amounts of samples (15 µg protein) were loaded in each lane based on fresh weight.

SDS-PAGE analysis of sour cherry polypeptides: The amount of proteins in fruits in general, is relatively low and protein degradation occurs during ripening by the activation of proteases. The presence of proteins in the nanoparticles was confirmed by their susceptibility to trypsin. Proteins in fruits and the homogenates were isolated with TRIzol™, a universal reagent which is ideal for nucleic acid and protein extraction in fruits (Tiwari and Paliyath, 2011). Under these conditions where protease activity is inhibited (as in the presence of phenol, guanidinium isothiocyanate), protein degradation was minimal and the proteins existed in the organic phase after the addition of water which resulted in the phase separation of TRIzol extract. The proteins in the original fruit, homogenate, and the pellet from centrifuged homogenate were subjected to trizol extraction, and the organic phase (chloroform: phenol) which normally contains the proteins analyzed by SDS-PAGE. Results are shown in FIG. 11. A clear separation of protein bands can be seen (see FIG. 11, lanes 2, 3, 4) in the gel, which represents the proteins in fruit (lane 2), proteins in the total water homogenate (lane 3), and the pellet obtained after the centrifugation of homogenate (lane 4). However, after trizol extraction of the supernatant of fruit homogenate obtained after centrifugation, the organic phase was almost devoid of proteins and primarily contained low molecular mass peptides (25 kD) (lane 5). Lyophilized powder of the dialyzed extract, when directly analyzed without TRIzol extraction, did not show discrete bands of proteins as in fruit, or its homogenate, but showed a smear (lane 6) of polypeptides when visualized after SDS-PAGE and coomassie-blue staining. However, after TRIzol extraction of the dialyzed extract powder, the organic phase showed no staining with coomassic brilliant blue suggesting that proteins/peptides may have migrated to the aqueous phase because of enhanced hydrophilicity due to association with carbohydrates and polyphenols (lane 7).

SDS-PAGE analysis of polypeptides in nanoparticles: Since the nanoparticles were constituted by polypeptides of various molecular masses (FIG. 11, lane 6), further analyses were conducted to delineate the nature of their association with other components such as carbohydrates and polyphenol components. If these structural components were tightly associated in the nanoparticle, it was hypothesized that they should co-migrate during SDS-PAGE. Sour cherries were extracted in water or in buffer (potassium citrate, 300 mM, pH, 6, final pH after homogenization was pH 5), and dialyzed against water or buffer. Dialyzed extracts were lyophilized and the powder resuspended in the loading buffer. Equivalent amounts (15 µg) of protein (resuspended in 15% glycerol in water) were loaded on the gel and subjected to SDS-PAGE. After electrophoresis, the gel was removed and incubated in 10% (v/v) acetic acid in water. Panel A (FIG. 12) shows the gel after separation of peptides and before staining with Coomassie brilliant blue to reveal the pink trailing colour in the lanes due to the presence of polyphenols. Panel B shows the same gel that was stained with Coomassie brilliant blue to reveal polypeptides. Lane 2 shows the staining pattern of the dialyzed extract powder. A comparison of lane 2 in panel A and B reveals the similarity in the migration of peptides (lane 2, panel B) to that of polyphenols (lane 2, panel A) suggesting that the polyphenols are tightly bound to the polypeptides in the nanoparticles. Polyphenols are small and uncharged molecules compared to peptides, and these will be eluted from the gel if they were not complexed. The dialyzed extract powder containing nanoparticles (obtained from water extract) was subjected to trizol extraction and phase separation, and lane 3 (panel A, B) corresponding to the aqueous supernatant fraction shows the presence of both polypeptides and polyphenols indicating their tight association. This property also revealed the hydrophilic nature of peptide-carbohydrate-polyphenol complexes, because, in the absence of complex formation, polypeptides by themselves would have partitioned in the organic phase of TRIzol extract (phenol: chloroform). However, as shown earlier (FIG. 11, lane 7), the organic phase from trizol extract of the nanoparticles did not possess any polypeptides. The association of peptides and polyphenols is clear in dialyzed buffer extract powder as well (FIG. 12, lane 4). Lanes 5, 6 and 7 correspond to the aqueous supernatant, interphase and organic phase of the dialyzed buffer extract powder obtained after TRIzol extraction. Polypeptides that are normally retained in the chloroform: phenol phase, have migrated into the aqueous phase (Lane 5) where the bulk of polypeptides and polyphenols can be visualized. The interphase shows the presence of polypeptides, but very little of the polyphenols (Lane 6, panel B, A). Lane 7 corresponding to the organic phase shows neither the presence of anthocyanin nor that of the peptide. Lanes 8, 9 and 10 correspond to the supernatant, interphase and the organic phase obtained after TRIzol extraction of dialyzed extract powder from ethanol bleached cherries where most of the polyphenols have been removed. Even though the removal of polyphenols lead to a structural transition of nanoparticles from spherical to filamentous structure nanofibres, the polypeptides are still an integral part of the nanofibres (lane 8, panel B). The interphase and the organic phase of bleached cherry dialyzed extract showed minimal staining for peptides (lanes 9, 10; panel B).

Carbohydrate composition of Nanoparticles and Nanofilments: The pectin nature of carbohydrates and their association with polypeptides in the nanoparticles was revealed by the similarity in staining with propidium iodide and coomassie brilliant blue after SDS-PAGE. Propidium iodide has been reported to be a stain for pectic acid (Rounds et al., 2011). Panel C (FIG. 12) shows the staining pattern of nanoparticles with propidium iodide (10 micromolar in water). The lower panel (D) shows a corresponding gel stained with Coomassie brilliant blue. Lane 1 corresponds to a standard sample of commercially available pectin, which shows minimal staining with propidium iodide. The staining of pectin with propidium iodide is due to the presence of negatively charged free carboxylic acid groups. If the carboxylic acid groups are blocked by methylation as naturally occur in some pectin samples, staining will be reduced. Lane 2 shows the migration pattern of components in the lyophilized powder of the dialyzed extract dissolved in 15% glycerol showing the distribution of pectin in nanoparticles (Panel A), and polypeptides (Panel B). Lane 3 corresponds to the pectin/polyphenol/peptide fraction obtained after lyophilizing the dialyzate fraction, and this fraction shows relatively more intense staining for polypeptides. Lane 4 corresponds to a standard of polygalacturonic acid which shows staining with propidium iodide, and not for polypeptides. The jelly like pellet of sour cherry homogenate also shows the presence of pectin and polypeptides (lane 5).

Figure 13:
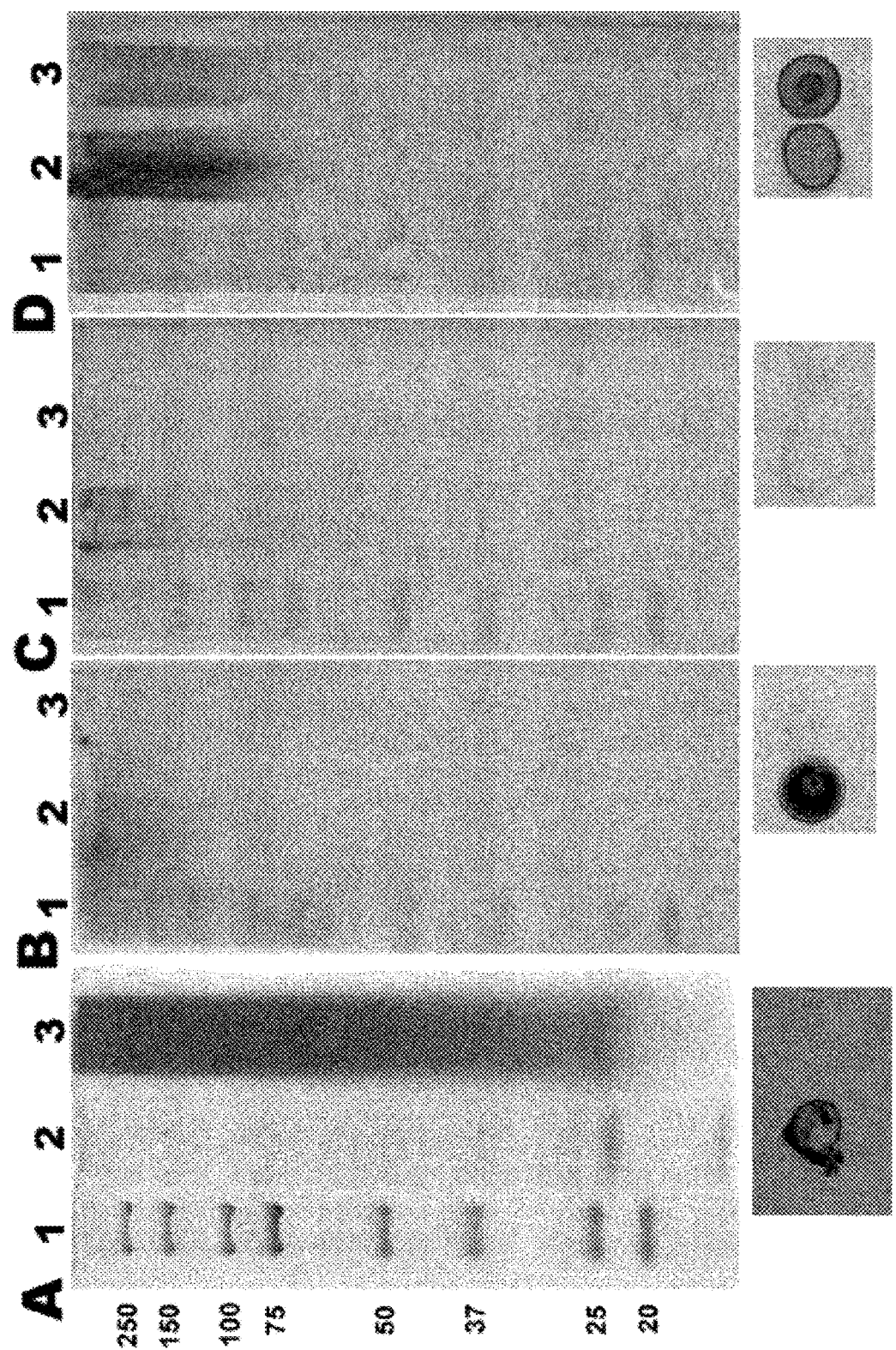
FIG. 13 shows dialyzed extract from ethanol-bleached cherry and unbleached cherry containing nanofibres and nanoparticles, respectively, which were subjected to SDS-PAGE and immunolocalization with structure specific monoclonal antibodies (rat IgM, www.Plant Probes.net). The bound antibodies were detected with alkaline phosphatase conjugated goat-anti rat IgG. Panel A shows the staining of polypeptides in nanofibres (lane 2) and nanoparticles (lane 3) by coomassie brilliant blue. The nanofibres from bleached cherry are very hygroscopic and become a jelly which does not readily enter the gel. Panel B shows the reactivity of antibodies against homogalacturonan (oligo 1, 4-linked galacturonic acid methyl esters; LM 20). The bleached cherry dialyzed extract shows reactivity towards this antibody indicating exposed homogalacturonan units in the nanofibres. However, the reactivity towards dialyzed extract from unbleached cherry (containing spherical nanoparticles) is much lower (Panel B, lane 3). This is again reflected in the intensity of dot blots shown below panel B. In spherical nanoparticles, the pectic moieties form the shells, and are potentially masked by peptides, hemicelluloses and polyphenols (anthocyanins). These may hinder the accessibility of the anti-homogalacturonan antibody to the interior. While in nanofibres, the pectic moieties are potentially exposed which enable strong interaction with the anti-homogalacturonan antibody. Both nanofibres and nanoparticles showed only a mild reactivity towards anti-extensin (which recognises the LM1 epitope that is carried by a range of HRGP [Hydroxyproline rich Glycoproteins]), suggesting that extensin, which is the major cell wall protein in fruits (Panel C) may not be intact, but may contain peptides derived from extensin. Very strong reaction was observed against anti-arabinogalactan-protein (glycoprotein; LM14 epitope) (hemicellulose-protein) in both complexes and fibres suggesting that this may be a major component of the basic structure of nanoparticles or nanofibres (Panel D). Bottom panel below panel A shows cross reactivity of nanoparticles and nanofibres against anti-xyloglucan (LM 15; recognizes the XXXG motif of xyloglucan). There was no reaction between the antibodies and molecules transferred from the gel during blot. Dot blots revealed strong reaction by nanofibres against anti-xyloglucan, but not to nanoparticles.

Further analysis of the chemical nature of the nanoparticles was conducted by Western blot analysis (FIG. 13). Sour cherry fruits were extracted in water, before and after bleaching in ethanol (removing polyphenols) and nanoparticles and nanofibres isolated by dialysis against water. The dialyzed extracts were lyophilized and the complexes dissolved in glycerol: water and subjected to SDS-PAGE and immunolocalization with structure specific monoclonal antibodies (rat IgM) raised against homogalacturonan (a twentymer of α-1,4-galacturonic acid with intervening methylated units which forms a principal backbone structure of pectin), extension (the major cell wall glycoprotein), and arabinogalactan-protein (a major pectin-linked to protein). The bound antibodies were detected with alkaline phosphatase conjugated goat-anti rat IgG. Panel A shows the staining of nanofibres/nanoparticles from bleached cherry (lane 2; nanofibres) and unbleached cherry (lane 3; nanoparticles) respectively, by coomassie brilliant blue. Staining with coomassie brilliant blue is considerably lowered after ethanol extraction of polyphenols suggesting potential loss of polypeptides along with polyphenols (lane 2). This may also be due to the lowered penetration of gel by the nanofibres from bleached cherry. Panel B shows the reactivity of antibodies raised against homogalacturonan against nanofibres/nanoparticles from bleached cherry (Panel B, lane 2) and those from unbleached cherry (lane 3). Interestingly, reactivity towards homogalacturonan was more intense in nanofibres from bleached cherry as compared to nanoparticles from unbleached cherry (Panel B, lane 3). This is again reflected in the intensity of dot blots shown below panel B. This may potentially reflect the differences in accessibility of homogalacturonan moieties by the antibodies in the nanoparticles/nanofibres. A key difference between the nanoparticles from unbleached cherry to nanofibres from bleached cherry is the presence of polyphenols. By the removal of polyphenols through bleaching, the homogalacturonan moieties may become exposed to a greater extent that can lead to increased reactivity to the antibody. As well, these results demonstrate that polyphenols are an integral part of the nanoparticles from unbleached cherry, while its removal can lead to structural transformations. Incubating filamentous nanofibres with cherry polyphenols did not reverse the transformation from the filamentous to the spherical form (data not shown), however, both forms are structurally stable. Both nanoparticles and nanofibres showed a mild reactivity towards anti-extensin, an antibody raised against the major cell wall protein in fruits (Panel C). The dot blots against anti-extensin also showed minimal reactivity. However, a very strong reaction was observed against anti-arabinogalactan-protein (pectin-protein) by both nanoparticle/nanofibre types, suggesting that this may be a major component of the basic structure of nanoparticles/nanofibres (Panel D, lanes 2, 3; dot blots). Western blots against anti-xyloglucan did not show any cross reactivity in the gels, but showed strong reaction against nanofibres (bottom panel, Panel A, forming filamentous aggregates. It appears that the polypeptides are stripped from the nanoparticles and nanofibres during solubilisation by SDS, but carbohydrates may remain as aggregates, that do not effectively enter the gel due to large size and lack of charge.

Figure 10:
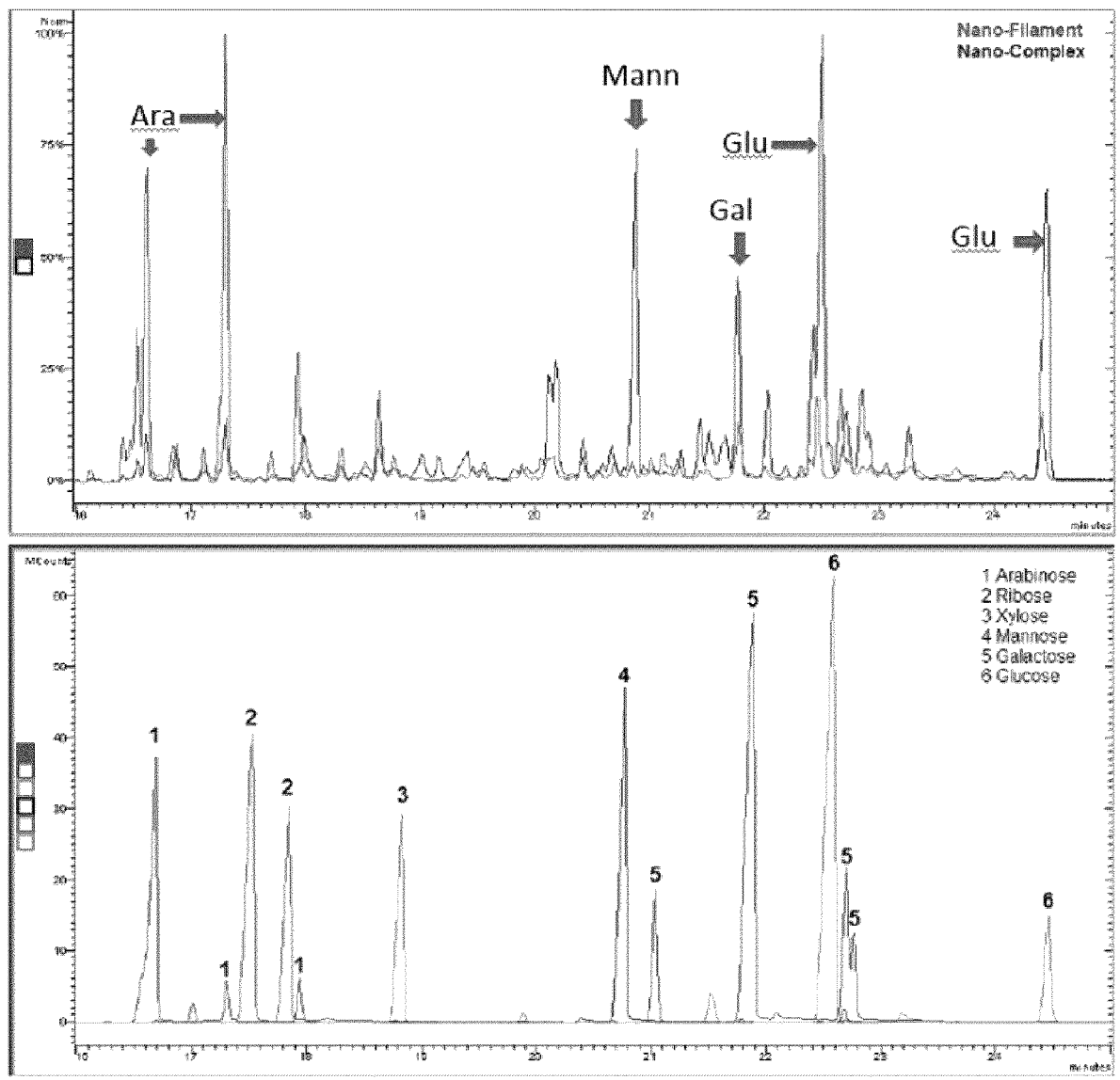
FIG. 10 shows trimethylsilyl derivatives of sugars in the nanoparticles (referred to as nano-complex in the Figure) and nanofibres (referred to as Nano-filament in the Figure) (top panel) and sugar standards (bottom panel). Nanoparticles and nanofibres were subjected to digestion using trifluoroacetic acid (TFA), before derivatization with BSTFA. Major sugars in nanoparticles are mannose, galactose/galacturonic acid, and glucose. The nanofibres are enriched in arabinose and minor amounts of glucose, and galactose/galacturonic acid. The amounts are relative, as the TFA-digestion is harsh, and may degrade some components. Galactose and galacturonic acid provide similar peak distribution, hence the peak may represent both compounds. The results primarily indicate the predominance of hexoses in nanoparticles and pentoses in nanofibres.

Qualitative analysis of carbohydrate composition of nanoparticles and nanofibres were conducted after digestion with trifluoroacetic acid (8.6M) and trimethylsilylation of liberated sugars using BSTFA: TMCS (Sigma, 99:1). A qualitative profile of sugars separated and identified by GC-MS is shown in FIG. 10 (top panel) along with that of common sugars as standards (bottom panel). There are similarities as well as differences in the sugar composition of nanoparticles (blue; labelled as nano-complex) and nanofibres (red; labelled as nano-filament). Glucose, galactose/galacturonic acid, and mannose were the major components in nanoparticles, with relatively low amounts of arabinose. Sugars of nanofibres were enriched in arabinose, with lower amounts of galactose/galacturonic acid, and glucose. There may be other sugars present in the nanoparticles and nanofibres that are not identified, and some of the peaks may also originate from sugars that were modified during TFA digestion. The results suggest that during nanofibre formation, several oligomers enriched in glucose, galactose/galacturonic acid, and mannose may be stripped off leaving primarily arabinose oligomers-enriched nanofibres, still derived from arabinogalactans of pectin.

Figure 14:
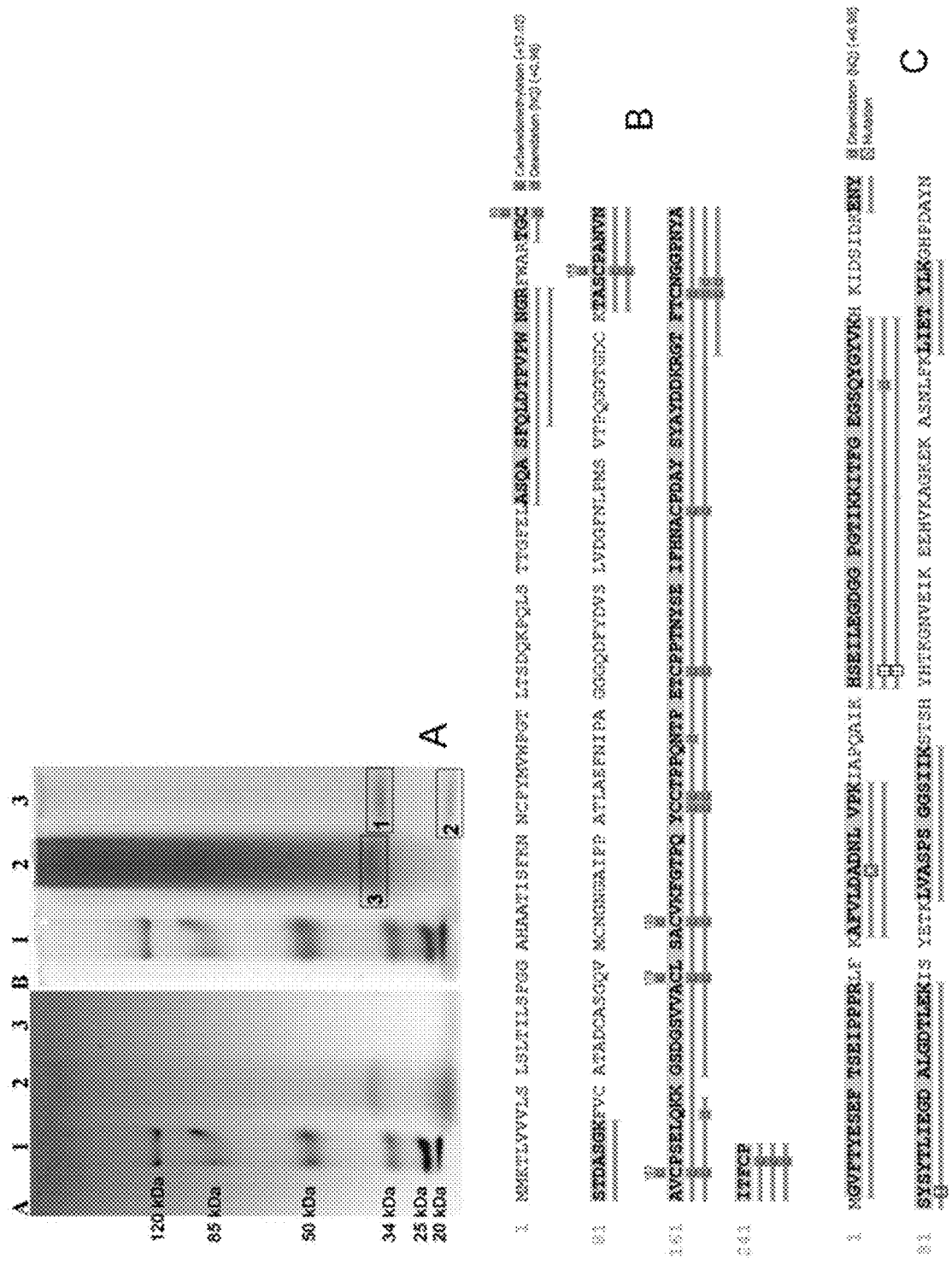
FIG. 14 shows reducing SDS-PAGE of Nanoparticle (Lane 2) and Nanofiber (Lane 3). 100 µg each were resolved on 10% gel. (A) The gel A was incubated in 10% acetic acid and later stained with coomassie brilliant blue (gel B). The gel bands highlighted in numbers were identified by LC/MS/MS as follows: Band 1: PR protein fragment; Glucan endo-1,3-beta-glucosidase (Accession #P50694) from Cherry; Band 2: PR protein fragment; major cherry allergen Pru a1 (Accession #O24248); Band 3: Most likely to be a fragment of band 1. Panels B and C show the amino acid sequences of the beta-glucosidase (Accession number P50694) (SEQ ID NO: 27) and Pru a1 (Accession number O24248) (SEQ ID NO: 28), respectively.

Identification of peptides derived from Pathogenesis Related proteins in nanofibres: During SDS-PAGE analysis, occurrence of peptides of various molecular masses could be detected in both nanoparticles and nanofibres, originating by the action of native protease activity during homogenization of cherries (FIG. 14, Panel A; lanes 2, 3; gels A, B). Among these, at least two bands were distinct in nanofibers (lane 3; B) with relative molecular masses of 40 kD and 20 kD (labeled 1, 3, FIG. 14; Panel A). A polypeptide band with slightly stronger intensity and a molecular mass of about 40 kD (labeled 2, gel B) was also observed. In unstained gel these 3 polypeptides were found to be associated with polyphenols (purple coloured) (gel A, lane 2). These bands were dissected and subjected to peptide fingerprinting after trypsin digestion and LC-MS/MS. Sequences of major peptides identified are shown in FIG. 14 (Panel B and C). The band 1 with ~40 kD molecular mass in lane 3 (Nanofibre) showed sequence similarity to the PR protein Glucan endo-1,3-beta-glucosidase (Accession #P50694) from Cherry (Panel B). The sequences identified by LC-MS-MS (indicated as highlighted fragments and deduced sequences from the genbank corresponded to a 246 amino acid long peptide of the protein (SEQ ID NO: 27). The second band at ~20 kD in lane 3 (nanofibers), showed sequence similarity to another PR protein (major cherry allergen Pru al (Accession #O24248) with a total of 161 amino acids in the polypeptide (SEQ ID NO: 28) (Panel B). The 40 kD band in nanoparticles corresponding to band in nanofibres did not yield hydrolytic products, potentially due to interference from bound polyphenols. These identified peptide fragments are a small fraction of all the polypeptides separated on the gel. This potentially suggests the high activities of proteases that results in the generation of peptides which may form integral components of nanoparticles and nanofibers.

FT-IR analysis of the nanoparticles: FT-IR spectrum of the nanoparticle/nanofibre powder from unbleached and bleached cherry fruits revealed complex spectra, with a high degree of similarity to each other and with similarity to macromolecular structures such as that of protein and cell wall polysaccharides (FIG. 15; nano-complex=nanoparticle, nano-filament=nanofibre). The figure also shows the spectra of polygalacturonic acid (PGA) (homogalacturonan, pectin), and albumin (BSA). The major absorption bands of the nanoparticles were observed as a broad band between 3000 nm to 3600 nm, between 2600 nm to 3000 nm, and several peaks in the fingerprint region between 1750 nm to 800 nm. Because of the macromolecular nature of nanoparticles, absorption peaks characteristic to individual functional groups or structural feature become merged. Comparison to spectral characteristics of polypeptides, pectin and polyphenols, several structural features of nanoparticles can be elucidated. The proportion of components such as protein (>10%), carbohydrates (~70%) and the presence of polyphenols (~10-15%) in the nanoparticles, may also influence the peaks and peak shapes, revealing an overall dominance of peaks characteristic to carbohydrates. FT-IR analysis of cell wall carbohydrate components showed features characteristic to cellulose, hemicellulose and pectin (Kacurakova et al, 2000; Urias-Orona, 2010). In ripening fruits, increased activity of cellulolytic and pectinolytic enzymes result in the catabolism of cell wall components leading to small molecular mass oligomers with characteristic linkages. Among these, pectins are complex molecules with α-1, 4-linked galacturonic acid with intermittent hairy regions (i.e. bristle-shaped) comprised of rhamnogalacturonans, galactans, arabinans and arabinogalactans (Negi and Handa, 2008). Xyloglucans, xylans, glucomannans and galactomannans are the hemicellulosic components of cell wall. Thus, during homogenization of fruits, any of these components may become integrated into the nanoparticles. The Western blot studies have shown the presence of homogalacturonan and arabinogalactan in the nanoparticles suggesting the predominant involvement of pectin in its formation. The FT-IR spectra from both type of nanoparticles/nanofibres from cherry show intense absorption in the carbohydrate region spanning 900 cm$^{-1}$ and 1200 cm$^{-1}$. Nanofibres from bleached cherry show a sharp peak at ~1017 cm$^{-1}$, which is characteristic to pectin with a high proportion of homogalacturonan (Kacurakova et al., 2000). The shoulder between 1045 cm$^{-1}$ and 1074 cm$^{-1}$ may originate from the β-linked arabinogalactans. Absorption from rhamnogalacturonans, as well as hemicelluloses occurs in this broad region.

Figure 15:
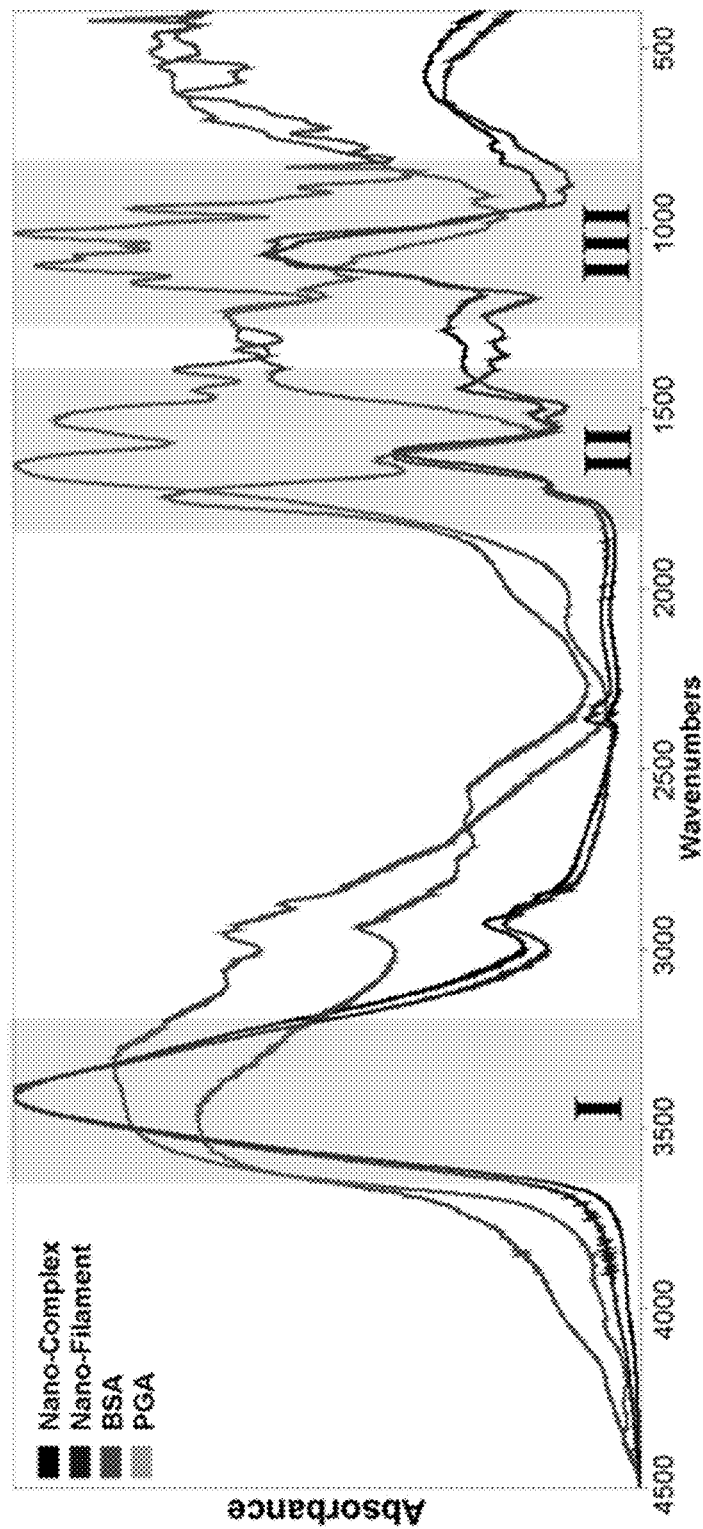
FIG. 15 shows FT-IR spectra of lyophilized powders of the dialyzed extracts from ethanol-bleached and unbleached cherry (top panel) as compared to several components having structural similarities (bottom panel). Because of the complex nature of components in the extract, it is difficult to obtain precise assignments of structures and functional groups. A comparison with spectra of standards suggest the presence of OH stretching (carbohydrates, polyphenols, 3000-3500 cm$^{-1}$), and several peaks due to CH—, COO, CN, etc., extending from 500-2000 cm$^{-1}$. Similarities to authentic pectin, protein, peptide backbone (C—N—C—N), are evident. BSA and PGA are included as standards in the Figure for comparison.

While the absorption in the carbohydrate region primarily originates from the glycosidic linkages (C—O—C), the anomeric region provides information on the type of linkages between sugar moieties. α-linkages are characterized by an absorption band at 834 cm$^{-1}$, and the β-linkages by a band at 898 cm$^{-1}$. Both type of nanoparticles show a broad absorption maximum at ~834 nm suggesting that the carbohydrates of the complexes predominantly possess an a type linkage, as common in pectin, again suggesting that the carbohydrates in nanoparticles are primarily of pectin origin (FIG. 15).

The broad bands observed between ~1550 cm$^{-1}$ and ~1800 cm$^{-1}$, are characteristic to pectin as observed in other plant tissues (McCann et al., 1994). In general, the FT-IR spectral pattern of pectin isolated from tobacco cells between 900 cm$^{-1}$ and 1800 cm$^{-1}$ including the fingerprint region are nearly identical to that observed for the nanoparticles. Two major structural elements of pectin are the ester linkages (1740 cm$^{-1}$) and the carboxylic acid groups (1600 and 1414 cm$^{-1}$). The broad peak at 1740 cm$^{-1}$ is distinct in both types of nanoparticles indicating the presence of esterified pectins, with slightly lower intensity in the nanoparticles from bleached cherries (FIG. 15).

The absorption bands of proteins in the nanoparticles are probably masked to a large extent by those arising from pectin (Gorinstein et al., 2009). However, certain characteristics of secondary structure can be observed in these spectra. FT-IR spectra of proteins are characterized by specific amide absorptions, termed as amide A, B bands and the amide I to VII. Amide A (~3500 cm$^{-1}$) and Amide B bands (~3100 cm$^{-1}$) arising from —NH stretching is potentially overlapped with the —OH stretching of carbohydrate hydroxyls (3400 cm$^{-1}$) forming a broad peak between 3600 cm$^{-1}$ and 3000 cm$^{-1}$ in the nanoparticle spectra. Amides I and II absorption arises from stretching vibrations of the —C—O, and —C—N groups (1600-1700 cm$^{-1}$) which overlap with the ester absorption from pectins, and NH stretching (1510-1580 cm 1) respectively. Amide I absorption is characteristic to the backbone structure, primarily beta-sheet that absorbs at ~1629 cm$^{-1}$. Cell wall glycoproteins such as extension has a larger component of β sheets, however, Western analysis using extension antibodies did not show a prevalence of extensin in the nanoparticles (FIG. 13). However, a highly positive reactivity to antibodies raised against arabinogalactan-protein was observed in both type of nanoparticles and nanofibres. This may suggest that arabinogalactan-linked proteins which are amphiphilic in nature (Seifert and Roberts, 2007) may provide the carbohydrate-polypeptide components to the nanoparticles (FIG. 15).

Polyphenols are an integral part of the nanoparticles. The relative amount of polyphenols is in the range of 12-15% in the nanoparticles. The FT-IR spectrum of nanoparticles containing polyphenols and the nanofibres isolated from bleached cherries devoid of polyphenols did not show major differences. The polyphenols show characteristic spectra in pure form, with major absorbance in the carbohydrate region, —C═H stretching (~2850-3000 cm$^{-1}$), and hydroxyl stretching from the polyphenol hydroxyls and the sugar hydroxyl groups (free 3200-3600 cm$^{-1}$) (David et al., 2009). Since the relative amount of polyphenols is low, the absorption of the polyphenol functional group is difficult to decipher from that of the carbohydrates, and protein (FIG. 15).

Figure 16:
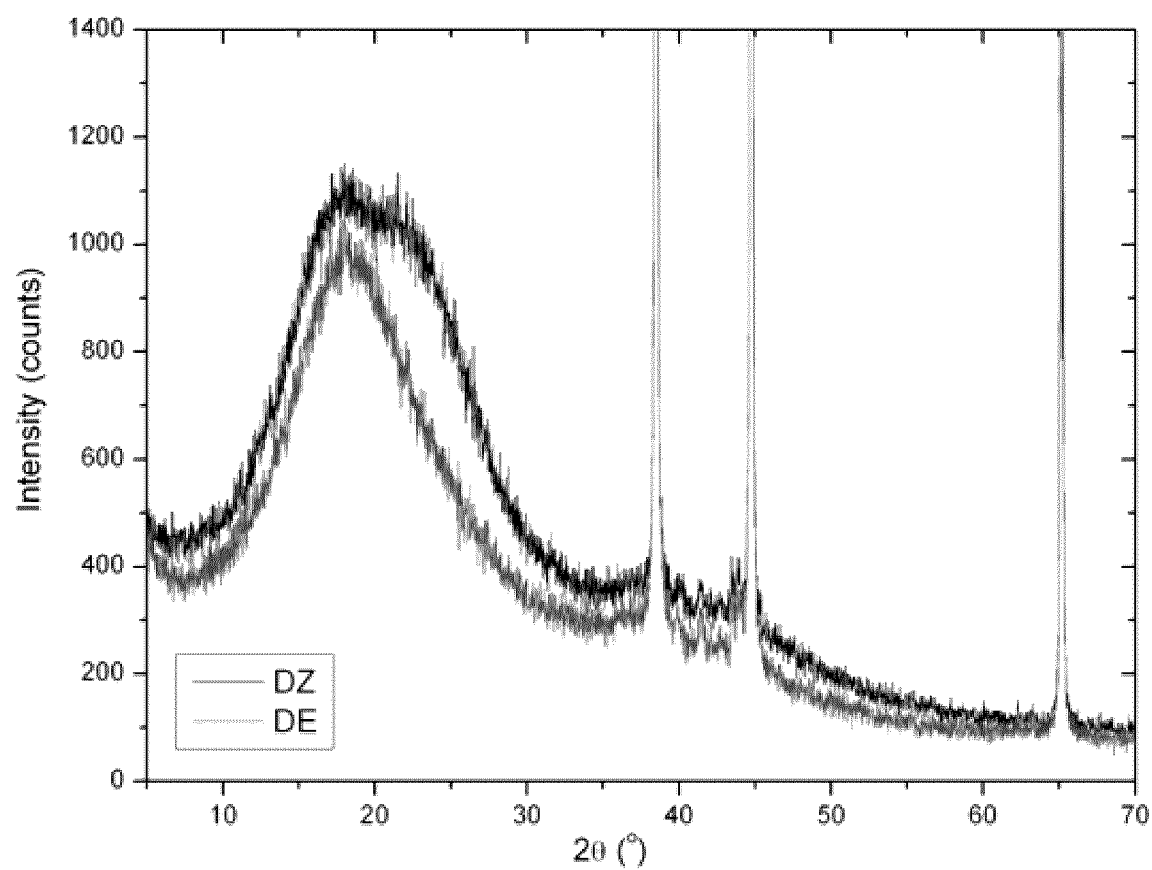
FIG. 16 shows wide angle X-ray diffraction of lyophilized powders of dialyzed extract (nanoparticles) and dialysate (pectin) obtained after water extraction of sour cherries. The sharp peaks arise from deflections from the sample holder. Both dialyzed extract and dialysate powders show a very diffuse band extending from 2θ 10° to 30° indicating the absence of crystalline structures in dialyzed extract (DE) and dialysate (DZ). Cellulose (β-1,4-glucan) is the only carbohydrate that exists as a crystalline structure in cell walls. This result suggests that there are no cellulose products (β-1,4-glucan moieties) in the nanoparticles as major components. Pectins have amorphous structure that enable them to form sheets, vesicles and filaments, and do not show a clear sharp diffraction pattern.

X-Ray diffraction of nanoparticles: The prevalence of pectin in fruits can potentially give rise to nanoparticles through structural transitions as shown in this Example. As the nanoparticles are highly susceptible to pectinase treatment, and undergo complete organizational dissolution, it appears that pectin is a predominant component of the nanoparticles. Pectin can form gels which is dependent on the degree of methoxylation and the presence of sugars and low pH, and divalent ions such as calcium (Fu and Rao, 2001; Strom et al., 2007). Beta-1,4-glucans such as cellulose occur as crystalline entities, but can also exist in an amorphous state. The susceptibility of the nanoparticles to cellulose treatment suggests that components that possess β-1, 4-glycosidic linkages are also a part of the nanoparticle structure and these may include amorphous cellulose and/or hemicellulosic components (xyloglucans) which link cellulose microfibrils. Previous studies on tamarind seed xyloglucans have shown that xyloglucans can be masked by pectin and dissolution of pectin exposes the xyloglucan (Marcus et al., 2008). Therefore, simultaneous presence of pectin and cellulose in the nanoparticles is a likely event. X-ray diffraction of crystalline cellulose shows sharp peaks centred at a diffraction angle (2θ) at 22.5°, while that of amorphous cellulose shows a characteristic broad peak at 20.7° (Park et al., 2010). X-Ray diffraction of the nanoparticle powder (FIG. 16) shows a peak centred around 20° suggesting the presence of amorphous cellulose in the nanoparticles. The diffractogram of the dialysate powder shows a much broader peak centred at 20°, as it may contain multiple types of carbohydrate components. The x-ray diffraction pattern of the nanoparticles and the dialysate are also similar to the gelatin-pectin composites (Sharma et al, 2011). As the fruit ripens, cellulase and pectinase activities increase leading to the dissolution of cell wall components, potentially releasing several types of cell wall polymers that can get integrated into the nanoparticles. Thus, it appears that the nanoparticles originate from pectin components such as polygalacturonic acid containing, both free and esterified carboxy groups, arabinogalactans, xyloglucans, amorphous cellulose, etc. Further assembly with peptides and polyphenols during the extraction process may result in the self-assembly of these components to form of the nanoparticles.

Proposed model for structural organization of spherical nanoparticles: The organization of macromolecules and the polyphenols to form the nanoparticles may be elucidated from several results. The electron micrograph of a single nanoparticle from the dialyzed fraction of unbleached cherry is shown in FIG. 17A. Though most of the nanoparticles are in the size range of about 25 to about 50 nm in diameter, and are very stable spherical structures, occasionally large complexes are formed exceeding 100 nm in diameter. It is likely that the larger size may make such complexes structurally less stable in comparison to the smaller nanoparticles. The large nanoparticles that appear spherical under normal conditions become collapsed occasionally revealing structural details. In the micrograph, the collapsed area is shown in the centre (arrow 1; Panel A, FIG. 17). This observation is consistent with results obtained after enzyme (trypsin, cellulase) treatment where nanoparticles are stripped off from their outer structures revealing a spherical, pliable, pectin core. The core is likely formed by homogalacturonan moieties and unexposed, as the nanoparticle does not show cross reactivity to antibodies raised against homogalacturonan. The collapsed structure suggests that the interior of the core may be hollow. The core is surrounded by filaments assembled in a spiral organization (FIG. 17, Panel A, arrow 2) constituted by homogalacturonan and protein as deduced by its susceptibility to pectinase and trypsin. Polyphenols may have a significant role in stabilizing the helical organization of the filaments since the removal of polyphenols with ethanol results in a totally different organization, unwinding the helical structures into long filaments. These filaments show strong reactivity to homogalacturonan antibodies when polyphenols are removed which suggests that polyphenols may mask the helical structures. Exterior to the spiral filaments covering the pectin core, there appears to be another distinct layer of fibrils which appears to be different from the interior fibril layer (FIG. 17, Panel A, arrow 3). It is likely that the composition of this layer is different from that of the interior layer (arrow 2), since this may primarily be constituted by arabinogalactans coupled with polypeptides, as the nanoparticles from unbleached cherry shows strong reactivity against arabinogalactan-protein antibodies indicating their exterior location and enhanced accessibility to the antibodies. Arabinogalactan-proteins are also a part of the filament structures isolated from bleached cherry. Thus, the nanoparticles isolated from unbleached cherry and the nanofibres isolated from bleached cherry may possess similar components, but are organized as physically distinct structures. An enlarged view of the nanoparticle (FIG. 17, Panel B) shows the helical structures on the inner layer of the nanoparticle (arrows).

The development of nanomaterials based on natural products is increasingly being explored since there are potential cytotoxic effects emerging from the use of engineered nanomaterials such as iron oxide nanoparticles, dendrimers, gold- and silver nanoparticles, carbon nanotubes etc., which have still not been fully evaluated (Maynard, 2006). The issue with engineered nanomaterials is that the human body may not have a mechanism to eliminate these from the system. In cell culture studies, it has been observed that toxicity from fullerene type nanomaterials decrease as the hydroxylation of the structure increases (Lewinski et al., 2008). A primary application of engineered nanomaterials is in diagnostics and biomedicine (Kunzmann et al, 2011). Silica nanoparticles of 70 nm were able to penetrate placental barrier and enter the fetus, while those 300 nm and 900 nm in size did not accumulate in the fetal tissue (Yamashita et al., 2011). Similarly, drug loaded polymeric micelles 30 nm in diameter were more efficient in penetrating tumours with low permeability, than 50 nm, 70 nm or 100 nm micelles (Cabral et al., 2011). Understanding the mechanisms of uptake, distribution and elimination of engineered nanomaterials may also help understand these mechanisms in nanomaterials of biological origin.

Biological nanomaterials of different shapes and sizes have been proposed to provide benefits in drug delivery and retention. Nanoliposomes, nanocochleates, micelles, filasomes etc., are potential morphovariants of biological nanostructures with potential applications in biomedicine (Nishiyama, 2007). Among these, filamentous polymeric micelles referred to as filomicelles which are 22 to 60 nm in diameter and 2-8 μm in length, have been observed to remain in the blood longer than spherical nanomicelles (Discher and Eisenberg, 2002). Proteins such as fibrinogen surround gold nanoparticles coated with polyacrylic acid, and this appears to be a structural change which is a part of its elicitation of inflammation (Deng et al., 2011). Daidzein loaded solid lipid nanoparticles were more efficient than daidzein alone in cardio-cerebrovascular protection in animal models through enhancing bioavailability and increased circulation time (Gao et al., 2008).

Nanoparticles are likely to be absorbed by endocytotic mechanisms and hence may undergo several type of modifications during binding to the cell surface, internalization, transport, and release in the cell. During endocytosis, the nanoparticles may bind to the cell surface followed by internalization by vesiculation of plasma membrane through endosomes, phagosomes and macropinosomes. There may be different types of mechanisms involved in these processes. Vesicular structures of plasma membrane origin may become multivesicular bodies and fuse with lysosomes. The lysosomal pH is acidic and provides an ideal condition for the degradation of nanoparticles by proteases and hydrolases releasing the contents. The absorption of nanoparticles by cells depends upon the surface characteristics of the cell (Iverson et al., 2011). Nanoparticles that are 20 to 50 nm in diameter appear to be taken up much more than those that are larger or smaller. The uptake can also depend on surface charge of the recipient cell, in general, positively charged nanoparticles being taken up more efficiently. The nanostructures from sour cherry may show both characteristics, being positively charged owing to the potential exposure of peptide amino groups in the periphery and hidden carboxylic acids of polygalacturonic acid when in the spherical nanoparticle form, while being negatively charged as nanofibers with greater abundance of polygalacturonic acids (acidic groups) exposed to the near neutral aqueous medium they are suspended in. Nanoparticles with hidden polygalacturonate moieties react poorly with anti-homogalacturonan antibody. In comparison, nanofibres with highly exposed polygalacturonate moieties react very intensely against anti-homogalacturonan antibody, as seen in FIG. 13.

As an omnipresent biological macromolecule in plants, and especially abundant in fruits and vegetables, the physicochemical properties of pectin has been well studied, and its potential utility in medicine for drug encapsulation, targeted delivery, development of hydrogels for applications as skin protectants, either alone or in combination with proteins or synthetic molecules such as polyvinyl pyrrolidone, polylactic acid etc., is increasingly being explored (Mishra et al., 2012). An advantage of pectin based materials is that it has been consumed by humans throughout evolution and has confirmed biological properties as a food matrix for transporting encapsulated materials into the colon where the polysaccharides are digested by probiotic bacteria, releasing the contents. Pectin can also bind and help remove cholesterol from the gastrointestinal system. Pectin based delivery systems have been explored for drug delivery through multiple roots (Yadav, 2009; Sriamornsak, 2011). The three dimensional structure of pectin matrices may be influenced by the free carboxylic acid groups (homogalacturonans and rhamnogalacturonans), since, based on pH of the embedded solution, pectin chains can exist as anionic chains which can get stabilized by divalent ions such as calcium adopting various forms. Again, the ratio of methylated carboxyl groups to free carboxyls may influence the capacity of pectin to form 3D structures. Thus, pectin formulations such as films, hydrogels, nanostructures etc., have been explored for multiple medical applications. However, exclusively pectin based matrices may have some disadvantages such as low mechanical strength, low shear stability, low drug loading efficacy, and premature drug release. For this reason, chemical and physical alterations of pectin by blending or co-polymerization with biodegradable polymers such as chitosan, polylactic acid, starch, gelatin, soy protein, β-lactoglobulin, human serum albumin etc., may provide a higher charge density (positive primary amine and negative carboxyl group). Production of ZnO-pectin nanoparticles ranging in size between 70-200 nm in diameter has been achieved to explore the possibility of enhancing Zn uptake in Zn-deficient population segment (Shi and Gunasekaran, 2008). Such molecules have been observed to penetrate into the tissue deeper and able to provide better drug delivery. Thiolated nanoparticles of pectin have been prepared for better ocular drug delivery. SPIONs (superparamagnetic iron based nanoparticles) and oxaliplatin were encapsulated in Pectin-Ca2+ to form pectin based spherical nanostructures 100-200 nm in diameter with magnetic function. The cancer drug paclitaxel has been conjugated with pectin nanostructures, and the process has been suggested to be influenced by the hydrophilicity of pectin (—OH and —COOH groups) as well as positively charged amide groups of asparagines (Verma et al., 2011). Attempts have also been made to deliver several classes of drugs such as thiazoles with low solubility, cancer drugs, neuro- and mood active drugs, and insulin through pectin based nanostructures (Sharma et al., 2012).

By contrast to synthetic methods for producing pectin based nanoparticles, the present Example indicates the potential of using an in vivo fruit-based system for producing nanoparticles and nanofibres with unique characteristics. The fruit serves as a self-contained factory for forming nanoparticles and nanofibres. As the fruit ripens, catabolic processes are activated which leads to fruit softening, and results in the production of cell wall components of lower molecular mass, including cellulose, pectins and polypeptides derived from cell wall glycoproteins with positive, negative and amphiphilic character, as well as calcium ions and low pH released during homogenization. Once the tissue is homogenized and various components are released, self-assembly of various components is observed to take place. It should be noted that without external influence, the nanoparticles formed in this Example were substantially uniform in size, shape and physicochemical characteristics. Fruits with different characteristics such as sour cherry, blueberry and grape, all show potential for such self-assembly of the basic cellular components to form substantially identical type of nanoparticles.

An interesting feature that has become evident from this Example is the role of anthocyanins and possibly malic acid in determining the self-assembly of the components to form nanoparticles. In the presence of anthocyanins, the nanoparticles are spherical with a central pectin core that is woven around with galacturonan-xyloglucan-arabinogalactan-polypeptide filaments. These filaments are helical in nature in the presence of anthocyanins and comprise of fibrillar structures. Anthocyanins are amphiphilic molecules and may serve as bridging structures between various components. However, once the anthocyanins are removed, the nanoparticles instead form film-type (planar structures of pectin, FIG. 7), and fibre-like tructures (filomicelle-type), referred to as nanofibres. Irrespective of their shape, both spherical nanoparticles, and nanofibres were highly stable, and may be capable of binding with a variety of drugs (Paclitaxel, Vincristine), and/or minerals with high efficiency and uptake capacity. In terms of function, spherical nanoparticles may also serve as carriers of anthocyanins for targeted delivery of anthocyanins into the colon, for example, as anthocyanins may be protected inside a spherical complexed structure much more by comparison to free anthocyanins, thus shielding these from pH changes during transition between stomach and intestine.

In the present Example, nanoparticles and nanofibres were prepared from fruits, and physicochemical characteristics and functionalities of the nanoparticles and the nanofibres are investigated and described. These nanoparticles and nanofibres are unique in terms of their enormous surface area generated through tertiary structure formation from pectin, cellulose, and protein, in the presence or absence of polyphenols. These nanoparticles and nanofibres of biological origin may provide an alternative to engineered nanomaterials in several applications. As the building components have been consumed through food (juice, smoothies), and no adverse effects are observed, it may be suggested that biological elimination of the structural components may occur, just as any food macromolecules. The nanoparticles and nanofibres are internalized by mammalian cells indicating their potential to be used as, for example, delivery systems of small molecules, nutrients, drugs, minerals, or other such agents/cargo. Despite being derived from similar materials, the nanoparticles and nanofibres have significant differences, as described in detail herein.

EXAMPLE 2-Functions and Applications of Nanoparticles

Effect of Nanoparticle Treatment on Body Weight in Wild-Type and ETKO Mice

Materials and Methods

In Vivo Analyses-Animals and genotyping-Pcyt2+/− mice (also referred to herein as ETKO mice) were generated and genotyped as described previously (Fullerton M D, et al. 2007). Pcyt2 is a gene that is responsible for regulation the production of the phospholipid, phosphatidylethanolamine (PE), an important component of cell membranes and organelles. Completely knocking out the Pcyt2 gene (null animals) results in early embryonic lethal death (pups die before birth) whereas heterozygous animals (which only have one copy of the gene) are normal at and after birth. Heterozygous mice however experience a chronic weight gain as a result of the altered phospholipid metabolism. There is a redirection of the components, which make up the phospholipids and the cell machinery changes from making PE to triglyceride (fat). This means the mice have increased weight, more fat in the liver and plasma and ultimately a decreased sensitivity to insulin (insulin resistance).

Pcyt2+/− mice were crossbred, and the heterozygous colony was maintained at the University of Guelph, according to procedures approved by the University Animal Care Committee. Mice were housed with a 12-h light/12-h dark cycle, had free access to water, and were fed a standardized chow diet (catalog number S-2335; Harlan Teklad). Mice were divided into 4 experimental groups (n=3-6/groups): (i) Wild type (C57BL/6)-Untreated (WT-U), (ii) Wild type (C57BL/6)-Treated (WT-T), (iii) Pcyt2 Knockout-Untreated (KO-U), and (iv) Pcyt2 Knockout-Treated (KO-T). Samples taken for biochemical assays (blood serum and tissues (liver)) were snap-frozen in liquid nitrogen and stored at −80° C. for later use.

Blood analysis. After clinical death, the terminal blood was collected from the heart. Serum was separated immediately and sent to the Animal Health Laboratory (University of Guelph; an accredited Facility for analysis) for biochemical analyses such as those for Albumin, Globulin, A: G, Total protein, ALT, AST, Cholesterol, CK, Glucose, Phosphorus, Triglycerides and Urea.

Chemicals and reagents. L-Type Triglyceride M kit was purchased from Wako Diagnostics (Osaka, Japan and Neuss, Germany). Antibodies against p65 NF-kB and B-Tubulin were from Santa Cruz. Biotechnology and Cell Signaling Technology, respectively. RNeasy Plus kit for RNA isolation was from Qiagen (Valencia, CA, USA). The High-Capacity cDNA Reverse Transcription Kit for cDNA preparation was from Applied Biosystems (Foster city, CA, USA). The primers used are listed below.

TABLE 4

Primer Sequences used for PCT for Estimating Expression Levels of Particular Genes after Treatment with Nanoparticles. F = Forward, R = Revserse.

| Primers | Sequence | SEQ ID NO: | TM (° C.) | Amplicon Size (bp) |
|---|---|---|---|---|
| STAT4 | F-5' AGGTTAAGCTGGCTGTCCTG3' | 1 | 62 | 150 |
| | R-5'AGATCTCTTGTCTTCTGGTTTGTTG3' | 2 | | |
| TNF-α | F-5' CCGATGGGTTGTACCTTGTC 3' | 3 | 60 | 300 |
| | R-5' GGGCTGGGTAGAGAATGGAT 3' | 4 | | |

TABLE 4-continued

Primer Sequences used for PCT for Estimating Expression Levels of Particular Genes after Treatment with Nanoparticles. F = Forward, R = Revserse.

| Primers | Sequence | SEQ ID NO: | TM (° C.) | Amplicon Size (bp) |
|---|---|---|---|---|
| IL-6 | F-5' CAAGGGTGTTACACTGG 3' | 5 | 62 | 200 |
| | R-5' CTGGTCTCATCCGAACCCTG 3' | 6 | | |
| FAS | F-5' CTTCGAGATGTGCTCCCAGCTGC 3' | 7 | 59 | 268 |
| | R-5' CTTAGTGATAAGGTCCACGGAGGC 3' | 8 | | |
| ATGL | F-5' CAACGCCACTCACATCTACGG 3' | 9 | 57 | 106 |
| | R-5' GGACACCTCAATAATGTTGGCAC 3' | 10 | | |
| HSL | F-5' ACGCTACACAAAGGCTGCTT 3' | 11 | 59 | 125 |
| | R-5' TCGTTGCGTTTGTAGTGCTC 3' | 12 | | |
| LPL | F-5' GCTCGCACGAGCGCTCCATT 3' | 13 | 59 | 350 |
| | R-5' CCTCGGGCAGGGTGAAGGGAA 3' | 14 | | |
| PGC1-α | F-5' TTGACTGGCGTCATTCGGG 3' | 15 | 59.5 | 396 |
| | R-5' GAAGGACTGGCCTCGTTGTC 3' | 16 | | |
| PPAR-α | F-5' CGCATGTGAAGGCTGTAAGGGC 3' | 17 | 57 | 289 |
| | R-5' GTCATCCAGTTCTAAGGCATTG 3' | 18 | | |
| PPAR-Y | F-5' CAGAAGTGCCTTGCTGTGGGG 3' | 19 | 57 | 157 |
| | R-5' CTTGGCTTTGGTCAGCGGG 3' | 20 | | |
| CTL1 | F-5' GAACGCTCTGCGAGTGGCTGC 3' | 21 | 49 | 376 |
| | R-5' TTCTTATGTTCTTGACTGCC 3' | 22 | | |
| PCYT1 | F-5' ATGCACAGAGAGTTCAGCTAAAG 3' | 23 | 50 | 170 |
| | R-5' GGGCTTACTAAAGTCAACTTCAA 3' | 24 | | |
| PSS2 | F-5' GAGTGGCTGTCCCTGAAGAC 3' | 25 | 59 | 305 |
| | R-5' TCGTAGATCTCACGCATGGC 3' | 26 | | |

Nanoparticle treatment. The experiments were performed with 24-30 weeks old Pcyt2 knock out mouse and littermate controls. Untreated groups of KO and control mouse (wild type; n=3-6 each) were provided with 100 uL water 3 times per week (by gavage). The treatment group of KO and control mouse (n-3-6 each; ~40 g average weight) were administered with 100 mg/kg/4 week polyphenol equivalent of the nanoparticle solution in 100 uL water 3 times per week (133 μg polyphenol equivalent per dose). Oral gavage for all groups lasted 4 weeks. Trials were repeated twice, and at the end of trials the mouse were sacrificed and used for blood and tissue analysis.

Immunoblotting. NF-kB was determined by immunoblotting using 10% SDS-PAGE, western blotting and detection of the band by chemiluminescence. Membranes were blocked with 5% milk in 1×PBST and incubated overnight at 4° C. with anti-NF-kB (Santa Cruz Biotechnology, Santa Cruz, California, USA) antibody. Membranes were then incubated with the anti-rabbit IgG and visualized by chemiluminescence (Sigma-Aldrich). Membrane rehybridization with β-Tubulin was conducted to check loading accuracy. The density of the specific bands was quantified with an imaging densitometer (Image J).

Liver Triglycerides Determination. The TG content of the liver was measured using L-Type TG M reagents according to the kit (Wako) procedure.

Total RNA Isolation and Gene Expression. Total RNA was isolated using the RNeasy Plus kit (Qiagen, Valencia, CA, USA) and cDNA was prepared using the High-Capacity cDNA Reverse Transcription Kit (Applied Biosystems, Foster city, CA, USA). Genes of interest were analyzed in the exponential phase of PCR amplification, using the optimal amount of cDNA and the reaction cycle number. Each gene level is expressed relative to the internal GAPDH control. The genes tested include pro-inflammatory genes (STAT4, TNF-α, and IL-6) and lipolysis genes (FAS, ATGL, HSL, LPL, PGC1-α, PPAR-α, PPAR-γ, CTL1, PCYT1, and PSS2). The experiments were performed by using liver samples collected from Pcyt2+/− and Pcyt2+/+, male and female mice. Reaction products were subjected to electrophoresis and bands visualized with ethidium bromide staining. ImageJ 1.46 software was used to quantify band density, and gene levels are expressed as fold changes relative to the controls. The primers used are listed in the Table above.

NF-kB was determined by immunoblotting by SDS-PAGE, western blotting and detection of the band by chemiluminiscence. Membranes were blocked with 5% milk in 1×PBST and incubated overnight at 4° C. with anti-NF-kB (Santa Cruz Biotechnology, Santa Cruz, California, USA) antibody. Membranes were then incubated with the anti-rabbit IgG and visualized by chemiluminescence (Sigma-Aldrich). Membrane rehybridization with β-Tubulin was conducted to check loading accuracy. The density of the specific bands was quantified with an imaging densitometer (Image J).

Statistical analysis. Statistical analysis was completed using Prism GraphPad. Data are expressed as mean±S.E. Statistical significance was calculated using either Student's t test (P values <0.05 were considered significant) or multifactorial ANOVA. When a significant effect was found, post hoc comparisons were carried out using the Tukey's honestly significant difference test. Differences were considered significant at P<0.05.

Figure 18:
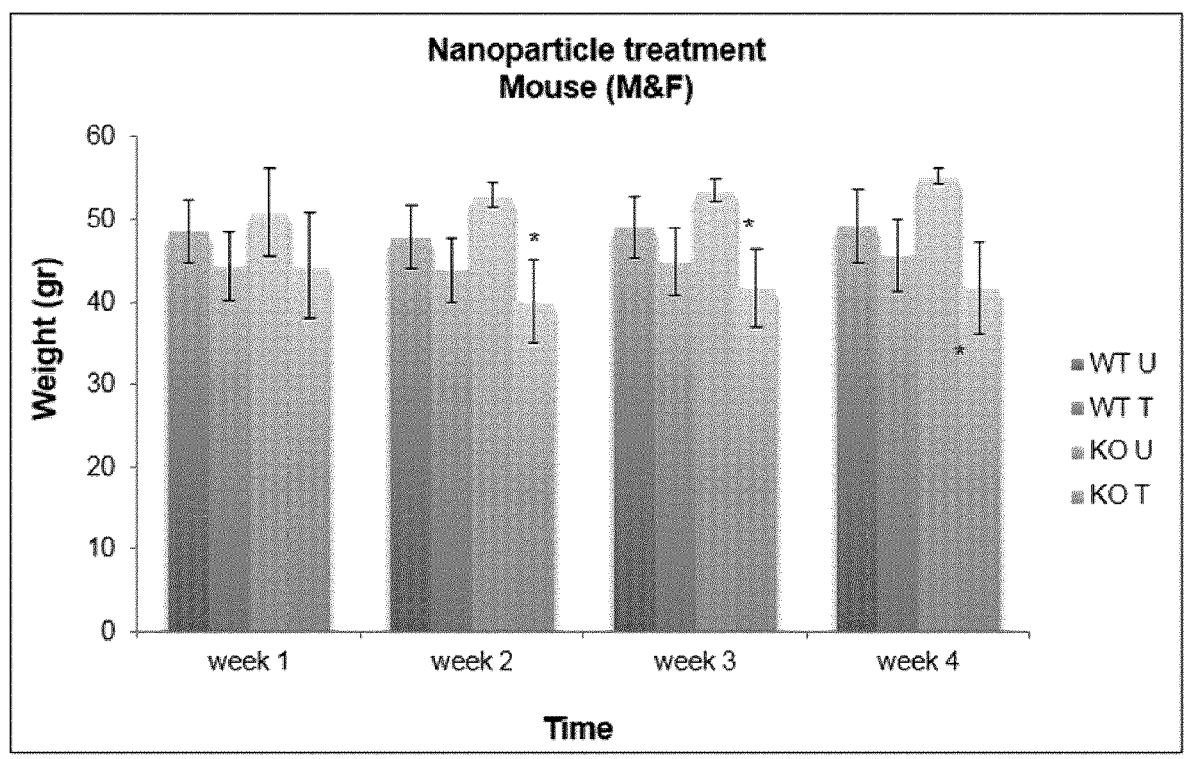
FIG. 18 shows effect of feeding mice a solution of nanoparticles (NP) on body weight changes in wild type and ETKO mice. Mice (6-7 month old) were divided into four groups of 5-6 each (Wild type Untreated (WT U), Wild type treated (WT T), Knock out Untreated (KO U) and Knock out Treated (KO T)). Treated mice received a dose of 133 µg equiv. NP solution/40 g body weight/day (100 mg extract/kg body weight) by gavage 5 times a week. Untreated mice received water. The experiment lasted for 4 weeks. First week of the NP treatment had no effect on the mice body weight among the tested groups, however, after week 2, 3 and 4, the continuation of the NP treatment prevented weight gain in the ETKO mice. Although there was no significant change in weight loss between WT untreated and treated at these particular doses/conditions, the reduction of the weight gain between KO untreated and KO treated was statistically significant ($P<0.05$)

Results and Discussion: Experiments were performed to study the effects of nanoparticle treatment on body weight in wild-type mice, and in ETKO mice. FIG. 18 shows effect of feeding mice a solution of nanoparticles (NP) on body weight changes in wild type and ETKO mice. Mice (6-7 month old) were divided into four groups of 5-6 each (Wild type Untreated (WT U), Wild type treated (WT T), Knock out Untreated (KO U) and Knock out Treated (KO T)). Nanoparticle-treated mice received a dose of 133 µg equiv. NP solution/40 g body weight/day (100 mg extract/kg body weight) by gavage 5 times a week. Untreated mice received water. The experiment lasted for 4 weeks. First week of the NP treatment had no effect on the mice body weight among the tested groups, however, after weeks 2, 3 and 4, the continuation of the NP treatment prevented weight gain in the ETKO mice. Although there was no significant change in weight loss between WT untreated and treated at these particular doses/conditions, the reduction of the weight gain between KO untreated and KO treated was statistically significant ($P<0.05$).

These results support use of the nanoparticles in treatment and/or management of obesity and/or weight loss.

Effect of Nanoparticle Treatment on Triglyceride Levels in the Liver, on Liver Tissue Histopathology, on Serum Biochemical Parameters, and on Gene Expression Materials and Methods Histological analysis. To examine liver histology, tissues were fixed in 10% neutral buffered formalin+phosphate-buffered saline, and embedded in paraffin. 10 µm liver sections were stained with hematoxylin and cosin (H&E) and visualized by light microscopy. Tissue lipids were analyzed with an imaging densitometer (Image J) as previously described (Fullerton et al. 2007).

Liver Triglycerides Determination. The TG content of the liver was measured using L-Type TG M reagents according to the kit (Wako) procedure.

Blood analysis. After mouse clinical death, the terminal blood was collected from the heart. Serum was separated immediately and sent for biochemical analyses such as those for Albumin, Globulin, A: G, Total protein, ALT, AST, Cholesterol, CK, Glucose, Phosphorus, and Triglycerides.

Results and Discussion

Figure 19:
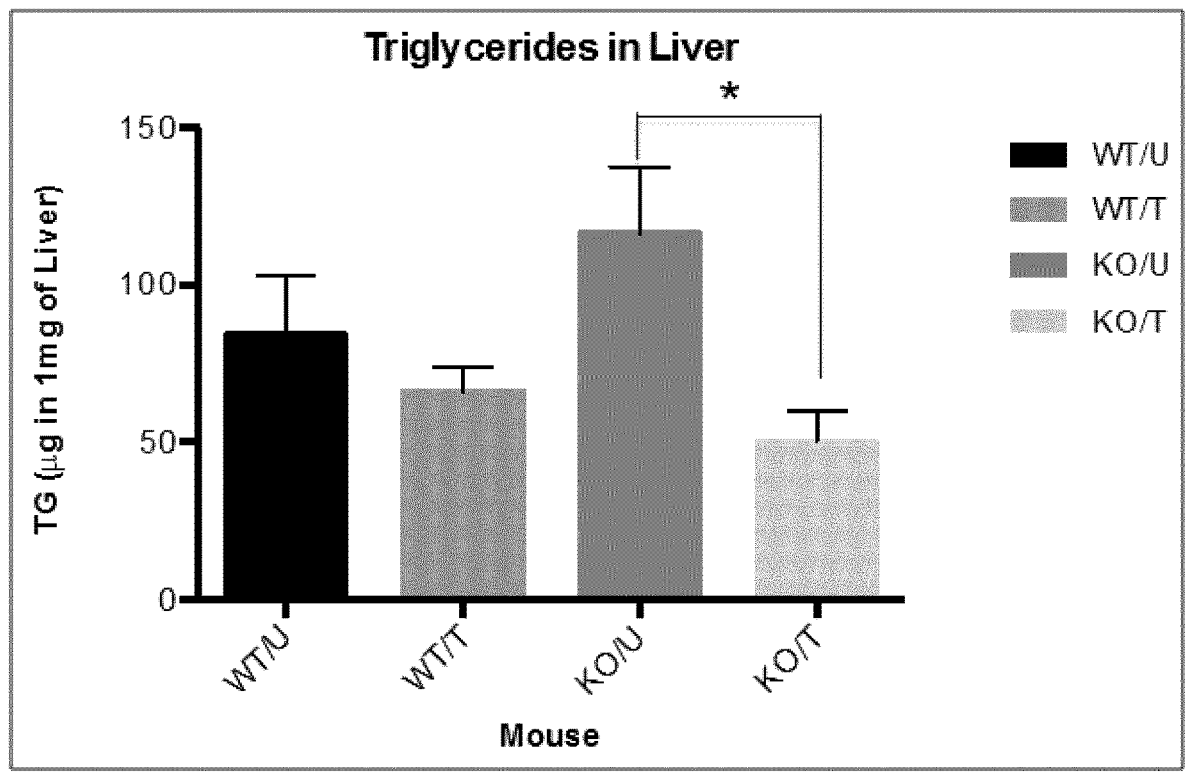
FIG. 19 shows effect of nanoparticle (NP) treatment on changes in triglyceride levels in the liver. The tissue originated from the trial described in Example 2. Triglyceride levels of liver tissue were estimated by procedures described in using Wako L-type TG M assay kit (Wako Life Sciences, CA, USA). There was a significant reduction in triglyceride levels in the ETKO mice subjected to NP treatment. The top panel shows data obtained from both male and female mice. The bottom panel shows data obtained from male mice. A reduction in liver triglycerides by NP treatment supports use of NP for prevention of lipid deposition in the liver and associated pathological symptoms as defined by marker enzyme activity such as that of Alanine aminotransferase and aspartate aminotransferase, and a reversion of structure closer to that of the wild type mouse liver structure, for example. Similar abnormalities are also observed in humans in non-alcoholic steatosis and/or NASH, suggesting that nanoparticles and/or food powder as described herein may provide an option for treating and/or reversing such conditions.
Figure 19:
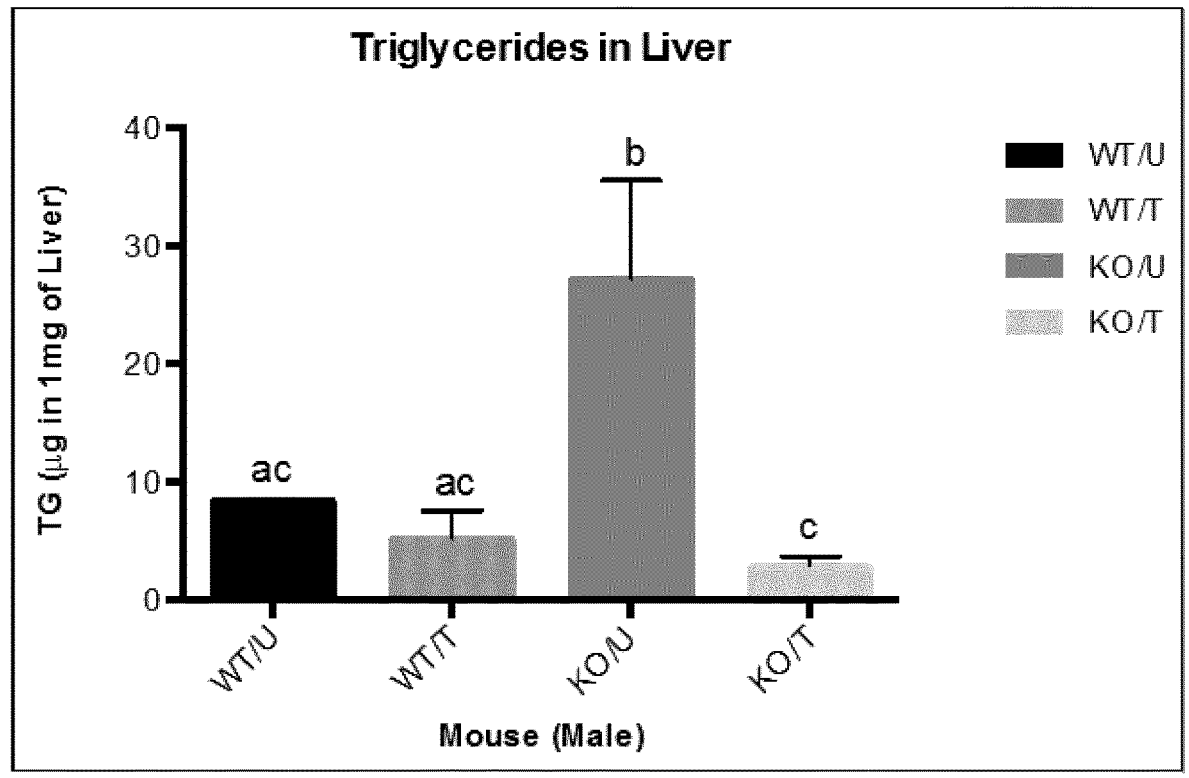

Studies were performed to investigate the effect of nanoparticle treatment on Triglyceride levels in the liver of wild type and ETKO mice. Under normal physiological conditions, the hepatic triglycerides level is relatively low, as liver is not involved in storage of the fat. Triglycerides of non-alcoholic fatty liver depend on the rate of fatty acid uptake from plasma into cells and hepatocellular capacity (Bradbury MW. 2006, Kawano Y 2013). Due to accumulation of triglycerides in obese mice liver tissue, the level of the triglycerides was investigated in WT and ETKO mice with or without nanoparticle (NP) treatment. FIG. 19 shows effect of nanoparticle (NP) treatment on changes in triglyceride levels in the mouse liver. Triglyceride levels of liver tissue were estimated by procedures described in using Wako L-type TG M assay kit (Wako Life Sciences, CA, USA). There was a significant reduction in triglyceride levels in the ETKO mice subjected to NP treatment. The top panel shows data obtained from both male and female mice. The bottom panel shows data obtained from male mice. A reduction in liver triglycerides by nanoparticle (NP) treatment supports use of NP for decreasing triglyceride levels in obese mouse liver, or liver of another animal or subject in need thereof.

Figure 20:
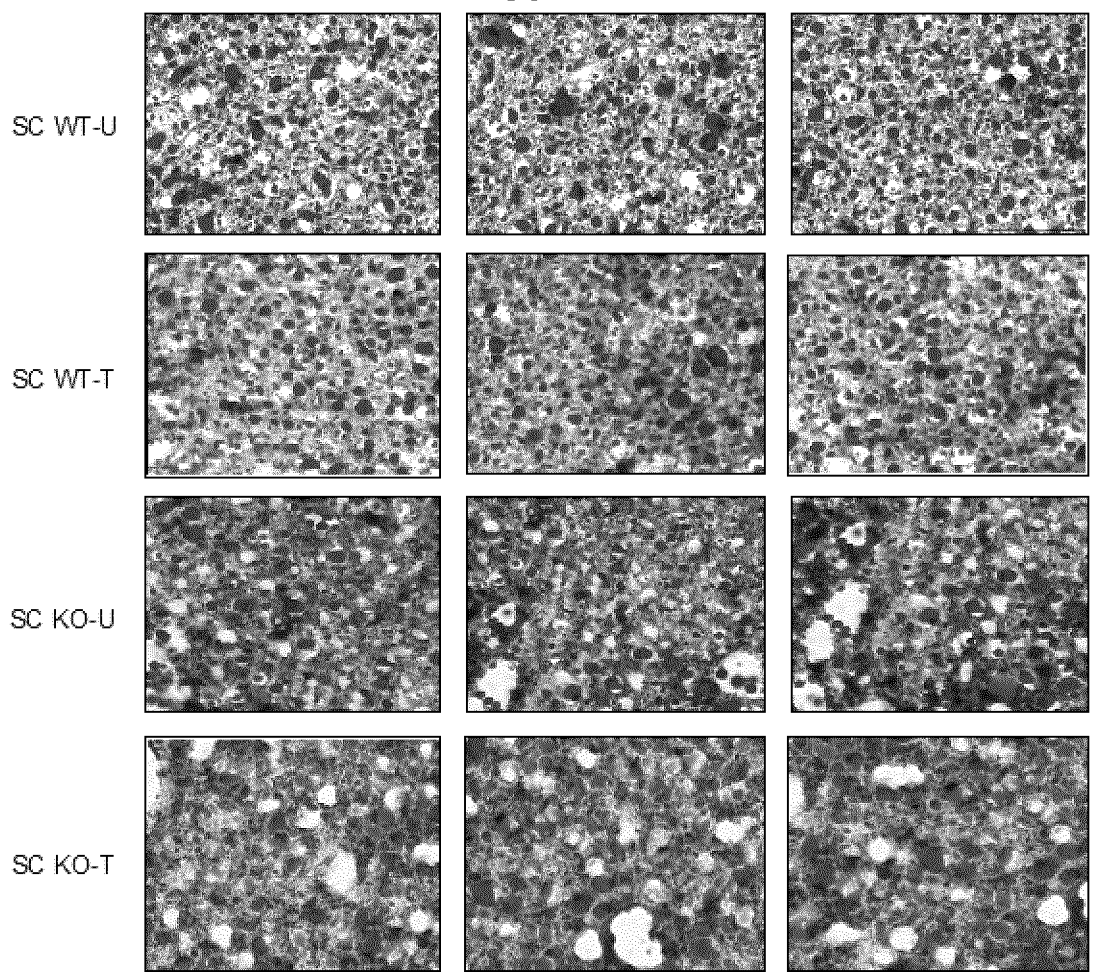
FIG. 20 shows histopathology of liver sections from mice subjected to treatments as described in Example 2. Frozen sections were stained with Oil-red-O stain (Sigma-Aldrich) to make the lipid droplets containing triglycerides visible as red droplets. The top two panels/rows represent the images of the stained liver sections from wild type (Untreated-top; Nanoparticle Treated, bottom) mice. Quantification of the red stained areas shows very little change in the control and treated sets of mice. Each panel/row represents sections from 3 independent mice. Bottom two panels/rows show the appearance of liver sections from ETKO untreated (top) and NP-treated (bottom) mice. In general the liver sections from ETKO mice show several vacant areas. These areas are reduced in treated ETKO mice. Also the structure of the liver tend to be similar to the WT (relatively more purple areas than control). The area of oil red stained regions are significantly reduced after treatment (Bottom Panel of the Figure). Abbreviations: Wild type Untreated (WT-U), Wild type treated (WT-T), Knock out Untreated (KO-U) and Knock out Treated (KO-T). "SC" appearing in the Figure labels indicates "Sour Cherry"
Figure 20:
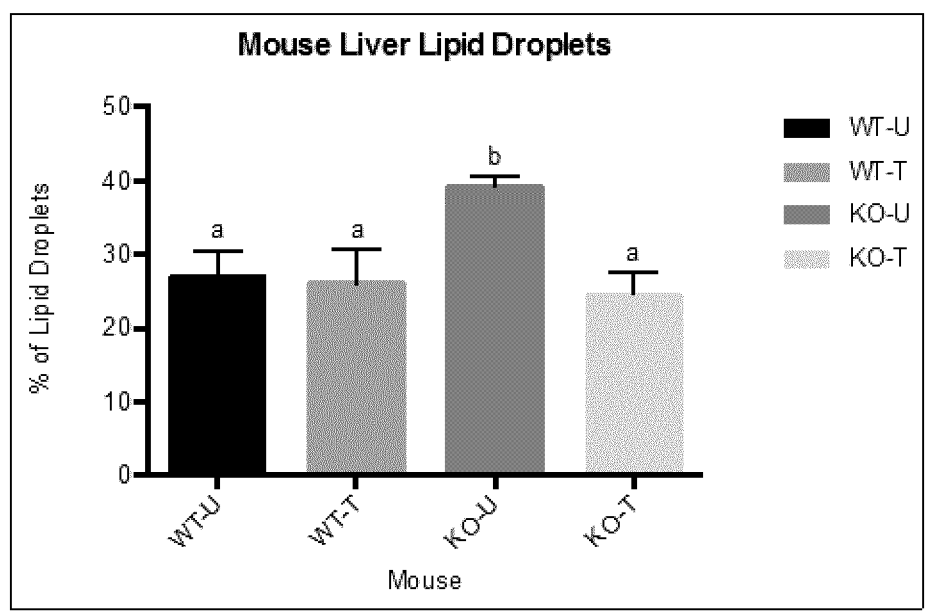

Studies were also performed to investigate the effect of nanoparticle treatment on liver tissue histopathology. Lipid droplets are considered as hepatocyte lipid storage organelles (Mashek DG, 2015). Certain metabolic syndrome diseases are believed to be developed due to the abnormal lipid accumulation in the liver (Gluchewaski 2017). Accordingly, studies were performed to investigate the effect of nanoparticle treatment on liver tissue histopathology, and on liver lipid droplets in wild-type and knockout (ETKO) mice. FIG. 20 shows histopathology of liver sections from mice (WT and KO) subjected to nanoparticle treatment. Frozen sections were stained with Oil-red-O stain (Sigma-Aldrich) to make the lipid droplets containing triglycerides visible as red droplets. The top two panels/rows represent the images of the stained liver sections from wild type (Untreated-top; Nanoparticle Treated, bottom) mice. Quantification of the red stained areas shows very little change in the control and treated sets of mice. Each panel/row represents sections from 3 independent mice. Bottom two panels/rows show the appearance of liver sections from ETKO untreated (top) and NP-treated (bottom) mice. In general the liver sections from ETKO mice show several vacant areas. These areas are reduced in treated ETKO mice. Also the structure of the liver tend to be similar to the WT (relatively more purple areas than control). The area of oil red stained regions are significantly reduced after treatment (Bottom Panel of the Figure). Following treatment, although no significant change was observed in WT-T/WT-U groups, there was a significant reduction in the amount of the lipid droplets in KO-T (treated) mice compared to KO-U (untreated) mice. These data show that NP treatment decreased the percentage of the lipid droplets in the obese mouse liver.

Considering the decrease in liver triglycerides in obese mice after treatment with nanoparticles, and the results from histopathological examination of the liver, it appears that nanoparticle treatment may be an effective means of controlling lipid deposition in the liver. Such conditions as observed under Non-Alcoholic Steatosis (i.e. NASH) resemble those that are observed in the obese mice. Accordingly, intake of anti-inflammatory plant products such as nanoparticles as described herein may be a way of controlling and/or managing NASH in an animal, mammal, or human subject, for example.

Studies were also performed to investigate the effects of nanoparticle treatment on serum biochemical parameters in mice (wild type, WT, and knockout, KO). Serum parameters are an important indicator of the nutritional status of an individual. An increase in the levels of circulating fatty acids can cause their binding to albumin causing conformational changes (Yamato M 2007). The levels of Globulin can be altered due to obesity and liver disease. Fluctuations in total protein amount can indicate liver and kidney disorders, heart failure and malnutrition. The elevated hepatic enzymes, alanine aminotransferase (ALT) and aspartate aminotransferase (AST) are also key indicators of abnormal liver function, observed in cases of non-alcoholic fatty liver disease and obesity (Marchesini G 2008). High blood levels of cholesterol and triglycerides are results of lipid metabolic disorders, hyperlipidemia or hypercholesterolemia. Increased amount of Creatine Kinase (CK) in blood serum is an indicator of muscle damage, heart disease, chronic kidney disease and acute renal failure (kidney). Phosphorus levels in the serum are usually associated with malnutrition, malabsorption and kidney dysfunction (phosphorus). High levels of glucose usually indicate diabetes, however, it may be associated with many other diseases.

Figure 21:
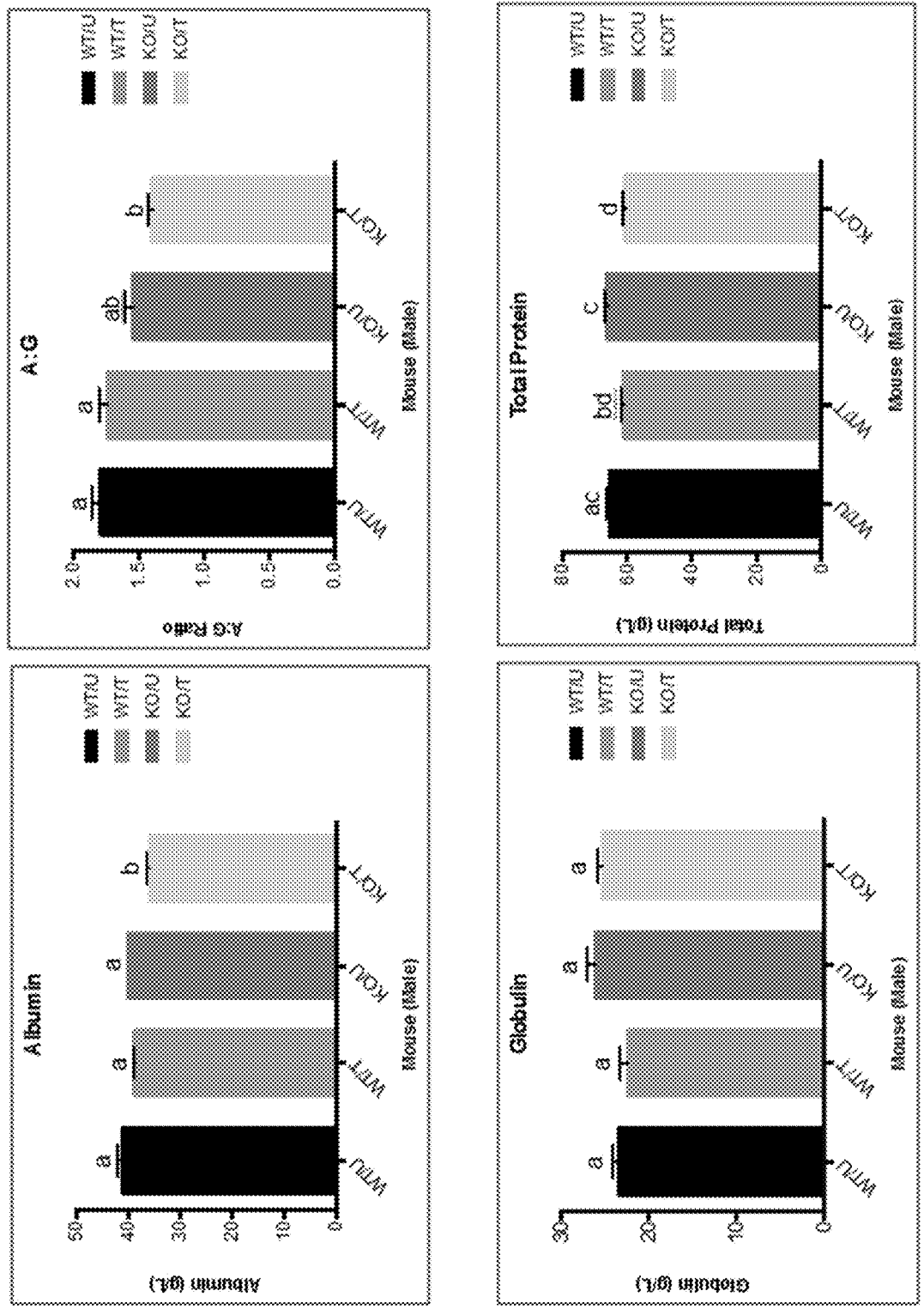
FIG. 21 shows blood serum parameters of nanoparticle (NP)-treated, and Untreated mice. There were no major changes in the levels of albumin, globulin and their ratios. There appears to be a slight decrease in the total protein levels in the serum. Values are Mean±SEM from 3 independent treatments. Abbreviations: Wild type Untreated (WT/U), Wild type treated (WT/T), Knock out Untreated (KO/U) and Knock out Treated (KO/T)
Figure 22:
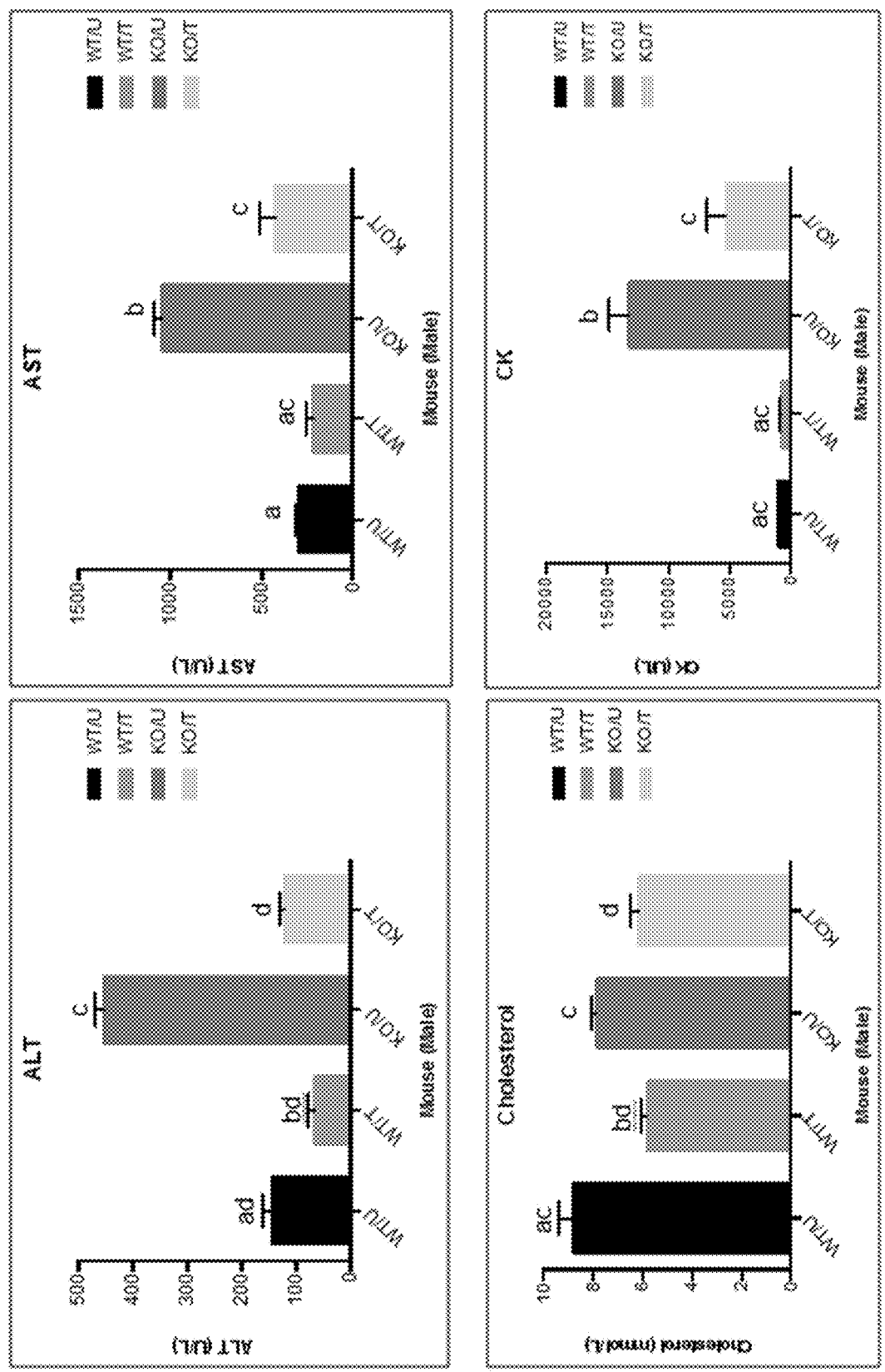
FIG. 22 shows changes in the levels of serum physiological function markers (ALT, AST, Cholesterol, and CK) of control and NP-treated mice. The analyses were conducted by standard procedures using test kits at the Pathology lab, Laboratory Services Division, University of Guelph. Alanine aminotransferase and Aspartate aminotransferase are enzymes that indicate the functional status of liver. If the liver function is poor or if liver is inflamed, more of these enzymes are secreted into the blood. There was a significant and substantial drop in the levels of both ALT and AST in response to NP treatment in obese mice. Even in wild type mice where these enzyme levels were low, NP treatment resulted in decline. NP treatment appears to normalize the liver function in obese mice. Cholesterol levels in the serum were also reduced in response to NP treatment in both wild type and obese mice. High Creatine Kinase levels are an indicator of muscle damage, which also showed a large decline in NP-treated obese mice. These results support an anti-inflammatory function of the NP. Abbreviations: Wild type Untreated (WT/U), Wild type treated (WT/T), Knock out Untreated (KO/U) and Knock out Treated (KO/T)
Figure 23:
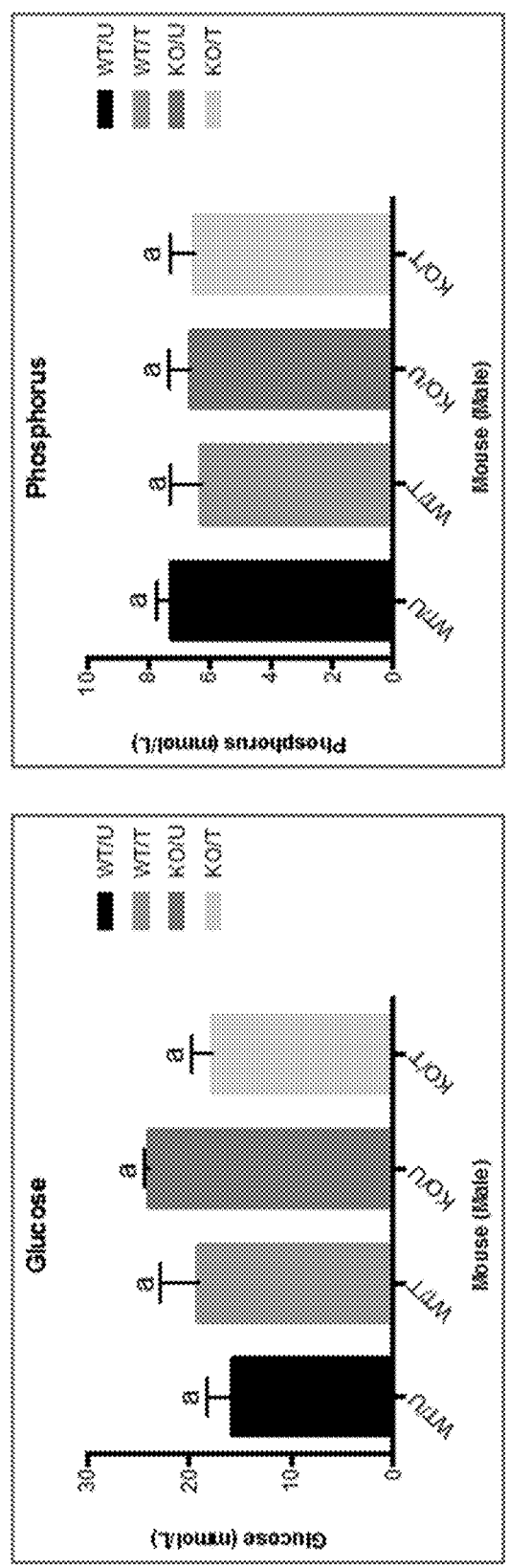
FIG. 23 shows the levels of glucose and phosphorus in the blood of untreated and nanoparticle treated mice. There were no major changes in the levels of phosphorus in the serum of both untreated and treated wild type and ETKO mouse. The glucose levels were similar in the wild-type and showed a declining trend in the obese mouse after treatment with the NP solution.

To investigate the effects of NP treatment on serum concentration of Albumin, Globulin, A: G, Total protein, ALT, AST, Cholesterol, CK, Glucose, Phosphorus, and Triglycerides in the four experimental groups (wild type nanoparticle-treated and untreated-WT-T, WT-U, and knockout nanoparticle-treated and untreated, KO-T and KO-U), the mice were treated with 100 mg/kg body weight of NP solution over a 4 week period. FIG. 21 shows blood serum parameters of nanoparticle (NP)-treated, and Untreated mice. There were no major changes in the levels of albumin, globulin and their ratios. There appears to be a slight decrease in the total protein levels in the serum. Values are Mean±SEM from 3 independent treatments. FIG. 22 shows changes in the levels of serum physiological function markers (ALT, AST, Cholesterol, and CK) of control and NP-treated mice. The analyses were conducted by standard procedures using test kits at the Pathology lab, Laboratory Services Division, University of Guelph. Alanine aminotransferase and Aspartate aminotransferase are enzymes that indicate the functional status of liver. If the liver function is poor or if liver is inflamed, more of these enzymes are secreted into the blood. There was a significant and substantial drop in the levels of both ALT and AST in response to NP treatment in obese mice. Even in wild type mice where these enzyme levels were low, NP treatment resulted in decline. NP treatment appears to normalize the liver function in obese mice. Cholesterol levels in the serum were also reduced in response to NP treatment in both wild type and obese mice. High Creatine Kinase levels are an indicator of muscle damage, which also showed a large decline in NP-treated obese mice. These results support an anti-inflammatory function of the NP treatment. FIG. 23 shows the levels of glucose and phosphorus in the blood of untreated and nanoparticle treated mice. There were no major changes in the levels of phosphorus in the serum of both untreated and treated wild type and ETKO mouse. The glucose levels were similar in the wild-type and showed a declining trend in the obese mouse after treatment with the NP solution.

Effect of Nanoparticle Treatment on Gene Expression

Results and Discussion

Studies were performed to investigate effects of nanoparticle treatment on expression levels of various key genes involved in various relevant biological pathways and/or conditions. Mice (Wild Type, WT, and ETKO Knockout, KO) were treated with nanoparticles, and changes in gene expression levels were analyzed.

Figure 24:
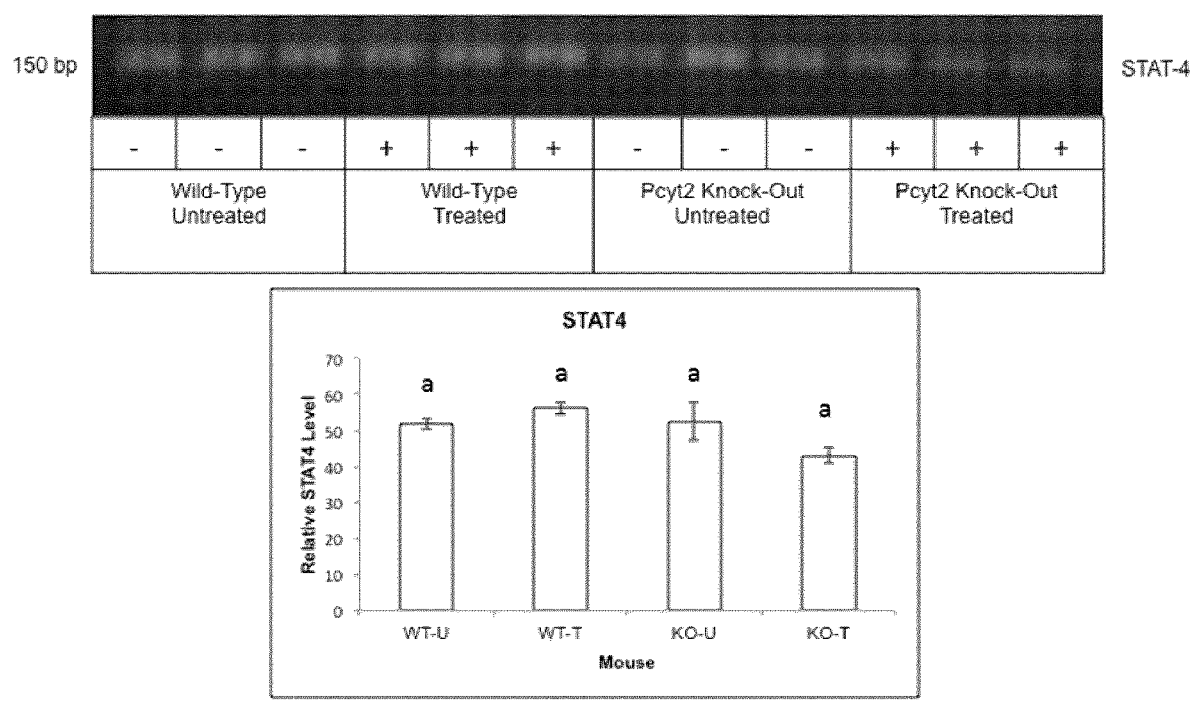
FIG. 24 shows evaluation of the changes in STAT4 gene expression in response to treatment with nanoparticle solution as described in Example 2. The quantification was made by Agarose gel electrophoresis of PCR products and staining with ethidium bromide. There are no significant changes in the levels of STAT4 between untreated, and treated wild type mice. There is a declining trend in STAT 4 expression in the ETKO mice fed with NP solution. Values were not significantly different from the levels in untreated ETKO mice in this testing, but a declining trend was observed. The values are Mean±SEM, from 4-5 mice in each group. STAT4 (Signal Transducer and Activator of transcription 4) is a transcription factor of the STAT family of proteins. STAT 4 is phosphorylated by Janus Kinases, which enables its dimerization, and translocation into nucleus during cytokine signaling, and increases gene expression. Increase in Stat 4 related gene expression is an indication of activated inflammatory pathways.

STAT4 (Signal Transducer and Activator of transcription 4) is a transcription factor of the STAT family of proteins. STAT 4 is phosphorylated by Janus Kinases, which enables its dimerization, and translocation into nucleus during cytokine signalling, and increases gene expression. Increase in Stat 4 related gene expression is an indication of activated inflammatory pathways. FIG. 24 shows evaluation of the changes in STAT4 gene expression in response to treatment with nanoparticle solution. The quantification was made by Agarose gel electrophoresis of PCR products and staining with ethidium bromide. There are no significant changes in the levels of STAT4 between untreated, and treated wild type mice. There is a declining trend in STAT 4 expression in the ETKO mice fed with NP solution. Values were not significantly different from the levels in untreated ETKO mice in this testing, but a declining trend was observed. The values are Mean±SEM, from 4-5 mice in each group. This suggests that the nanoparticle solution may show potential in reducing inflammation status of the body.

Figure 25:
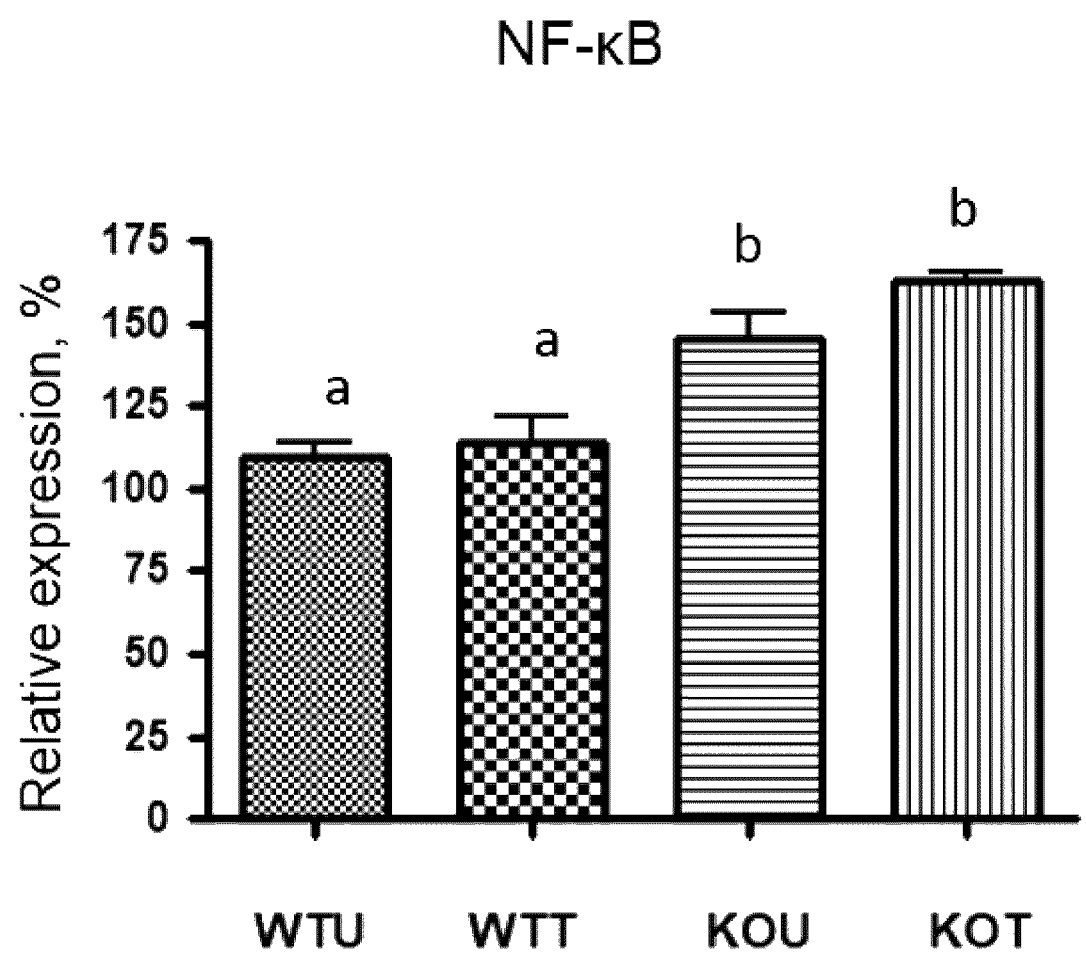
FIG. 25 shows evaluation of the changes in NF-kB gene expression in response to treatment with Nanoparticle solution as described in Example 2. NF-kB band intensity was quantified by Western blot, and chemiluminiscent detection. Expression of NF-kB was up-regulated in obese mice, suggesting increased inflammatory pathway function. Treatment with nanoparticle solution did not result in a significant change in the levels of NF-kB in either wild type or obese mice. The values are Mean±SEM, from 4-5 mice in each group. Nuclear Factor-kB (NF-kB) is a key protein involved in the initiation of inflammation signalling through cytokines such as interleukins and tumor necrosis factor-α. The pathway is complicated and may have both pro-inflammatory and anti-inflammatory roles based on conditions. A lowered NF-kB signalling is considered as an indication of lowered degree of inflammation.

Nuclear Factor-kB (NF-kB) is a key protein involved in the initiation of inflammation signalling through cytokines such as interleukins and tumor necrosis factor-$\alpha$. The pathway is complicated and may have both pro-inflammatory and anti-inflammatory roles based on conditions. A decline in NF-kB signalling is considered favorable for the down-regulation of inflammation related chronic disorders. FIG. 25 shows evaluation of the changes in NF-kB gene expression in response to treatment with Nanoparticle solution. NF-kB band intensity was quantified by Western blot, and chemiluminiscent detection. There were no significant changes in the levels of NF-kB between untreated, and treated wild type mice. Similar observations were made in the case of obese mice. However, there was an increase in the NF-kB expression levels in the obese mice when compared to the wild type mice. These results suggest an increase in inflammatory status of the obese mice, as compared to wild-type. The values are Mean±SEM, from 4-5 mice in each group.

Figure 26:
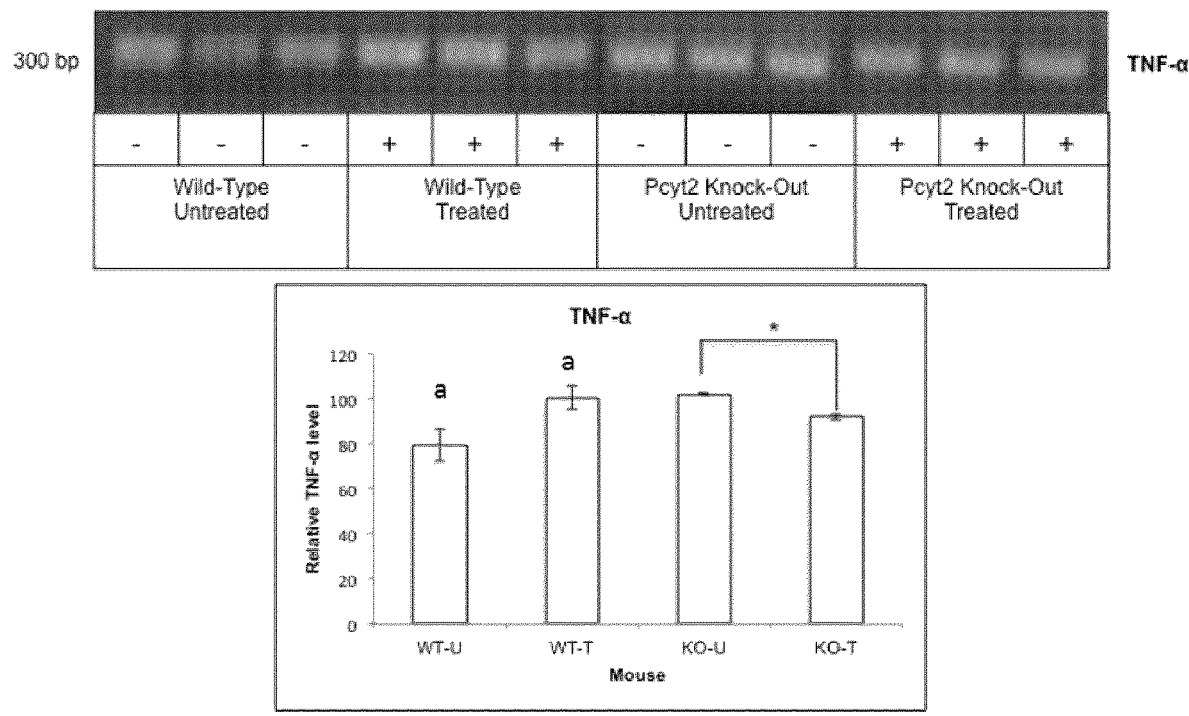
FIG. 26 shows evaluation of the changes in the expression of TNF α gene in response to treatment of mice with Nanoparticle solution as described in Example 2. The quantification was made by RT-PCR and separation of products by agarose gel electrophoresis and ethidium bromide staining. There are no significant changes in the levels of TNF α gene expression between untreated, and treated wild type mice. There is a significant decrease in TNF α expression in the ETKO mice fed with NP solution. The values are Mean±SEM, from 4-5 mice in each group. TNF α is a key protein involved in the signalling pathways related to inflammation, caused by infection, as well as by autoimmune activation. A down regulation of TNFα is typically desirable for controlling chronic autoimmune diseases, for example. A reduction in TNFα is desirable in the reduction of obesity, which is also linked to inflammation state in the body.

TNF $\alpha$ is a key protein involved in the signalling pathways related to inflammation, caused by infection, as well as by autoimmune activation. A down regulation of TNF$\alpha$ is considered ideal for controlling chronic autoimmune diseases such as arthritis. A reduction in TNF$\alpha$ is desirable in the reduction of obesity which is also linked to inflammation state in the body. FIG. 26 shows evaluation of the changes in the expression of TNF $\alpha$ gene in response to treatment of mice with Nanoparticle solution. The quantification was made by RT-PCR and separation of products by agarose gel electrophoresis and ethidium bromide staining. There are no significant changes in the levels of TNF $\alpha$ gene expression between untreated, and treated wild type mice. There is a significant decrease in TNF $\alpha$ expression in the ETKO mice fed with NP solution. The values are Mean±SEM, from 4-5 mice in each group.

IL6 is a cytokine that mediates both pro-inflammatory and anti-inflammatory pathways. Activation of IL6 has been known to lead to the development of a chronic inflammatory state leading to several disorders. There are multiple roles for IL6. Monoclonal antibodies to IL6-receptor (Tocilizumab) are targeted to rheumatoid arthritis, an inflammatory disease.

Figure 27:
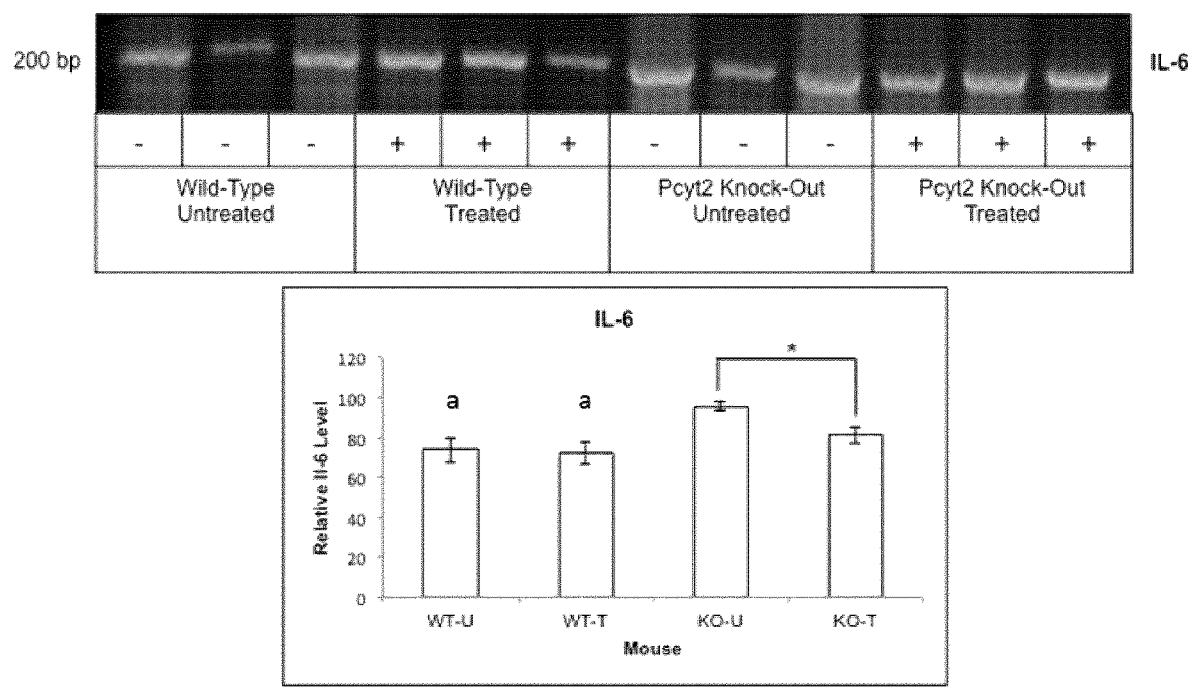
FIG. 27 shows evaluation of the changes in the expression of IL6 gene in response to treatment of mice with Nanoparticle solution as described in Example 2. There are no significant changes in the levels of IL6 between untreated, and treated wild type mice. There is a significant decrease in IL6 expression in the ETKO mice fed with NP solution. The values are Mean±SEM, from 4-5 mice in each group. IL6 is a cytokine that mediates both pro-inflammatory and anti-inflammatory pathways. Activation of IL6 has been known to lead to the development of a chronic inflammatory state leading to several disorders. Downregulation of IL6 may help reduce inflammation and chronic conditions, such as obesity.

Downregulation of IL6 can help reduce chronic conditions, such as obesity. FIG. 27 shows evaluation of the changes in the expression of IL6 gene in response to treatment of mice with Nanoparticle solution. There are no significant changes in the levels of IL6 between untreated, and treated wild type mice. There is a significant decrease in IL6 expression in the ETKO mice fed with NP solution. The values are Mean±SEM, from 4-5 mice in each group.

Figure 28:
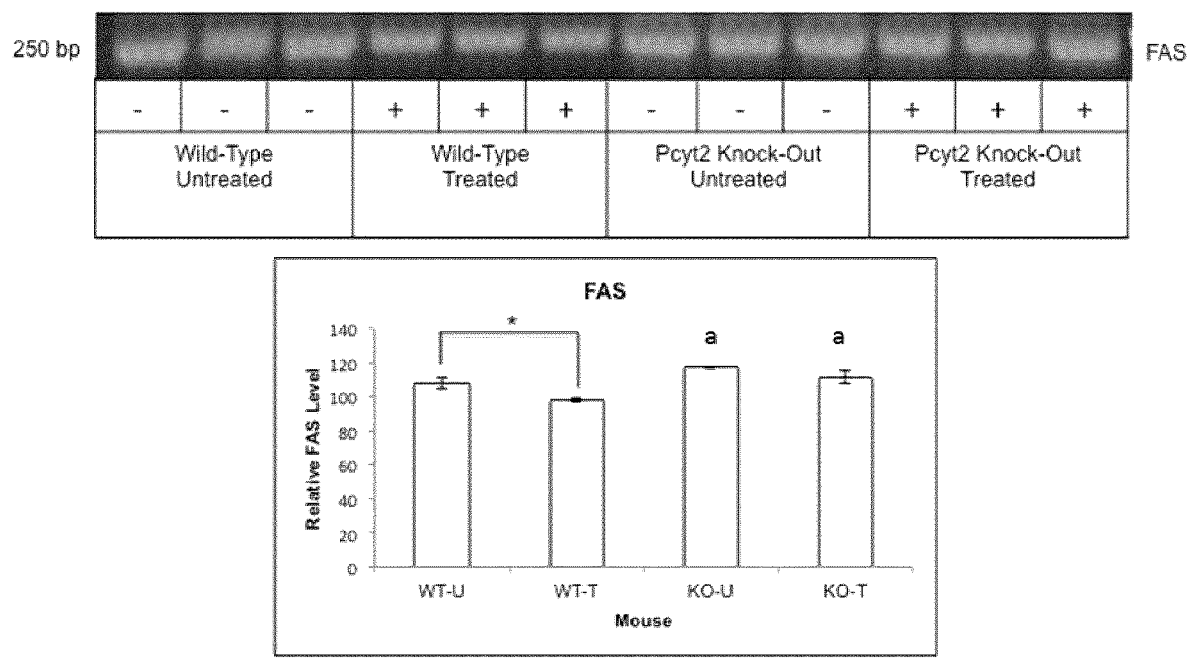
FIG. 28 shows evaluation of the changes in FASN gene expression in response to treatment with Nanoparticle solution as described in Example 2. The quantification was made by separating the PCR products on agarose gel, and ethidium bromide staining for visualizing the band. There was a significant reduction in the level of FAS in NP-treated wild type mice. There was a declining trend in FAS expression in the ETKO mice fed with NP solution. Values were not significantly different from the levels in untreated ETKO mice in this testing. The values are Mean±SEM, from 4-5 mice in each group. FAS (Fatty Acid Synthase) is an enzyme involved in the biosynthesis of fatty acids. Fatty acid are converted to triglycerides, and the increased levels of fatty acids may cause deposition of fat leading to obesity. Thus, a reduction in this enzyme level may favour reduced triglyceride biosynthesis and deposition.

FAS (Fatty Acid Synthase) is an enzyme involved in the biosynthesis of fatty acids. Fatty acids are converted to triglycerides, and the increased levels of fatty acids may cause deposition of fat leading to obesity. Thus, a reduction in this enzyme level may favour reduced triglyceride biosynthesis and deposition. FIG. 28 shows evaluation of the changes in FASN gene expression in response to treatment with Nanoparticle solution. The quantification was made by separating the PCR products on agarose gel, and ethidium bromide staining for visualizing the band. There was a significant reduction in the level of FAS in NP-treated wild type mice. There was a declining trend in FAS expression in the ETKO mice fed with NP solution. Values were not significantly different from the levels in untreated ETKO mice in this testing. The values are Mean±SEM, from 4-5 mice in each group.

Figure 29:
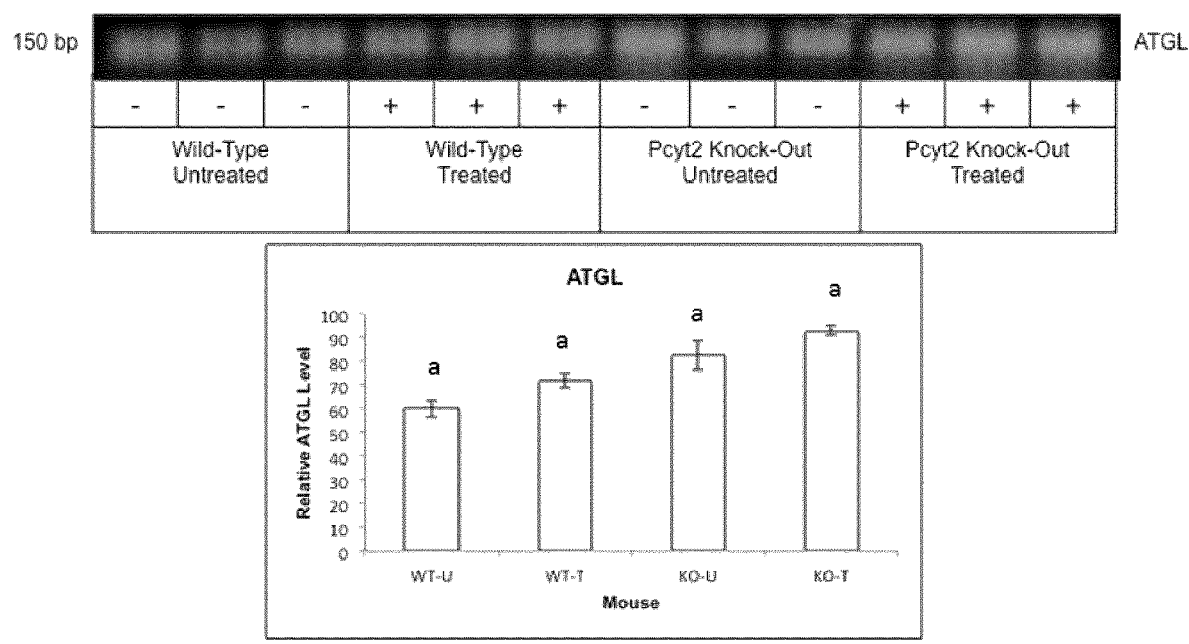
FIG. 29 shows evaluation of the changes in ATGL gene expression in response to treatment with Nanoparticle solution as described in Example 2. The quantification was made by separating the PCR products on agarose gel, and ethidium bromide staining for visualizing the band. There was no significant difference in the level of ATGL between the control and the NP-treated wild type mice. Similarly the levels of ATGL expression was the same in the Untreated and the NP-treated ETKO mice. The values are Mean±SEM, from 4-5 mice in each group; ATGL (Adipose Triglyceride Lipase) is an enzyme involved in the initiation of triglyceride catabolisminto fatty acids. ATGL function is potentially involved in the development of metabolic syndrome.

ATGL (Adipose Triglyceride Lipase) is an enzyme involved in the initiation of triglyceride catabolisminto fatty acids. ATGL function is potentially involved in the development of metabolic syndrome. FIG. 29 shows evaluation of the changes in ATGL gene expression in response to treatment with Nanoparticle solution. The quantification was made by separating the PCR products on agarose gel, and ethidium bromide staining for visualizing the band. There was no significant difference in the level of ATGL between the control and the NP-treated wild type mice. Similarly the levels of ATGL expression was same in the Untreated and the NP-treated ETKO mice. The values are Mean±SEM, from 4-5 mice in each group.

Figure 30:
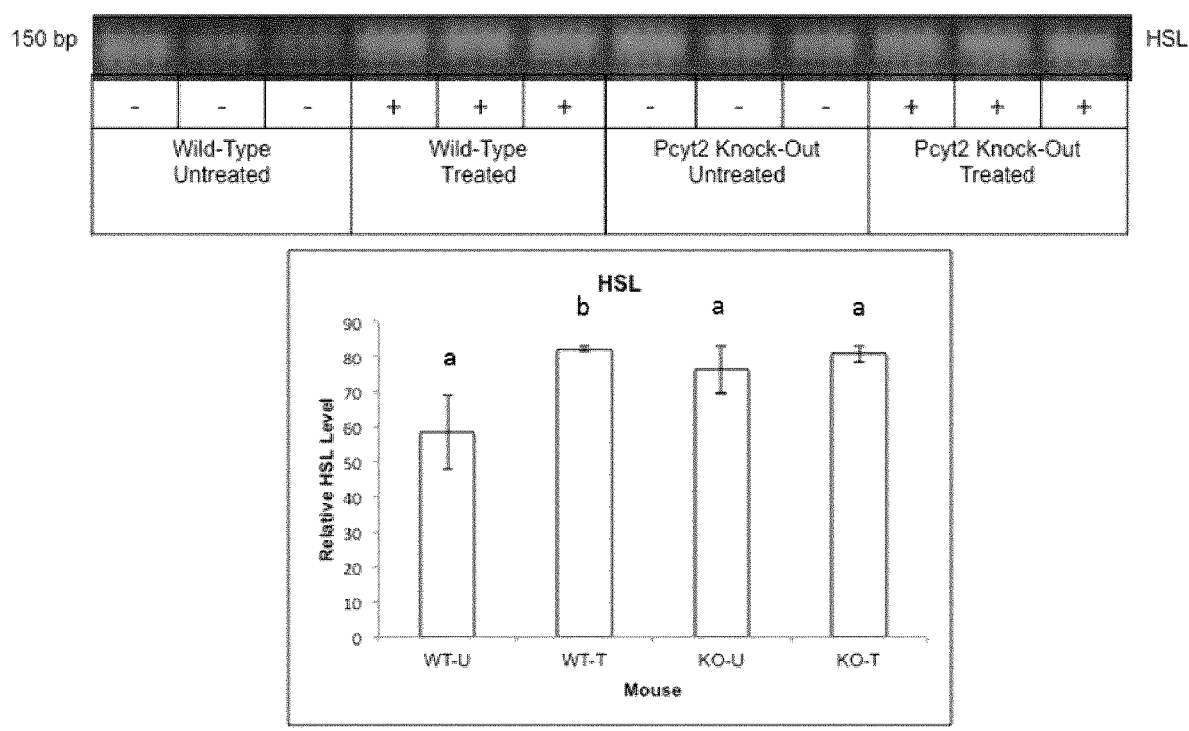
FIG. 30 shows evaluation of the changes in HSL gene expression in response to treatment with Nanoparticle solution as described in Example 2. The quantification was made by separating the PCR products on agarose gel, and ethidium bromide staining for visualizing the band. There was a significant increase in the HSL transcript levels between the control and the NP-treated wild type mice. The levels of HSL expression was the same in the untreated and the NP-treated ETKO mice. The values are Mean±SEM, from 4-5 mice in each group. HSL (Hormone Sensitive Lipase) is a key enzyme involved in the hydrolysis of triglycerides in adipose tissue, and a key enzyme involved in energy generation. HSL acts in conjunction with ATGL to liberate free fatty acids from triglycerides. The enzyme is typically activated in response to catecholamines when energy is needed, as during fasting, and thus functions in mobilizing stored lipids. It also liberates fatty acids from cholesterol esters in steroid biogenesis.

HSL (Hormone Sensitive Lipase) is a key enzyme involved in the hydrolysis of triglycerides in adipose tissue, and a key enzyme involved in energy generation. HSL acts in conjunction with ATGL to liberate free fatty acids from triglycerides. The enzyme is activated in response to catecholamines when energy is needed, as during fasting, and thus functions in mobilizing stored lipids. It also liberates fatty acids from cholesterol esters in steroid biogenesis. HSL may have a function in reducing atherosclerosis by breaking down cholesterol esters in foam cells. FIG. 30 shows evaluation of the changes in HSL gene expression in response to treatment with Nanoparticle solution. The quantification was made by separating the PCR products on agarose gel, and ethidium bromide staining for visualizing the band. There was a significant increase in the HSL transcript levels between the control and the NP-treated wild type mice. The levels of HSL expression was the same in the untreated and the NP-treated ETKO mice. The values are Mean±SEM, from 4-5 mice in each group.

Figure 31:
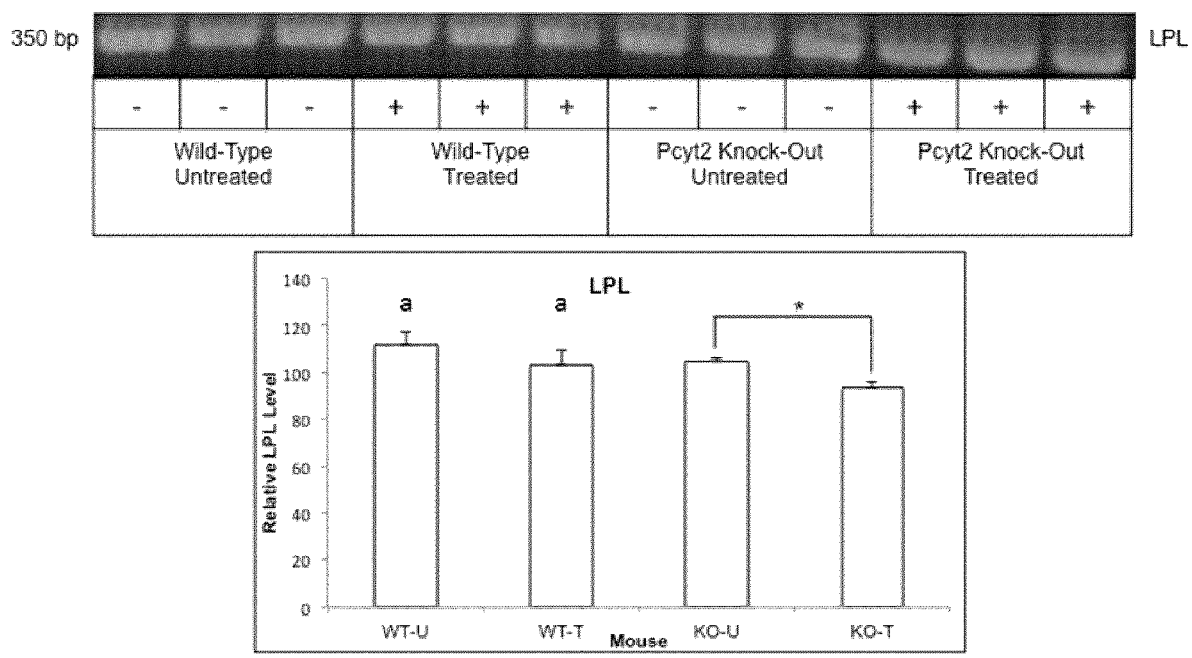
FIG. 31 shows evaluation of the changes in LPL gene expression in response to treatment with Nanoparticle solution as described in Example 2. The quantification was made by separating the PCR products on agarose gel, and ethidium bromide staining for visualizing the band. There was no change in the level of LPL transcripts in response to NP treatment in wild type mice. By contrast, there was a significant decrease in the levels of LPL expression in the NP-treated ETKO mice. The values are Mean±SEM, from 4-5 mice in each group. LPL (Lipoprotein lipase) is an enzyme that hydrolyzes triglycerides bound to lipoproteins, liberating free fatty acids and monoacylglycerol. LPL is similar to other lipases such as pancreatic, and hepatic lipases. LPL is present is several tissues such as heart, muscle and adipose tissue, and they are present in the cell layers close to the lumen in capillaries. LPL may influence the lipoprotein metabolism in capillaries. LPL activity is regulated differentially by hormones such as insulin and adrenalin. LPL level is known to increase after a high fat diet or a high carbohydrate diet, and may have a function in development of obesity.

LPL (Lipoprotein lipase) is an enzyme that hydrolyzes triglycerides bound to lipoproteins, liberating free fatty acids and monoacylglycerol. LPL is similar to other lipases such as pancreatic, and hepatic lipases. LPL is present in several tissues such as heart, muscle and adipose tissue, and they are present in the cell layers close to the lumen in capillaries. LPL may influence the lipoprotein metabolism in capillaries. LPL activity is regulated differentially by hormones such as insulin and adrenalin. LPL level is known to increase after a high fat diet or a high carbohydrate diet, and may have a function in development of obesity. FIG. 31 shows evaluation of the changes in LPL gene expression in response to treatment with Nanoparticle solution. The quantification was made by separating the PCR products on agarose gel, ethidium bromide staining for visualizing the band. There was no change in the level of LPL transcripts in response to NP treatment in wild type mice. By contrast, there was a significant decrease in the levels of LPL expression in the NP-treated ETKO mice. The values are Mean±SEM, from 4-5 mice in each group.

Figure 32:
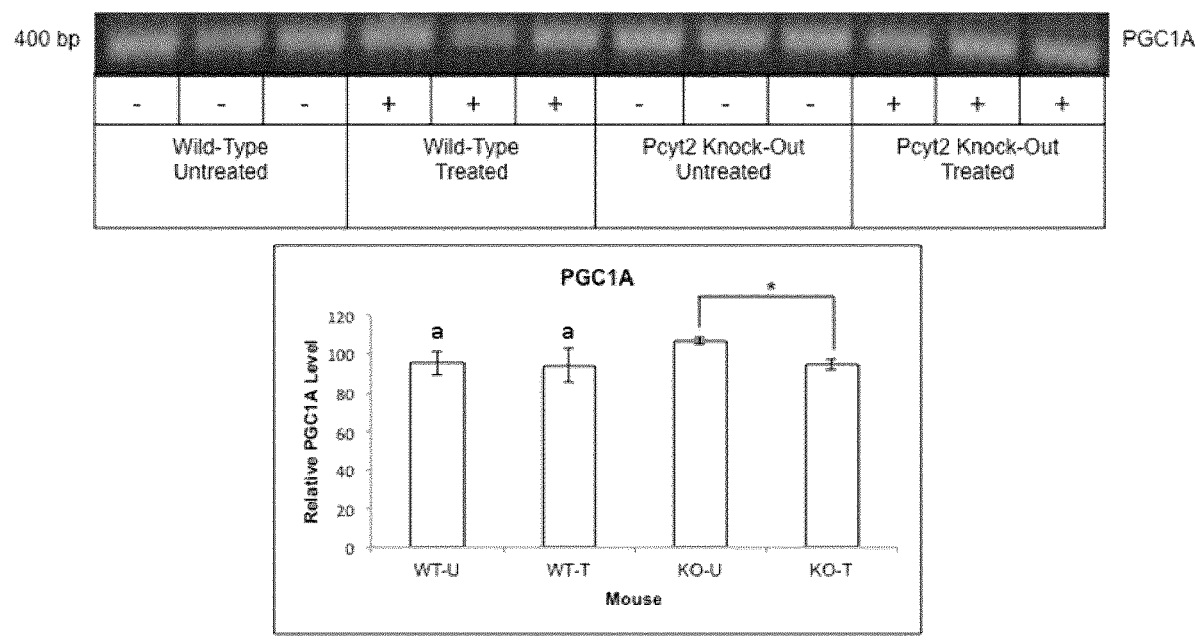
FIG. 32 shows evaluation of the changes in PGC1-α gene expression in response to treatment with Nanoparticle solution as described in Example 2. The quantification was made by separating the PCR products on agarose gel, ethidium bromide staining for visualizing the band. There is no change in the level of PGC1-Alpha transcripts in response to NP treatment in wild type mice. By contrast, there was a significant decrease in the levels of PGC1-Alpha expression in the NP-treated ETKO mice. The values are Mean±SEM, from 4-5 mice in each group. PGC1-α (Peroxisome proliferator-activated receptor-gamma coactivator) belongs to a family of transcription co-activators, involved in the regulation of energy metabolism related to carbohydrates and lipids. PGC1-A is activated under stress conditions. This protein is also known to activate NF-kB, which is involved in enhancing inflammation pathway. A decline in the levels of PGC1-A may thus downregulate inflammation.

PGC1-α (Peroxisome proliferator-activated receptor-gamma coactivator) belongs to a family of transcription co-activators, involved in the regulation of energy metabolism related to carbohydrates and lipids. PGC1-A is activated under stress conditions. This protein is also known to activate NF-kB, which is involved in enhancing inflammation pathway. A decline in the levels of PGC1-A may thus downregulate inflammation. FIG. 32 shows evaluation of the changes in PGC1-α gene expression in response to treatment with Nanoparticle solution. The quantification was made by separating the PCR products on agarose gel, ethidium bromide staining for visualizing the band. There is no change in the level of PGC1-Alpha transcripts in response to NP treatment in wild type mice. By contrast, there was a significant decrease in the levels of PGC1-Alpha expression in the NP-treated ETKO mice. The values are Mean±SEM, from 4-5 mice in each group.

Figure 33:
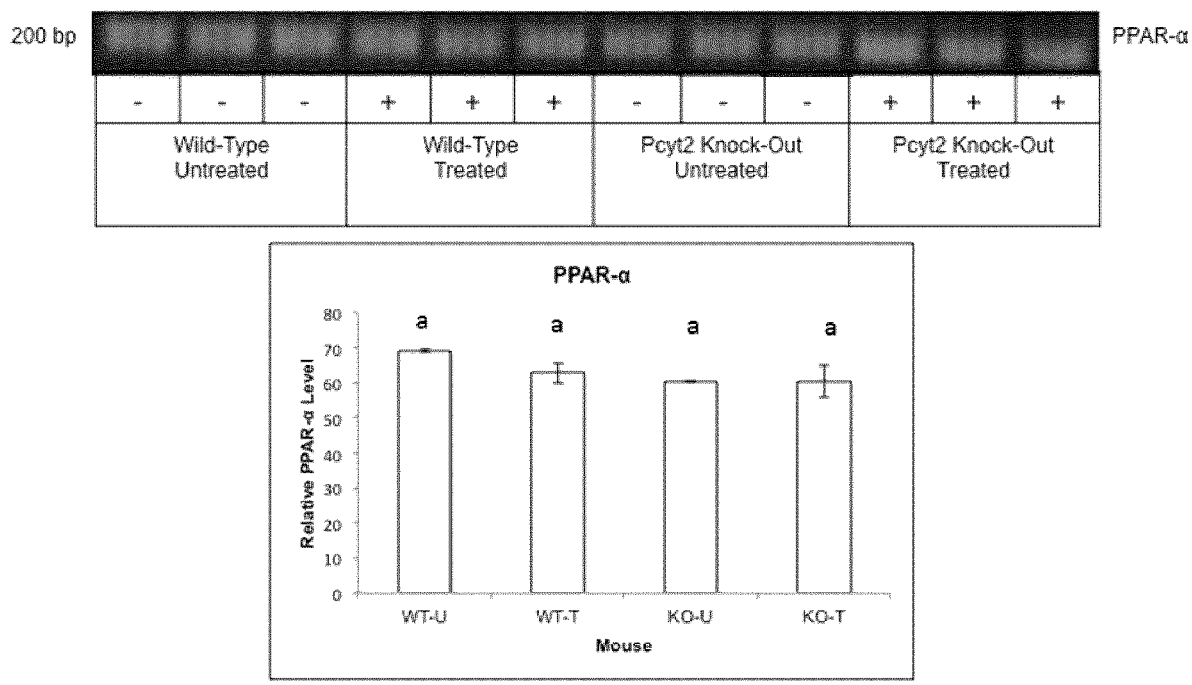
FIG. 33 shows evaluation of the changes in PPAR-α gene expression in response to treatment with Nanoparticle solution as described in Example 2. The quantification was made by separating the PCR products on agarose gel, and ethidium bromide staining for visualizing the band. There was no change in the level of PPAR-α transcripts in response to NP treatment in wild type mice, as well as the ETKO obese mice. The values are Mean±SEM, from 4-5 mice in each group. PPAR-α (Peroxisome Proliferator Activated Receptor-Alpha) belongs to a group of nucleus-localized transcription factors. PPAR-Alpha has a key regulatory function in the lipid metabolism in liver, including the stimulation of genes involved in fatty acid uptake, transport and catabolism.

PPAR-α (Peroxisome Proliferator Activated Receptor-Alpha) belongs to a group of nucleus-localized transcription factors. PPAR-Alpha has a key regulatory function in the lipid metabolism in liver, including the stimulation of genes involved in fatty acid uptake, transport and catabolismpPR-Alpha Knock-out mice have abnormal lipid metabolism leading to fatty liver disease. FIG. 33 shows evaluation of the changes in PPAR-α gene expression in response to treatment with Nanoparticle solution. The quantification was made by separating the PCR products on agarose gel, and ethidium bromide staining for visualizing the band. There was no change in the level of PPAR-α transcripts in response to NP treatment in wild type mice, as well as the ETKO obese mice. The values are Mean±SEM, from 4-5 mice in each group.

Figure 34:
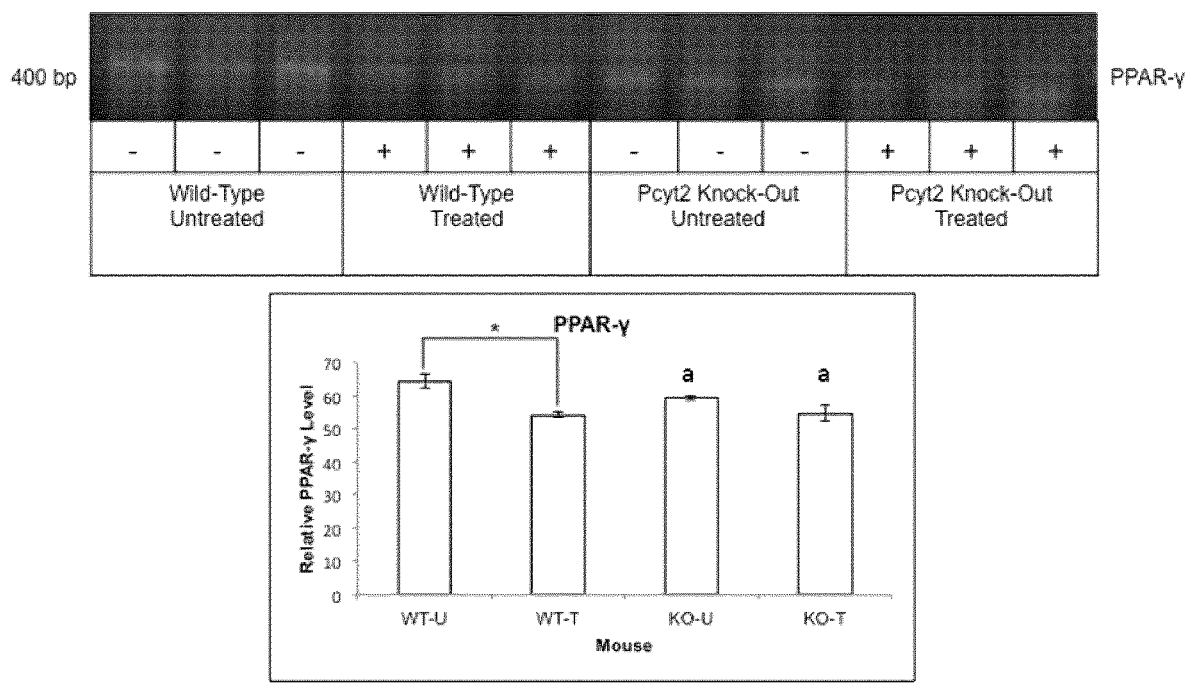
FIG. 34 shows evaluation of the changes in PPAR-y gene expression in response to treatment with Nanoparticle solution as described in Example 2. The quantification was made by separating the PCR products on agarose gel, ethidium bromide staining for visualizing the band. There is a significant reduction of PPAR-gamma transcripts, in NP-treated wild type mice. There was no major change in the level of PPAR gamma in the obese mice after NP-treatment. The values are Mean±SEM, from 4-5 mice in each group. PPAR-gamma (Peroxisome Proliferator Activated Receptor-gamma) is another transcription factor located in the nucleus. This protein is involved in the proliferation of adipocytes, enhancing obesity development. PPAR gamma is expressed in adipose tissue and at a lower level in muscles. PPAR gamma is known to influence the development of obesity and type II diabetes.

PPAR-gamma (Peroxisome Proliferator Activated Receptor-gamma) is another transcription factor located in the nucleus. This protein is involved in the proliferation of adipocytes, enhancing obesity development. PPAR gamma is expressed in adipose tissue and at a lower level in muscles. PPAR gamma is known to influence the development of obesity and type II diabetes. FIG. 34 shows evaluation of the changes in PPAR-y gene expression in response to treatment with Nanoparticle solution. The quantification was made by separating the PCR products on agarose gel, ethidium bromide staining for visualizing the band. There is a significant reduction of PPAR-gamma transcripts, in NP-treated wild type mice. There was no major change in the level of PPAR gamma in the obese mice after NP-treatment. The values are Mean±SEM, from 4-5 mice in each group.

Figure 35:
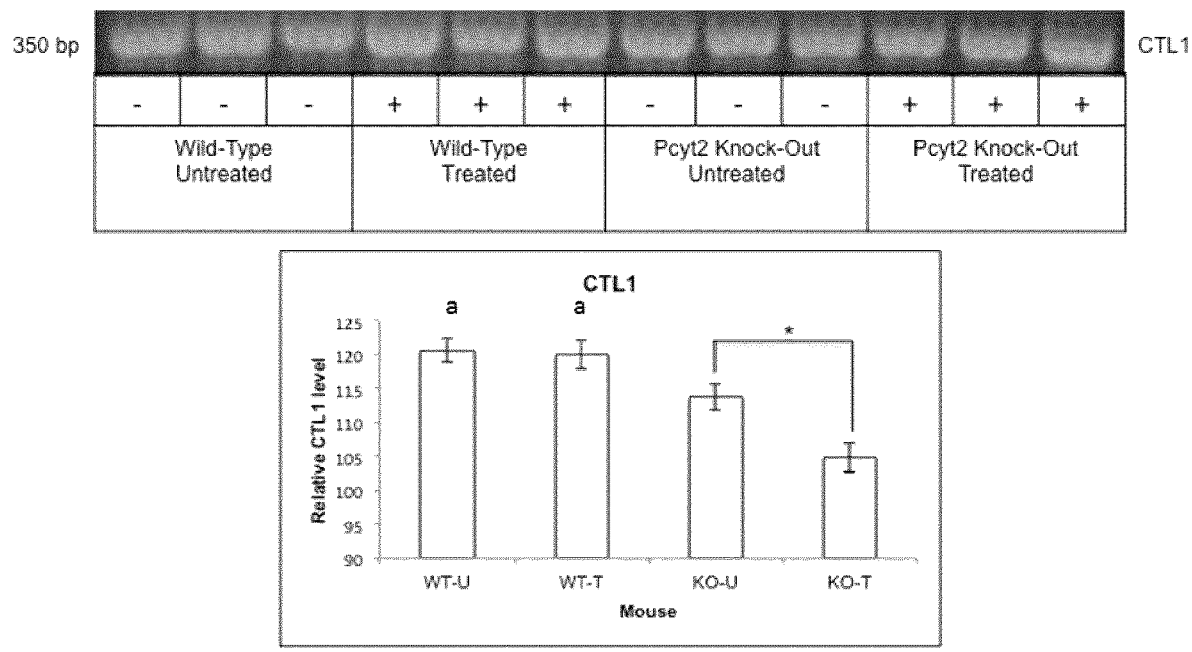
FIG. 35 shows evaluation of the changes in CTL1 gene expression in response to treatment with Nanoparticle solution as described in Example 2. The quantification was made by separating the PCR products on agarose gel, ethidium bromide staining for visualizing the band. There is no change in the level of CTL-1 transcripts in response to NP treatment in wild type mice. By contrast, there was a significant decrease in the levels of CTL1 expression in the NP-treated ETKO mice. The values are Mean±SEM, from 4-5 mice in each group. CTL-1 (Choline Transporter Like Protein 1) is a membrane bound enzyme, and is found in plasma membrane of brain cells and in mitochondria. It is involved in the transport of choline in mitochondria, which is used in phosphatidylcholine biosynthesis and membrane biogenesis. Enhanced production of macrophages by inflammation resulted in overexpression of CTL-1, and appears to be related to increased inflammation. A reduction in high levels of membrane biogenesis may help reduce the enlargement of cells, and obesity related changes.

CTL-1 (Choline Transporter Like Protein 1) is a membrane bound enzyme, and found in plasma membrane of brain cells and in mitochondria. It is involved in the transport of choline in mitochondria, which is used in phosphatidylcholine biosynthesis and membrane biogenesis. Enhanced production of macrophages by inflammation resulted in overexpression of CTL-1, and appears to be related to increased inflammation. A reduction in high levels of membrane biogenesis may help reduce the enlargement of cells, and obesity related changes. FIG. 35 shows evaluation of the changes in CTL1 gene expression in response to treatment with Nanoparticle solution. The quantification was made by separating the PCR products on agarose gel, ethidium bromide staining for visualizing the band. There is no change in the level of CTL-1 transcripts in response to NP treatment in wild type mice. By contrast, there was a significant decrease in the levels of CTL1 expression in the NP-treated ETKO mice. The values are Mean±SEM, from 4-5 mice in each group.

Figure 36:
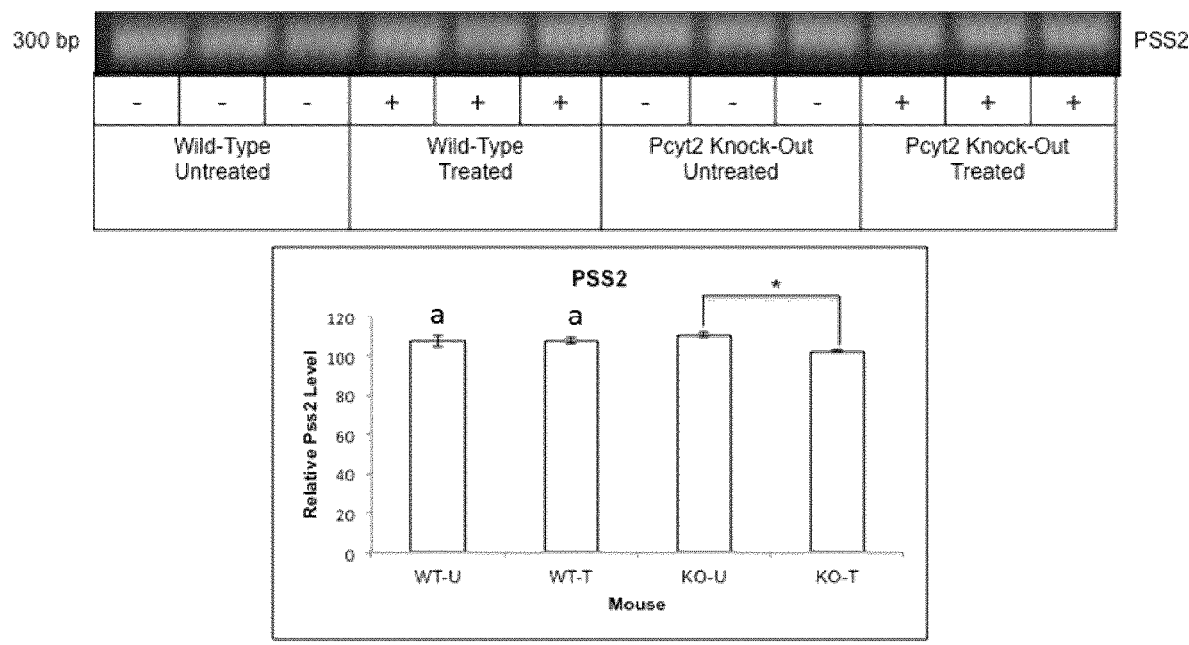
FIG. 36 shows evaluation of the changes in PSS 2 gene expression in response to treatment with Nanoparticle solution as described in Example 2. The quantification was made by separating the PCR products on agarose gel, and ethidium bromide staining for visualizing the band. There was no change in the level of PSS 2 transcripts in response to NP treatment in wild type mice; but showed a low but significant reduction in ETKO mice. The values are Mean±SEM, from 4-5 mice in each group. PSS 2 (CDP-diacylglycerol—serine O-phosphatidyltransferase 2; phosphatidylserine synthase 2) is an enzyme involved in phosphatidylserine biosynthesis. This protein is localized in mitochondria. PSS 2 Knockout mice showed a normal lifespan. The results suggest that the effect of nanoparticle solution treatment may be targeted to specific genes and not to all genes involved in pathways involved in lipid biosynthesis.

PSS 2 (CDP-diacylglycerol—serine O-phosphatidyltransferase 2; phosphatidylserine synthase 2) is an enzyme involved in phosphatidylserine biosynthesis. This protein is localized in mitochondria. PSS 2 Knockout mice showed a normal lifespan. FIG. 36 shows evaluation of the changes in PSS 2 gene expression in response to treatment with Nanoparticle solution. The quantification was made by separating the PCR products on agarose gel, and ethidium bromide staining for visualizing the band. There was no change in the level of PSS 2 transcripts in response to NP treatment in wild type mice; but a low but significant reduction was observed in ETKO mice. The values are Mean±SEM, from 4-5 mice in each group.

The functional (antioxidative, anti-inflammatory) and disease preventive nature of fruits, fruit juices, and fruit powders have been attributed to the presence of various ingredients such as anthocyanins, phenolic components, vitamin C, etc., that are present in these fruits. By virtue of their nature, however, anthocyanins are not absorbed into the body efficiently. As well, anthocyanins undergo structural rearrangements during their transit through the gastro-intestinal system. Alkaline conditions in the intestine causes the ring breakage of anthocyanins. Anthocyanins that are complexed with nanoparticles may be more readily transported across the intestinal epidermis and may potentially release the anthocyanins within the body. Internalized anthocyanins may alter the gene expression favouring a reduction in inflammation as antioxidants (by scavenging ROS), as well as altering the gene expression by downregulating inflammatory pathways involving proteins (TNF alpha, STAT, Interleukins, and their receptors), as well as the effector enzymes that regulate and participate in metabolic pathways.

These results demonstrate a direct effect of the treatment with nanoparticles and reduction in obesity. Supportive effects include a reduction in triglycerides liver, a reduction in the pathology of the liver (reduction in lipid droplets), reduction in liver function marker enzymes such as ALT and AST, a marked reduction in body mass (>10% within 4 weeks), downregulation of inflammation-promoting gene expression, etc, Reduction of chronic degenerative diseases has been associated with increased consumption of fruits and vegetables. Since the availability of functional ingredients depends upon the consumption of a variety of products including fruits, vegetables, nuts, spices etc., these studies aim, at least in part, to provide such combination of ingredients through a single concentrated high potency dose, and the effectiveness in terms of reduction of inflammation markers and prevention of weight gain was observed at a daily dose of ~2.5 mg/kg body weight (mouse trials). A projection of this data to humans suggests a daily dose of ~175 mg for a person with a weight of 70 kg, for example.

Example 3—Functions and Applications of Nanofibres

Nanofibres (and Nanoparticles) as Delivery Vehicles, and Cytotoxicity of Nanoparticles and Nanofibres from Sour Cherry (*Prunus cerasus* L.) Fruit Against Colorectal Cancer Cells Materials and Methods Sour cherry: The fruits used in this Example came from the Vineland Research Station, Vineland, Ontario, where these are maintained as germplasm. All the varieties are high polyphenol containing varieties, ranging in polyphenol content in the range of 300-500 mg/100 g fresh weight. The major variety used for the present studies was V 70151, others such as V 71261, Hymann Conserva and Hymann Rubisn also showed high levels of nanoparticle formation.

Isolation of nanoparticles and nanofibres: The extraction method involves homogenizing the fruit using a polytron homogenizer and a PTA 10 probe in a medium (preferably water, may use absolute or diluted methanol or ethanol), in 1:1 w/w proportion (1 g tissue to 1 ml water or alcohol), at an intermediate setting (4-5) setting until the fruit tissue is completely homogenized. The homogenate was filtered through 4 layers of cheese cloth to remove debris. The resulting homogenate was centrifuged (18,000×g) in a Sorvall RC 6 Plus centrifuge for 20 minutes. The supernatant was decanted. Five ml of the supernatant was dialyzed (spectra-Por, 6-8 kD cut off) against water (1 litre) for 12 hours at 4° C. The dialyzed extract within the dialysis bag was stored frozen at −20C, just as the supernatant (termed crude extract). Polyphenols that leach into water are diluted considerably, so, for experimental purposes, this was concentrated by hydrophobic interaction chromatography by passing through a sep-pak C18 cartridge, and eluting with methanol.

Polyphenol estimation and analysis: Polyphenols were estimated by Folin-Ciocalteau method as routinely performed in our lab (Jacob and Paliyath, 2008). A suitable aliquot of the extract was diluted to a final volume of 100 μl with 50% (v/v) of ethanol in water. Distilled water (0.5 ml) and 50 μl of Folin Ciocalteau reagent (2N) was added to the mixed solution. Sodium carbonate (100 μl of 5% (w/v)) was added to each sample, mixed by vortexing, and incubated in the dark for 1 h. After mixing the samples thoroughly the absorbance was measured at $\lambda_{max}$=725 nm using a Beckman Coulter DU 800 spectrophotometer (Beckman Coulter Inc, USA). A standard curve was generated using gallic acid with concentrations ranging from 0 to 200 μg/ml. The polyphenol concentrations are expressed as gallic acid equivalent per gram fresh weight of fruit.

Polyphenols were purified and concentrated when needed using Sep-Pak C18 chromatography. Usually, 1-2 mg polyphenol equivalent of extract was loaded on to a 1 ml cartridge, washed with 1-2 ml water, and polyphenols eluted with 100% methanol. Methanol was removed in a stream of nitrogen at 45° C. The resulting dry polyphenols were dissolved in methanol (for HPLC-MS) analysis or in water for antioxidant assays and cell culture studies after removing methanol, and redissolving in water.

HPLC-MS analysis of anthocyanins isolated from the crude extracts, the dialyzed extracts and the dialyzate fractions was performed using an Agilent 1100 series HPLC-MS. Separation was conducted using an X-Terra® MS C-18 column (5 μm, 150×3.0 mm, Waters Corporation, MA, USA). Anthocyanins were eluted with a gradient of methanol (solvent A) and 2.0% (v/v) formic acid (solvent B) at a flow rate of 0.8 ml/min. The gradient used was as follows: 0-2 min, 93% B; 2-30 min, 80% B; 30-45 min, 70% B; 45-50 min; 65% B, 50-60 min, 50% B; 60-65 min, 20% B; 65-70 min, 93% B. Detection was carried out at 520 nm for anthocyanins and at 260 nm for phenolic acids. Electrospray ionization (ESI) was performed with an API-ES mass spectrometer. Nitrogen was used as the nebulizing and drying gas, at a flow rate of 12 l/min at 350° C.; an ion spray voltage of 4000 V and a fragmenter voltage of 80 V. Ions generated were scanned from m/z 150 to 700. Spectra were acquired in the positive and negative ion mode. A sample injection volume of 20 μl (20 μg) was used for all the samples. Structure identification of the compounds was achieved by matching their molecular ions (m/z) obtained by LC-ESI-MS with literature data (www.metabolomics.jp). Three independent samples were analyzed and the quantity of ingredients expressed as mean±SEM per g. fresh weight of tissue equivalent.

Estimation of Antioxidant Capacity:

Antioxidant properties (ability to scavenge reactive oxygen species, or activated radicals) were conducted by evaluating the efficiency in scavenging of superoxide anion radicals, hydroxyl anion radicals and DPPH radicals under in vitro assay conditions (Jacob and Paliyath, 2008). The efficiency in scavenging these radicals is denoted by the specific rate of quenching.

Cell culture: Three cell lines derived from colon, CRL 1790, a normal cell line, HT 29, a colorectal cancer cell line and CRL 2158 a multidrug resistant colorectal cancer cell line (ATCC) were used to evaluate the cytotoxicity of nanocomplexes. Cells were cultured in media specifically recommended for each cell line. For HT 29, the medium used was DMEM (Dulbecco's modified Eagle's medium, Sigma), for CRL 2158, the medium used was RPMI, and for CRL 1790, the medium used was EMEM (Eagle's minimum essential medium; Cedarlane Labs, Burlington, ON, Canada). All the media were supplemented with FBS, Penicillin/streptomycin, and L-glutamine. At confluency (~80%), cells were washed with 1×PBS twice. Cells were incubated with trypsin-EDTA for 5 minutes and then diluted in respective media supplemented with 10% FBS before staining with trypan blue (50 ul of cells and 450 ul of trypan blue) and counting viable cells to evaluate cytotoxicity. The cytotoxicity was determined by trypan blue exclusion by living cells and blue staining of dead cells. The number of dead cells in a unit area was counted and expressed as a percentage of total cells in the area.

Confocal studies: $2 \times 10^5$ cells were plated on cell culture dish (35 mm×10 mm) and media changed every two days until the plate reaches confluency. Cells were examined under a confocal microscope after staining with appropriate reagents. Dylight 650 (Excitation 650 nm. Emission 700 nm, Thermo Scientific Pierce Biology Products) was found to provide superior performance and stability during uptake exteriments. Lyophilized powder of the dialyzed extract containing nanocomplexes (4 mg) was mixed with a 10 μM solution of Dylight 650 ester dissolved in dimethylformamide and incubated for 1 h at 25° C. for conjugation. After the reaction, the mixture was dialyzed against water (3×) using a 6-8 kD dialysis membrane until the free reagents were completely removed. The binding of Dylight to the nanocomplexes was evaluated by monitoring the fluorescence of dialyzed nanocomplexes.

Calcein uptake into HT 29, CRL 1790 cells: Uptake of calcein-loaded nanoparticles into mammalian cells. Calcein by itself is impermeable through membrane, and may be taken up at a low level by endocytosis. Ethanol-bleached cherry was homogenized in water, also containing 1 mg/g fresh weight equivalent of calcein, and the supernatant dialyzed against water. Calcein complexed to nanofilaments is retained within the dialysis bag, and used for uptake measurements by confocal microscopy. Calcein-loaded nanoparticles are taken up into discrete compartments in both HT 29 and CRL 1790 cells.

Conjugation of Dylight with nanocomplexes and nanofilaments and their uptake into HT 29, CRL 1790 and CRL 2158 cells: Demonstartion of the uptake of nanocomplexes isolated from unbleached sour cherry and nanofilaments isolated from ethanol bleached sour cherry into mammalian cells (HT-29, CRL 2158, CRL1790). The nanocomplexes and nanofilaments were conjugated with Dylight 650, and dialyzed against water extensively (3×) to remove unconjugated dye. The cells were seeded and allowed to grow for 48 hours. The conjugated nanocomplexes and filaments (~5 μM Dylight equivalent in 3 ml culture medium) were added to the medium and the cells were incubated for a further 24 h. The cells were maintained in petri plates (3.5 cm diameter), and observed under a confocal microscope (Leica) with excitation at 633 nm and emission monitored at 680 nm. Panels A and B respectively show the uptake of Dylight conjugated nanocomplexes and nanofilaments by HT 29 cells; Panels C and D respectively show the uptake of Dylight conjugated nanocomplexes and nanofilaments by CRL 2158 cells; and Panels E and F respectively show the uptake of the conjugated nanocomplexes by CRL 1790 cells, respectively. The inserts in the panels are enlarged composite images of cells. (Size bar)

Live-Dead cell analysis: Cells were grown as confluent and subconfluent monolayers for 24 h as described previously (Hakimuddin et al., 2004). Cells were treated with paclitaxel, or paclitaxel along with nanofibers for 12 h (Appropriate amounts of paclitaxel and nanofibers were mixed in 5% DMSO in water, and added to the cells). Cells were washed with phosphate buffer and cell viability tests performed on CRL 1790, CRL 2158 and HT 29 cells using a live/dead cell viability kit (Invitrogen, Mississauga, Ontario) as described by the manufacturer. Live dead cells were visualized under a confocal microscope. The assay kit contains two fluorescent dyes, calcein AM ester (Ex 494 nm, Em 517 nm) which specifically enters live cells, gets de-esterified and stains the live cells green. The dying cells as well as dead cells are membrane compromised (leaky plasma membrane) and allows the entry of ethidium homodimer Ex 517 nm/Em 617), which stains the nucleus red. The cells were observed at 517 nm (green channel) which differentiated live cells, and at 617 nm which enabled visualization of dead cells. The composite image of the two wavelengths shows the cells in transition to loss of cell viability.

In this Example, nanofibers were coupled with paclitaxel by mixing a 10× solution of paclitaxel (in 50% DMSO) with an appropriate amount of nanofibres in a vial. Appropriate amounts were dispensed into the culture plate under sterile conditions.

Nanoparticles or nanofibres with spherical or fibrous nature formed by spontaneous assembly were isolated from sour cherry fruits. Functional properties of these nanoparticles/nanofibres constituted primarily by carbohydrates, proteins and polyphenols (nanoparticles) were evaluated, and differences investigated. Nanoparticle-enriched fraction of sour cherry extract showed strong antioxidant activity as well as increased cytotoxicity against HT 29 colorectal cancer cells, while the nanofibres from ethanol bleached cherry devoid of polyphenols were inactive in this regard under the conditions tested. Both nanoparticles and nanofibres were internalized by normal human colon cells and cancer cells. Cytotoxicity analyses revealed that HT-29 cells treated with paclitaxel either in the presence, or absence, of nanofibres resulted in a high level of cytotoxicity. While the multidrug resistant colorectal cancer cells were resistant to paclitaxel treatment, in the presence of nanofibres, the treatment resulted in nearly complete cytotoxicity. Under similar conditions of treatment, normal colon cells showed very little cytotoxicity either in the presence of paclitaxel or paclitaxel mixed with nanofibres. These results suggest that nanofibres may be an efficient tool for the internalization of drugs and inducing cytotoxicity in cancer cells and multi-drug resistant cancer cells, for example.

Nanoparticles, as well as Nanofibres, conjugated with Dylight 650 were localized in discrete but similar organelles when mammalian cells were treated with these conjugated particles, suggesting that components conjugated to either nanoparticle or nanofiber may have similar chances of being absorbed and accumulated in a similar manner. It is contemplated that these results with Dylight may be extrapolated to applications when nanoparticles or nanofibers are conjugated with other pharmaceuticals, nutraceuticals, or other biologically active agents (rather than Dylight).

Estimation of antioxidant capacity: Antioxidant properties (ability to scavenge reactive oxygen species, or activated radicals) were conducted by evaluating the efficiency in scavenging of superoxide anion radicals, hydroxyl anion radicals and DPPH radicals under in vitro assay conditions (Jacob and Paliyath, 2008). The efficiency in scavenging these radicals is denoted by the specific rate of quenching.

Results and Discussion

Morphology of Nanoparticles and Nanofibres: Nanoparticles and nanofibres isolated from original sour cherry fruits and ethanol bleached sour cherry fruits showed distinct characteristics (see discussion in Examples 1 and 3, and FIGS. 1 and 17 (nanoparticles) and FIG. 37 (Nanofibre)). Nanoparticles from the original cherry extract where spherical in morphology. Detailed analysis shows that the spherical complexes may in certain embodiments be formed by a pectin core, surrounded by fiber-like structures comprising pectin components, hemicellulose derived molecules, peptides derived from cell wall proteins, anthocyanin and malic acid. These complexes were 50-250 nm in diameter in solution. After ethanol bleaching of sour cherry fruits when the anthocyanins and other small molecules (i.e., malic acid, in certain embodiments) are removed, the resulting fruits formed fiber-like structures during homogenization that were several micrometers in length and 5-10 nm in diameter (see FIG. 37). Both nanoparticles and nanofibres were used to evaluate their functional properties.

Polyphenol content in the nanoparticles: Cherry homogenates were obtained from elite lines of sour cherries containing high levels of polyphenols. During extractions using different cherry cultivars, the homogenates contained 0.88 to 0.94 mg/g fresh weight of polyphenols in aqueous extracts, while in methanol extracts, polyphenol content ranged from 1.04-1.13 mg/g fresh weight (see Example 1, Table 1). Subjecting sour cherry homogenates prepared in water or alcohol (methanol, ~50% v/v final) to dialysis against water resulted in the retention of nearly 80% of polyphenols within the dialysis bag in a complexed state (see Example 1, Table 1). Extraction of fruits with methanol increased polyphenol content in crude extract by nearly 20%, however the amount remaining in dialyzed extract was comparable to that obtained after dialyzing the water extract. The amount of free polyphenols that move out of the dialysis bag ($M_r$ cut off 6000-8000) into the dialysate was very low (less than 3%). In general, from multiple extractions, the polyphenol content of dialyzed extract ranged from 0.63-0.65 mg/g fresh weight in aqueous extracts, while in dialyzed extracts of methanol extracts, this ranged from 0.70-0.80 mg/g fresh weight. Polyphenol content in the dialysate was very low, ranging from 0.03 to 0.06 mg/g fresh weight in aqueous, and methanol extracts, respectively.

Polyphenol composition of the dialyzed extract and the dialysate was analyzed by HPLC-MS (see Example 1, Table 2) and the components. Polyphenols constituted a major proportion of phenolic components (>90%) with a minor proportion of phenolic acids (<10%). Cyanidin-3-rutinoside was the major anthocyanin (~70%) followed by peonidin-3-rutinoside. Pelargonidin-3-rutinoside and cyanidin-3-sophoroside were present at ~10-12%. Chlorogenic acid and p-coumaroylquinic acid were the major phenolic acids. The qualitative composition of the dialysate was very similar to that of the dialyzed extract. In terms of quantity, the dialyzed extract had a higher content of cyanidin-3-rutinoside (~25-30% higher), showing specific enrichment by forming nanoparticles.

Antioxidant capacity of free and complexed polyphenols: Antioxidant activities of crude extract, dialyzed extract and the dialysate were measured from both water and methanol extracts. The specific quenching of superoxide, hydroxyl radicals and the DPPH radicals is shown in Example 1, Table 3. The crude aqueous or methanolic cherry extracts showed very strong superoxide, hydroxyl radical, and DPPH scavenging abilities. Despite being a part of the nanoparticles, the polyphenols showed high antioxidant activities, much higher than the free polyphenols in the dialyzate, suggesting that the complex formation has not hindered the antioxidant activities of polyphenols. Thus, the entry of nanoparticles containing polyphenols into the body tissues crossing the GIT membrane is not likely to reduce their antioxidant function based on these results.

Figure 37:
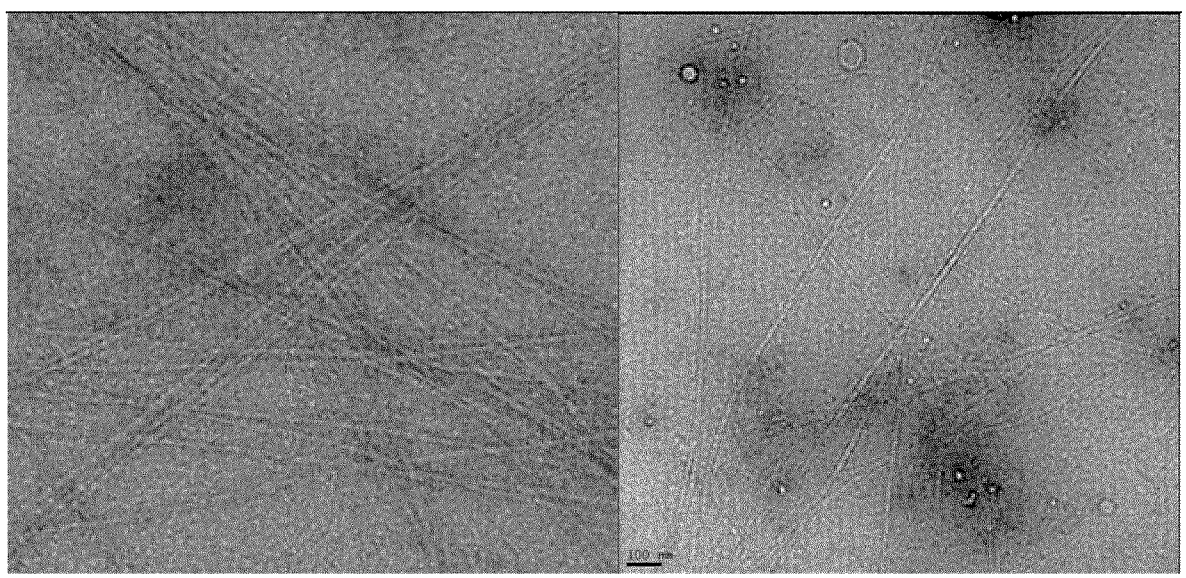
FIG. 37 shows transmission electron micrographs (TEMs) of nanofibres from 2 independent preparations of nanofibres. The left panel shows the nanofibres isolated from ethanol bleached sour cherry using freeze drying (lyophilisation). The right panel shows the nanofibres isolated by nano-spray drying.

In this Example, experiments were preformed to study cellular uptake of nanofibres (and nanoparticles), and to study the application of nanofibres (and nanoparticles) as delivery vehicles for various cargo. FIG. 37 shows examples of nanofibres, representative of those used in these experiments. FIG. 37 shows transmission electron micrographs (TEMs) of nanofibres from 2 independent preparations of nanofibres. The left panel shows the nanofibres isolated from ethanol bleached sour cherry using freeze drying (lyophilisation). The right panel shows the nanofibres isolated by nano-spray drying. Nanofibres such as these were used to study cellular uptake and applications as delivery vehicles, as described in further detail below.

Figure 38:
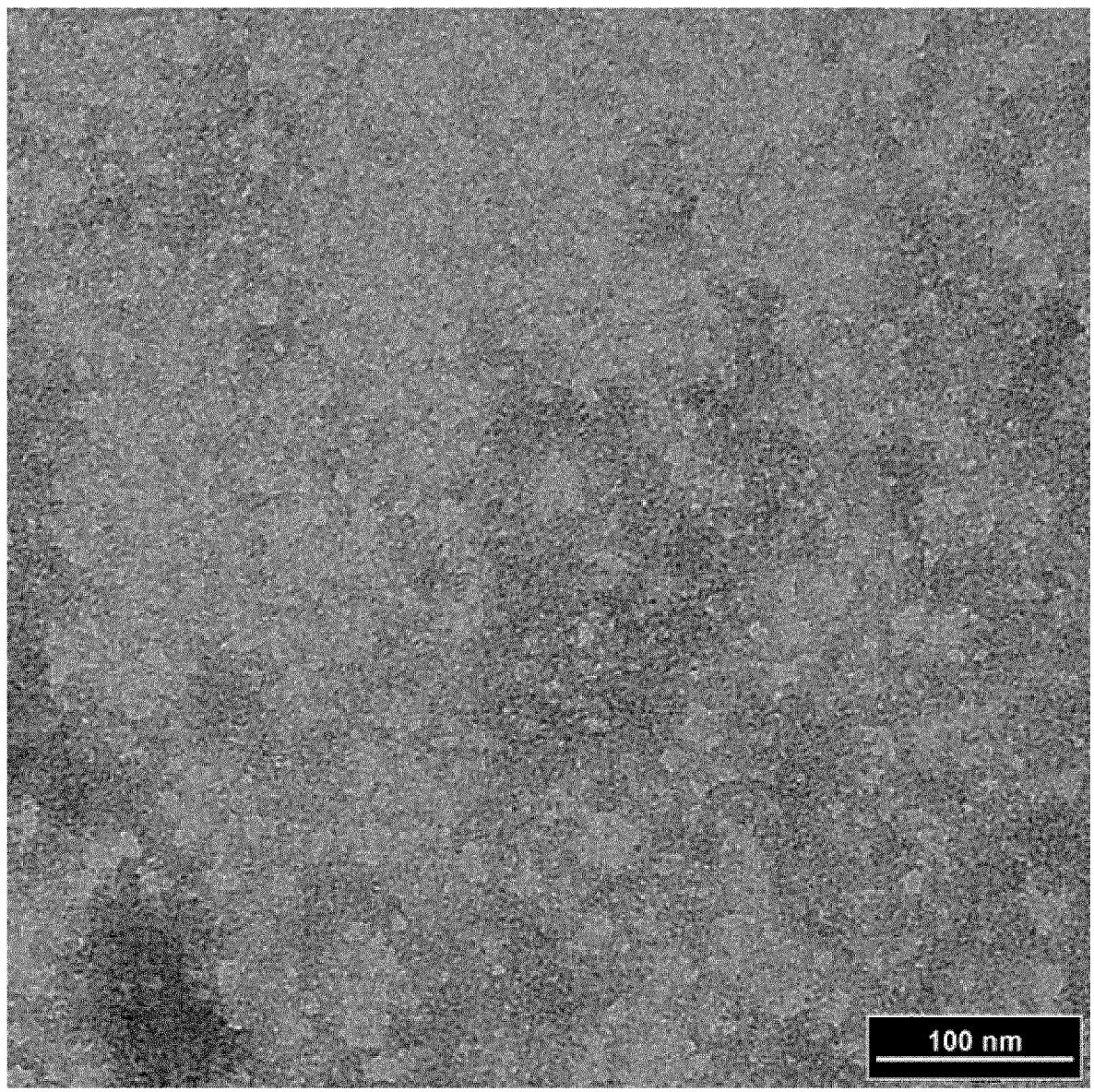
FIG. 38 shows nanofibre complexes with iron. Nanofibre preparation (2 mg) was dissolved in 2 ml water and mixed with 1 mM ferrous chloride. The solution was incubated for 2 hours and dialyzed overnight against water (2×) to remove unbound iron. The dialyzed solution was examined under an electron microscope without heavy metal staining (i.e. without staining with uranyl acetate, which is normally used to increase contrast). The nanofibre complexes were stained with iron (instead of uranyl acetate), showing the potential of nanofibres to be used as carriers of iron.

Studies were performed to investigate application of nanofibres for carrying a mineral cargo, such as iron. FIG. 38 shows nanofibre complexes formed with iron. Nanofibre preparation (2 mg) was dissolved in 2 ml water and mixed with 1 mM ferrous chloride. The solution was incubated for 2 hours and dialyzed overnight against water (2×) to remove unbound iron. The dialyzed solution was examined under an electron microscope without uranyl acetate staining. The nanofibre complexes were stained with iron (instead of uranyl acetate), showing the potential of nanofibres to be used as carriers of iron.

Figure 39:
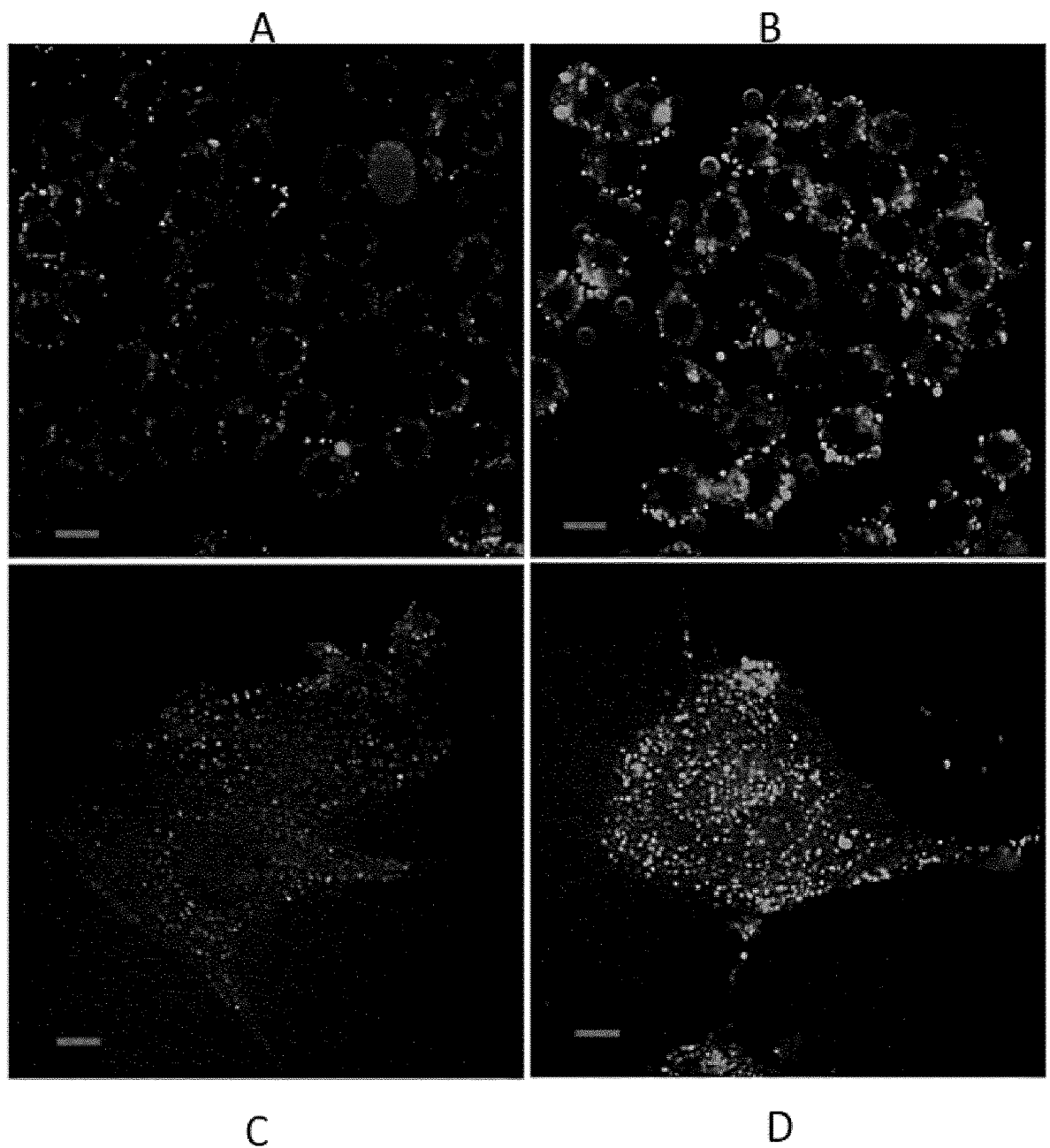
FIG. 39 shows uptake of calcein-loaded nanofibres into mammalian cells (calcein-nanofibre adduct). Calcein (Ex 494 nm/Em 517 nm) by itself is impermeable through membrane, and may be taken up at a low level by endocytosis (A,C). Ethanol-bleached cherry was homogenized in water, also containing 1 mg/g fresh weight equivalent of calcein, and the supernatant dialyzed against water. Calcein complexed to nanofibres is retained within the dialysis bag, and used for uptake measurements by confocal microscopy. Uptake of calcein alone was comparatively very low (Panels A and C) in both HT 29 cells (Top left panel) and normal intestinal cells (bottom left panel). Calcein-loaded nanofibres are taken up into discrete compartments in both colorectal cancer cell line HT 29 (Top right, B) and normal human intestinal CRL 1790 (bottom right, D) cells. (Size bar—10 µm). Panels B and D shows enhanced uptake of Nanofibre-calcein complex into both type of cells.

Studies were also performed to investigate use of nanofibres as delivery vehicles for a cargo of interest, where the cargo was non-covalently complexed with the nanofibres. In this study, nanofibres were used for cellular delivery of calcein. FIG. 39 shows uptake of calcein-loaded nanofibres into mammalian cells (calcein-nanofibre adduct). Calcein (Ex 494 nm/Em 517 nm) by itself is impermeable through membrane, and may be taken up at a low level by endocytosis (FIG. 39, A, C). Ethanol-bleached cherry was homogenized in water, also containing 1 mg/g fresh weight equivalent of calcein, and the supernatant dialyzed against water. Calcein complexed to nanofibres is retained within the dialysis bag, and used for uptake measurements by confocal microscopy. Uptake of calcein alone was comparatively very low in HT 29 cells (Panel A) and normal human intestinal cells (Panel C). Calcein-loaded nanofibres are taken up much more efficiently into discrete compartments in both colorectal cancer cell line HT 29 (B) and normal human intestinal CRL 1790 (D) cells. (Size bar-10 μm).

Cytotoxicity of nanoparticles and nanofibres against cancer cells: These studies evaluate the cytotoxic effects of the purified nanoparticles and the nanofibres isolated from sour cherry using normal human colonic epithelial cells (CRL 1790), human colorectal cancer cells (HT 29) and multidrug resistant human colorectal cancer cells (CRL 2158) in the presence or absence of paclitaxel. Nanoparticles were added as polyphenol equivalent aliquots, while the nanofibres were added on a weight basis. The cells were allowed to multiply for a period of 48 h and treated with paclitaxel (32 nM) and 4 μg/ml of nanofibres per petri plate, and cytotoxicity evaluated by trypan blue exclusion. The effects of the treatments are given in the following Table as % surviving cells after treatment for various time periods.

TABLE 5

Cytotoxicity of nanoparticles and nanofibres. The values are means of 3 replicates. Replicate to replicate variation in general was between 1-2%. Data in Treatment B were obtained by counting the live/dead cells from 4-6 random frames, after staining with calceinAM/Ethidium homodimer.

| A-Treatment | % Living cells Normal Cell Line CRL 1790 | % Living cells Colorectal Cancer Cell Line HT 29 | % Living cells Colorectal MDR cell line CRL 2158 |
|---|---|---|---|
| Nanoparticle (µg/ml) | | | |
| 0 | 100 | 100 | 100 |
| 5 | 87.58 | 75.64 | 89.65 |
| 20 | 81.50 | 66.02 | 83.44 |
| 80 | 72.54 | 58.33 | 74.48 |
| Nanofibre 4 µg/ml | 99-100 | 98-100 | 100 |
| Paclitaxel (nM) | | | |
| 0 | 100 | 100 | 100 |
| 2 | 86.66 | 70.93 | 90.86 |
| 8 | 74.28 | 59.11 | 86.17 |
| 32 | 66.79 | 48.27 | 83.76 |
| B-Live/Dead cell analysis | | | |
| -Paclitaxel-Fibre | 100 | 100 | 100 |
| Paclitaxel 32 nM, 24 h | 97.6 | 10.78 | 46.00 |
| Paclitaxel + Nanofibre (4 µg/ml) | 117.3 | 10.57 | 4.2 |

Nanoparticles by themselves showed mild toxicity to the cells (Table above). HT 29 was the most sensitive to nanoparticles while the normal CRL 1790 cells were the least affected. Multidrug resistant cell line CRL 2158 showed nearly 25% decrease in surviving cells, at a polyphenol concentration of 80 µg/ml. A similar degree of susceptibility was also observed in the normal cells. HT 29 cells treated at 80 µg/ml polyphenols showed nearly a 42% decrease in surviving cells. Nanofibres were not cytotoxic to any of the cell lines at the concentration used (4 µg/ml). When nanoparticles and nanofibres were mixed, there was a marginal increase in cytotoxicity in HT 29 and MDR cell lines at 80 µg/ml polyphenol concentration. Paclitaxel by itself was cytotoxic to HT 29 cells (50% survival at 32 nM) while the normal cells and the MDR cells showed a low level of cytotoxicity (Table above). When nanoparticles were included along with paclitaxel, the cytotoxicity did not change to a great extent under the conditions tested. When paclitaxel and nanofibres were added together, cytotoxicity of the MDR cells were increased to nearly 50%, at 32 nM paclitaxel. While the HT 29 cells showed a high level of cytotoxicity to paclitaxel alone, a combination of paclitaxel and nanofibres did not change the survival rate of cells under the conditions tested.

Uptake of complexed molecules by nanofibres: Nanofibres are extremely long (micrometers in length, ~5 nm in diameter; see FIG. 37, for example), and their ability to cross the plasma membrane was investigated. In this experiment, the ability of nanofibres to form natural complexes with a membrane impermeable fluorescent dye, calcein, was investigated. Nanofibres where prepared from ethanol-bleached cherry by procedures described herein above. While homogenizing, 1 mg/g fresh weight equivalent of calcein was mixed with the cherry. After homogenization and removal of debris, the homogenate was dialyzed (3×) against water until the dialysate showed no fluorescence. At the same time, the extract within the dialysis bag showed a high degree of fluorescence. HT-29 and CRL-1790 cells were incubated in the presence of calcein alone, and calcein-complexed nanofibres (of equal fluorescence intensity). Uptake of calcein and calcein complexed with nanofibres were monitored by confocal microscopy. Results are shown in FIG. 39. Panels A and B show the uptake of uncomplexed calcein, and nanofibre-complexed calcein respectively, into HT 29 cells. As can be seen from the figure, calcein complexed with nanofibres were preferentially taken up by cells (panel B) and these appear to be localized in vesicular structures. Far reduced uptake of calcein was observed, as calcein is a relatively membrane impermeant molecule. While most of the fluorescence was localized in regions close to the plasma membrane in HT 29 cells, uptake was more intense in CRL 1790 cells incubated with calcein-nanofibre complex (Panel D). As well, distribution of calcein fluorescence was seen in internal regions of the cell. Uptake of calcein alone was very low by CRL 1790 cells. Similar experiments were also conducted with nanoparticles, however, because of quenching of fluorescence by polyphenols, successful acquisition of images was not achieved. It is contemplated that nanoparticles as described herein may be as efficient in taking up calcein (or any other molecule of a drug/supplement nature), as further investigated hereinbelow.

Uptake of conjugated Dylight 650 by nanoparticles and nanofibres by cells: Additional studies were performed to investigate use of nanofibres (and nanoparticles) as delivery vehicles for a cargo of interest, where the cargo was covalently complexed with the nanofibres (or nanoparticles). In this study, nanofibres (and nanoparticles) were used for cellular delivery of Dylight 650. To further evaluate the ability of the nanoparticles and nanofibres to enter the cells, these were isolated from unbleached cherry and ethanol-bleached cherry, respectively, and chemically conjugated with a fluorescent dye Dylight 650 (excitation 650 nm, emission 670 nm). HT 29, CRL 2158 and CRL 1790 cells were grown and incubated with the dye solution and examined under a confocal microscope (FIG. 40).

Both the nanoparticles and nanofibres conjugated with the dye were taken up by the cells during incubation, and were clearly visible compartmentalized in vesicular structures in the cytoplasm and surrounding the nucleus. FIG. 40, Panels A and B respectively show the uptake of nanoparticles and nanofibres by HT 29 cells. Both conjugates are taken up by the cells as revealed in the insert (magnified view of a cell). Multidrug resistant CRL 2158 cells incubated with conjugated nanoparticles (C) and nanofibres (D) showed equally similar uptake as shown by the HT-29 cells, the relative intensity may be higher in the cells incubated with nanoparticles (panel C). The inserts show enlarged view of a composite image of a cell, again showing the accumulation of nanoparticles in organelles surrounding the nucleus. CRL 1790 cells showed a much higher uptake of the nanoparticles (E) as judged by the visual intensity than that of nanofibres (F). These results indicate that the nanoparticles and nanofibres isolated from unbleached and bleached cherry were able to cross the cell membrane and accumulate in specific organelles.

Figure 40:
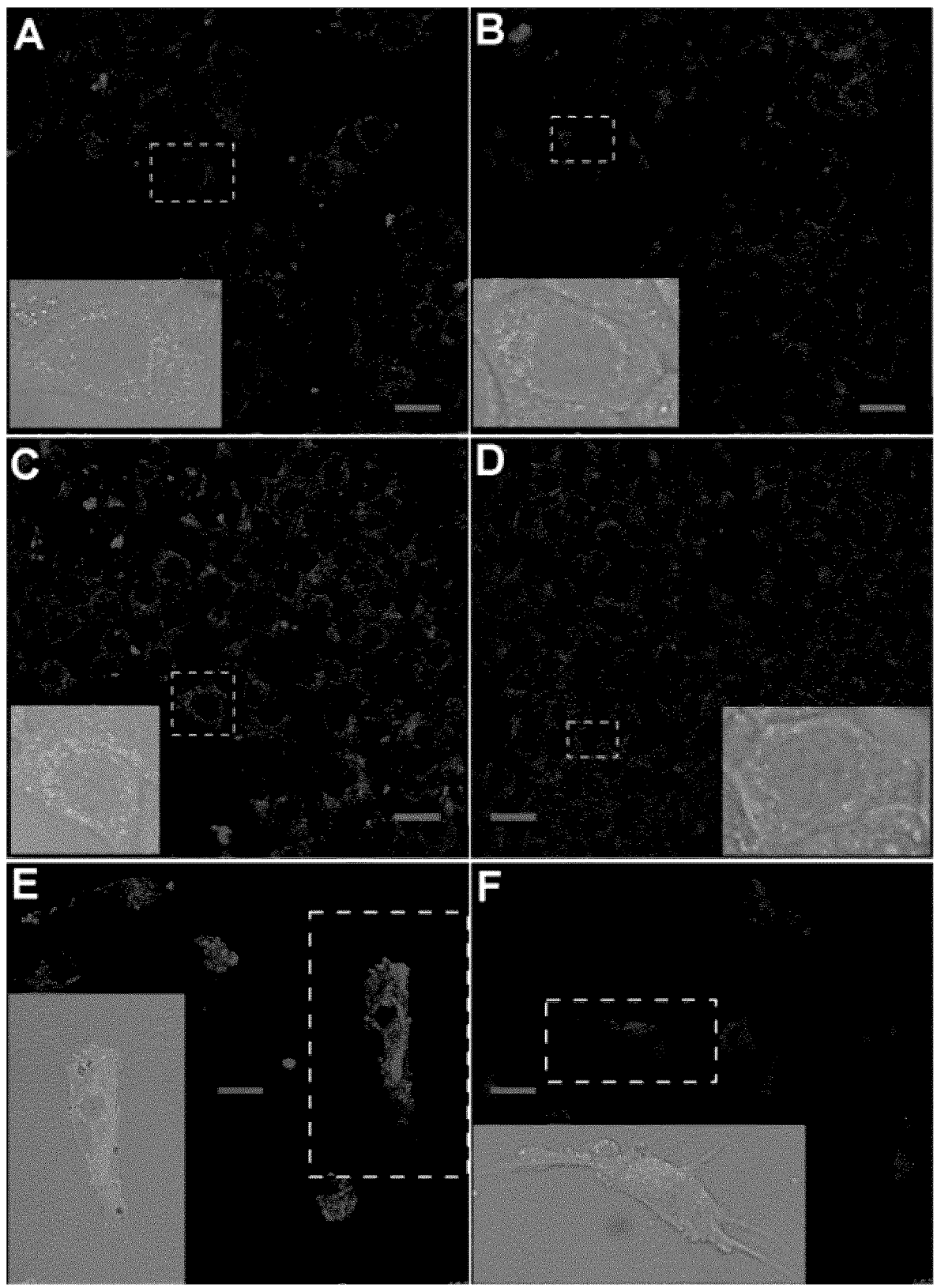
FIG. 40 shows a demonstration of the uptake of nanoparticles (A, C, E) isolated from unbleached sour cherry, and nanofibres (B, D, F) isolated from ethanol bleached sour cherry into human cells (HT-29, CRL 2158, CRL1790). The nanoparticles and nanofibres were chemically conjugated with Dylight 650, and dialyzed against water extensively (3×) to remove unconjugated dye. Dylight was conjugated to the nanoparticles and nanofibres using a method similar to that which is normally used to label the amino-group of antibodies and described in detail in the SOP sheet provided (Thermofisher). In short, Dylight was activated with N-hydroxysuccinimmide esters, which react with primary amines, which forms a stable covalent amide bond. The nanoparticle and nanofiber conjugated with Dylight was removed by using a size exclusion column. The conjugated products were stored in dark at −20° C., protected from light. The cells were seeded and allowed to grow for 48 hours. The conjugated nanoparticles and nanofibres (~5 µM Dylight equivalent in 3 ml culture medium) were added to the medium and the cells were incubated for a further 24 h. The cells were maintained in petri plates (3.5 cm diameter), and observed under a confocal microscope (Leica) with excitation at 633 nm and emission monitored at 680 nm. Panels A and B respectively show the uptake of Dylight conjugated nanoparticles and nanofibres by HT 29 cells (colorectal cancer cell line); Panels C and D respectively show the uptake of Dylight conjugated nanoparticles and nanofibres by CRL 2158 cells (MDR colorectal cell line); and Panels E and F respectively show the uptake of the conjugated nanoparticles by CRL 1790 cells (normal human intestinal cells), respectively. The inserts in the panels are enlarged composite images of cells. (Size bar—10 µm)

FIG. 40 shows a demonstration of the uptake of nanoparticles (A,C,E) isolated from unbleached sour cherry and nanofibres (B,D,F) isolated from ethanol bleached sour cherry into human cells (HT-29, CRL 2158, CRL1790). The nanoparticles and nanofibres were chemically conjugated with Dylight 650, and dialyzed against water extensively (3×) to remove unconjugated dye. The cells were seeded and allowed to grow for 48 hours. The conjugated nanoparticles and nanofibres (~5 μM Dylight equivalent in 3 ml culture medium) were added to the medium and the cells were incubated for a further 24 h. The cells were maintained in petri plates (3.5 cm diameter), and observed under a confocal microscope (Leica) with excitation at 633 nm and emission monitored at 680 nm. Panels A and B respectively show the uptake of Dylight conjugated nanoparticles and nanofibres by HT 29 cells (colorectal cancer cell line); Panels C and D respectively show the uptake of Dylight conjugated nanoparticles and nanofibres by CRL 2158 cells (MDR colorectal cell line); and Panels E and F respectively show the uptake of the conjugated nanoparticles by CRL 1790 cells (normal human intestinal cells), respectively. The inserts in the panels are enlarged composite images of cells. (Size bar-10 μm).

Figure 41:
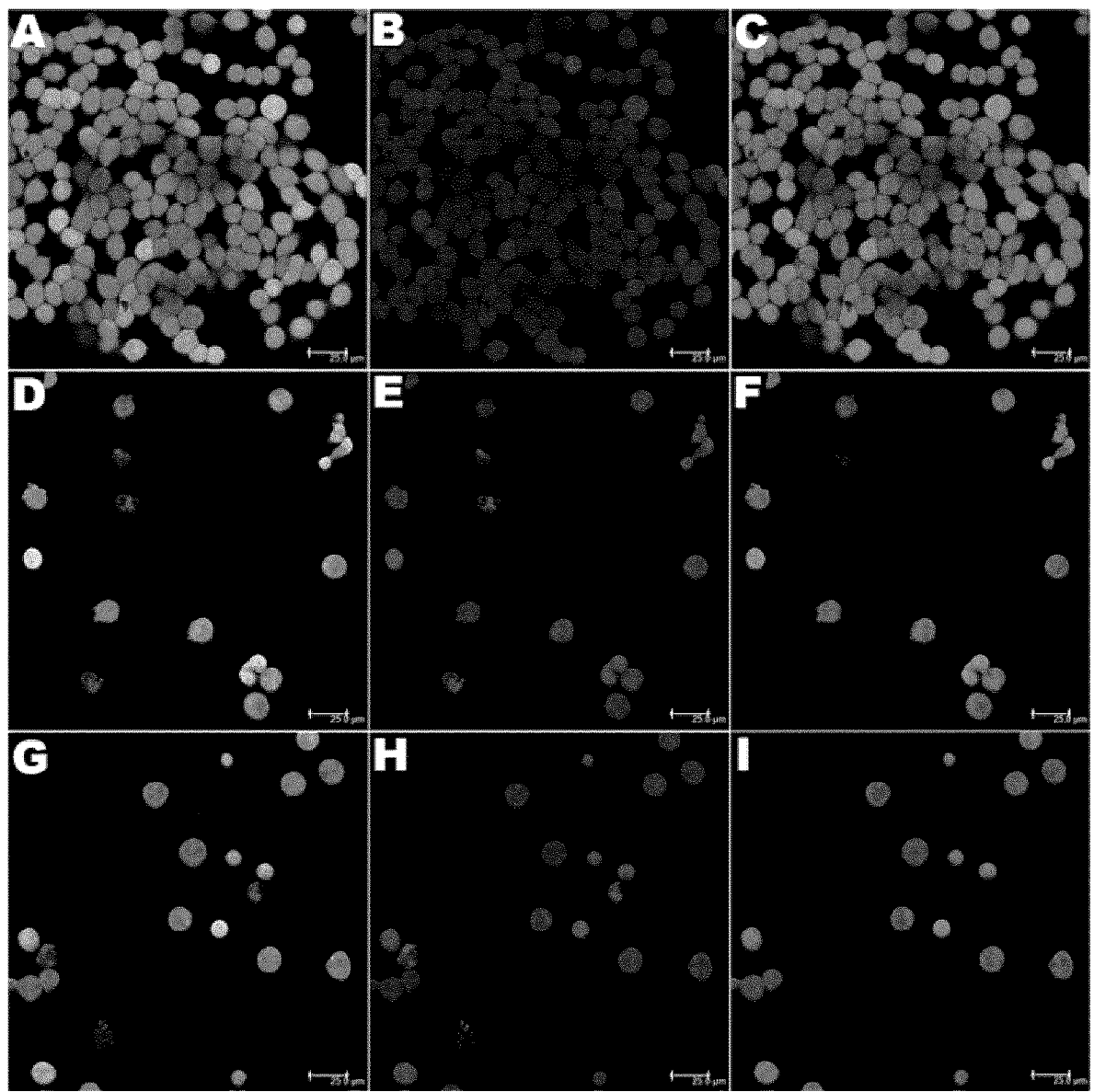
FIG. 41 shows cytotoxicity of Nanofibre-Paclitaxel to Human colorectal cancer Cells (HT 29). Live-Dead cell analysis of HT 29 colorectal cancer cells as were visualized under a confocal microscope is shown. The assay kit (Invitrogen) contains two fluorescent dyes, calcein AM ester (Ex 494 nm, Em 517 nm) which specifically enters live cells, gets de-esterified and stains the live cells green. The dying cells as well as dead cells are membrane compromised (leaky plasma membrane) and allows the entry of ethidium homodimer (Ex 517 nm/Em 617), which stains the nucleus red. The cells were observed at 517 nm (green channel) which differentiated live cells, and at 617 nm which enabled visualization of dead cells. The composite image of the two wavelengths show the cells in transition to loss of cell viability (A,D,G; yellow). Panels B,C represent control cells visualized at 617 nm (red, dead cells) and at 517 nm (green, live cells), respectively. Panel A is a composite image of untreated cells. Panels E, F represent the images of cells treated with paclitaxel (32 nM) recorded at the two wavelengths 617 and 517 nm respectively. Panel D is a composite image. Panels H and I show the cells treated with paclitaxel+nanofibres (32 nM+4 µg/ml nanofibres). Panel G is a composite of the red and green images.
Figure 42:
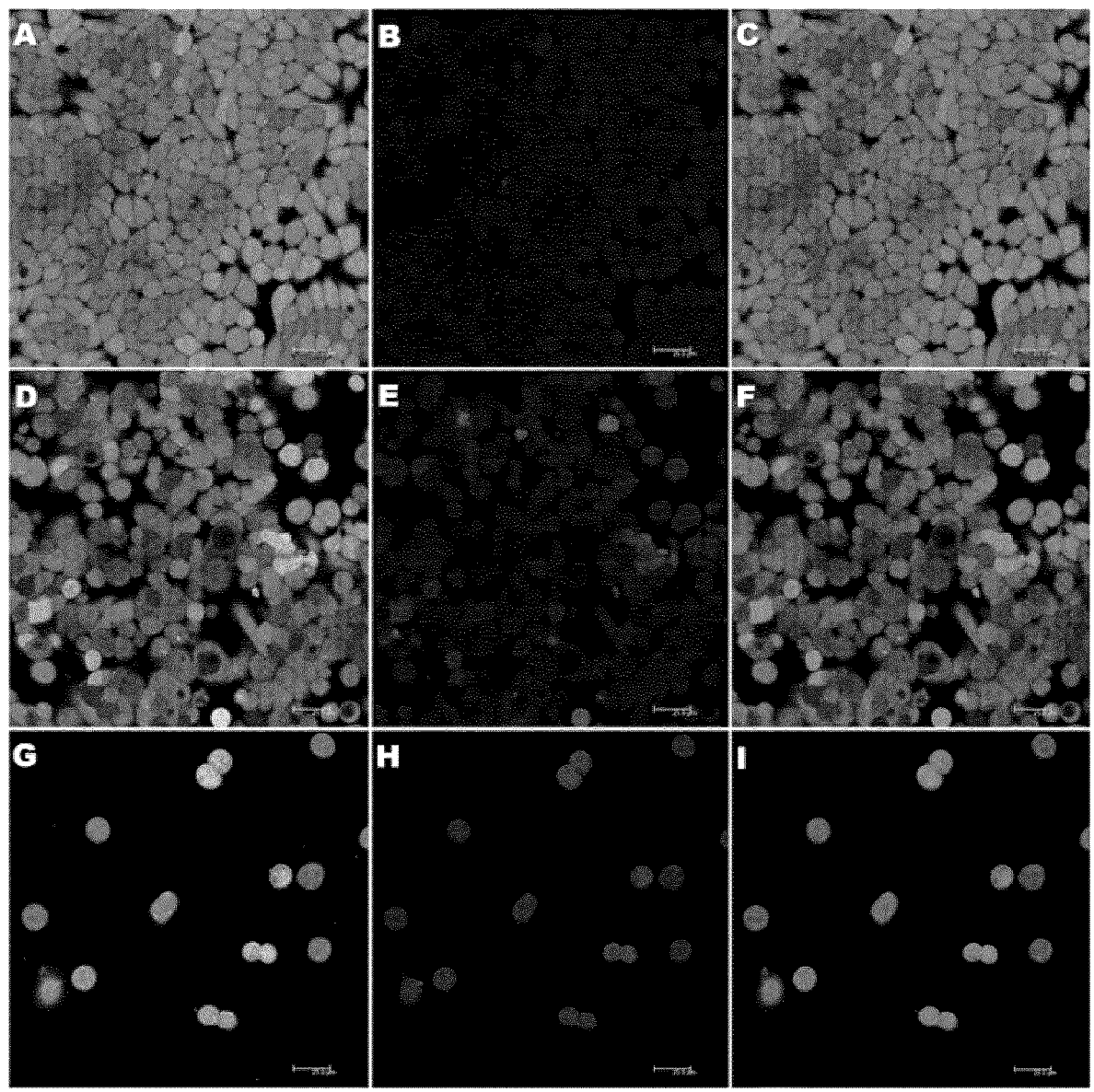
FIG. 42 shows cytotoxicity of Nanofibre-Paclitaxel to Human colorectal MDR cancer Cells (CRL 2158). Live-Dead cell analysis of CRL 2158 multidrug resistant colon cancer cells as were visualized under a confocal microscope is shown. The assay kit (Invitrogen) contains two fluorescent dyes, calcein AM ester (Ex 494 nm, Em 517 nm) which specifically enters live cells, gets de-esterified and stains the live cells green. The dying cells as well as dead cells are membrane compromised (leaky plasma membrane) and allows the entry of ethidium homodimer (Ex 517 nm/Em 617), which stains the nucleus red. The cells were observed at 517 nm (green channel) which differentiated live cells, and at 617 nm which enabled visualization of dead cells. The composite image of the two wavelengths show the cells in transition to loss of cell viability (A,D,G; yellow). Panels B,C represent control cells visualized at 617 nm (red, dead cells) and at 517 nm (green, live cells), respectively. Panel A is a composite image of untreated cells. Panels E, F represent the images of cells treated with paclitaxel (32 nM) recorded at the two wavelengths 617 and 517 nm respectively. Panel D is a composite image. Panels H and I show the cells treated with paclitaxel+nanofibres (32 nM+4 µg/ml nanofibres). Panel G is a composite of the red and green images.
Figure 43:
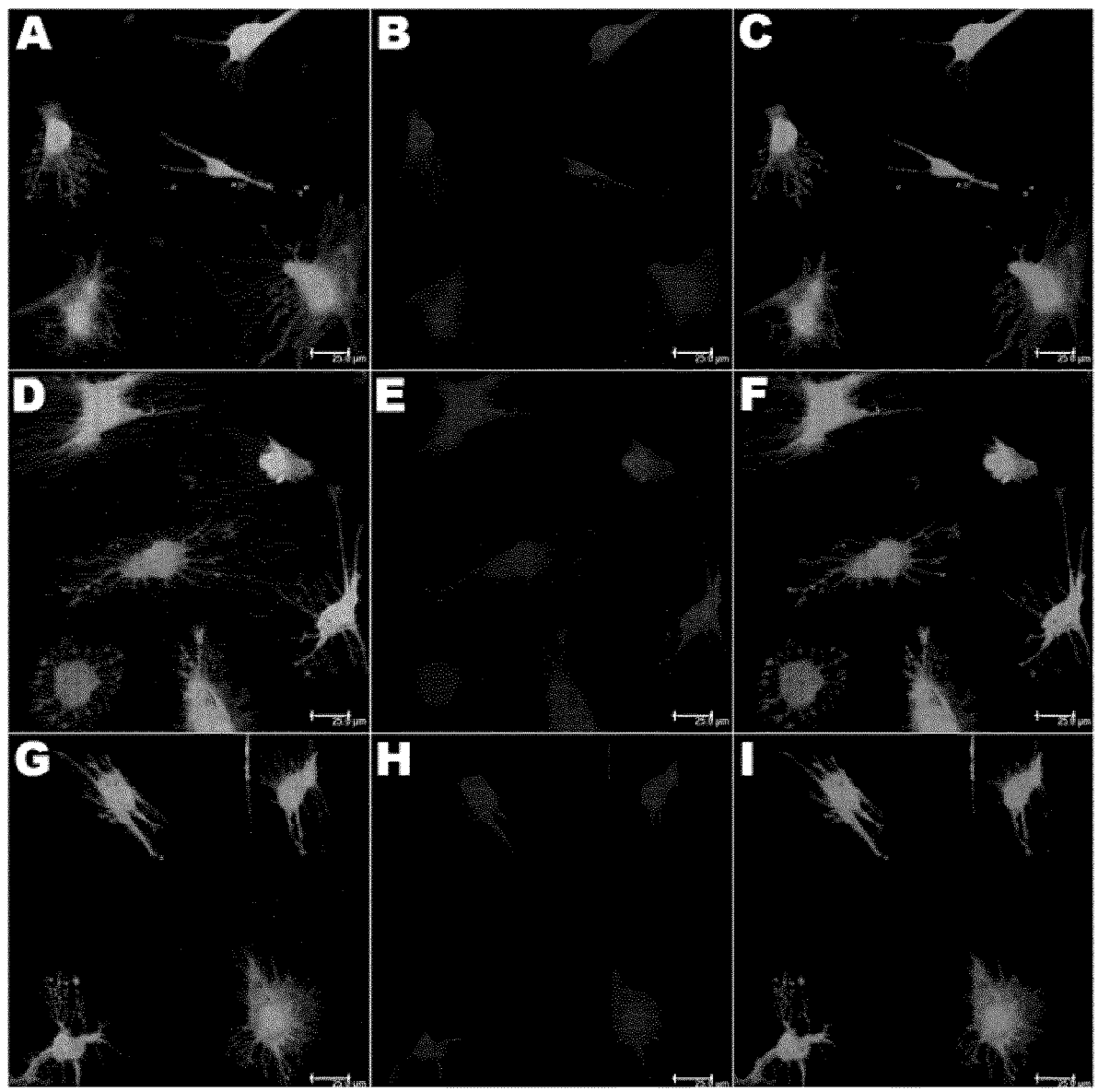
FIG. 43 shows cytotoxicity of Nanofibre-Paclitaxel to Normal Human Intestinal Cells (CRL 1790). Live-Dead cell analysis of CRL 1790 human colonic normal epithelial cells as were visualized under a confocal microscope is shown. The assay kit (Invitrogen) contains two fluorescent dyes, calcein AM ester (Ex 494 nm, Em 517 nm) which specifically enters live cells, gets de-esterified and stains the live cells green. The dying cells as well as dead cells are membrane compromised (leaky plasma membrane) and allows the entry of ethidium homodimer (Ex 517 nm/Em 617), which stains the nucleus red. The cells were observed at 517 nm (green channel) which differentiated live cells, and at 617 nm which enabled visualization of dead cells. The composite image of the two wavelengths show the cells in transition to loss of cell viability (A,D,G; yellow). Panels B,C represent control cells visualized at 617 nm (red, dead cells) and at 517 nm (green, live cells), respectively. Panel A is a composite image of untreated cells. Panels E, F represent the images of cells treated with paclitaxel (32 nM) recorded at the two wavelengths 617 and 517 nm respectively. Panel D is a composite image. Panels H and I show the cells treated with paclitaxel+nanofibres (32 nM+4 µg/ml nanofibres). Panel G is a composite of the red and green images.

Differentiating cytotoxicity by Live-Dead cell analysis: Further studies were performed to investigate delivery of paclitaxel using nanofibres into various cell lines. To further evaluate the efficiency of nanofibres in enhancing cytotoxicity of paclitaxel, live-dead cell analysis was conducted. Normal cells (CRL 1790), cancer cells (HT-29) and the MDR cells (CRL 2158) were cultured and exposed to paclitaxel alone, and paclitaxel along with nanofibres. The cells were cultured for 24 h at which time point, paclitaxel and the nanofibres were added to the culture. Live dead cell analysis was performed 24 h after exposure to the drug. The results are shown in FIGS. 41-43. FIG. 41 shows cytotoxicity of Nanofibre-Paclitaxel to Human colorectal cancer Cells (HT 29). Live-Dead cell analysis of HT 29 colorectal cancer cells as were visualized under a confocal microscope is shown. The assay kit (Invitrogen) contains two fluorescent dyes, calcein AM ester (Ex 494 nm, Em 517 nm) which specifically enters live cells, gets de-esterified and stains the live cells green. The dying cells as well as dead cells are membrane compromised (leaky plasma membrane) and allows the entry of ethidium homodimer (Ex 517 nm/Em 617), which stains the nucleus red. The cells were observed at 517 nm (green channel) which differentiated live cells, and at 617 nm which enabled visualization of dead cells. The composite image of the two wavelengths show the cells in transition to loss of cell viability (A,D,G; yellow). Panels B, C represent control cells visualized at 617 nm (red, dead cells) and at 517 nm (green, live cells), respectively. Panel A is a composite image of untreated cells. Panels E, F represent the images of cells treated with paclitaxel (32 nM) recorded at the two wavelengths 617 and 517 nm respectively. Panel D is a composite image. Panels H and I show the cells treated with paclitaxel+nanofibres (32 nM+4 μg/ml nanofibers, the fibers and appropriate amount of paclitaxel were mixed in 5% DMSO and added to the culture medium of cells and allowed to incubate for 12 h). Panel G is a composite of the red and green images. These results show use of nanofibres to deliver paclitaxel (complexed with the nanofibres, not conjugated) to cells, which resulted particular in cytotoxicity in the MDR cells, for example. Paclitaxel alone achieved an effect, but only in HT29 cancer cell line, not MDR. Nanofibres provided a better effect in MDR. It is contemplated that nanoparticles may be similarly efficient in taking up one or more drugs (or any other molecule of a drug/supplement nature), as supported in the earlier example using calcein and dylight.

FIG. 42 shows cytotoxicity of Nanofibre-Paclitaxel to Human colorectal MDR cancer Cells (CRL 2158). Live-Dead cell analysis of CRL 2158 multidrug resistant colon cancer cells as were visualized under a confocal microscope is shown. The assay kit (Invitrogen) contains two fluorescent dyes, calcein AM ester (Ex 494 nm, Em 517 nm) which specifically enters live cells, gets de-esterified and stains the live cells green. The dying cells as well as dead cells are membrane compromised (leaky plasma membrane) and allows the entry of ethidium homodimer (Ex 517 nm/Em 617), which stains the nucleus red. The cells were observed at 517 nm (green channel) which differentiated live cells, and at 617 nm which enabled visualization of dead cells. The composite image of the two wavelengths show the cells in transition to loss of cell viability (A,D,G; yellow). Panels B,C represent control cells visualized at 617 nm (red, dead cells) and at 517 nm (green, live cells), respectively. Panel A is a composite image of untreated cells. Panels E, F represent the images of cells treated with paclitaxel (32 nM) recorded at the two wavelengths 617 and 517 nm respectively. Panel D is a composite image. Panels H and I show the cells treated with paclitaxel+nanofibres (32 nM+4 μg/ml nanofibres). Panel G is a composite of the red and green images.

FIG. 43 shows cytotoxicity of Nanofibre-Paclitaxel to Normal Human Intestinal Cells (CRL 1790). Live-Dead cell analysis of CRL 1790 human colonic normal epithelial cells as were visualized under a confocal microscope is shown. The assay kit (Invitrogen) contains two fluorescent dyes, calcein AM ester (Ex 494 nm, Em 517 nm) which specifically enters live cells, gets de-esterified and stains the live cells green. The dying cells as well as dead cells are membrane compromised (leaky plasma membrane) and allows the entry of ethidium homodimer (Ex 517 nm/Em 617), which stains the nucleus red. The cells were observed at 517 nm (green channel) which differentiated live cells, and at 617 nm which enabled visualization of dead cells. The composite image of the two wavelengths show the cells in transition to loss of cell viability (A,D,G; yellow). Panels B,C represent control cells visualized at 617 nm (red, dead cells) and at 517 nm (green, live cells), respectively. Panel A is a composite image of untreated cells. Panels E, F represent the images of cells treated with paclitaxel (32 nM) recorded at the two wavelengths 617 and 517 nm respectively. Panel D is a composite image. Panels H and I show the cells treated with paclitaxel+nanofibres (32 nM+4 μg/ml nanofibres). Panel G is a composite of the red and green images.

These results provide information on the use of nanofibers (and potentially nanoparticles) for delivery of pharmaceuticals into the cells. In the present example, a cancer cell model HT 29, which is a colorectal cancer cell line, and a multidrug resistant colorectal cancer cell line CRL 2158, was used to study the efficacy of nanofiber-complexed paclitaxel. Cytotoxic effects of paclitaxel alone, and paclitaxel complexed with nanofibers were nearly the same in HT 29 cells. This cell line being non-multidrug resistant, is susceptible to cytotoxicity by paclitaxel alone. These cells also responded to nanofiber complexed paclitaxel, suggesting that the drug is released from the complex inside the cell, and not retained by the nanofiber. Multidrug resistance development is a major problem with cancer chemotherapy, where the cells actively pumps out the drugs, thus eliminating cytotoxicity. In the case of CRL 2158, the multidrug resistance capacity was revealed by its resistance to treatment with paclitaxel. However, multidrug resistance was overcome by complexing with the nanofibers where nearly 100% of the MDR cells showed cytotoxicity. Thus, complexing with nanofibers may provide an avenue to combat multidrug resistant cells. Interestingly, the normal intestinal cells (CRL 1790) did not show cytotoxicity to either paclitaxel alone or paclitaxel-nanofiber complex at the concentration of paclitaxel used, indicating the safety of such treatment to cells.

Interestingly, it was difficult to find cytotoxicity in normal colon cells (CRL 1790) either in the absence, or presence of paclitaxel, even when treated with the nanofibre (FIG. 43, panels A-I). These cells retained their morphology in the presence of paclitaxel (panels D, E, F), or paclitaxel and nanofibre (panels G, H, I), and no loss in membrane integrity could be observed.

A quantitative estimate of living cells in CRL 1790, HT 29 and CRL 2158 during cell culture in the presence or absence of paclitaxel, as well as paclitaxel and nanofibre, is given in the above Table of this Example. The normal cell line did not show any cytotoxicity to 32 nM paclitaxel either provided alone or in the presence of nanofibre. HT 29 cells showed high levels of cytotoxicity to paclitaxel as well as paclitaxel and nanofibre supplied together. CRL 2158 cells showed some degree of resistance to paclitaxel when supplied alone (~50% survival), while in the presence of nanofibres, the degree of survival was reduced to 4%. Live-dead analysis of cells was a more accurate way of determining the survival of cells during treatment with various components.

The above-mentioned results provide insight on the use of nanofibers (and potentially nanoparticles by extension) for delivery of pharmaceuticals into cells. In the present example, a cancer cell model HT 29 was used which is a colorectal cancer cell line, and a multidrug resistant colorectal cancer cell line CRL 2158, to study the efficacy of nanofiber-complexed paclitaxel. Cytotoxic effects of paclitaxel alone, and paclitaxel complexed with nanofibers were nearly the same in HT 29 cells. This cell line being non-multidrug resistant, is susceptible to cytotoxicity by paclitaxel alone. These cells also responded to nanofiber complexed paclitaxel suggesting that the drug is released from the complex inside the cell, and not retained by the nanofiber. Multidrug resistance development is a major problem with cancer chemotherapy, where the cells actively pumps out the drugs, thus eliminating cytotoxicity. In the case of CRL 2158, the multidrug resistance capacity was revealed by its resistance to treatment with paclitaxel. However, multidrug resistance was overcome by complexing with the nanofibers where nearly 100% of the MDR cells showed cytotoxicity. Thus, complexing with nanofibers provide an avenue to combat multidrug resistant cells. Interestingly, the normal intestinal cells (CRL 1790) did not show cytotoxicity to either paclitaxel alone or paclitaxel-nanofiber complex at the concentration of paclitaxel used, indicating the safety of such treatment to cells.

Discussion

The compositional and structural features of the nanoparticles and nanofibres formed during the homogenization of sour cherry fruits through self-assembly of cellular components including those originating from cell wall (cellulose, pectin, protein) and vacuolar components such as anthocyanins and malic acid is evaluated. Nanoparticles were spherical complexes about 50 to about 250 nm in diameter comprising a pectin core wound around by spiral fiber shaped structures. In contrast, nanofibres formed from ethanol-bleached cherry fruits were fiber-like (about 5 to about 10 nm in breadth) and micrometers in length. Anthocyanins and malic acid were removed from the fruits to facilitate nanofibre formation in these studies. Fruits low in anthocyanins may thus have a preferential tendency to form nanofibres according to the presently described methods. Because of the presence of anthocyanins in the nanoparticle, these show high antioxidant activity and thus may be a nutritionally relevant structural complex. In cytotoxicity tests, nanofibres showed much higher activity when complexed to anticancer drugs. The present Example describes potential functional effects of the nanoparticles and nanofibres in mammalian cells.

Polyphenols in food and medicine/interactions with drugs: Nutritional and dietary interventions have recently become potential complimentary strategies for downregulating various inflammatory diseases (Willcox et al., 2004). Dietary intake of fruits that are rich in polyphenols resulted in the downregulation of several inflammation markers in animal models and humans (Gonzalez-Galego et al., 2010). Consumption of fruit juices and products from grape and pomegranate at moderate level resulted in increased antioxidant function and the reduction of lipid peroxidation in the plasma (Garcia-Alonso et al., 2006; Jensen et al, 2008). The results from several studies show an inverse correlation between fruit and vegetable consumption and the expression of inflammation markers in blood, such as CRP (C-Reactive protein) and IL6 (interleukin 6) and several other inflammation markers such as CRP, IL-6, and TNF $\alpha$ (Holt et al., 2009). In a group of 120 men and women between the ages of 40-74, intake of polyphenol-rich blueberry extracts (300 mg/day for 3 weeks) caused a significant reduction in plasma levels of pro-inflammatory cytokines and chemokines (IL-4, IL-13, IL-8 and IFN-$\alpha$) of the NF-$\kappa$B pathway (Karlsen et al., 2007). Similarly, increased consumption of sweet bing cherries (280 g/day) resulted in lowered levels of CRP and NO (Kelley et al., 2006). Sour cherry polyphenols are strong inhibitors of the enzyme cyclooxygenase a key enzyme involved in inflammatory pathway (Chandra et al., 2002). A study involving elderly 70-year old men, increased intake of food rich in antioxidants resulted in lowered cyclooxygenase, cytokine-mediated inflammation and oxidative stress (Helmersson et al., 2009). Thus polyphenol-containing foods have the property of downregulating the inflammatory pathway and thereby prevent chronic degenerative diseases such as cancer, cardiovascular diseases, and neurodegenerative diseases.

A major issue that has been raised regarding the biological effect of polyphenols is that these are believed to be very poorly absorbed (0.5%-1.5%) through the gastro-intestinal system. As well, alkalinisation of food during the transit from stomach to intestine by mixing with pancreatic and bile juice, destabilizes anthocyanin structure resulting in ring opening and partial degradation.

In the present Example, effective internalization of nanoparticles (and nanofibres) by human cells is demonstrated. Since the anthocyanins are stabilized in the nanoparticle, and may be resistant to pH changes, internalization of nanoparticles may be an alternative form of polyphenol delivery in the GIT. Thus, the formation of nanoparticles containing polyphenols may enhance the bioavailability of polyphenols, as they may bypass the typical carrier mediated absorption in the jejunum, enabling their absorption in pre-intestinal sites. Complex formation may also help transport the polyphenols to downstream areas of intestine such as the distal parts of small intestine and colon where they may exert beneficial effects. In certain embodiments, it is contemplated that these may involve antioxidant function to protect the intestinal tissue from reactive oxygen species generated by colonic microbiota, modulate cell proliferation, and/or enable the formation of metabolites that may provide additional health benefits.

Drug delivery, importance of Bionanoparticles: Tremendous advances have been made in developing nanotechnology-based strategies in medicine and health, utilizing both engineered nanomaterials as well those prepared from naturally existing biomolecules. Detection of cancer sites by in vivo targeting of nanostructures and nanostructure conjugates is an area of great interest, however, more information regarding the mechanism of uptake and biodistribution is needed. Nanostructures and their conjugates are believed to accumulate through multiple mechanisms including endocytosis, non-specific entry, vesiculation etc. (Iversina et al., 2011). However, recent studies also bring evidences for specific uptake mechanisms. SWNTs were found to be specifically sequestered into an immune cell group, Ly6c monocytes (Smith et al., 2014). Conjugation of the SWNTs with a targeting peptide RGD further enhanced entry of nanostructures into the monocytes. The monocytes thus provided the delivery of SWNTs through a Trojan horse mechanism into the tumour site, enabling the accumulation of nearly 25% of the SWNTs at the target site. Thus, targeting tumour cells with immune cells may provide an effective strategy for cancer drug delivery.

Mitochondria is a critical organelle involved in determining the survival or apoptosis of cancer cells. Disrupting mitochondrial energy generation is a key step in directing the cancer cells to apoptotic pathways. Targeting apoptosis inducing peptides to mitochondria is of great interest to kill cancer cells, however, the limitations include the non-specificity of delivery and lack of solubility. Increasing delivery of apoptosis inducing, mitochondria targeting amphipathic tail-anchoring peptides (ATAP) to malignant brain and metastatic cancer cells by conjugating with magnetic core-shell nanoparticles was found to be an efficient way of enhancing chemotherapeutic efficacy (Shah et al., 2014). Delivering siRNAs for simultaneous silencing of several genes that are up-regulated in cancer cells could be achieved through polymeric nanostructures synthesized from low molecular weight polyamines and lipids (Dahlman et al., 2014) in vascular endothelial cells in mouse models (Dahlman et al., 2014).

Physicochemical characteristics such as composition, size, surface charge distribution, etc., can affect cellular uptake of nanostructures. In a recent study (Agarwala et al., 2013) have reported that, apart from these characteristics, the very shape of the nanostructures can influence their uptake. In this study, mammalian epithelial cells, endothelial cells and immune cells were observed to internalize negatively charged hydrophilic disc-shaped nanostructures preferentially. Nanodiscs with a high aspect ratio were preferred over nanodiscs of lower aspect ratio and rod shaped nanostructures. Spherical nanostructures are also internalized with a lesser efficiency even when their sizes are reduced. Cabral et al (2011) has also reported that accumulation of nanostructures in tumours is also dependent on size. Nanostructure internalization process may be complex involving interactions between the nanostructures and the membrane, energy for cell adhesion and membrane deformation, as well as the nanostructure concentration at the cell membrane surface.

The nanoparticles and nanofibres described herein isolated from cherry are structurally complex. Lyophilized powder of the nanoparticle was resistant to acid (4M HCl), alkali (1M NaOH), and freezing. Both nanoparticles and nanofibres formed complexes with small molecules (dyes, drugs), which did not dissociate. Drugs such as paclitaxel may also be conjugated with these structures. Paclitaxel is an effective drug for treatment against cancer. These studies indicate that effectiveness of paclitaxel may be enhanced when provided to mammalian cells along with nanofibres. Moreover, multidrug resistant cancer cells (CRL 2158) showed resistance to paclitaxel. When provided along with nanofibres, paclitaxel showed similar cytotoxicity to MDR cells just as the normal HT 29 cancer cells. Thus, application of drugs along with nanofibres may bypass the paclitaxel exclusion, enhancing its efficacy. An interesting aspect is that the increase in efficiency may result from pure associations between nanofibres and paclitaxel. Apart from complex formation with organic molecules, nanofibres and nanoparticles may be able to bind to metals such as iron, zinc, Mg, Se, and/or others. It is contemplated that in certain embodiments, with the higher internalization efficiency of the nanoparticles and nanofibres, the efficiency of metal ion intake may be enhanced, thus reducing dosage.

The present Example results suggest that the nanoparticles and nanofibre structures have functional applications. Nanoparticles by themselves may be a high efficiency antioxidant, and may be suitable for therapeutic applications where localized antioxidant function is desirable. The nanofibres were highly potent in internalization of conjugated or complexed drugs.

Internalization of paclitaxel-nanofibre complexes may bypass the drug elimination capacity of multidrug resistant cancers, making them as susceptible to cancer drugs just as the cancer cells that are killed by simple drugs. Thus, results indicate that both the nanoparticles and nanofibres may have notable potential for enhancing the efficiency of cancer treatment, for example.

Results described in detail herein indicate that preparation of particular nanoparticles, nanofibres, and food powders may be achieved by processing of (for example) ripe fruits involving homogenization, during which the cell wall matrices such as cellulose, pectin and proteins, which are in a partially disassembled state, may spontaneously assemble into, for example, well-structured nanoparticles incorporating polyphenols (antioxidants, modulators of cell metabolism and gene expression), organic acids such as malic acid, and peptides resulting from proteolysis.

Nanoparticles with similar structure are formed during similar processing of other fruits. In blueberry for instance, the nanoparticles formed are structurally similar to those formed in sour cherry. In the present Example, the nutritional and antiproliferative activities of nanoparticles and nanofibres from sour cherry are investigated.

Nanotechnology has made great strides in medicine especially in targeted drug delivery. Though the use of engineered nanomaterials has been complicated because of toxicity and inability of the system to eliminate nanomaterials efficiently (Maynard, 2006; Lewinski et al., 2008; Kunzman et al., 2011; Yamashita et al., 2011), the use of nanoparticles derived from biological materials that are easily degradable in biological systems may provide novel avenues of targeted drug delivery.

In the present Example, the ability of nanoparticles (and nanofibres) isolated from sour cherry fruits to internalize into normal and cancer cells, and their ability to cause cytotoxicity when containing anthocyanins, or the anticancer drug paclitaxel, is described. The nanofibres were derived from sour cherry fruits that were devoid of anthocyanins. As the building components of the nanofibres are components derived from food, a pharmaceutical application of the food components may be considered to be less damaging to normal cells than when drugs conjugated with synthetic components are ingested, for example. As well, without wishing to be bound by theory, internalization of these structures by cells suggests that components (pectin, peptides, anthocyanins, organic acids, etc.) may have a different form of entry from the GIT. It may be that such nanoparticles may serve as facilitators for the absorption of anthocyanins which are very poorly absorbed as simple molecules, but show great antioxidant activity and cytotoxic potential under in vitro conditions.

Example 4—Studies of Food Powder Preparation, Structure, and Applications

Food Powder Preparation and Structural Investigation

In this Example, functional food powders made from extracts of broccoli, sour cherry, almond, soybean and/or turmeric, or any combination thereof (and particularly, all of these components), through high shear blending and nanospray-drying, are described. Each particle of the powder contained a substantially uniform blend of nutraceuticals originating from the raw materials (Sulphoraphane, indole-3-carbinol, polyphenols, phytosterols, isoflavones, curcumin etc.); as compared to a blend of individual dry powders originating from each raw component.

The food powder, in a form demonstrating high antioxidant activity, provided high bioavailability of ingredients, and in general showed a broad spectrum anti-inflammatory activity. Thus, consumption of the food powder may provide protection from developing chronic diseases, particularly when used in conjunction with appropriate healthy lifestyle.

Consumption of fruits and vegetables at recommended levels, in conjunction with an active healthy life style is well recognized to reduce the development of chronic diseases such as obesity, type II diabetes, cancer, joint inflammations etc. However, the consumption of adequate amounts of fruits and vegetables in the general public is lacking. Because of the current lifestyles, the incidence of obesity has increased, especially childhood obesity. In an effort to enhance the dietary intake of the active components commonly available in fruits and vegetables, the present food powders have been developed, with ingredients in a bioavailable form. The bioavailability of nutraceutical components is generally low from fruits and vegetables due to several reasons. With the presently described food powders, it may be possible to increase the bioavailability, and thereby, enhance the efficacy of these components.

The major food components (and some nutritional agents thereof) used in this Example include the following:

Broccoli—Contains the nutraceutical components (i.e. nutritional agents) such as precursors of sulphoraphane and indole-3-carbinol. Both components enhance the innate antioxidant system (KEAP-1/NRF2/ARE pathway) and phase 2 enzymes involved in elimination of xenobiotics.

Sour Cherry—Sour cherry contains cyanidin-3 glucoside/rutinoside as the major polyphenol. Sour cherry extract has been shown to be strongly anti-inflammatory to joint inflammations.

Almond—Almond contains essential unsaturated fatty acids and phytosterols and may reduce biosynthesis of cholesterol. It is also a high source of vitamin E.

Soymilk—Soybean is a source of isoflavones, and protein.

Turmeric—Turmeric is a spice and was recognized for its anti-inflammatory property. Turmeric contains curcumin, which is a strong cyclo-oxygenase inhibitor. Recent research has also confirmed its ability to reduce obesity in experimental in vivo models.

Materials and Methods: Food powder was prepared by mixing several components, along with sour cherry extracts (which is a main component in its preparation). Extracts of sour cherry and broccoli florets were prepared independently by blending these in water (1 g to 2 ml ratio) using a Reicht high speed blender at 4000 rpm for 5 minutes. The homogenate was filtered through 4 layers of cheese cloth and the debris discarded. The homogenated were stored chilled until use.

One hundred ml of sour cherry extract, 100 ml of broccoli extract, 100 ml of almond milk (~8% w/v; Silk™ Brand; distributed by Whitewave Foods, Colorado, USA); 50 ml soymilk (~10%), and 5 g turmeric powder were blended together in a Reicht high speed blender at 5000 rpm for 5 minutes. The blend was stored in cold for 2 hours and decanted. The solution was adjusted to a dilute consistency with water and subjected to nanospray drying as described earlier in Example 1 using similar settings. The dried powder was collected and stored cold in nitrogen atmosphere at −20° C. in brown bottles.

Results and Discussion: Experiments were preformed to prepare and structurally characterize food powders.

As described herein, the presently described food powders may be prepared with generally any suitable plant tissue which may be used for preparing nanoparticles and/or nanofibres as described herein. In certain embodiments, food powder may be prepared form a fruit, vegetable or another plant tissue or product capable of forming carbohydrate-based nanoparticles or nanofibers as described herein. Food powders may be prepared in any suitable medium comprising aqueous, organic, or a combination thereof. The food powders may, in certain embodiments, further comprise a nutrient-containing material (or a nutrient) that is desired to be included in the food powder product (which will typically be tailored for the intended application of the food powder), and may include fresh, processed, or concentrated powders, either alone or in any desired combinations by weight or volume.

In certain embodiments, food powder may be prepared by homogenization of the food powder starting materials. For example, homogenization may be achieved using a blender, preferably operating at a high rpm and capable of generating high shear forces, or any other suitable machine capable of high performance mixing such as a sonolator.

In certain embodiments, the food powder may be filtered to remove debris, or debris may be otherwise removed from the homogenized mixture. By way of example, a centrifugal device or filtration device (for example, a membrane filtration device, or tangential flow filtration device) capable of filtering the debris (i.e. particulate matter that has not gone into the homogenate and settles under gravity) may be used to remove debris.

In certain embodiments, the food powder may then be dehydrated, lyophilized, spray-dried, nano-spray-dried, or otherwise dehydrated or dried. By way of example, equipment that is capable of removing water (or another solvent being used) may be used, which may include a nanospray drier, or a lyophilizer for aqueous samples, or more preferably a high efficiency spray drier capable of spray drying large volumes may be used, for example. In certain embodiments, the drier may operate under reduced pressure.

In certain embodiments, the food powders described herein may be prepared from a plant tissue which is suitable for preparing a nanoparticle and/or a nanofibre as already described in detail herein, in combination with a nutrient-containing material. As will be understood, the nutrient-containing material will typically be tailored for the intended application of the food powder, and may include fresh, processed, or concentrated powders, either alone or in any desired combinations by weight or volume. In certain embodiments, the food powder may be developed with nutrient-containing components or with components targeted to address a particular physiological condition (such as a chronic condition, for example), and such nutrient-containing material may have preventive and/or curative properties, for example. As will be understood, the term nutrient as used herein may include any suitable active agent or compound appropriate for the particular indication (or material comprising said active agent or compound), and is not limited to those entities typically considered as nutrients such as those found in food. By way of example, in certain embodiments, a nutrient may include any suitable natural (or unnatural) ingredient having a health benefit.

In certain embodiments, the food powder may comprise:
1. Sour cherry (or sour cherry extract), or an another fruit or vegetable (or extract thereof) which is capable of forming carbohydrate-based nanoparticles or nanofibers as described herein;
2. A hydrophobic component (such as, but not limited to, almond milk) which can incorporate hydrophobic molecules from the added substances (other examples being coconut milk, or milk derived from edible nuts, for example); and
3. A nutrient-containing material (such as a functional food extract, for example) that contains one or more bioactive ingredient/ingredients tailored for the desired application of the food powder, for example.

Some non-limiting examples of nutrient-containing materials may include one or more of the following active compounds and/or plant families:
Carotenoids (i.e. beta-carotene, lycopene, lutein and other xanthophylls, astaxanthin, etc.);
Annonacins (i.e. polyketides derived from Annona fruits with anticancer properties);
Boswellia (which may act in conjunction with curcumin providing added anti-inflammatory function);
Ashwagandha (a herbal component containing with anoliides with anti-stress, and cancer preventive properties, primarily with a steroid structure);
Ginger family members that may include, for example, edible ginger (*Zingiber officinalis*), mango ginger (*Curcuma amada*), or others containing any of several bioactive ingredients including gingerols and shogaols; *Curcuma longa* (i.e. turmeric, containing curcumin);
Cannabinodiols (which are the medicinally active ingredients of *Cannabis* sp. without hallucinogenic activity);
Fructo-oligosaccharides and galacto-oligosaccharides, as well as inulin from Jerusalem artichoke, to enhance prebiotic content;
Piperaceae members such as *Piper nigrum* and its wild relatives containing piperine and several derivatives; and/or
any other suitable ingredient(s) (such as, but not limited to, those derived from plants) not already listed above; and/or any extract, derivative, product isolated therefrom, or material or plant tissue containing such component.

In this Example, a food powder was prepared from the following starting materials:
1. An aqueous extract of sour cherry;
2. A homogenate of almonds commercially available as almond milk;
3. A homogenate of soybeans commercially available as soymilk;
4. An aqueous extract of broccoli; and
5. Turmeric powder.

These starting materials were blended in a high speed blender (Recht, ATS scientific, Burlington) at 4500 rpm; and nanospray dried in a Buchi Nanospray drier under recommended settings. The volumes/weights used included:
One hundred ml of sour cherry extract (1-2 mg/ml polyphenol equivalent was used, although it is contemplated that a concentration ranging from about 0.1 mg/ml to a completely saturated solution of polyphenols in water or other solvent may be used);
One hundred ml of almond milk at ~8-10%, w/v;
50 ml of soymilk at about ~8-10% w/v;
One hundred ml of broccoli extract; and
5 g of turmeric powder.

As will be understood, while the volume of sour cherry extract was maintained at 100 ml in this Example, in other embodiments it is contemplated that the volume/weight of sour cherry and/or other ingredients may be varied as desired, and additional components may be included in any suitable proportions.

Figure 44:
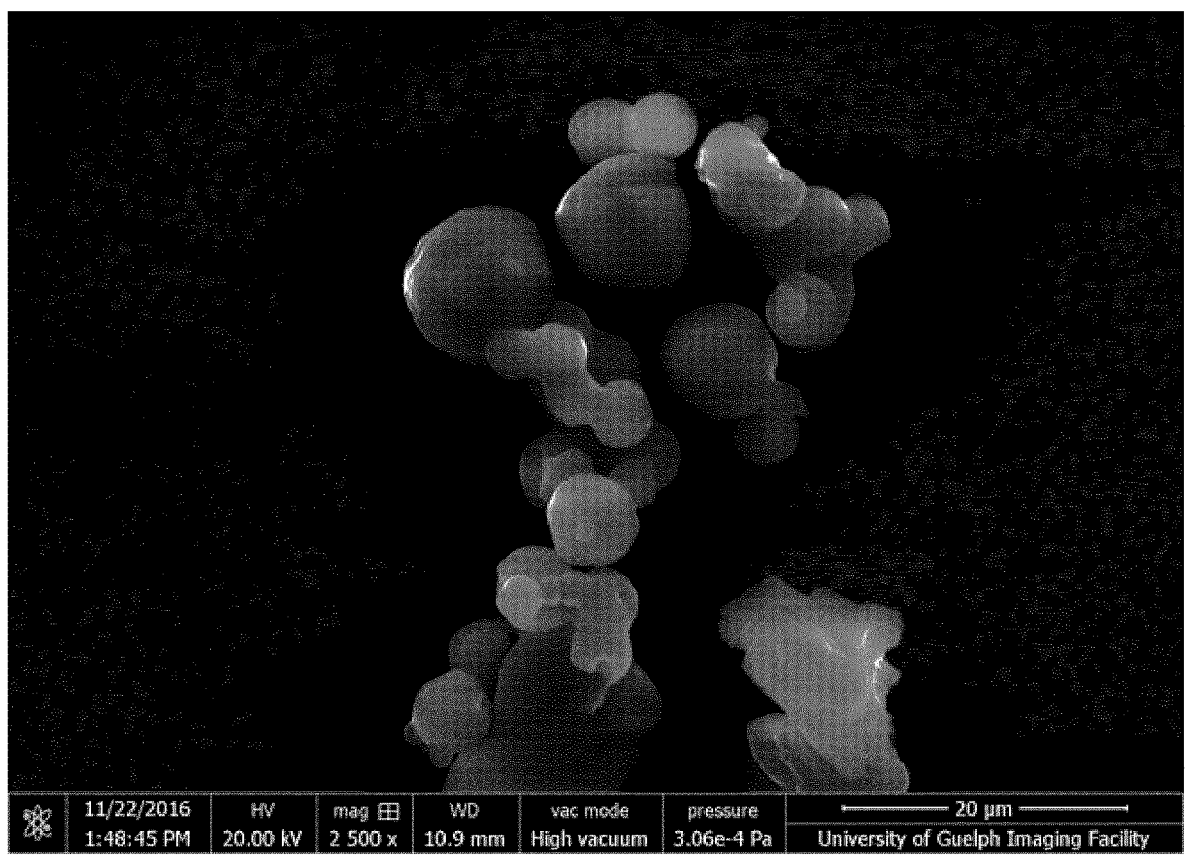
FIG. 44 shows a scanning electron micrograph of food powder prepared from sour cherry, broccoli and other food ingredients. Food powder was prepared by blending a mixture of homogenized solutions of individual components, and nano-spray drying of the blended mixture, as described in Example 4.

FIG. 44 shows a scanning electron micrograph of a food powder prepared from sour cherry, broccoli and other food ingredients as described herein. Food powder was prepared by blending a mixture of homogenized solutions of individual components, and nano-spray drying of the blended mixture. The food powder was prepared using the specific mixture described immediately above.

Figure 45:
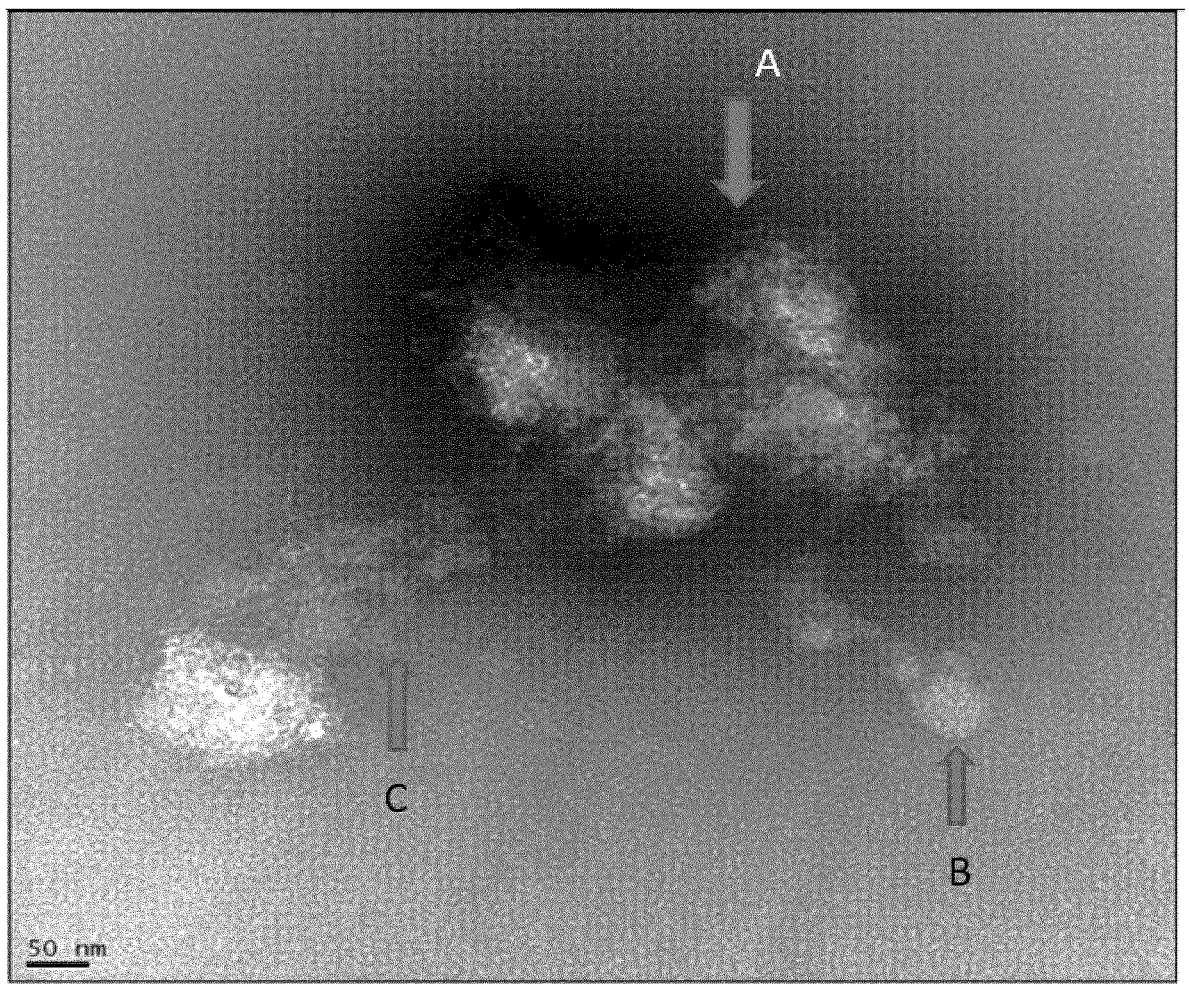
FIG. 45 shows a transmission electron micrograph of an aqueous solution of the food powder showing ultrastructural characteristics. The food powder appears as oblong to spherical masses of tightly wound fibre structures (see Arrow designated A). The structure resembles a nanoparticle without a structural organization as observed in sour cherry nanoparticles (see FIG. 17). However, a globular structure resembling a spherical core (Arrow designated B) can be observed with fibre structures emanating therefrom. The spirally organized structures (arrow C) is analogous to the spiral fibres observed in nanoparticles. A fifty microliter aliquot of the food powder suspension was placed on a glass slide, and a carbon coated grid was floated on the solution with the coated side down, for 30 seconds. The grid was blotted dry at the edges and stained with a 0.1% solution of Uranyl acetate. The picture shows a macroaggregate of food powder particle that is undergoing dissolution into much smaller nanoparticles (Arrow designated A). Arrow designated B shows the core of the nanoparticle with unwound fibres. The spiral nature of the winding fibres can be seen as denoted by arrow C.

FIG. 45 shows a transmission electron micrograph of an aqueous solution of the food powder showing ultrastructural characteristics. FIG. 45 depicts the same food powder as depicted in FIG. 44 described above. A fifty microliter aliquot of the food powder suspension was placed on a glass slide, and a carbon coated grid was floated on the solution with the coated side down, for 30 seconds. The grid was blotted dry at the edges and stained with a 0.1% solution of Uranyl acetate. The food powder appears as oblong to spherical masses of tightly wound fibre structures (see Arrow designated A). The structure resembles a nanoparticle, but without a structural organization as observed in sour cherry nanoparticles (see FIG. 17). Indeed, the structure could be considered as a nanosphere, defined by fibrous structures winding about themselves to form the nanosphere-like structure (not unlike a tangled ball of string, with one or more fibres tangled into a ball-like structure). A globular structure made of nano fibres wound around themselves (Arrow designated B) can be observed with fibre structures emanating therefrom. This structure is analogous to that of a nanosphere, where the fibres are wound together and capable of adsorbing several types of functional ingredients. The spirally organized structures (arrow C) is analogous to the spiral fibres observed in nanoparticles. In this food powder example, the food powder contains nutritional agents contributed by the broccoli extract and turmeric powder components. These nutritional agents are complexed with the above-described fibrous structures, and may contribute to food powder formation and/or resultant structure.

Food Powder Applications Using Obese Mouse Model In Vivo

Materials and Methods

Expression Analysis-Chemicals and reagents. L-Type Triglyceride M kit was purchased from Wako Diagnostics (Osaka, Japan and Neuss, Germany). RNeasy Plus kit for RNA isolation was from Qiagen (Valencia, CA, USA). The High-Capacity cDNA Reverse Transcription Kit for cDNA preparation was from Applied Biosystems (Foster city, CA, USA). RT$^2$ Profiler™ PCR Array Mouse Inflammatory Cytokines & Receptors kit was from Qiagen (Valencia, CA, USA). iQ SYBR Green Supermix was from Bio-rad (California, USA).

Food Powder treatment. The experiments were performed with 36 to 48 weeks old Pcyt2 knock out mouse and littermate controls. Untreated groups of KO and control mouse (n=3-6 each) were ingesting (via gavage) 100 uL water daily and treated groups of KO and control mouse (n=3-6 each) administered 100 μg of the food powder (in 100 uL water) 5 times per week. Oral gavage for all groups lasted 8 weeks. Trials were repeated twice, and at the end of trials the mouse were sacrificed and used for blood and tissue analysis.

Total RNA Isolation and Gene Expression. Total RNA was isolated using the RNeasy Plus kit (Qiagen, Valencia, CA, USA) and cDNA was prepared using the High-Capacity cDNA Reverse Transcription Kit (Applied Biosystems, Foster city, CA, USA). RT-qPCR was done using $RT^2$ Profiler™ PCR Array Mouse Inflammatory Cytokines & Receptors kit suitable for Bio-rad CFX96 RT-qPCR machine. $RT^2$ Profiler™ PCR Arrays in 96-well plates contain primer assays for 84 pathway or disease-focused genes. Genes of interest were analyzed in the exponential phase of PCR amplification, using the optimal amount of cDNA and the reaction cycle number. Each gene level is expressed relative to the internal B2 m (Beta-2-Microglobulin) control. The experiments were performed by using liver samples collected from Pcyt2+/– and Pcyt2+/+female mice. Gene levels are expressed as fold changes relative to the controls. The RT-qPCR results were analyzed by using the comparative ΔΔCt method.

Statistical analysis. Statistical analysis was completed using Prism GraphPad. Data are expressed as mean±S.E. Statistical significance was calculated using either Student's t test (P values <0.05 were considered significant) or multifactorial ANOVA. When a significant effect was found, post hoc comparisons were carried out using the Tukey's honestly significant difference test. Differences were considered significant at P<0.05.*

Results and Discussion: Experiments were preformed to investigate application of food powders as described herein. For these studies, the food powder prepared in the studies described immediately above was used.

Figure 46:
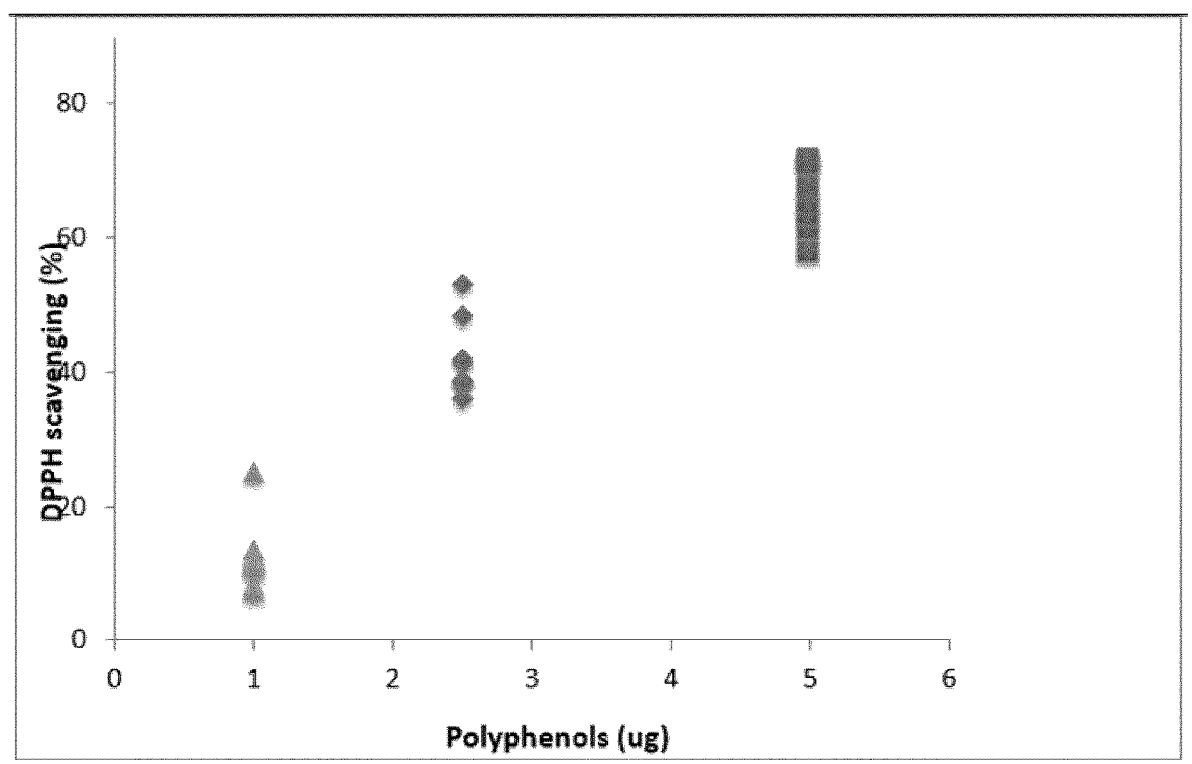
FIG. 46 shows evaluation of the antioxidant capacity of the food powder. The powder was dissolved in water and the antioxidant capacity of the solution was determined by estimating the DPPH Radical scavenging capacity of solution as polyphenol equivalent (estimated by Folin-Ciocalteau reagent) in micrograms. A 0.1 mM Folin-Ciocateau reagent was prepared in methanol, and the food powder solution was added in the specified amounts. The antioxidants were allowed to react with 1 ml of DPPH reagent, and the absorbance (purple, 517 nm absorption) was monitored. The decline in 517 nm absorbance was noted and expressed as % quenching in comparison to a control without polyphenol. Trolox was used as a positive control at the same concentrations as polyphenols and showed a TEAC value of 1. Each point at a concentration represents an individual sample of food powder prepared.

FIG. 46 shows evaluation of the antioxidant capacity of the food powder. The powder was dissolved in water and the antioxidant capacity of the solution was determined by estimating the DPPH Radical scavenging capacity of solution as polyphenol equivalent (estimated by Folin-Ciocalteau reagent) in micrograms. A 0.1 mM Folin-Ciocateau reagent was prepared in methanol, and the food powder solution was added in the specified amounts. The antioxidants were allowed to react with 1 ml of DPPH reagent, and the absorbance (purple, 517 nm absorption) was monitored. The decline in 517 nm absorbance was noted and expressed as % quenching in comparison to a control without polyphenol. Trolox was used as a positive control at the same concentrations as polyphenols and showed a TEAC value of 1. Each point at a concentration represents an individual sample of food powder prepared. The results show strong antioxidant capacity of the food powder. Since the bioavailability of antioxidant components (bound to the nanofiber backbone) is likely to be higher, these results suggest the food powder may have a greater impact in terms of scavenging free radicals and reducing inflammation as compared to the components that are free in solution.

Figure 47:
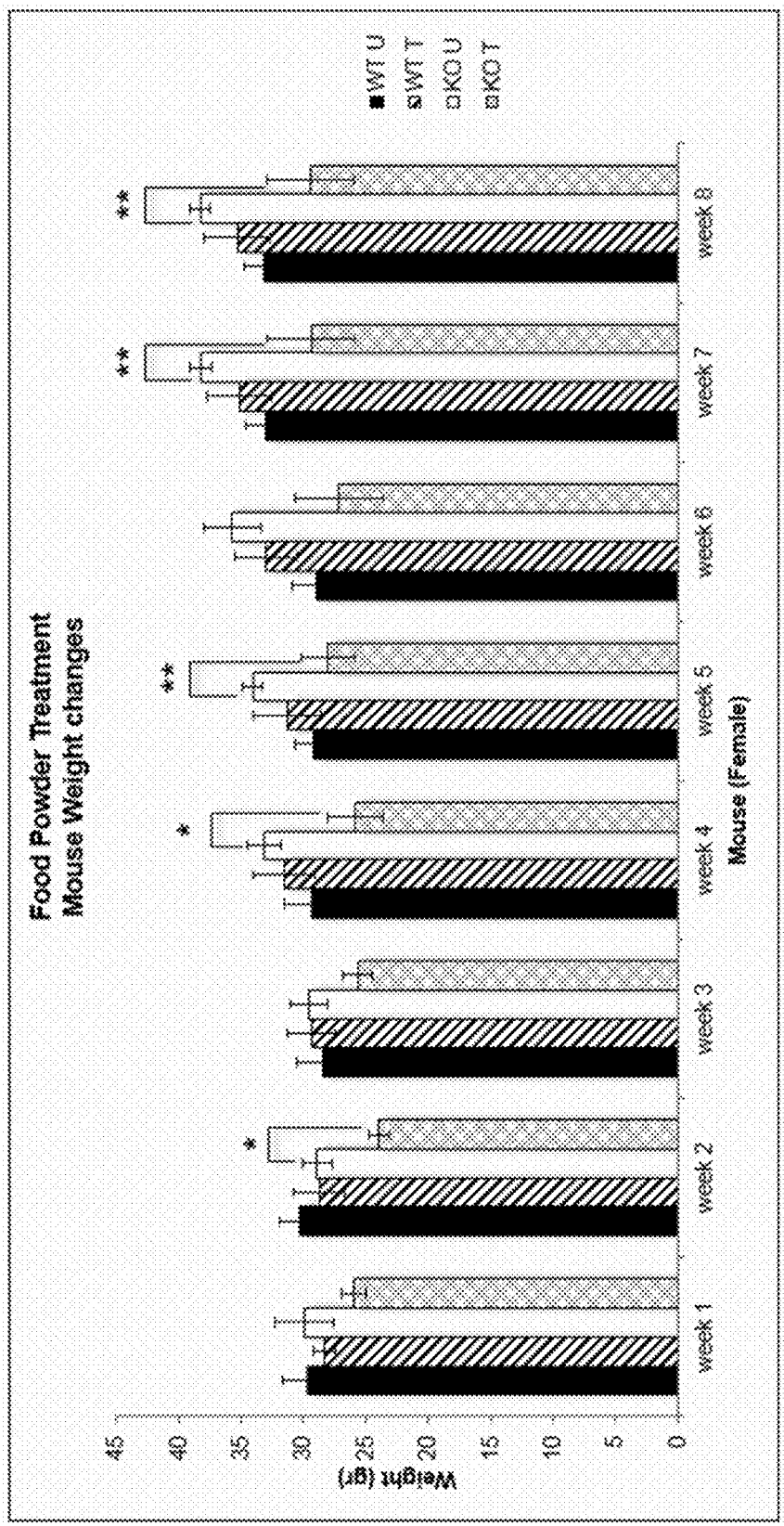
FIG. 47 shows evaluation of body mass changes in wild type (WT) and ethanolamine knockout mice (KO) treated with food powder and water. The experiments were performed with 24 weeks old Pcyt2 knock out mice (KO) and littermate controls. Untreated (U) groups of KO and wild type mouse (n=4-6 each) were given 100 µL of water by gavage at the time of treatment. The treated (T) groups of KO and wild type (WT) mice (n=4-6 each) were administered with 100 µg of the food powder (in 100 uL water) 5 times per week. Oral gavage for all groups lasted 8 weeks. At the end of the treatment period, the mice were sacrificed and blood and tissue samples were collected for analysis. The stars indicate significantly different values (*-$P<0.05$; **-$P<0.01$)

FIG. 47 shows evaluation of body mass changes in wild type (WT) and ethanolamine knockout mice (KO) treated with food powder and water. The experiments were performed with 24 week old Pcyt2 knock out mice (KO) and littermate controls. Untreated (U) groups of KO and wild type mouse (n=4-6 each) were given 100 μL of water by gavage at the time of treatment. The treated (T) groups of KO and wild type (WT) mice (n=4-6 each) were administered with 100 ug of the food powder (in 100 uL water) 5 times per week. Oral gavage for all groups lasted 8 weeks. At the end of the treatment period, the mice were sacrificed and blood and tissue samples were collected for analysis. The stars indicate significantly different values (*-P<0.05; **-P<0.01). These results suggest that the food powder treatment may have a significant effect in preventing weight gain. In systems that may be compromised genetically resulting in obesity, the food powder consumption may be an option in maintaining weight. Food powder treatment may also serve as an intervention in those who develop obesity because of unhealthy eating habits.

Figure 48:
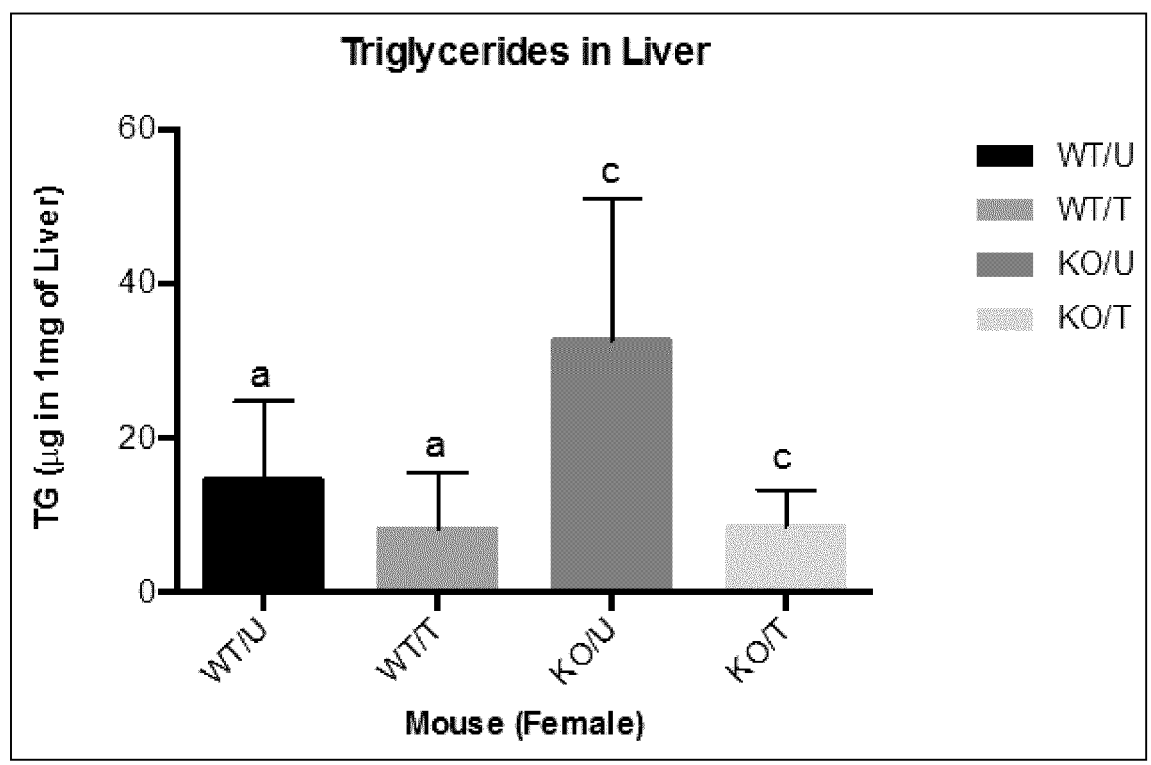
FIG. 48 shows effect of food powder treatment on changes in triglyceride levels in the liver. The tissue originated from the trial described in Example 4. Triglyceride levels of liver tissue were estimated by procedures described in using Wako L-type TG M assay kit (Wako Life Sciences, CA, USA). There is no significant reduction in triglyceride levels in both the wild-type and the ETKO mice subjected to food powder treatment. Values are Mean±SEM from three separate samples. There appears to be a trend in the reduction of triglycerides in the food powder treated obese mice. A reduction in liver triglycerides by food powder treatment may be beneficial in individuals showing metabolic syndrome. Abbreviations: Wild type Untreated (WT/U), Wild type treated (WT/T), Knock out Untreated (KO/U) and Knock out Treated (KO/T)

FIG. 48 shows effect of food powder treatment on changes in triglyceride levels in the liver. Triglyceride levels of liver tissue were estimated by procedures described in using Wako L-type TG M assay kit (Wako Life Sciences, CA, USA). There is no significant reduction in triglyceride levels in both the wild-type and the ETKO mice subjected to food powder treatment. Values are Mean±SEM from three separate samples. There appears to be a trend in the reduction of triglycerides in the food powder treated obese mice. A reduction in liver triglycerides by food powder treatment may be beneficial in individuals showing metabolic syndrome and tendency to develop obesity. Accumulation of lipids in the liver is a syndrome associated with fatty liver disease. It is possible that the food powder components may at least partially reverse such syndrome and associated health issues.

Figure 49:
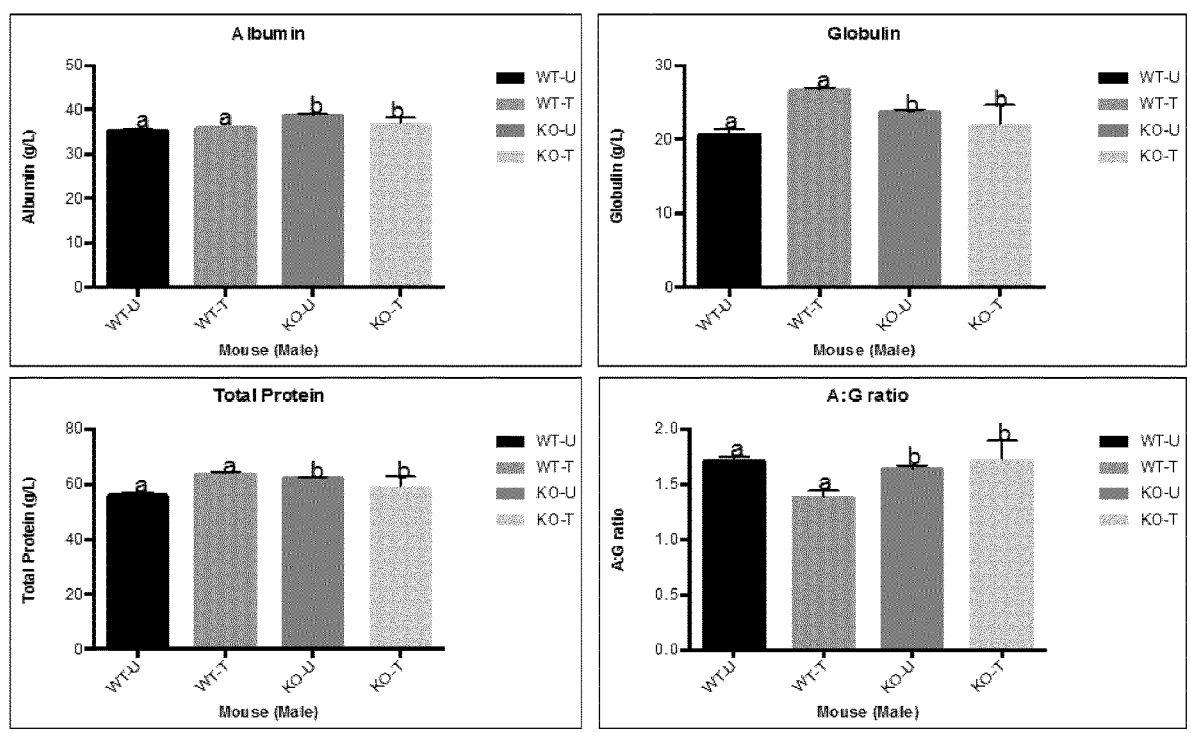
FIG. 49 shows blood serum parameters of food powder-treated, and Untreated wild type and ETKO mice. There were no major changes in the levels of albumin, globulin and their ratios. There as no significant difference between the control and treatment group in terms of total protein. Values are Mean±SEM from 3 independent treatments. Abbreviations: Wild type Untreated (WT/U), Wild type treated (WT/T), Knock out Untreated (KO/U) and Knock out Treated (KO/T)

FIG. 49 shows blood serum parameters of food powder-treated, and Untreated wild type and ETKO mice. There were no major changes in the levels of albumin, globulin and their ratios. There was no significant difference between the control and treatment group in terms of total protein. Values are Mean±SEM from 3 independent treatments. This data suggests that food powder treatment does not cause significant changes in several physiological parameters, which suggests that its action may be relatively more specific to certain conditions.

Figure 50:
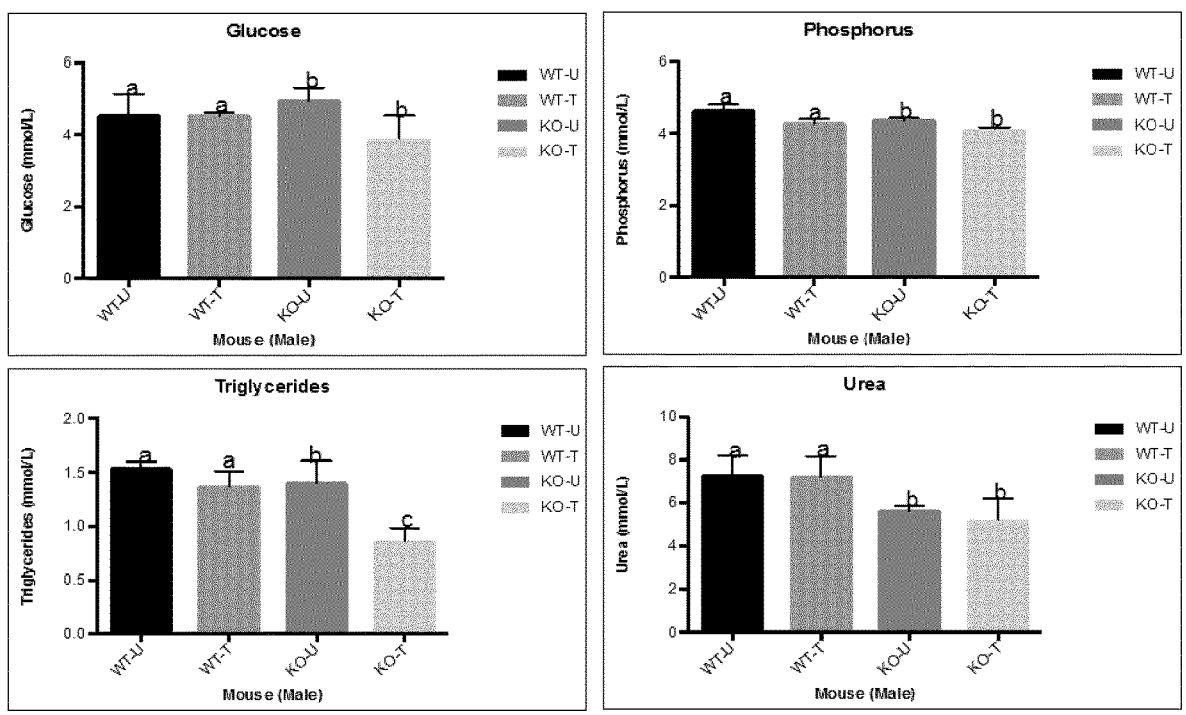
FIG. 50 shows blood serum parameters of food powder-treated, and Untreated wild type and ETKO mice. There are no major changes in the levels of glucose, phosphorus, and urea. There appears to be a slight decrease in the triglyceride levels in the obese mice treated with food powder. Values are Mean±SEM from 3 independent samples. Abbreviations: Wild type Untreated (WT-U), Wild type treated (WT-T), Knock out Untreated (KO-U) and Knock out Treated (KO-T)

FIG. 50 shows blood serum parameters of food powder-treated, and Untreated wild type and ETKO mice. There are no major changes in the levels of glucose, phosphorus, and urea. There appears to be a slight decrease in the triglyceride levels in the obese mice treated with food powder. Values are Mean±SEM from 3 independent samples. These data suggest that food powder treatment does not cause significant changes in several physiological parameters, which suggests that its action may be relatively more specific to certain conditions.

Figure 51:
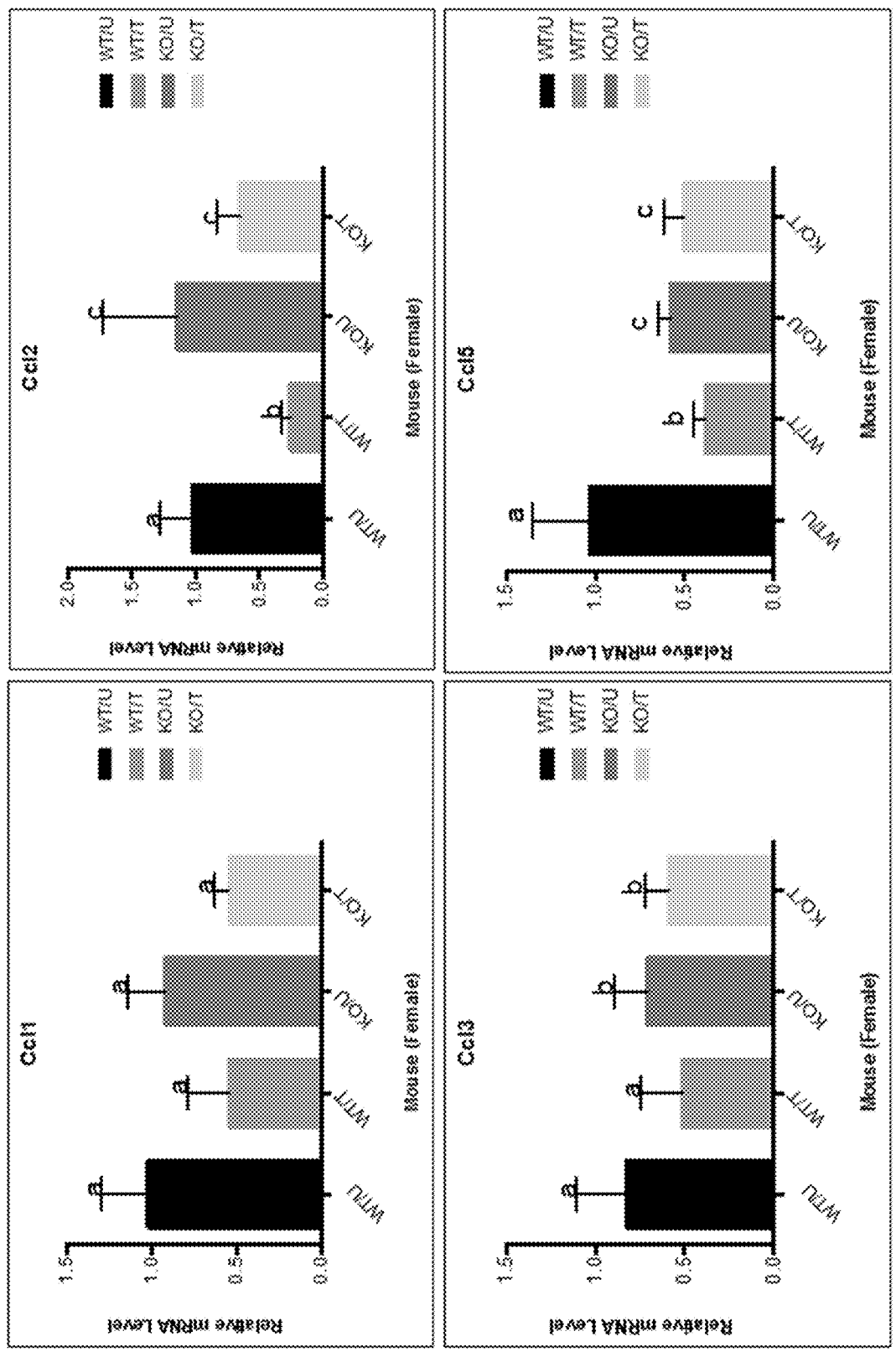
FIG. 51 shows changes in transcript levels of chemokines (chemotactic cytokines) in wild type and ETKO mice treated with the food powder. CCL type chemokines are small glycoproteins secreted by activated T cells that cause attraction of monocytes to the site of inflammation. CCL1 (C-C motif chemokine ligand 1) and its family members (CCL2, CCL3, CCL5 . . . ) are involved in inflammation processes. A significant reduction in CCL2 and CCL 5 was observed in wild-type mice in response to food powder treatment. There is a trend showing a reduction of these chemokines after food powder treatment in ETKO mice, but are not significantly different in this testing. The data are Mean±SEM of transcript levels in samples from three independent mice. CCLI binds to CCR8 for it function. CCL2 (Monocyte Chemoattractant Protein 1; MCP1) is also involved in attraction of monocytes to sites of inflammation and binds to receptors CCR2 and CCR4. CCL3 (Macrophage inflammatory protein—Alpha; MIP1-α) is involved in acute inflammation and an attractant of white blood cells. It binds to receptors CCR1, CCR4 and CCR 5). CCL5 binds to CCR5 surface receptor, and is involved in inflammation and cancer progression. Abbreviations: Wild type Untreated (WT/U), Wild type treated (WT/T), Knock out Untreated (KO/U) and Knock out Treated (KO/T)

FIG. 51 shows changes in transcript levels of chemokines (chemotactic cytokines) in wild type and ETKO mice treated with the food powder. CCL type chemokines are small glycoproteins secreted by activated T cells that cause attraction of monocytes to the site of inflammation. CCL1 (C-C motif chemokine ligand 1) and its family members (CCL2, CCL3, CCL5 . . . ) are involved in inflammation processes. A significant reduction in CCL2 and CCL 5 was observed in wild-type mice in response to food powder treatment. There is a trend showing a reduction of these chemokines after food powder treatment in ETKO mice, but are not significantly different in this testing. The data are Mean±SEM of transcript levels in samples from three independent mice.

CCL1 binds to CCR8 for it function. CCL2 (Monocyte Chemoattractant Protein 1; MCP1) is also involved in attraction of monocytes to sites of inflammation and binds to receptors CCR2 and CCR4. CCL3 (Macrophage inflammatory protein-Alpha; MIP1-α) is involved in acute inflammation and an attractant of white blood cells. It binds to receptors CCR1, CCR4 and CCR 5). CCL5 binds to CCR5 surface receptor, and is involved in inflammation and cancer progression. These data suggest that the food powder treatment may result in the downregulation of these components of inflammation.

Figure 52:
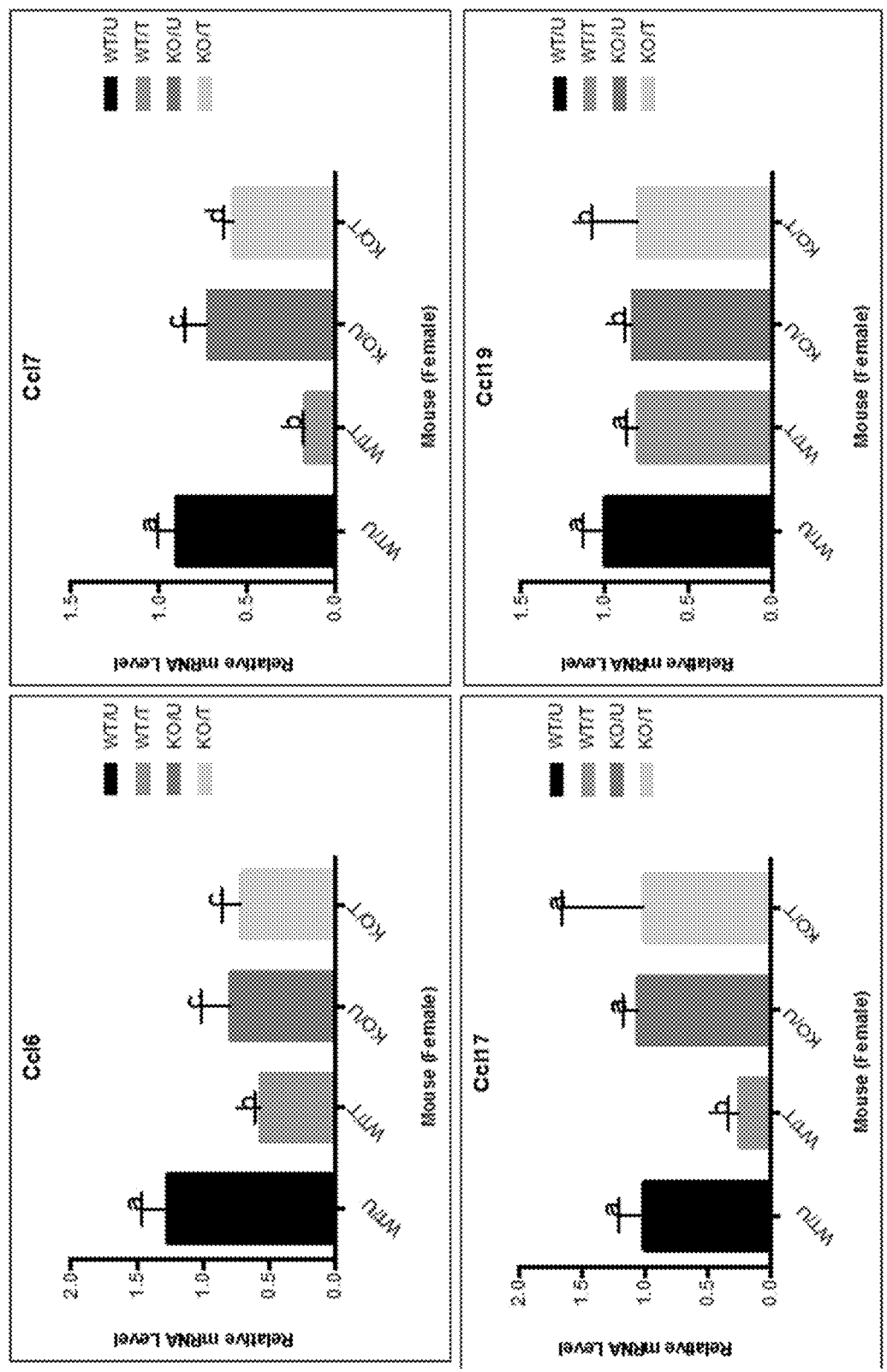
FIG. 52 shows changes in transcript levels of chemokines (chemotactic cytokines) in wild type and ETKO mice treated with the food powder. CCL type chemokines are small glycoproteins secreted by activated T cells that cause attraction of monocytes to the site of inflammation. The figure shows changes in transcript levels of CCL6, CCL7, CCL17 and CCL19. CCL6 is unique to rodents and may bind to CCR 1 during its action. CCL6 is expressed in macrophages during myeloid cell differentiation. A significant reduction in CCL6, CCL 7, and CCL17 was observed in wild-type mice in response to food powder treatment. A significant reduction in CCL7 was observed in ETKO mouse. CCL 19 showed no change in transcripts in both wild type and ETKO mouse. The data are Mean±SEM of transcript levels in samples from three independent mice. CCL6 binds to CCR1 for it function. CCL7 is also involved in attraction of monocytes to sites of inflammation and binds to CCR2 receptor. Abnormal levels of CCL7 expression is related to tumorigenesis and MMP-2 activation and metastasis. Thus, downregulation of CCL7 is likely to be highly beneficial in cancer prevention. CCL17 is involved in chemo attraction of lymphocytes, and is involved in the induction of inflammatory diseases such as atherosclerosis and inflammatory bowel diseases. CCL19 is involved in lymphocyte recirculation. Abbreviations: Wild type Untreated (WT/U), Wild type treated (WT/T), Knock out Untreated (KO/U) and Knock out Treated (KO/T)

FIG. 52 shows changes in transcript levels of chemokines (chemotactic cytokines) in wild type and ETKO mice treated with the food powder. CCL type chemokines are small glycoproteins secreted by activated T cells that cause attraction of monocytes to the site of inflammation. The figure shows changes in transcript levels of CCL6, CCL7, CCL17 and CCL19. CCL6 is unique to rodents and may bind to CCR 1 during its action. CCL6 is expressed in macrophages during myeloid cell differentiation. A significant reduction in CCL6, CCL 7, and CCL17 was observed in wild-type mice in response to food powder treatment. A significant reduction in CCL7 was observed in ETKO mouse. CCL 19 showed no change in transcripts in both wild type and ETKO mouse. The data are Mean±SEM of transcript levels in samples from three independent mice. CCL6 binds to CCR1 for it function. CCL7 is also involved in attraction of monocytes to sites of inflammation and binds to CCR2 receptor. Abnormal levels of CCL7 expression is related to tumorigenesis and MMP-2 activation and metastasis. Thus, downregulation of CCL7 is likely to be highly beneficial in cancer prevention. CCL17 is involved in chemo attraction of lymphocytes, and is involved in the induction of inflammatory diseases such as atherosclerosis and inflammatory bowel diseases. CCL19 is involved in lymphocyte recirculation. Overall these results are supportive of reducing the levels of components involved in increasing inflammation.

Figure 53:
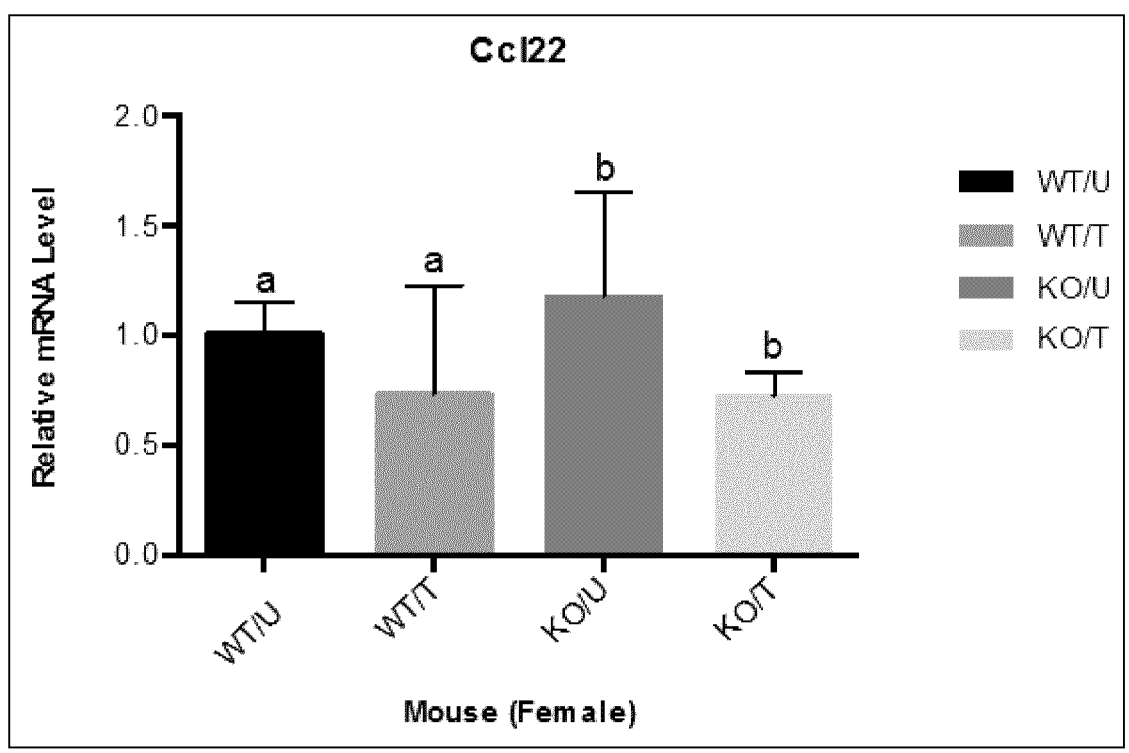
FIG. 53 shows changes in transcript levels of CCL22 chemokine (chemotactic cytokines) in wild type and ETKO mice treated with the food powder. CCL22 is produced by tumors and tumor infiltrating T-cells, causing immunosuppression and immune cell evasion by the tumor, helping tumor progression. CCL22 over-expression in immune cells is caused by Interleukin-alpha. There were no changes in the levels of CCL22 in both wild-type and ETKO mice in response to food powder treatment. The data are Mean±SEM of transcript levels in samples from three independent mice. Abbreviations: Wild type Untreated (WT/U), Wild type treated (WT/T), Knock out Untreated (KO/U) and Knock out Treated (KO/T)

FIG. 53 shows changes in transcript levels of CCL22 chemokine (chemotactic cytokines) in wild type and ETKO mice treated with the food powder. CCL22 is produced by tumors and tumor infiltrating T-cells, causing immunosuppression and immune cell evasion by the tumor, helping tumor progression. CCL22 over-expression in immune cells is caused by Interleukin-alpha. There were no changes in the levels of CCL22 in both wild-type and ETKO mice in response to food powder treatment. The data are Mean±SEM of transcript levels in samples from three independent mice. These results suggest that there were no major effects on the expression of CCL22 by the food powder treatment.

Figure 54:
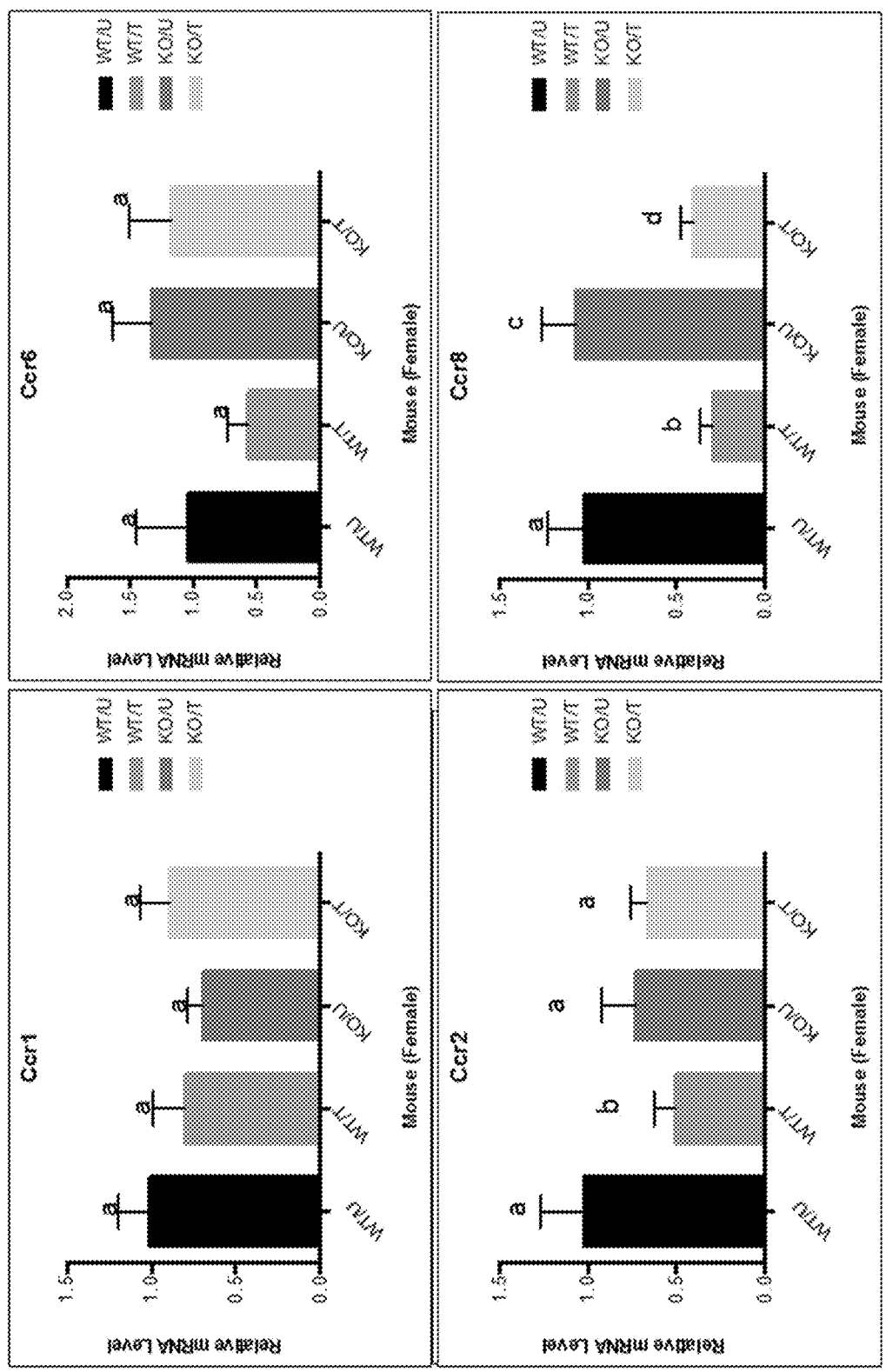
FIG. 54 shows evaluation of changes in transcript levels of CCR type receptors in wild type and ETKO mice subjected to treatment with food power. Chemokine receptors of the CCR family are expressed in blood cells such as cosinophils, basophils, lymphocytes, macrophages, and dendritic cells, and enhancement in their expression/activity is linked to increased inflammation. A number of signal transduction pathways are activated when CCR binds to a ligand chemokine (CCL family). Food powder treatment did not change the expression levels of CCR1 and CCR6 in both wild type and ETKO mice. CCR2 and CCR 8 in wild type mouse showed significant downregulation in response to food powder treatment suggesting that the food powder may downregulate the levels of inflammation causing CCRs. As well, there was significant downregulation of CCR8 in ETKO mice fed with the food powder. Thus, a decrease in both the levels of chemokines as well as their receptors appears to occur as a response to food powder treatment. The data are Mean±SEM of transcript levels in samples from three independent mice. Abbreviations: Wild type Untreated (WT/U), Wild type treated (WT/T), Knock out Untreated (KO/U) and Knock out Treated (KO/T)
Figure 55:
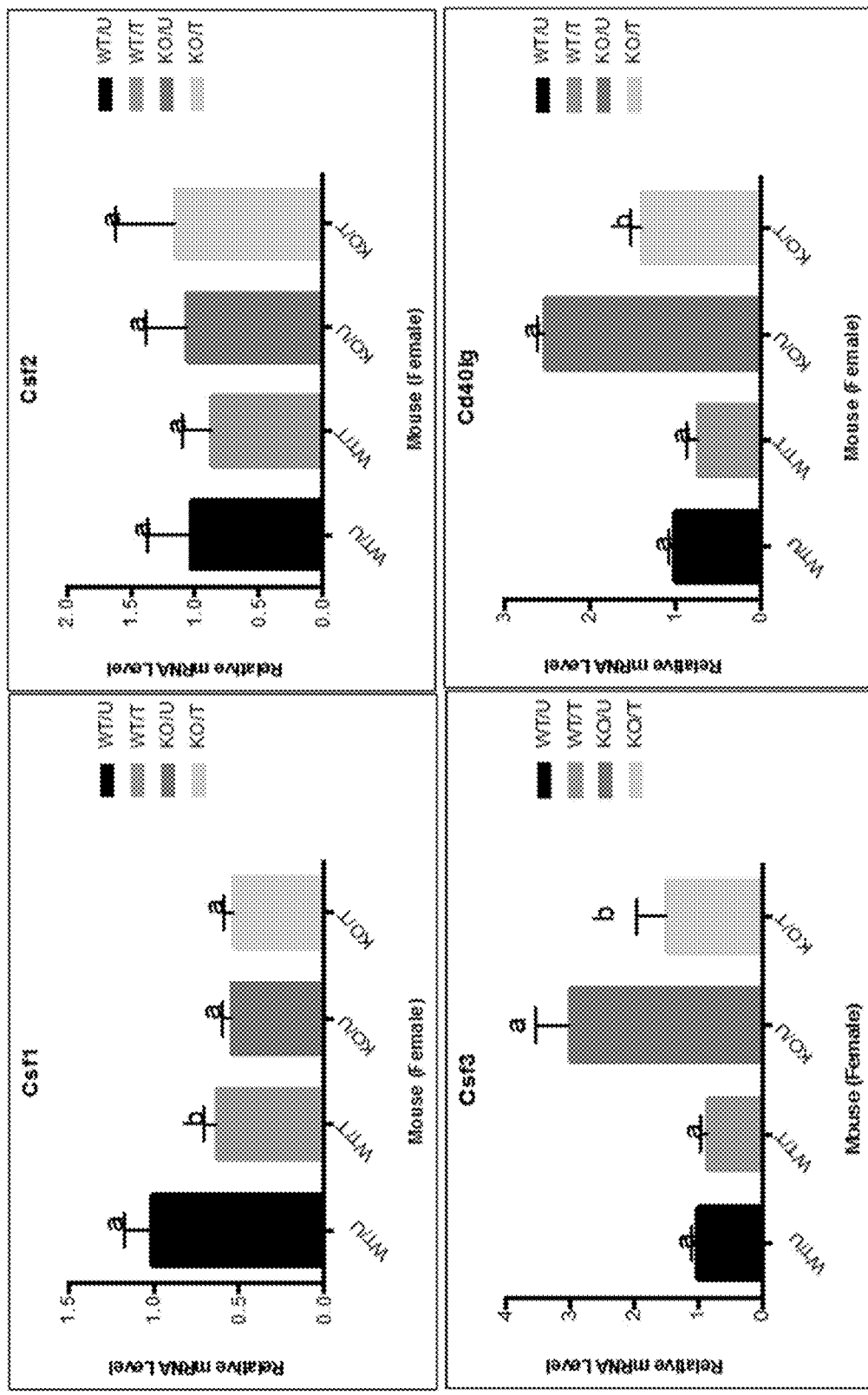
FIG. 55 shows evaluation of changes in transcript levels of CSF (Colony stimulating factor) in wild type and ETKO mice subjected to treatment with food power. CSFs are cytokines produced by granulocyte/macrophage (GM-CSF), macrophages (M-CSF), and granulocytes (G-CSF). Enhancement in their expression/activity is linked to increased inflammation, and downregulation helps in reducing inflammatory and autoimmune diseases. CSF levels were similar in the wild type mouse and those treated with the food powder. CSF3 was upregulated in the ETKO mouse, a potential link to development of obesity. Treatment with food powder brought the CSF levels closer to that observed in wild type mouse. A decrease in both the levels of chemokines as well as their receptors appears to occur as a response to food powder treatment. CD40LG is a ligand of CD40 protein localized on the surface of immune cells and an increase in the expression of this protein has been linked to increase in inflammation, in relation to development of several cancers. In vascular endothelium, an increase in the secretion of CD40 ligand by platelets appears to enhance the production of ROS that lead to the formation of plaque cells and blockage of arteries. There was a significant reduction in the expression of CD40 ligand in mouse treated with the food powder, bringing its level close to that in wild type. The data are Mean±SEM of transcript levels in samples from three independent mice. Abbreviations: Wild type Untreated (WT/U), Wild type treated (WT/T), Knock out Untreated (KO/U) and Knock out Treated (KO/T)

FIG. 54 shows evaluation of changes in transcript levels of CCR type receptors in wild type and ETKO mice subjected to treatment with food power. Chemokine receptors of the CCR family are expressed in blood cells such as eosinophils, basophils, lymphocytes, macrophages, and dendritic cells, and enhancement in their expression/activity is linked to increased inflammation. A number of signal transduction pathways are activated when CCR binds to a ligand chemokine (CCL family). Food powder treatment did not change the expression levels of CCR1 and CCR6 in both wild type and ETKO mice. CCR2 and CCR 8 in wild type mouse showed significant downregulation in response to food powder treatment suggesting that the food powder may downregulate the levels of inflammation causing CCRs. As well, there was significant downregulation of CCR8 in ETKO mice fed with the food powder. Thus, a decrease in both the levels of chemokines as well as their receptors appears to occur as a response to food powder treatment. The data are Mean±SEM of transcript levels in samples from three independent mice. FIG. 55 shows evaluation of changes in transcript levels of CSF (Colony stimulating factor) in wild type and ETKO mice subjected to treatment with food power. CSFs are cytokines produced by granulocyte/macrophage (GM-CSF), macrophages (M-CSF), and granulocytes (G-CSF). Enhancement in their expression/activity is linked to increased inflammation, and downregulation helps in reducing inflammatory and autoimmune diseases. CSF levels were similar in the wild type mouse and those treated with the food powder. CSF3 was upregulated in the ETKO mouse, a potential link to development of obesity. Treatment with food powder brought the CSF levels closer to that observed in wild type mouse. A decrease in both the levels of chemokines as well as their receptors appears to occur as a response to food powder treatment. CD40LG is a ligand of CD40 protein localized on the surface of immune cells and an increase in the expression of this protein has been linked to increase in inflammation, in relation to development of several cancers. In vascular endothelium, an increase in the secretion of CD40 ligand by platelets appears to enhance the production of ROS that lead to the formation of plaque cells and blockage of arteries. There was a significant reduction in the expression of CD40 ligand in mouse treated with the food powder, bringing its level close to that in wild type. The data are Mean±SEM of transcript levels in samples from three independent mice.

Figure 56:
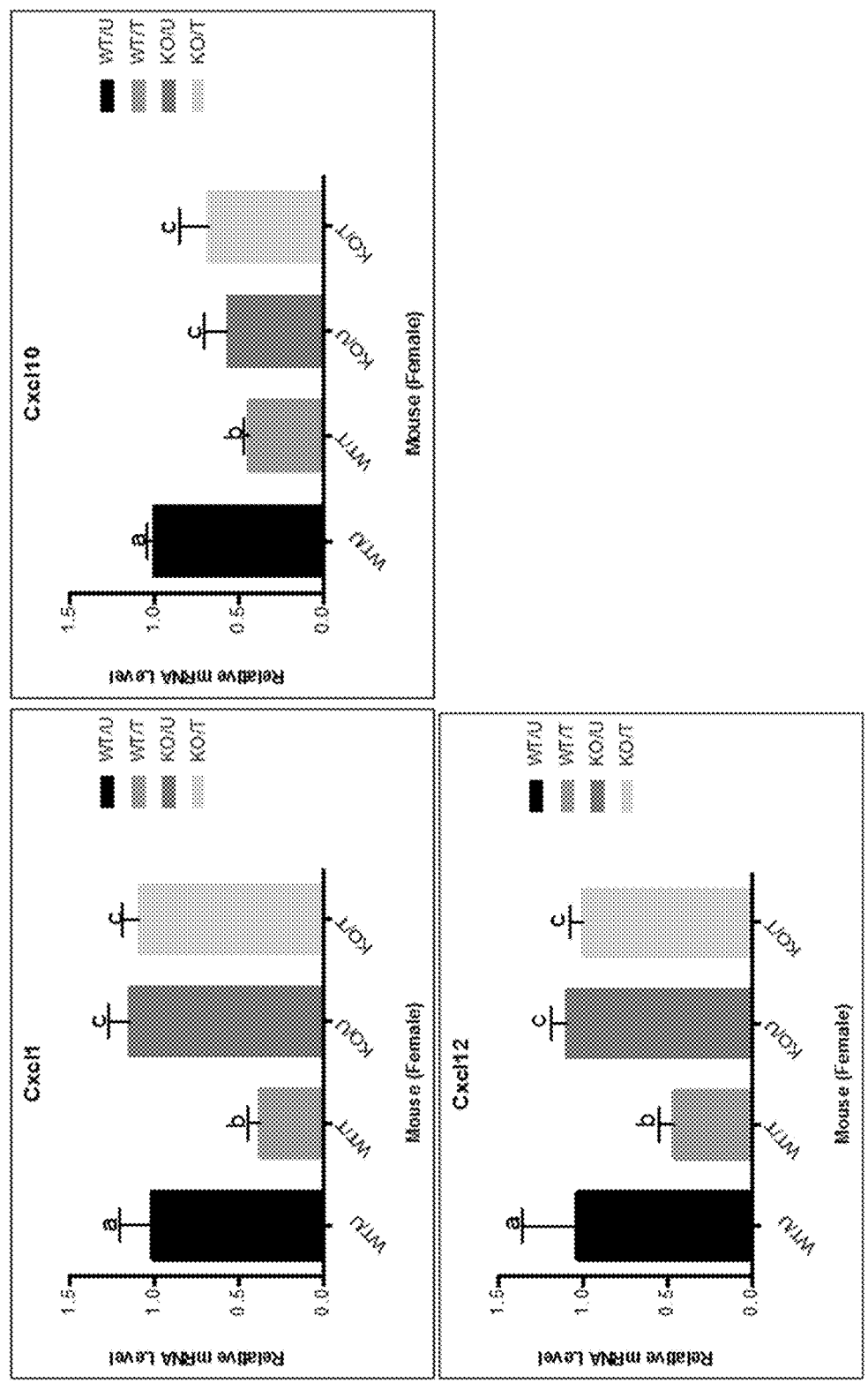
FIG. 56 shows evaluation in changes of CXC motif chemokines in response to food powder treatment in wild type and ETKO mice. CXCI type chemokines: CXCL chemokines bind to CXCR type receptors on surface of immunogenic cells and induce their action. CXCL1 (CXC motif ligand 1) and acts through its receptor CXCR-2 plays a key role in inflammation. CXCL 1 was downregulated in wild type mice significantly, while the ETKO mice did not show a significant change in response to food powder treatment. CXCL 10 and its receptor CXCR3 are implicated in pathologies that occur during autoimmune disease development, including organ specific diseases (type 1 diabetes), and systematic autoimmune diseases such as Rheumatoid arthritis. Interferons and TNF activate the production of CXCL10 resulting in the activation of TH1 lymphocytes. CXCL 10 was downregulated in wild-type mouse significantly, while the ETKO mice did not show any change in response to food treatment. CXCL-12 (CXC-motif ligand -12; stromal cell-derived factor 1 or SDF 1) is a chemokine which binds to its receptor CXC-R 4. CXCL-12 is expressed in a variety of tissues and is important in development. Overexpression of CXCL-12 leads to inflammation and is highly chemotactic to leukocytes (neuroinflammation). CXCL 12 is a clinical marker for pancreatic cancer, multiple sclerosis, Alzheimer's disease, etc. CXCL-12 was downregulated in wild-type mice in response to food powder treatment. The data are Mean±SEM of transcript levels in samples from 3 independent mice. Abbreviations: Wild type Untreated (WT/U), Wild type treated (WT/T), Knock out Untreated (KO/U) and Knock out Treated (KO/T)

FIG. 56 shows evaluation in changes of CXC motif chemokines in response to food powder treatment in wild type and ETKO mice. CXCI type chemokines: CXCL chemokines bind to CXCR type receptors on surface of immunogenic cells and induce their action. CXCL1 (CXC motif ligand 1) and acts through its receptor CXCR-2 plays a key role in inflammation. CXCL 1 was downregulated in wild type mice significantly, while the ETKO mice did not show a significant change in response to food powder treatment. CXCL 10 and its receptor CXCR3 are implicated in pathologies that occur during autoimmune disease development, including organ specific diseases (type 1 diabetes), and systematic autoimmune diseases such as Rheumatoid arthritis. Interferons and TNF activate the production of CXCL10 resulting in the activation of TH1 lymphocytes. CXCL 10 was downregulated in wild-type mouse significantly, while the ETKO mice did not show any change in response to food treatment. CXCL-12 (CXC-motif ligand -12; stromal cell-derived factor 1 or SDF 1) is a chemokine which binds to its receptor CXC-R 4. CXCL-12 is expressed in a variety of tissues and is important in development. Overexpression of CXCL-12 leads to inflammation and is highly chemotactic to leukocytes (neuroinflammation). CXCL 12 is a clinical marker for pancreatic cancer, multiple sclerosis, Alzheimer's disease, etc. CXCL-12 was downregulated in wild-type mice in response to food powder treatment. The data are Mean±SEM of transcript levels in samples from 3 independent mice. These results show differential responses of wild-type mouse and the ETKO mouse to the same treatment. Without wishing to be bound by theory, obesity as a condition may alter the pattern of response to anti-inflammatory agents.

Figure 57:
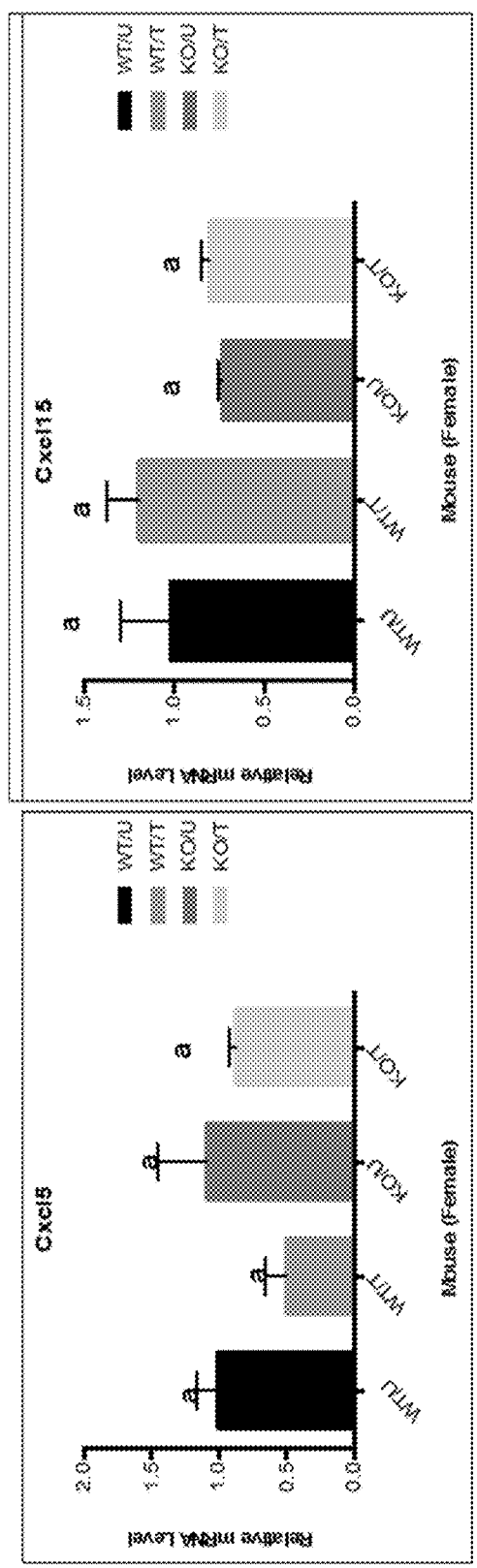
FIG. 57 shows evaluation of the effect of food treatment on CXC-Ligand transcription levels. CXC1-5 is produced during inflammation stimulated by interleukins and TNF alpha. It binds to CXC receptor 2. It is believed to play a role in cell proliferation, enhancing motility and angiogenesis. There no changes in CXCL 5 between untreated and food powder treated wild type and ETKO mice. CXCL 15 is a chemokine expressed in lung epidermal cells, intestinal cells etc. and is linked to inflammation. There were no changes in the transcript levels of CXL15 between untreated and food powder treated wild type and ETKO mice. The data are Mean±SEM of transcript levels in samples from three independent mice. Abbreviations: Wild type Untreated (WT/U), Wild type treated (WT/T), Knock out Untreated (KO/U) and Knock out Treated (KO/T)

FIG. 57 shows evaluation of the effect of food treatment on CXC-Ligand transcription levels. CXCI-5 is produced during inflammation stimulated by interleukins and TNF alpha. It binds to CXC receptor 2. It is believed to play a role in cell proliferation, enhancing motility and angiogenesis. There were no changes in CXCL 5 between untreated and food powder treated wild type and ETKO mice. CXCL 15 is a chemokine expressed in lung epidermal cells, intestinal cells etc. and is linked to inflammation. There were no changes in the transcript levels of CXL15 between untreated and food powder treated wild type and ETKO mice. The data are Mean±SEM of transcript levels in samples from three independent mice. These genes did not respond to food powder treatment, indicating a specific nature of its action.

Figure 58:
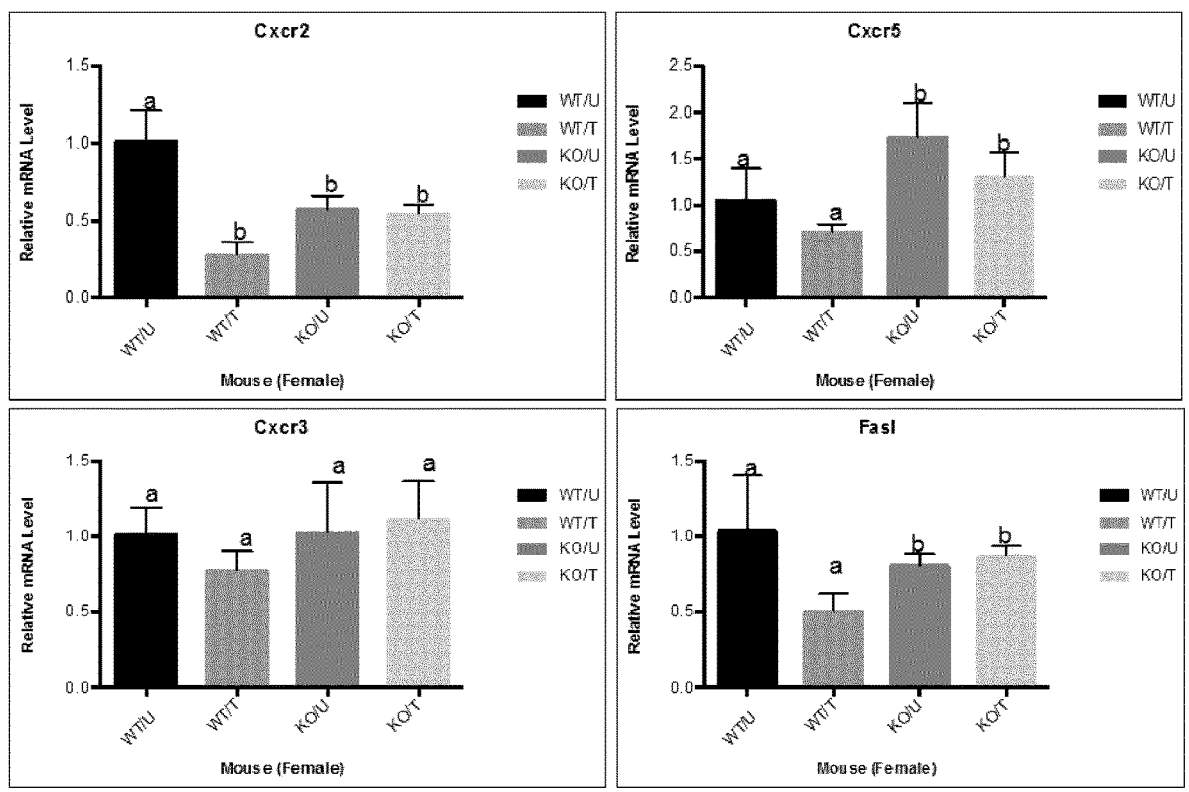
FIG. 58 shows CXCR (CXC motif chemokine receptors, binds to CXC ligands of the chemokine family and interleukins by attracting immunoactive blood cells and inducing inflammation). The levels of CXCR-2 was significantly reduced by food powder treatment in wild type mice. No change was observed in ETKO mice. There were no differences in CXCR-5 and 3 and CXCR5 in both wild type and ETKO mice. The results suggest that apart from the ligands (C-C; C-X-C-motif), the receptors can also be modulated by treatment with the food powder, that may provide better downregulation of inflammation. Receptors of the tumor necrosis factor family are another group of receptors involved in inflammation, and several natural products are known to downregulate TNF alpha linked signal transduction pathway. FAS Ligand (FAS L) belong to TNF superfamily and binding to its receptor initiates apoptosis. There is no significant difference in the levels of FAS L after food powder treatment, in both wild-type and ETKO mice. The data are Mean±SEM of transcript levels in samples from three independent mice. Abbreviations: Wild type Untreated (WT/U), Wild type treated (WT/T), Knock out Untreated (KO/U) and Knock out Treated (KO/T)

FIG. 58 shows CXCR (CXC motif chemokine receptors, which bind to CXC ligands of the chemokine family and interleukins by attracting immunoactive blood cells and inducing inflammation) results. The levels of CXCR-2 was significantly reduced by food powder treatment in wild type mice. No change was observed in ETKO mice. There were no differences in CXCR-5 and 3, and CXCR5 in both wild type and ETKO mice. The results suggest that apart from the ligands (C-C; C-X-C-motif), the receptors can also be modulated by treatment with the food powder, that may provide better downregulation of inflammation. Receptors of the tumor necrosis factor family are another group of receptors involved in inflammation, and several natural products are known to downregulate TNF alpha linked signal transduction pathway. FAS Ligand (FAS L) belong to TNF superfamily and binding to its receptor initiates apoptosis. There was no significant difference in the levels of FAS L after food powder treatment, in both wild-type and ETKO mice. The data are Mean±SEM of transcript levels in samples from three independent mice. Food powder treatment did not appear to affect the expression of these genes under the conditions tested.

Figure 59:
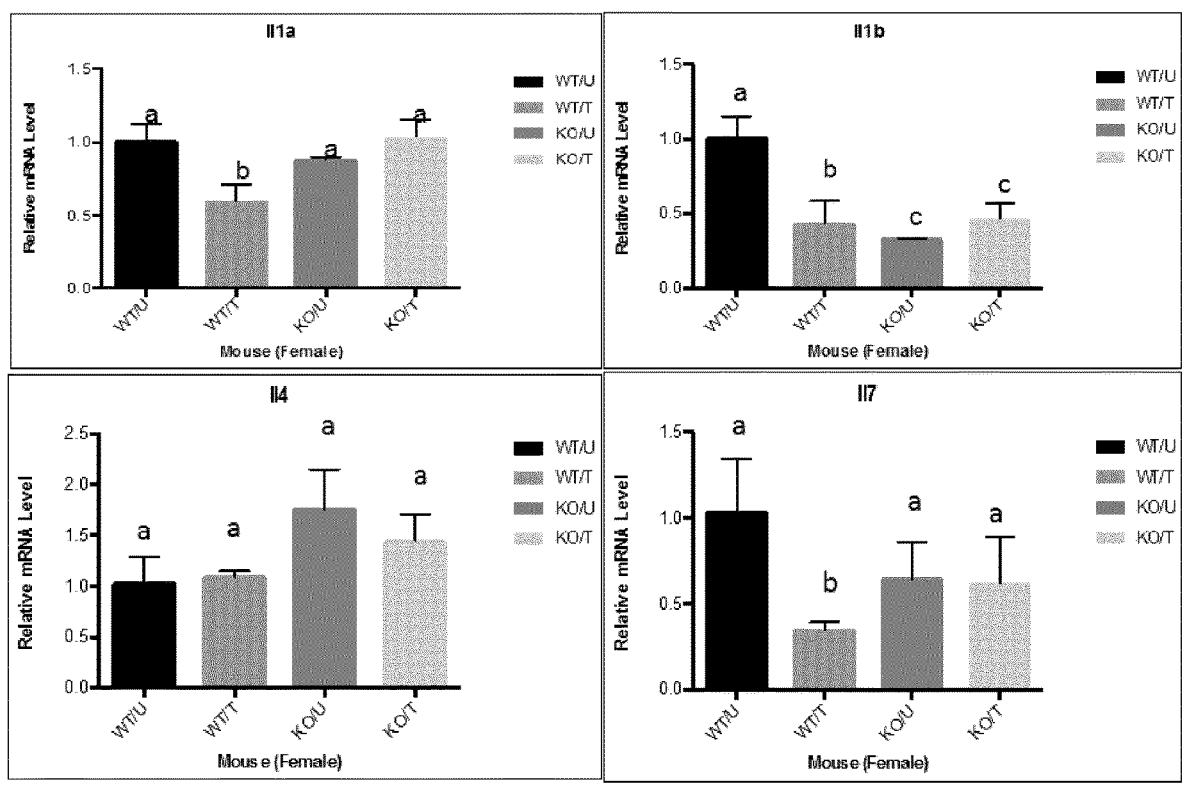
FIG. 59 shows evaluation of the changes in interleukins as a response to food powder treatment in wild type and ETKO mouse. Interleukins are cytokines involved in immune function, some interleukins are proinflammatory (IL17) and others have antiinflammatory function (IL10). They mediate the immune function under normal conditions and when challenged with disease causing organisms. A significant reduction was observed in the expression levels of IL 1A, IL 1B, and IL 7, of wild type mice treated with food powder. The levels of these interleukins remained similar in response to food powder treatment. The expression levels of IL4 remained similar in untreated and food powder treated wild type and ETKO mice. The data are Mean±SEM of transcript levels in samples from three independent mice. Abbreviations: Wild type Untreated (WT/U), Wild type treated (WT/T), Knock out Untreated (KO/U) and Knock out Treated (KO/T)

FIG. 59 shows evaluation of the changes in interleukins as a response to food powder treatment in wild type and ETKO mouse. Interleukins are cytokines involved in immune function, some interleukins are proinflammatory (IL17) and others have antiinflammatory function (IL10). They mediate the immune function under normal conditions and when challenged with disease causing organisms. A significant reduction was observed in the expression levels of IL 1A, IL 1B, and IL 7, of wild type mice treated with food powder. The levels of these interleukins remained similar in ETKO mice in response to food powder treatment. The expression levels of IL4 remained similar in untreated and food powder treated wild type and ETKO mice. The data are Mean±SEM of transcript levels in samples from three independent mice. The results suggest differences in the expression pattern between wild type mouse and ETKO mouse.

Figure 60:
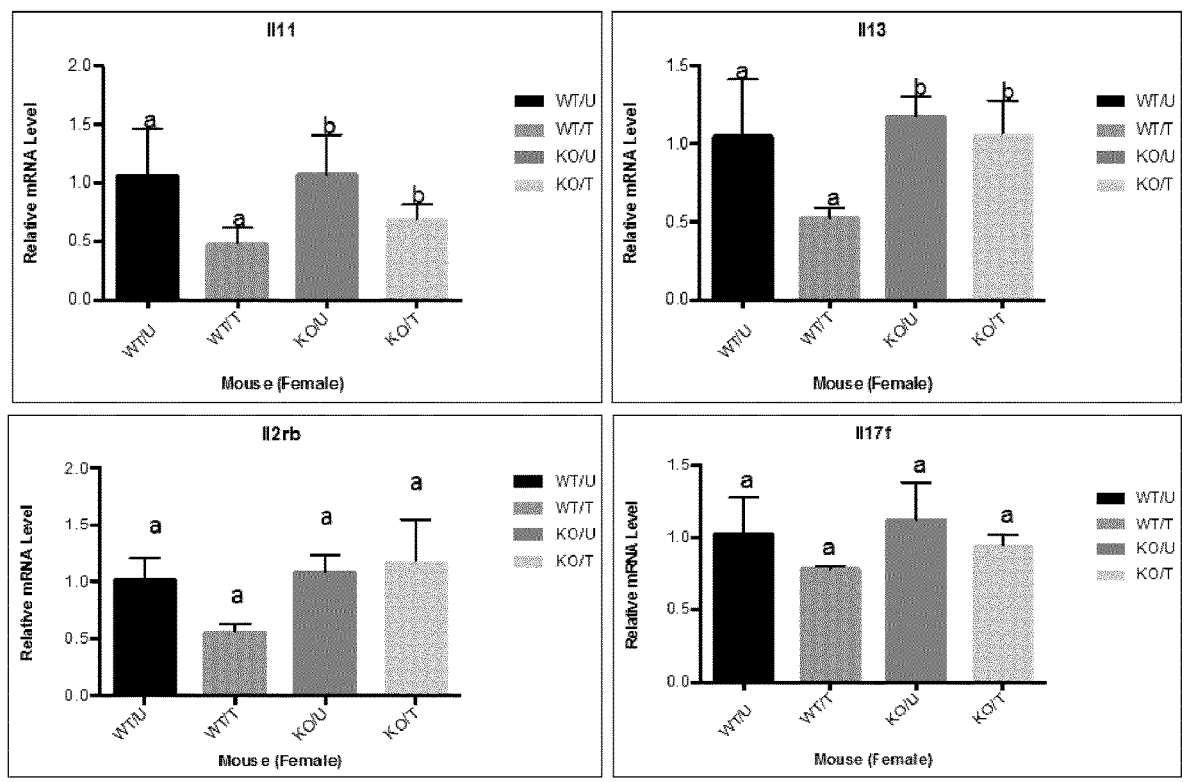
FIG. 60 shows evaluation of the changes in interleukins as a response to food powder treatment in wild type and ETKO mouse. Interleukins mediate the immune function under normal conditions and when challenged with disease causing organisms. There were no changes in the expression levels of IL11, IL13, IL2rb and IL17f did not change after food powder treatment in both wild type and ETKO mice. The data are Mean±SEM of transcript levels in samples from three independent mice. Abbreviations: Wild type Untreated (WT/U), Wild type treated (WT/T), Knock out Untreated (KO/U) and Knock out Treated (KO/T)
Figure 61:
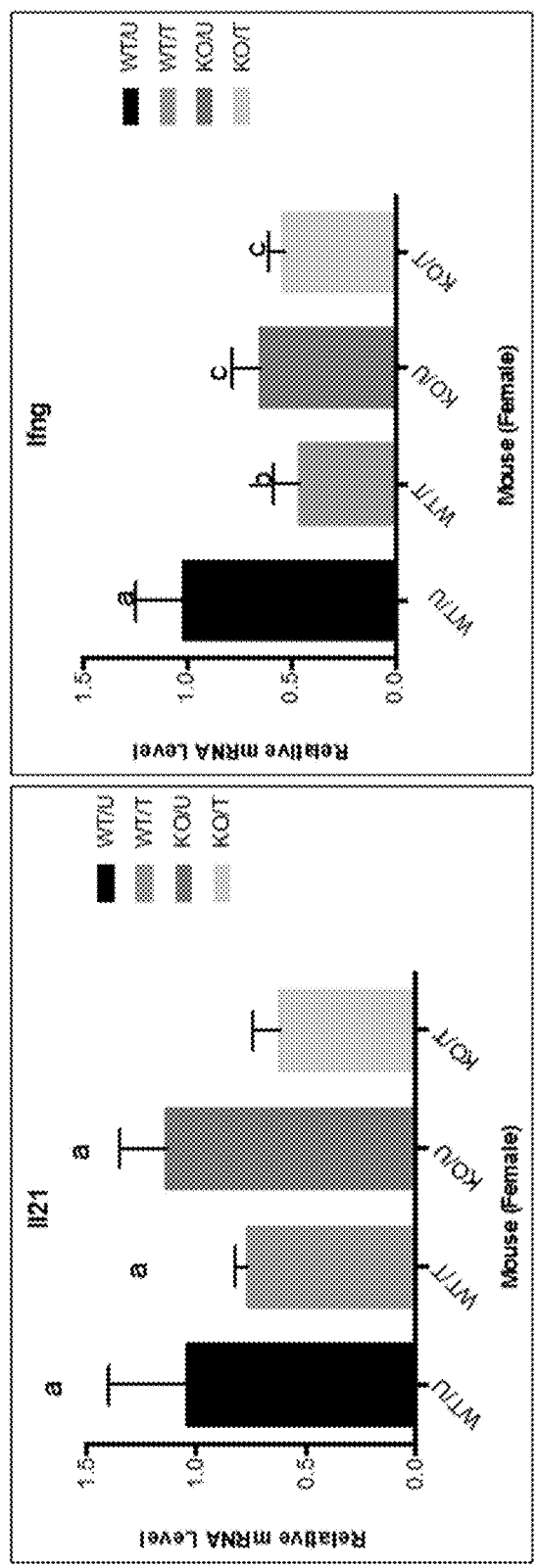
FIG. 61 shows evaluation of the changes in interleukins as a response to food powder treatment in wild type and ETKO mouse. There were no changes in the expression levels of IL21 after food powder treatment in both wild type and ETKO mice. Interferon gamma (IFNG) is another cytokine which is involved in responses against viral agents. There was no change in the levels of IFNG in response to food powder treatment in both wild type and ETKO mice. The data are Mean±SEM of transcript levels in samples from three independent mice. Abbreviations: Wild type Untreated (WT/U), Wild type treated (WT/T), Knock out Untreated (KO/U) and Knock out Treated (KO/T)

FIG. 60 shows evaluation of the changes in interleukins as a response to food powder treatment in wild type and ETKO mouse. Interleukins mediate the immune function under normal conditions and when challenged with disease causing organisms. There were no changes in the expression levels of IL11, IL13, IL2rb and IL171 in response to food powder treatment in both wild type and ETKO mice. The data are Mean±SEM of transcript levels in samples from three independent mice. These results suggest that food powder treatment does not cause changes in all gene expression, but are relatively more targeted, in both wild type mouse and ETKO mouse. FIG. 61 shows evaluation of the changes in interleukins as a response to food powder treatment in wild type and ETKO mouse. There were no changes in the expression levels of IL17 after food powder treatment in both wild type and ETKO mice. Interferon gamma (IFNG) is another cytokine which is involved in responses against viral agents. There was no change in the levels of IFNG in response to food powder treatment in both wild type and ETKO mice. The data are Mean±SEM of transcript levels in samples from three independent mice. These results suggest targeted action of food powder in altering gene expression.

Figure 62:
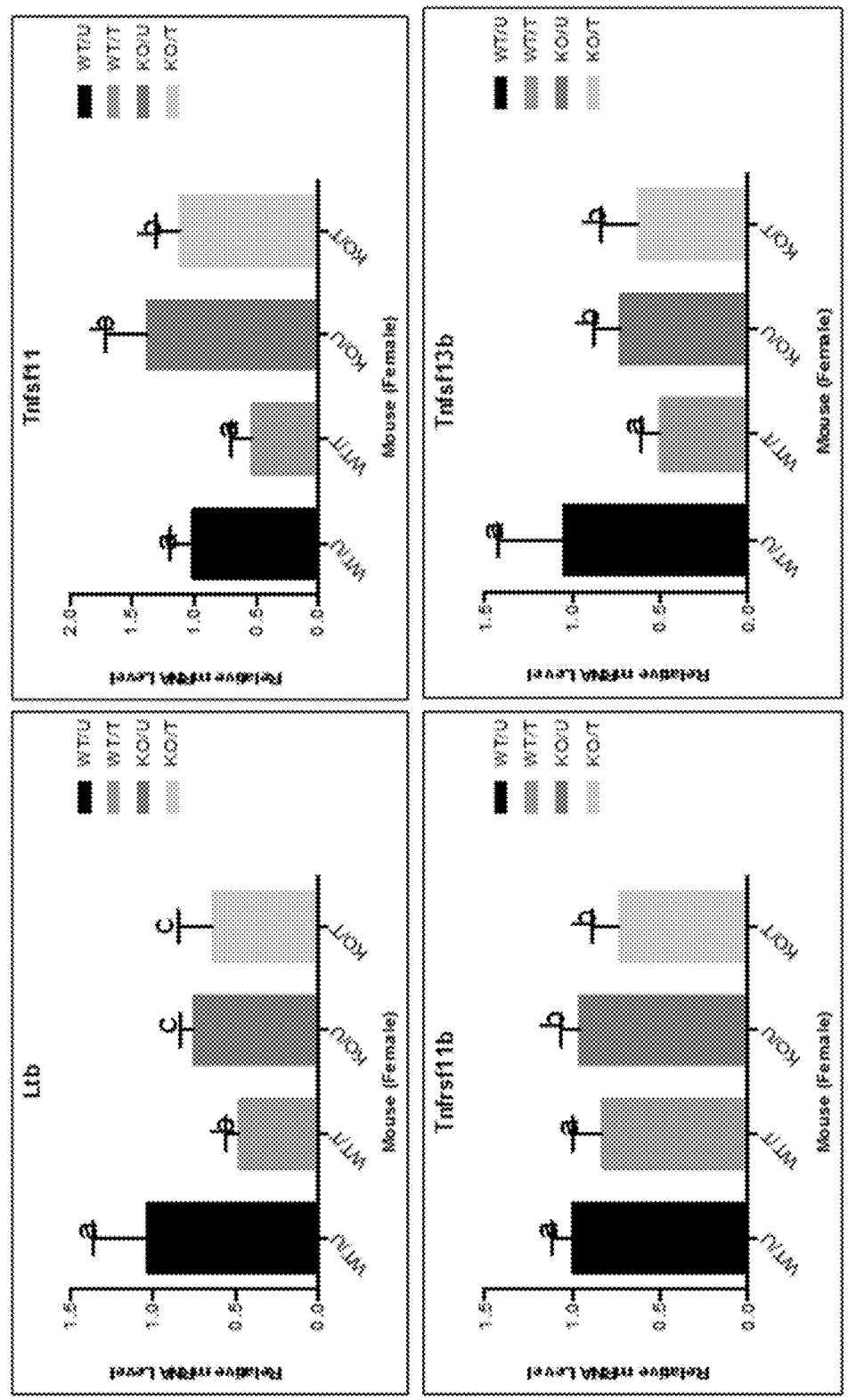
FIG. 62 shows evaluation of changes in transcript levels of Tumor Necrosis Factor superfamily members in relation to their responses during treatment with food powder in wild type and ETKO mice. LTB (Lymphotoxin B: Lymphotoxin Beta (TNF Superfamily, Member 3) is a membrane protein and an inducer of inflammatory response. The levels of LTB transcripts were downregulated in wild type mice in response to food powder treatment. There were no changes in LTB transcript levels in ETKO mice treated with food powder. Transcript levels of other members of TNF superfamily such as TNFSF11, TNFSF11b and TNFS113b did not change after food powder treatment in both wild-type and ETKO mice. The data are Mean±SEM of transcript levels in samples from three independent mice. Abbreviations: Wild type Untreated (WT/U), Wild type treated (WT/T), Knock out Untreated (KO/U) and Knock out Treated (KO/T).

FIG. 62 shows evaluation of changes in transcript levels of Tumor Necrosis Factor superfamily members in relation to their responses during treatment with food powder in wild type and ETKO mice. LTB (Lymphotoxin B: Lymphotoxin Beta (TNF Superfamily, Member 3) is a membrane protein and an inducer of inflammatory response. The levels of LTB transcripts were downregulated in wild type mice in response to food powder treatment. There were no changes in LTB transcript levels in ETKO mice treated with food powder. Transcript levels of other members of TNF superfamily such as TNFSF11, TNFSF11b and TNFS113b did not change after food powder treatment in both wild-type and ETKO mice. The data are Mean±SEM of transcript levels in samples from three independent mice.

It is interesting to note that the wild-type mice also responded to food powder treatment by downregulating inflammatory cytokines and their receptors, in some cases much more than in the obese mice. This suggests that the food powder may be particularly effective in downregulating inflammation even in normal mice. Since down regulation of inflammation is highly relevant to the prevention of several chronic diseases, similar such food powder treatments (i.e. intake) may be beneficial for several such chronic diseases in humans and/or other animals.

Example 5—pH Dependence of Binding of Organic Molecules to Nanoparticles and Nanofibres Experiments were performed to evaluate the binding capacity of organic molecules to nanofibres and nanoparticles under aqueous conditions. The major ingredients of both the nanofibers and nanoparticles are polygalacturonic acid (PG) polymers (see below) along with other minor carbohydrate polymers such as xylans and arabinans. The carboxylic acid moiety of PG provides a highly acidic property to PG in aqueous solutions with a pKa close to 4. At this pH, most of the carboxylic acid will be in the dissociated form (COO−). This may tend to repel individual strands in a multi-strand structure, and perhaps facilitate increased binding of ligand molecules.

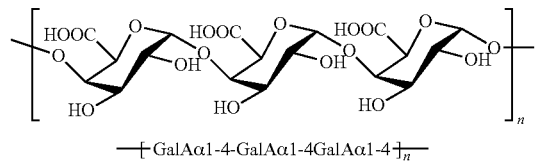

—$[$GalAα1-4-GalAα1-4GalAα1-4$]_n$—

To test this possibility, nanofibres and nanoparticles were incubated with dyes, and the binding capacity monitored. For nanofibres, Calcein (Ex 490; Em-515) was used and for nanoparticles, dylight was used (Ex 650; Em 680). Since nanoparticles contained polyphenols, they tend to quench emissions in the green-orange region of the spectrum. Therefore, dylight with absorption/emission characteristics beyond 600 nm was used. Both these dyes are incorporated by nanoparticles and nanofibres.

Nanofibres (10 mg) were dissolved in 10 ml of water. Nanoparticles also contained 10 mg of powder in 10 ml of water. (There is likely no equivalency in terms of composition, functional groups etc. between these two preparations). Nanofibres were mixed with 5 mg of calcein (in 10 ml). The nanoparticle solution was mixed with 200 μg equivalent of dylight in 10 ml.

The solutions were mixed gently for 3 hours and separated into fractions of 100 μl which were dialyzed overnight against buffers of different pH ranging from pH 4 to pH 7. The dialyzed nanofiber and nanoparticle solutions were diluted to 2 ml and absorbance measured at the Amax for the dyes (calcein at 490 nm; dylight at 652 nm). Calcein and dylight solutions were diluted proportionally as in the nanofibre and nanoparticle solutions to provide a control. The results are given in the following Tables 6 and 7.

TABLE 6

Nanofibres (NF) Sample - Calcein as Dye.

| Sample ID | λ Max | OD | % change over blank absorbance |
|---|---|---|---|
| Calcein + water | 491.5 | 1.121 | control |
| Calcein + buffer pH 4.0 | 472.5 | 0.444 | control |
| Dialyzed NF (pH 4.0 + calcein) | 472.5 | 1.090 | 145.5 |
| Calcein + buffer pH 6.0 | 491.5 | 0.927 | control |
| Dialyzed NF (pH 6.0 + calcein) | 491 | 2.010 | 116.83 |
| Calcein + buffer pH 6.5 | 492 | 1.250 | control |
| Dialyzed NF (pH 6.5 + calcein) | 492 | 2.230 | 78.4 |
| Calcein + buffer pH 7.0 | 492 | 1.390 | control |
| Dialyzed NF (pH 7.0 + calcein) | 491.5 | 2.474 | 78 |

There was a pH dependent increase in the calcein absorption from pH 4 to pH 7. Calcein absorbance was the highest at pH 4-6 region, above which the conjugation was probably reduced. The binding was maximal in the pH 4-6 range, with 145% and 116% increase over the control without nanofibres. The effective binding tends to decrease as the pH increases when all the carboxylic acid groups are fully dissociated. Without wishing to be bound by theory, this may also be due to the dissociation of structural organic acids (eg. Malic acid, ascorbic acid etc.) in the nanofiber structure at higher pH.

TABLE 7

Nanoparticles Sample - Dylight 650 as Dye.

| Sample ID | λ Max | OD | % change blank absorbance |
|---|---|---|---|
| Dylight + buffer pH 4.0 | 652.5 | 0.3154 | control |
| Dialyzed NP (pH 4.0 + Dylight) | 652.5 | 0.2545 | 80.95 |
| Dylight + buffer pH 6.0 | 652.5 | 0.3620 | control |
| Dialyzed NP (pH 6.0 + Dylight) | 652.5 | 0.2760 | 76.24 |
| Dylight + buffer pH 6.5 | 652.5 | 0.4309 | control |
| Dialyzed NP (pH 6.5 + Dylight) | 652.5 | 0.2504 | 58.00 |
| Dylight + buffer pH 7.0 | 652.5 | 0.3788 | control |
| Dialyzed NP (pH 7.0 + Dylight) | 652.5 | 0.3053 | 80.47 |

Aqueous solutions of nanoparticles and dylight were mixed gently for 3 hours and separated into fractions of 100 μl which were dialyzed overnight against buffers of different pH ranging from pH 4 to pH 7. The dialyzed nanoparticle solutions were diluted to 2 ml and absorbance measured at the Amax (652.5 nm). Dylight solutions were also diluted proportionally as in the dialyzed nanoparticle solutions to provide a control for each pH set. In the presence of nanoparticle, under the conditions tested, the absorbance from dylight tends to decrease irrespective of pH and no clear relation to pH was noticeable. Without wishing to be bound by theory, this is probably because the nanoparticle is a tightly associated structure and may not allow the interior parts to bind to certain components with high efficiently, after its self-assembly. In both cases, however, the dyes were retained despite extensive dialysis, suggesting that a chemical conjugate may not be needed for cargo delivery by nanoparticles and nanofibres. It certain embodiments, conjugation may, however, be preferred where the cargo is large, such as in the case of antibodies, such as monoclonal antibodies, and/or other large molecules.

Example 6—Mouse Study of Liver Sections Treated with Food Powder

A study was carried out in mice to evaluate the effect of food powder treatment in a mouse model of obesity. Experimental conditions are as described above. Sections were stained with Eosin/hematoxylin.

Figure 63:
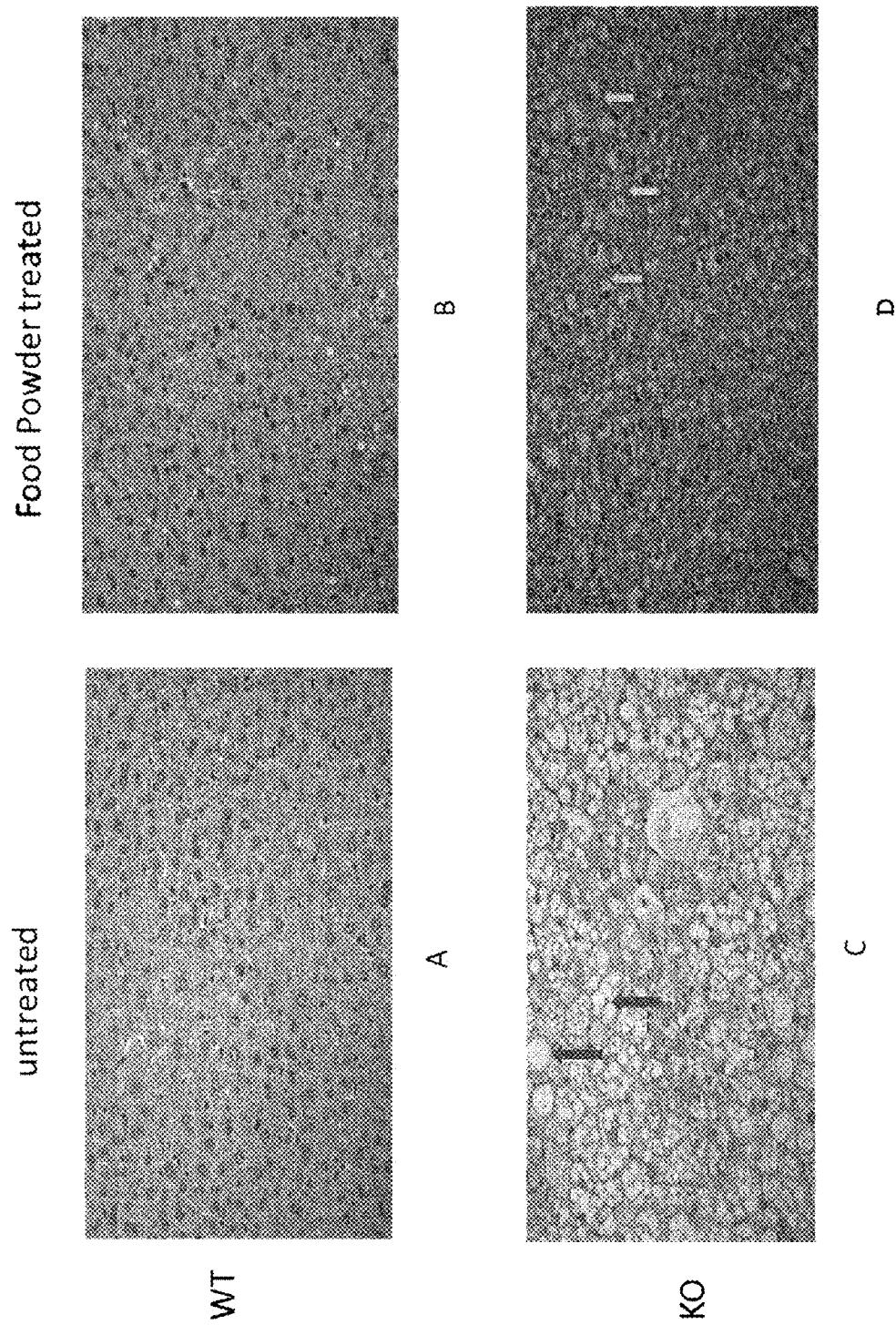
FIG. 63 shows histopathology results of liver sections in mice with and without food powder treatment. Panel (A) illustrates untreated Wild Type (WT) mouse liver section stained with Hematoxylin and Eosin; very few lipid bodies are visible. Panel (B) illustrates Wild Type (WT) mouse liver section, treated with food powder and stained with Hematoxylin and Eosin; very few lipid bodies are visible. Panel (C) illustrates untreated obese (KO) mouse liver section stained with Hematoxylin and Eosin; the clear circular areas are lipid bodies widely distributed in the liver. Panel (D) illustrates (KO) mouse liver section, treated with food powder and stained with Hematoxylin and Eosin; the clear circular areas are lipid bodies. Potential areas of tissue regeneration are shown by arrows.

FIG. 63 shows liver sections in mice with and without food powder treatment. Panel (A) illustrates untreated Wild Type (WT) mouse liver section. As can be seen, very few lipid bodies are visible. Panel (B) illustrates Wild Type (WT) mouse liver section treated with food powder. Again, very few lipid bodies are visible. Panel (C) illustrates untreated obese (KO) mouse liver section. In this panel the clear circular areas are lipid bodies widely distributed in the liver. Panel (D) illustrates (KO) mouse liver section treated with food powder. The clear circular areas are lipid bodies. Potential areas of tissue regeneration are shown by arrows. These results show a clear reduction in lipid bodies in obese mice treated with food powder as described herein.

One or more illustrative embodiments have been described by way of example. It will be understood to persons skilled in the art that a number of variations and modifications can be made without departing from the scope of the invention as defined in the claims.

REFERENCES

Aprikian, O., Duclos, V., Guyot, S., Besson, C., Manach, C., Bernalier, A., Rémésy, C. and Demigné, C. (2003) Apple pectin and a polyphenol-rich apple concentrate are more effective together than separately on cecal fermentations and plasma lipids in rats. J. Nutr., 133, 1860-1865.

Azeredo, H. M. C., Mattoso, L. H. C., Wood, D., Williams, T. G., Avena-Bustillos, R. J. and McHugh, T. H. (2009) Nanocomposite edible films from mango puree reinforced with cellulose nanofibers. J. Food. Sci., 74, Nr 5, N31-N35.

Cabral, H., Matsumoto, Y., Mizuno, K., Chen, Q., Murakami, M., Kimura, M., Terada, Y., Kano, M. R., Miyazono, K., Uesaka, M., Nishiyama, N. and Kataoka, K. (2011) Accumulation of sub-100 nm polymeric micelles in poorly permeable tumours depends on size., Nature Nanotechnol., 6., 815-823.

Clifford, M. and Brown, J. E. (2006) Dietary flavonoids and health-Broadening the perspective In Flavonoids Chemistry biochemistry and applications, Andersen O M, Markham K R (Eds.); Taylor and Francis, New York, NY: 320-370.

Dangles, O. and Dufour, C. (2006). Flavonoid-protein interactions. In Flavonoids: Chemistry, biochemistry & applications, ed. Andersen O, Markham K. 443-69. Boca Raton, FL: CRC Press.

David, I., Ştefănuţ, M. N., Căta, A, Ienaşcu, I., Pop, R., Tănasie, C., and Balcu, I. (2009) Study of polyphenols from *Vaccinium Myrtillus* L. frozen fruits. J. Agroalimentary Processes and Technol. 15 (3), 348-352.

Del Rio, D., Borges, G. and Crozier, A. (2010) Berry Flavonoids and phenolics: bioavailability and evidence of protective effects. Brit. J. Nutr., 104: S 67-S90.

Deng, Z. J., Liang, M., Monteiro, M., Toth, I. and Minchin, R. F. (2011) Nanoparticle-induced unfolding of fibrinogen promotes Mac-1 receptor activation and inflammation. Nature Nanotech. 6, 39-44.

Discher, D. E. and Eisenberg, A. (2002) Polymer vesicles. Science 297, 967-973. Fu, J. T.; Rao, M. A. (2001) Rheology and structure development during gelation of low-methoxyl pectin gels: The effect of sucrose. Food Hydrocolloid., 15, 93-100.

Gao, Y., Gu, W., Chen, L., Xu, Z., Li, Y. (2008). The role of daidzein-loaded sterically stabilized solid lipid nanoparticles in therapy for cardio-cerebrovascular diseases. Biomaterials., 29, 4129-4136.

Gorinstein, S., Haruenkit, R., Poovarodom, S., Park, Y-S., Vearasilp, S., Suhaj, M., Ham, K-S., Heo, B-G., Cho, J. Y., and Jang, H. G. 2009. The comparative characteristics of snake and kiwi fruits. Food and Chem. Toxicol., 47, 1884-1891.

IOM (Institute of Medicine) (2009) Nanotechnology in food products: Workshop Summary. Washington, DC: The National Academies Press.

Iversena, T. G., Skotlanda, T. and Sandvig, K. (2011). Endocytosis and intracellular transport of nanoparticles: Present knowledge and need for future studies. Nano Today, 6, 176-185.

Jacob, J. K. and Paliyath, G. (2008) Physico-chemical characteristics of nanovesicle-carbohydrate complexes in grape juice, J. Agr. Food Chem., 56, 1305-1315.

Kacurakova, M., Capek, P., Sasinkova, N., Wellner, A., and Ebrigerova, A. (2000) FT-IR study of plant cell wall model compounds: pectic polysaccharides. Carbohydrate Polym., 43, 195-203.

Kunzmann, A., Andersson, B., Thurnherrm, T., Krug, H, Scheynius, A. and Fadeel, B. (2011) Toxicology of engineered nanomaterials: Focus on biocompatibility, biodistribution and biodegradation. Biochim. Biophys. Acta., 1810, 361-373.

Lewinski, N., Colvin, V. and Drezek, R. (2008) cytotoxicity of nanoparticles. Small, 4, 26-49.

Manach, C., Scalbert, A., Morand, C., Remesy, C. and Jimenez, L. (2004). Polyphenols: food sources and bioavailability. Amer. J. Clin. Nutr., 79:727-747.

Marcus, S. E., Verhertbruggen, Y., Hervé, C., Ordaz-Ortiz, J. J., Farkas, V., Pedersen, H. L., Willats, W. G. T. and Knox, J. P. (2008). Pectic homogalacturonan masks abundant sets of xyloglucan epitopes in plant cell walls. BMC Plant Biol., 8, 60-72.

Maynard, A. D. (2006) Nanotechnology: Assessing the risks. Nanotoday, 1, 22-33.

McCann, M. C., Shi, J., Roberts, K. And Carpita, N. C. (1994) Changes in pectin structure and localization during the growth of unadapted and NaCl-adapted tobacco cells. Plant J., 5, 773-785.

Mishra, R. K., Banthia, A. K. and Majeed, A. B. A. (2012) Pectin based formulations for biomedical applications: A Review. Aian J. Pharm. Clin. Res., 5, 1-7.

Mishra, R. K., Banthia, A. K. and Majeed, A. B. A. (2011). Development and characterization of pectin/gelatin hydrogel membranes for wound dressing. Int. J. Plast. Technol., 15, 82-95.

Negi, P. S. and Handa, A. K. (2008) Structural deterioration of the produce: The breakdown of cell wall components. In, Post Harvest Biology and Technology of Fruits, Vegetables and Flowers (Eds)

Paliyath, G., D. P. Murr, A. K. Handa and S. Lurie, Blackwell Publications, Iowa, pp 162-194.

Nishiyama N (2007) Nanocarriers shape up for long life. Nature Nanotechnol., 2, 203-205.

Padayachee, A., Netzel, G., Netzel, M., Day, L., Zabaras, D., Mikkelsen, D. and Gidley, M. (2012) Binding of polyphenols to plant cell wall analogues-Part 1: Anthocyanins. Food Chemistry, 134, 155-161.

Palashuddin, Md. S. K., Jaiswal, A., Paul, A., Ghosh, S. S. and Chattopadhyay, A. (2012) Presence of amorphous carbon nanoparticles in food caramels. Nature Scientific Reports, 2, Article number: 383. doi:10.1038/srep00383

Paliyath, G., Bakovic, M. and Shetty, K. (2011). Functional foods, nutraceuticals and degenerative disease prevention. Wiley-Blackwell, Oxford, UK, 392 pages.

Park, S., Baker, J. O., Himmel, M. E., Parilla, P. A., Johnson, D. K. (2010). Cellulose crystallinity index: measurement techniques and their impact on interpreting cellulase performance. BMC Biotechnol. Fuels, 3, 10-20.

Ramasamy, T., Kandasamy, U, Hinabindhu, R. and Kona, K. (2009) Nanocochleate-A New Drug Delivery System. FABAD J. Pharm. Sci., 34, 91-101.

Rico, C. M., Majumdar, S., Duarte-Gardea, M., Peralta-Videa, J. R. and Gardea-Torresdey, J. L. (2011) Interaction of Nanoparticles with Edible Plants and Their Possible Implications in the Food Chain. J. Agr. Food. Chem., 59, 3485-3498.

Rounds, C. M., Lubeck, E., Hepler, P. K. and Winship, L. J. (2011) Propidium iodide competes with Ca2+ to label pectin in pollen tubes and *Arabidopsis* root hairs. Plant Physiol., 157, 175-187.

Saura-Calixto, F. and Diaz-Rubio, M. E. (2007a). Polyphenols associated with dietary fibre in wine-A wine polyphenols gap? Food Res Int.; 40:613-619.

Saura-Calixto, F., Serrano, J. and Goni, I. (2007b). Intake and bioaccessibility of total polyphenols in a whole diet. Food Chemistry, 101:492-501.

Scalbert, A., Manach, C., Morand, C., Rémésy, C. and Jiménez, L. (2005). Dietary polyphenols and the prevention of diseases. Crit Rev Food Sci Nutr 45 (4): 287-306

Seifert, G. J. and Roberts, K. (2007) The Biology of Arabinogalactan Proteins. Annu. Rev. Plant Biol., 58, 137-161.

Sessa, M., Tsao, R., Liu, R., Ferrari, G. and Donsì, F. (2011). Evaluation of the stability and antioxidant activity of nanoencapsulated resveratrol during in vitro digestion. J. Agr. Food Chem., 59, 12352-12360.

Shi, L. and Gunasekaran, S. (2008) Preparation of pectin-ZnO nanocomposites. (2008). Nanoscale Research Letters, 3:491-495.

Spencer, J. P. E. and Rice-Evans, C. A. (2003) Metabolism in the small intestine and gastrointestinal tract. In Flavonoids in Health and disease, Rice-Evans C, Packer L (Eds.); Marcel Dekker, Inc. New York: 363-389.

Sriamornsak, P. (2011) Application of pectin in oral drug delivery. Expert Opinion on Drug. Deliv., 8, 1009-1023.

Ström, A.; Ribelles, P.; Lundin, L.; Norton, I.; Morris, E. R.; Williams, A. K. Influence of pectin fine structure on the mechanical properties of calcium-pectin and acid-pectin gels. Biomacromolecules 2007, 8, 2668-2674.

Urias-Orona, V., Rascón-Chu, A., Lizardi-Mendoza, J., Carvajal-Millán, E., Gardea, A. A., and Ramírez-Wong, B. (2010). A Novel Pectin Material: Extraction, Characterization and Gelling Properties, 11, 3686-3695.

Verma, A. K., Chanchal, A., Kumar, A. (2011) Potential of Negatively charged pectin nanoparticles encapsulating Paclitaxel: Preparation & Characterization. IEEE., 978, 1-8.

Yadav, N., Morris, G. A., Harding, S. E., Ang, S. and Adams, G. G. (2009) Various non-injectable delivery systems for the treatment of diabetes mellitus. Endo. Metabol. & Imm. Disord. -Drug Targ. 2009, 9, 1-13.

Yamashita, K. et al. (2011) Silica and titanium dioxide nanoparticles cause pregnancy complications in mice Nature Nanotech., 6, 321-328.

Zhao, N., Bagaria, H. G., Wong, M. S. and Zu, Y. (2011) A nanoparticle that is both tumor cell-selective and cancer gene-specific for anaplastic large cell lymphoma. J. Nanobiotechnol., 9, 1-12.

Zhang, H. Y., Arab Tehrany, E., Kahn, C. J. F., Ponc, ot, M. and Cleymand, L. F. (2012) Effects of nanoliposomes based on soya, rapeseed and fish lecithins on chitosan thin films designed for tissue engineering. Carbohydrate Polymers., 88, 618-627.

Agarwala, R., Singh, V., Jurney, P., Shib, L., Sreenivasan, S. V., and Roya, K. (2013). Mammalian cells preferentially internalize hydrogel nanodiscs over nanorods and use shape-specific uptake mechanisms. Proc. Natl. Acad. Sci. (USA), 110, 17247-17252.

Barenholz, Y. (2012) Doxil®—The first FDA-approved nano-drug: Lessons learned. J. Controlled Release, 160, 117-134., Cabral, H., Matsumoto, Y., Mizuno, K., Chen, Q., Murakami, M., Kimura, M., Terada, Y., Kano, M. R., Miyazono, K., Uesaka, M., Nishiyama, N. and Kataoka, K. (2011) Accumulation of sub-100 nm polymeric micelles in poorly permeable tumours depends on size., Nature Nanotechnol., 6., 815-823.

Chandra, A., Nair, M. G. and Lezzoni, A. (1992). Evaluation and characterization of the anthocyanin pigments in tart cherries (*Prunus cerasus* L.). J. Agric. Food Chem., 40, 967-969.

Kai-Hua Chow, E. and Ho, D. (2013) Cancer nanomedicine: From drug delivery to imaging. Sci. Trasl. Medicine., 5, (216) 1-12.

Clifford, M. and Brown, J. E. (2006) Dietary flavonoids and health-Broadening the perspective In Flavonoids Chemistry biochemistry and applications, Andersen O M, Markham K R (Eds.); Taylor and Francis, New York, NY: 320-370.

Dahlman, J. E. Barnes, C. et al. (2014) In vivo endothelial siRNA delivery using polymeric nanoparticles with low molecular weight. Nature Nanotechnol., 2014, 9, 648-654.

Del Rio, D., Borges, G. and Crozier, A. (2010) Berry Flavonoids and phenolics: bioavailability and evidence of protective effects. Brit. J. Nutr., 104: S 67-S90.

Gao, Y., Gu, W., Chen, L., Xu, Z., Li, Y. (2008). The role of daidzein-loaded sterically stabilized solid lipid nanoparticles in therapy for cardio-cerebrovascular diseases. Biomaterials., 29, 4129-4136.

Garcia-Alonso, J., Rosa, G., Vidal-Guevera, M. L. and Periago, M. J. (2006) Acute intake of phenolic rich juice improves antioxidant status in healthy subjects. Nutr. Res., 26:330-339.

Gonzalez-Gallego, J., Victoria Garcia-Mediavilla, M., Sanchez-Campos, S. and Tunon, M. J. (2010) Fruit polyphenols, immunity and inflammation. British J. Nutr., 104: S15-S27.

Hakimuddin, F, Paliyath, G. and Meckling, K. (2004). Selective cytotoxicity of a red grape wine flavonoid fraction against MCF-7 cells, Breast Cancer Res. Treatment. 85:65-79.

Hakimuddin, F., Paliyath, G. and Meckling, K. (2006). Red wine polyphenols cause selective cytotoxicity in MCF-7 cells by disrupting calcium signaling, mitochondrial function and the cell cycle. J. Agric. Food Chem., 54:7912-7923.

Hakimuddin, F., Tiwari, K., Paliyath, G. and Meckling, K. (2008). Grape and wine polyphenols down-regulate the expression of signal transduction genes and inhibit the growth of estrogen receptor-negative mda-mb231 tumors in nu/nu mouse xenografts. Nutr. Res., 28:702-713.

Hakimuddin, F. and Paliyath, G. (2011). Cancer prevention by polyphenols: Influence on signal transduction and gene expression. In Functional foods, nutraceuticals and degenerative disease prevention. Eds Paliyath G, Bakovic M, Shetty K. Wiley-Blackwell, Oxford, UK, pp 283-321.

Holt, E. M., Steffen, L. M., Moran, A., Basu, S., Steinberger, J., Ross, J., Hong, C. P. and Sinaiko, A. R. (2009). Fruit and vegetable consumption and its relation to markers of inflammation and oxidative stress in adolescents. J Am Diet Assoc., 109:414-421.

Iversena, T. G., Skotlanda, T. and Sandvig, K. (2011). Endocytosis and intracellular transport of nanoparticles: Present knowledge and need for future studies. Nano Today, 6, 176-185.

Jacob, J. K. and Paliyath, G. (2008) Physico-chemical characteristics of nanovesicle-carbohydrate complexes in grape juice, J. Agr. Food Chem., 56, 1305-1315.

Jacob, J. K., Tiwari, K, Correa-Betanzo, J., Misran, A, Chandrasekaran, R and G. Paliyath. (2012) Biochemical basis for functional ingredient design from fruits. Annu. Rev. Food Sci. Technol., 3, 79-104.

Jensen, G. S., Wu, X, Patterson, K. M, Barnes, J., Carter, S. G., Scherwitz, L. S., Beaman, R., Endres, J. R. and Schauss, A. G. (2008) In vitro and in vivo antioxidant and antiinflammatory capacities of an antioxidant rich fruit and berry juice blend. Results of a pilot and randomized double blind, placebo controlled, crossover study. J. Agric. Food Chem., 56:8326-8333.

Karlsen, A., Retterstol, L., Laake, P., Paur, I., Kjolsrud-Bohn, S., Sandvik, L. and Blomhoff, R. (2007) Anthocyanins inhibit, Nuclear Factor kappa B-activation in monocytes and reduce plasma concentration of pro-inflammatory mediators in healthy adults. Journal of Nutrition, 137, 1951-1954.

Kelley, D. S., Rasooly, R., Jacob, R. A., Kader, A. A., and Mackey, B. E. (2006). Consumption of bing sweet cherries lowers circulating concentrations of inflammation markers in healthy men and women. J.Nutr., 136: 981-986.

Kunzmann, A., Andersson, B., Thurnherrm, T., Krug, H., Scheynius, A. and Fadeel, B. (2011) Toxicology of engineered nanomaterials: Focus on biocompatibility, biodistribution and biodegradation. Biochim. Biophys. Acta., 1810, 361-373.

Lewinski, N., Colvin, V. and Drezek, R. (2008) cytotoxicity of nanoparticles. Small, 4, 26-49.

Manach, C., Scalbert, A., Morand, C., Remesy, C. and Jimenez, L. (2004). Polyphenols: food sources and bioavailability. Amer. J. Clin. Nutr., 79:727-747 Maynard, A. D. (2006) Nanotechnology: Assessing the risks. Nanotoday, 1, 22-33.

Morton, S. W., Lee, M. J., Deng, Z. J., Dreaden, E. C. Siouve, E., Shopsowitz, K. E., Shah, N. J., Yaffe, M. B., Hammond, P. T. (2014) A Nanoparticle-Based Combination Chemotherapy Delivery System for Enhanced Tumor Killing by Dynamic Rewiring of Signaling Pathways. Science Signalling., 7, 1-11.

Palashuddin, Md. S. K., Jaiswal, A., Paul, A., Ghosh, S. S. and Chattopadhyay, A. (2012) Presence of amorphous carbon nanoparticles in food caramels. Nature Scientific Reports, 2, Article number: 383. doi: 10.1038/srep00383

Ramasamy, T., Kandasamy, U, Hinabindhu, R. and Kona, K. (2009) Nanocochleate--A New Drug Delivery System. FABAD J. Pharm. Sci., 34, 91-101.

Saura-Calixto, F. and Diaz-Rubio, M. E. (2007a). Polyphenols associated with dietary fibre in wine-A wine polyphenols gap? Food Res Int.; 40:613-619.

Sessa, M., Tsao, R., Liu, R., Ferrari, G. and Donsì, F. (2011). Evaluation of the stability and antioxidant activity of nanoencapsulated resveratrol during in vitro digestion. J. Agr. Food Chem., 59, 12352-12360.

Shah, B. P., Pasquale, N., De, G., Tan, T., Ma, J. and Lee, K-B. (2014). Core shell nanoparticle-based peptide therapeutics and combined hyperthermia for enhanced cancer cell apoptosis. ACS Nano, 8, 9379-9387.

Smith, B. R., Ghosn, E. E. B., Rallapalli, H., Prescher, J. A., Larson, T., Herzenberg, L. A. and Gambhir, S. S. (2014) Selective uptake of single-walled carbon nanotubes by circulating monocytes for enhanced tumour delivery. Nature Nanotechnol., 9, 481-487.

Verma, A. K., Chanchal, A., Kumar, A. (2011) Potential of Negatively charged pectin nanoparticles encapsulating Paclitaxel: Preparation & Characterization. IEEE., 978, 1-8.

Willcox, J. K., Ash, S. L. and Catignani, G. L. (2004). Antioxidants and prevention of chronic disease. Critical Reviews in Food Science and Nutrition, 44:275-295.

Yamashita, K. et al. (2011) Silica and titanium dioxide nanoparticles cause pregnancy complications in mice Nature Nanotech., 6, 321-328.

Zhao, N., Bagaria, H. G., Wong, M. S. and Zu, Y. (2011) A nanoparticle that is both tumor cell-selective and cancer gene-specific for anaplastic large cell lymphoma. J. Nanobiotechnol., 9, 1-12.

Zhu, G., Mei, L., and Tan W. (2014) Nanomedicine. The Scientist Magazine, August 22nd 2014.

Atkins, M. B.; Regan, M.; McDermott, D. Update on the role of interleukin 2 and other cytokines in the treatment of patients with stage IV renal carcinoma. Clin. Cancer Res. 2004, 10, 6342S-6346S.

Atkins, M. B.; Lotze, M. T.; Dutcher, J. P.; Fisher, R. I.; Weiss, G.; Margolin, K.; Abrams, J.; Sznol, M.; Parkinson, D.; Hawkins, M.; et al. High-dose recombinant interleukin 2 therapy for patients with metastatic melanoma: Analysis of 270 patients treated between 1985 and 1993. J. Clin. Oncol. 1999, 17, 2105-2116.

Balkwill, F. (2006). TNF-α in promotion and progression of cancer. Cancer and Metastasis Reviews, 25: pp. 409-416.

Balkwill, F. (2009). Tumour necrosis factor and cancer. Nat. Rev. Cancer 9, 361-371.

Chang, K. J., Reid, T., Senzer, N., et al., (2012). Phase I evaluation of TNFerade Biologic plus chemoradiotherapy before esophagectomy for locally advanced resectable esophageal cancer, Gastrointestinal Endoscopy, 75: pp. 1139-1146, 2012.

Commins S P, Borish L & Steinke J W (2010) Immunologic messenger molecules: cytokines, interferons, and chemokines. J Allergy Clin Immunol 125(2 Suppl 2): S53-72.

Dougan, M., and Dranoff, G. (2009). Immune therapy for cancer. Annual Review of Immunology 27:83-117.

Eferl, R., and Wagner, E. F. (2003). AP-1: a double-edged sword in tumorigenesis. Nat. Rev. Cancer 3:859-868.

Heikkila, K., Ebrahim, S., and Lawlor, D. A. (2008) Systematic review of the association between circulating interleukin-6 (IL-6) and cancer. European Journal of Cancer 44: pp. 937-945.

Herman, J. M., Wild, A. T., Wang H., et al., 2013. Randomized phase III multi-institutional study of TNFerade biologic with fluorouracil and radiotherapy for locally advanced pancreatic cancer: final results. Journal of Clinical Oncology, 31: pp. 886-894.

Hodge, D. R., Hurt, E. M., and Farrar, W. L. 2005. The role of IL-6 and STAT3 in inflammation and cancer. European Journal of Cancer, 41: pp. 2502-2512.

Karin, M. (2006). Nuclear factor-kappa B in cancer development and progression. Nature 441, 431-436.

Laveti, D., Kumar, M., Hemalatha, R., Sistla, R., Naidu, V. G., Talla, V., Verma, V., Kaur, N., and Nagpal, R., (2013) Anti-inflammatory treatments for chronic diseases: a review, Inflamm. Allergy Drug Targets 12:349-361.

Lee S and Margolin K (2011) Cytokines in cancer immunotherapy. Cancers 3:3856-3893.

Lust, J. A., Lacy, M. Q., Zeldenrust, S. R., Dispenzieri, A., Gertz, M. A., Witzig, T. E., Kumar, S., Hayman, S. R., Russell, S., Buadi, F. K., et al. (2009). Induction of a chronic disease state in patients with smoldering or indolent multiple myeloma by targeting interleukin 1beta-induced interleukin 6 production and the myeloma proliferative component. Mayo Clin. Proc. 84, 114-122.

Popa, C., Netea, M. G., Van Riel, J P. L. C. M., Van Der Meer, W. M., and Stalenhoef, A. F. H. (2007) The role of TNF-α in chronic inflammatory conditions, intermediary metabolism, and cardiovascular risk. Journal of Lipid Research vol. 48: pp. 751-762.

Thornton, A. M.; Donovan, E. E.; Piccirillo, C. A.; Shevach, E. M. Cutting edge: IL-2 is critically required for the in vitro activation of CD4+CD25+ T cell suppressor function. J. Immunol. 2004, 172, 6519-6523.

Waldner, M. J., and Neurath, M. F. (2009). Colitis-associated cancer: the role of T cells in tumor development. Semin. Immunopathol. 31, 249-256.

Zhang, J. Y., Green, C. L., Tao, S., and Khavari, P. A. (2004). NF-kappa B RelA opposes epidermal proliferation driven by TNFR1 and JNK. Genes Dev. 18, 17-22.

Zitvogel, L., Apetoh, L., Ghiringhelli, F., and Kroemer, G. (2008). Immunological aspects of cancer chemotherapy. Nat. Rev. Immunol. 8, 59-73.

Aprikian, O., Duclos, V., Guyot, S., et al., (2003) Apple pectin and a polyphenol-rich apple concentrate are more effective together than separately on cecal fermentations and plasma lipids in rats. J. Nutr., 133, 1860-1865.

Azeredo, H. M. C., Mattoso, L. H. C., Wood, D., Williams, T. G., Avena-Bustillos, R. J. and McHugh, T. H. (2009) Nanocomposite edible films from mango puree reinforced with cellulose nanofibers. J. Food. Sci., 74, Nr 5, N31-N35.

Cabral, H., Matsumoto, Y., Mizuno, K., Chen, Q., Murakami, M., Kimura, M., Terada, Y., Kano, M. R., Miyazono, K., Uesaka, M., Nishiyama, N. and Kataoka, K. (2011) Accumulation of sub-100 nm polymeric micelles in poorly permeable tumours depends on size., Nature Nanotechnol., 6., 815-823.

Clifford, M. and Brown, J. E. (2006) Dietary flavonoids and health-Broadening the perspective In Flavonoids Chemistry biochemistry and applications, Andersen O M, Markham K R (Eds.); Taylor and Francis, New York, NY: 320-370.

Dangles, O. and Dufour, C. (2006). Flavonoid-protein interactions. In Flavonoids: Chemistry, biochemistry & applications, ed. Andersen O, Markham K. 443-69. Boca Raton, FL: CRC Press.

David, I., Ştefănuţ, M. N., Căta, A, Ienaşcu, I., Pop, R., Tănasie, C., and Balcu, I. (2009) Study of polyphenols from *Vaccinium Myrtillus* L. frozen fruits. J. Agroalimentary Processes and Technol. 15 (3), 348-352.

Del Rio, D., Borges, G. and Crozier, A. (2010) Berry Flavonoids and phenolics: bioavailability and evidence of protective effects. Brit. J. Nutr., 104: S 67-S90.

Deng, Z. J., Liang, M., Monteiro, M., Toth, I. and Minchin, R. F. (2011) Nanoparticle-induced unfolding of fibrinogen promotes Mac-1 receptor activation and inflammation. Nature Nanotech. 6, 39-44.

Discher, D. E. and Eisenberg, A. (2002) Polymer vesicles. Science 297, 967-973.

Fu, J. T.; Rao, M. A. (2001) Rheology and structure development during gelation of low-methoxyl pectin gels: The effect of sucrose. Food Hydrocolloid., 15, 93-100.

Gao, Y., Gu, W., Chen, L., Xu, Z., Li, Y. (2008). The role of daidzein-loaded sterically stabilized solid lipid nanoparticles in therapy for cardio-cerebrovascular diseases. Biomaterials., 29, 4129-4136.

Gorinstein, S., Haruenkit, R., Poovarodom, S., Park, Y-S., Vearasilp, S., Suhaj, M., Ham, K-S., Heo, B-G., Cho, J. Y., and Jang, H. G. 2009. The comparative characteristics of snake and kiwi fruits. Food and Chem. Toxicol., 47, 1884-1891.

IOM (Institute of Medicine) (2009) Nanotechnology in food products: Workshop Summary. Washington, DC: The National Academies Press.

Iversena, T. G., Skotlanda, T. and Sandvig, K. (2011). Endocytosis and intracellular transport of nanoparticles: Present knowledge and need for future studies. Nano Today, 6, 176-185.

Jacob, J. K. and Paliyath, G. (2008) Physico-chemical characteristics of nanovesicle-carbohydrate complexes in grape juice, J. Agr. Food Chem., 56, 1305-1315.

Kacurakova, M., Capek, P., Sasinkova, N., Wellner, A., and Ebrigerova, A. (2000) FT-IR study of plant cell wall model compounds: pectic polysaccharides. Carbohydrate Polym., 43, 195-203.

Kunzmann, A., Andersson, B., Thurnherrm, T., Krug, H., Scheynius, A. and Fadeel, B. (2011) Toxicology of engineered nanomaterials: Focus on biocompatibility, biodistribution and biodegradation. Biochim. Biophys. Acta., 1810, 361-373.

Lewinski, N., Colvin, V. and Drezek, R. (2008) cytotoxicity of nanoparticles. Small, 4, 26-49.

Manach, C., Scalbert, A., Morand, C., Remesy, C. and Jimenez, L. (2004). Polyphenols: food sources and bioavailability. Amer. J. Clin. Nutr., 79:727-747.

Marcus, S. E., Verhertbruggen, Y., Hervé, C., Ordaz-Ortiz, J. J., Farkas, V., Pedersen, H. L., Willats, W. G. T. and Knox, J. P. (2008). Pectic homogalacturonan masks abundant sets of xyloglucan epitopes in plant cell walls. BMC Plant Biol., 8, 60-72.

Maynard, A. D. (2006) Nanotechnology: Assessing the risks. Nanotoday, 1, 22-33.

McCann, M. C., Shi, J., Roberts, K. And Carpita, N.C. (1994) Changes in pectin structure and localization during the growth of unadapted and NaCl-adapted tobacco cells. Plant J., 5, 773-785.

Mishra, R. K., Banthia, A. K. and Majeed, A. B. A. (2012) Pectin based formulations for biomedical applications: A Review. Aian J. Pharm. Clin. Res., 5, 1-7.

Mishra, R. K., Banthia, A. K. and Majeed, A. B. A. (2011). Development and characterization of pectin/gelatin hydrogel membranes for wound dressing. Int. J. Plast. Technol., 15, 82-95.

Negi, P. S. and Handa, A. K. (2008) Structural deterioration of the produce: The breakdown of cell wall components. In, Post Harvest Biology and Technology of Fruits, Vegetables and Flowers (Eds) Paliyath, G., D. P. Murr, A. K. Handa and S. Lurie, Blackwell Publications, Iowa, pp 162-194.

Nishiyama N (2007) Nanocarriers shape up for long life. Nature Nanotechnol., 2, 203-205.

Padayachee, A., Netzel, G., Netzel, M., Day, L., Zabaras, D., Mikkelsen, D. and Gidley, M. (2012) Binding of polyphenols to plant cell wall analogues-Part 1: Anthocyanins. Food Chemistry, 134, 155-161.

Palashuddin, Md. S. K., Jaiswal, A., Paul, A., Ghosh, S. S. and Chattopadhyay, A. (2012) Presence of amorphous carbon nanoparticles in food caramels. Nature Scientific Reports, 2, Paliyath, G., Bakovic, M. and Shetty, K. (2011). Functional foods, nutraceuticals and degenerative disease prevention, Wiley-Blackwell, Oxford, UK, 392 pages.

Park, S., Baker, J. O., Himmel, M. E., Parilla, P. A., Johnson, D. K. (2010). Cellulose crystallinity index: measurement techniques and their impact on interpreting cellulase performance. BMC Biotechnol. Fuels, 3, 10-20.

Ramasamy, T., Kandasamy, U, Hinabindhu, R. and Kona, K. (2009) Nanocochleate-A New Drug Delivery System. FABAD J. Pharm. Sci., 34, 91-101.

Rico, C. M., Majumdar, S., Duarte-Gardea, M., Peralta-Videa, J. R. and Gardea-Torresdey, J. L. (2011) Interaction of Nanoparticles with Edible Plants and Their Possible Implications in the Food Chain. J. Agr. Food. Chem., 59, 3485-3498.

Rounds, C. M., Lubeck, E., Hepler, P. K., and Winship, L. J., (2011) Propidium iodide competes with Ca2+ to label pectin in pollen tubes and *Arabidopsis* root hairs. Plant Physiol., 157, 175-187.

Saura-Calixto, F. and Diaz-Rubio, M. E. (2007a). Polyphenols associated with dietary fibre in wine-A wine polyphenols gap? Food Res Int.; 40:613-619.

Saura-Calixto, F., Serrano, J. and Goni, I. (2007b). Intake and bioaccessibility of total polyphenols in a whole diet. Food Chemistry, 101:492-501.

Scalbert, A., Manach, C., Morand, C., Rémésy, C. and Jiménez, L. (2005). Dietary polyphenols and the prevention of diseases. Crit Rev Food Sci Nutr 45 (4): 287-306

Seifert, G. J. and Roberts, K. (2007) The Biology of Arabinogalactan Proteins. Annu. Rev. Plant Biol., 58, 137-161.

Sessa, M., Tsao, R., Liu, R., Ferrari, G. and Donsì, F. (2011). Evaluation of the stability and antioxidant activity of nanoencapsulated resveratrol during in vitro digestion. J. Agr. Food Chem., 59, 12352-12360.

Shi, L. and Gunasekaran, S. (2008) Preparation of pectin-ZnO nanocomposites. (2008). Nanoscale Research Letters, 3:491-495.

Spencer, J. P. E. and Rice-Evans, C. A. (2003) Metabolism in the small intestine and gastrointestinal tract. In Flavonoids in Health and disease, Rice-Evans C, Packer L (Eds.); Marcel Dekker, Inc. New York: 363-389.

Sriamornsak, P. (2011) Application of pectin in oral drug delivery. Expert Opinion on Drug. Deliv., 8, 1009-1023.

Ström, A.; Ribelles, P.; Lundin, L.; Norton, I.; Morris, E. R.; Williams, A. K. Influence of pectin fine structure on the mechanical properties of calcium-pectin and acid-pectin gels. Biomacromolecules 2007, 8, 2668-2674.

Urias-Orona, V., Rascón-Chu, A., Lizardi-Mendoza, J., Carvajal-Millán, E., Gardea, A. A., and Ramírez-Wong, B. (2010). A Novel Pectin Material: Extraction, Characterization and Gelling Properties, 11, 3686-3695.

Verma, A. K., Chanchal, A., Kumar, A. (2011) Potential of Negatively charged pectin nanoparticles encapsulating Paclitaxel: Preparation & Characterization. IEEE., 978, 1-8.

Yadav, N., Morris, G. A., Harding, S. E., Ang, S. and Adams, G. G. (2009) Various non-injectable delivery systems for the treatment of diabetes mellitus. Endo. Metabol. & Imm. Disord. -Drug Targ. 2009, 9, 1-13.

Yamashita, K. et al. (2011) Silica and titanium dioxide nanoparticles cause pregnancy complications in mice Nature Nanotech., 6, 321-328.

Zhao, N., Bagaria, H. G., Wong, M. S. and Zu, Y. (2011) A nanocomplex that is both tumor cell-selective and cancer gene-specific for anaplastic large cell lymphoma. J. Nanobiotechnol., 9, 1-12.

Zhang, H. Y., Arab Tehrany, E., Kahn, C. J. F., Ponc, ot, M. and Cleymand, L. F. (2012) Effects of nanoliposomes based on soya, rapeseed and fish lecithins on chitosan thin films designed for tissue engineering. Carbohydrate Polymers., 88, 618-627.

Chang, D., Lei, J., Cui, H., Lu, N., Sun, Y, Zhang, X., Gao, C and Yin, Y. 2012. Carbohydrate Polymers., 88, 663-669.

Gao, Y., Gu, W., Chen, L., Xu, Z and Li, Y. 2008. The role of daidzein-loaded sterically stabilized solid lipid nanoparticles in therapy for cardio-vascular diseases. Biomaterials, 29, 4129-4136.

Gao, J and Xu, B. 2009. Applications of nanomaterials inside cells. Nano Today, 4, 37-51.

Jacob, J. K. and G. Paliyath (2008) Physico-chemical characteristics of nanovesicle-carbohydrate complexes in grape juice, J. Agr. Food Chem., 56, 1305-1315.

Lewinski, N., Colvin, V., and Rebekah, D. 2008. Cytotoxicity of nanoparticles. Small., 4, 26-49.

Maynard, A. 2006. Nanotechnology: Assessing the risks. Nanotoday, 1, 22-33.

Paliyath, G. and J. E. Thompson (1990) Evidence for early changes in membrane structure during post-harvest development of cut carnation flowers, New Phytologist, 114, 555-562

Ramasamy, T., Khandasamy, U, Hinabindhu, R and K. Kiran. (2009). Nanocochleate-a new drug delivery system, FABAD J. Pharm. Sci., 34, 91-101.

Sessa, M., R. Tsao, R. Liu, G. Ferrari, and F. Donsi. (2011) Evaluation of the stability and antioxidant activity of nanoencapsulated resveratrol during in vitro digestion, J. Agr. Food Chem., 59, 12352-12360.

Yao, K., G. Paliyath, R. W. Humphrey, F. R. Hallet and J. E. Thompson (1991) Identification and characterization of non-sedimentable lipid-protein microvesicles enriched in phospholipid degradation products, Proc. Natl. Acad. Sci. (USA), 88, 2269-2273

Yao, K., G. Paliyath and J. E Thompson (1991) Non-sedimentable microvesicles from senescing bean cotyledons contain gel phase-forming phospholipid degradation products, Plant Physiol., 97, 502-508.

Zhang, N., Ping, Q., Huang, G., Xu, W., Cheng, Y., and Han, X. 2006. Lectin-modified solid lipid nanoparticles as carriers for oral administration of insulin. Internat. J. Pharmaceut., 327, 153-159.

Zhang, H. Y., Tehrany E. A., Kahn, C. J. F., Poncot, M, Linder M and F, Cleymand. 2012. Effects of nanoliposomes basaed on spya, rapeseed and fish lecithinson chitosan thin film s designed for tissue engineering. Carb. Polymers., 88, 618-627.

Zhao, N., Bagaria, H. G., Wong, M. S. and Zu, Y. 2011. A nanocomplex that is both tumour cell selective and cancer gene specific for anaplastic large cell lymphoma. J. Nanobiotechnol., 9, 2-14.

Zheng, D., Gilijohann, A, Chen, D. L., Massich, M. D., Wang, X-Q., Lordanov, H., Mirkin, C. A. and Paller, A. S. 2012. Topical delivery of siRNA based spherical nucleic acid nanoparticle conjugates for gene requlation. Proc. Natl. Acad. Scii. (USA), 109, 11975-11980.

J. Correa-Betanzo a, E. Allen-Vercoe b, J. McDonald b, K. Schroeter b, M. Corredig a, G. Paliyath (2014) Stability and biological activity of wild blueberry (*Vaccinium angustifolium*) polyphenols during simulated in vitro gastrointestinal digestion. Food Chemistry 165 (2014) 522-531; Julieta Correa-Betanzo, Priya Padmanabhan, Milena Corredig, Jayasankar Subramanian, and Gopinadhan Paliyath (2015) Complex Formation of Blueberry (*Vaccinium angustifolium*) anthocyanins during Freeze-Drying and Its Influence on Their Biological Activity. J. Agric. Food Chem. 2015, 63, 2935-2946).

All references cited herein and elsewhere in the specification are hereby incorporated by reference in their entireties.

What is claimed is:

1. A nanoparticle comprising self-assembled cellular components derived from a homogenized plant tissue derived from cherry or sour cherry, the cellular components comprising one or more structural carbohydrates or cleavage products of one or more structural carbohydrates, wherein the nanoparticle is non-crystalline and has a spherical structure with a pectin based inner core, wherein the nanoparticle is lipid-free, and wherein the nanoparticle comprises pectin or a cleavage product of pectin, hemicellulose or a cleavage product of hemicellulose, peptide and/or protein or a cleavage product of peptide and/or protein, an organic acid, at least one polyphenol or a cleavage product of a polyphenol, or any combination thereof.

2. The nanoparticle of claim 1, wherein the nanoparticle further comprises:

an intermediate layer surrounding the inner core, the intermediate layer comprising macromolecules of pectin, a cleavage product of pectin, hemicellulose, a cleavage product of hemicellulose and/or polyphenol, and organic acid;

wherein the polyphenol comprises an anthocyanin;

wherein the organic acid comprises malic acid, ascorbic acid, or both; and a fibrillated outer layer comprising macromolecular carbohydrate and protein, optionally formed from catabolism during ripening and/or during homogenization of the plant tissue.

3. The nanoparticle of claim 1, wherein the cellular components comprise those liberated from the plant tissue during ripening or during homogenization of ripened fruit, which are capable of self-assembling into the nanoparticle; and the one or more structural carbohydrates comprise one or more of pectin or a cleavage product of pectin, pectic acid or a cleavage product of pectic acid, methyl ester of pectin or a cleavage product of methyl ester of pectin, a pectin derivative or a cleavage product of the pectin derivative, polygalacturonic acid or a cleavage product of polygalacturonic acid, rhamnogalacturonans or a cleavage product of rhamnoglacturonans, xylogucans or a cleavage product of xylogucans, hemicelluloses or a cleavage product of hemicelluloses, xyloglucans possessing β-(1→4)-linked backbones of glucose, mannose, or xylose, and/or arabinogalactans or a cleavage product of xyloglucans possessing β-(1→4)-linked backbones of glucose, mannose, or xylose, and/or arabinogalactans.

4. The nanoparticle of claim 1, wherein the nanoparticle has a diameter of about 50-250 nm.

5. The nanoparticle of claim 1, wherein the nanoparticle comprises:

an intermediate layer surrounding the inner core, the intermediate layer comprising one or more spiral fibril structures comprising pectin or a derivative thereof, and one or more hemicellulose-derived molecules or a derivative thereof; and a fibrillated outer layer comprising hemicellulose or a cleavage product of hemicellulose, and one or more peptides derived from cellular proteins.

6. The nanoparticle of claim 1, wherein the nanoparticle is stabilized by hydrogen-bonding interactions present at a pH ranging from about 3 to about 7 and formed between macromolecules derived from catabolism of cellular components of the plant tissue and possessing hydroxyl groups and/or amino groups and/or organic acid groups.

7. The nanoparticle of claim 1, further comprising a biologically active agent; wherein the biologically active agent is a pharmaceutically active drug, protein, enzyme, nutraceutical, or nutrient.

8. The nanoparticle of claim 1, in aqueous solution, in powder form, in dehydrated, lyophilized, freeze-dried, spray-dried, or nanospray-dried form.

9. A nanoparticle prepared by a method comprising:

preparing a homogenized plant tissue in solution, comprising cellular components liberated from the plant tissue;

removing debris from the homogenized plant tissue, if present; and optionally, dialyzing the homogenized plant tissue to remove non-complexed compounds, or removing the non-complexed compounds by size exclusion, thereby providing a solution comprising the nanoparticles which are formed by self-assembly of the cellular components.

10. A food powder prepared from the nanoparticle as defined in claim 1, optionally wherein the food powder is provided in a micro-scale fine powder form.

11. A food powder comprising self-assembled cellular components derived from a homogenized plant tissue derived from cherry or sour cherry, the cellular components comprising one or more structural carbohydrates or cleavage products of one or more structural carbohydrates, and further comprising at least one nutritional agent, wherein lipids are not a structural component of the food powder.

12. The food powder of claim 11, wherein the food powder comprises:

fibrous structures winding about themselves to form a nanosphere-like structure; and optionally a hydrophobic component, wherein the hydrophobic component comprises or is provided in almond milk, coconut milk, and/or milk derived from an edible nut.

13. The food powder of claim 11, wherein the nutritional agent comprises a naturally occurring active ingredient having a health benefit; wherein the nutritional agent comprises one or more carotenoids, annonacins, Boswelia, Ashwagandha, Ginger family members, cannabinodiols, fructo-oligosacchgarides, galacto-oligosaccharides, inulin, Jerusalem artichoke, Piperaceae family members, *Piper nigrum* or a wild relative containing piperine and/or derivatives thereof, or any active ingredient thereof having a health benefit, or any extract, derivative, or product isolated therefrom, or any combinations thereof.

14. The food powder of claim 11, wherein the food powder comprises:
sour cherry, or an aqueous extract thereof;
almond milk or another homogenate of almonds;
soymilk, or another homogenate of soybean;
broccoli, or an aqueous extract thereof; and
turmeric, or a powder thereof.

15. The food powder of claim 14, comprising:
about 25-30 v/v % sour cherry extract;
optionally wherein the sour cherry extract is about 1-2 mg/ml of polyphenol equivalent;
about 25-30 v/v % almond milk or other homogenate of almonds;
about 10-18 v/v % soymilk or other homogenate of soybean;
about 25-30 v/v % broccoli extract; and
about 0.5-2.5 w/v % turmeric or powder thereof.

16. A food powder produced by a method comprising:
preparing a homogenized plant tissue in solution, comprising cellular components liberated from the plant tissue, the cellular components comprising one or more structural carbohydrates or cleavage products thereof, and the homogenized plant tissue in solution further comprising at least one nutritional agent;
optionally, removing debris from the homogenized plant tissue in solution, if present; and
freeze-drying, lyophilizing, spray-drying, or nanospray drying the homogenized plant tissue in solution to form the food powder.

17. An antibacterial food powder, comprising a food powder as defined claim 11, complexed with or conjugated with an antibacterial agent.

18. The antibacterial food powder of claim 17, wherein the antibacterial agent comprises lysozyme, a tetracycline, or Nisin, or any combination thereof.

19. The food powder of claim 15, wherein the sour cherry extract is at least about 0.1 mg/ml of polyphenol equivalent.

* * * * *

SEQUENCE LISTING

<160> NUMBER OF SEQ ID NOS: 28

<210> SEQ ID NO 1
<211> LENGTH: 20
<212> TYPE: DNA

```
<213> ORGANISM: Artificial Sequence
<220> FEATURE:
<223> OTHER INFORMATION: Forward primer - STAT4

<400> SEQUENCE: 1
aggttaagct ggctgtcctg                                              20

<210> SEQ ID NO 2
<211> LENGTH: 25
<212> TYPE: DNA
<213> ORGANISM: Artificial Sequence
<220> FEATURE:
<223> OTHER INFORMATION: Reverse primer - STAT4

<400> SEQUENCE: 2
agatctcttg tcttctggtt tgttg                                        25

<210> SEQ ID NO 3
<211> LENGTH: 20
<212> TYPE: DNA
<213> ORGANISM: Artificial Sequence
<220> FEATURE:
<223> OTHER INFORMATION: Former primer - TNF-alpha

<400> SEQUENCE: 3
ccgatgggtt gtaccttgtc                                              20

<210> SEQ ID NO 4
<211> LENGTH: 20
<212> TYPE: DNA
<213> ORGANISM: Artificial Sequence
<220> FEATURE:
<223> OTHER INFORMATION: Revere primer - TNF-alpha

<400> SEQUENCE: 4
gggctgggta gagaatggat                                              20

<210> SEQ ID NO 5
<211> LENGTH: 17
<212> TYPE: DNA
<213> ORGANISM: Artificial Sequence
<220> FEATURE:
<223> OTHER INFORMATION: Forward primer - IL-6

<400> SEQUENCE: 5
caagggtgtt acactgg                                                 17

<210> SEQ ID NO 6
<211> LENGTH: 20
<212> TYPE: DNA
<213> ORGANISM: Artificial Sequence
<220> FEATURE:
<223> OTHER INFORMATION: Reverse primer - IL-6

<400> SEQUENCE: 6
ctggtctcat ccgaaccctg                                              20

<210> SEQ ID NO 7
<211> LENGTH: 23
<212> TYPE: DNA
<213> ORGANISM: Artificial Sequence
<220> FEATURE:
<223> OTHER INFORMATION: Forward primer - FAS

<400> SEQUENCE: 7
cttcgagatg tgctcccagc tgc                                          23
```

<210> SEQ ID NO 8
<211> LENGTH: 24
<212> TYPE: DNA
<213> ORGANISM: Artificial Sequence
<220> FEATURE:
<223> OTHER INFORMATION: Reverse primer - FAS

<400> SEQUENCE: 8
cttagtgata aggtccacgg aggc                                             24

<210> SEQ ID NO 9
<211> LENGTH: 21
<212> TYPE: DNA
<213> ORGANISM: Artificial Sequence
<220> FEATURE:
<223> OTHER INFORMATION: Forward primer - ATGL

<400> SEQUENCE: 9
caacgccact cacatctacg g                                                21

<210> SEQ ID NO 10
<211> LENGTH: 23
<212> TYPE: DNA
<213> ORGANISM: Artificial Sequence
<220> FEATURE:
<223> OTHER INFORMATION: Reverse primer - ATGL

<400> SEQUENCE: 10
ggacacctca ataatgttgg cac                                              23

<210> SEQ ID NO 11
<211> LENGTH: 20
<212> TYPE: DNA
<213> ORGANISM: Artificial Sequence
<220> FEATURE:
<223> OTHER INFORMATION: Forward primer - HSL

<400> SEQUENCE: 11
acgctacaca aaggctgctt                                                  20

<210> SEQ ID NO 12
<211> LENGTH: 20
<212> TYPE: DNA
<213> ORGANISM: Artificial Sequence
<220> FEATURE:
<223> OTHER INFORMATION: Reverse primer - HSL

<400> SEQUENCE: 12
tcgttgcgtt tgtagtgctc                                                  20

<210> SEQ ID NO 13
<211> LENGTH: 20
<212> TYPE: DNA
<213> ORGANISM: Artificial Sequence
<220> FEATURE:
<223> OTHER INFORMATION: Forward primer - LPL

<400> SEQUENCE: 13
gctcgcacga gcgctccatt                                                  20

<210> SEQ ID NO 14
<211> LENGTH: 21
<212> TYPE: DNA
<213> ORGANISM: Artificial Sequence
<220> FEATURE:

```
<223> OTHER INFORMATION: Reverse primer - LPL

<400> SEQUENCE: 14
cctcgggcag ggtgaaggga a                                              21

<210> SEQ ID NO 15
<211> LENGTH: 19
<212> TYPE: DNA
<213> ORGANISM: Artificial Sequence
<220> FEATURE:
<223> OTHER INFORMATION: Forward primer - PGC1-alpha

<400> SEQUENCE: 15
ttgactggcg tcattcggg                                                 19

<210> SEQ ID NO 16
<211> LENGTH: 20
<212> TYPE: DNA
<213> ORGANISM: Artificial Sequence
<220> FEATURE:
<223> OTHER INFORMATION: Reverse primer - PGC1-alpha

<400> SEQUENCE: 16
gaaggactgg cctcgttgtc                                                20

<210> SEQ ID NO 17
<211> LENGTH: 22
<212> TYPE: DNA
<213> ORGANISM: Artificial Sequence
<220> FEATURE:
<223> OTHER INFORMATION: Forward primer - PPAR-alpha

<400> SEQUENCE: 17
cgcatgtgaa ggctgtaagg gc                                             22

<210> SEQ ID NO 18
<211> LENGTH: 22
<212> TYPE: DNA
<213> ORGANISM: Artificial Sequence
<220> FEATURE:
<223> OTHER INFORMATION: Reverse primer - PPAR-alpha

<400> SEQUENCE: 18
gtcatccagt tctaaggcat tg                                             22

<210> SEQ ID NO 19
<211> LENGTH: 21
<212> TYPE: DNA
<213> ORGANISM: Artificial Sequence
<220> FEATURE:
<223> OTHER INFORMATION: Forward primer - PPAR-Y

<400> SEQUENCE: 19
cagaagtgcc ttgctgtggg g                                              21

<210> SEQ ID NO 20
<211> LENGTH: 19
<212> TYPE: DNA
<213> ORGANISM: Artificial Sequence
<220> FEATURE:
<223> OTHER INFORMATION: Reverse primer - PPAR-Y

<400> SEQUENCE: 20
cttggctttg gtcagcggg                                                 19
```

```
<210> SEQ ID NO 21
<211> LENGTH: 21
<212> TYPE: DNA
<213> ORGANISM: Artificial Sequence
<220> FEATURE:
<223> OTHER INFORMATION: Forward primer - CTL1

<400> SEQUENCE: 21
gaacgctctg cgagtggctg c                                             21

<210> SEQ ID NO 22
<211> LENGTH: 20
<212> TYPE: DNA
<213> ORGANISM: Artificial Sequence
<220> FEATURE:
<223> OTHER INFORMATION: Reverse primer - CTL1

<400> SEQUENCE: 22
ttcttatgtt cttgactgcc                                               20

<210> SEQ ID NO 23
<211> LENGTH: 23
<212> TYPE: DNA
<213> ORGANISM: Artificial Sequence
<220> FEATURE:
<223> OTHER INFORMATION: Forward primer - PCYT1

<400> SEQUENCE: 23
atgcacagag agttcagcta aag                                           23

<210> SEQ ID NO 24
<211> LENGTH: 23
<212> TYPE: DNA
<213> ORGANISM: Artificial Sequence
<220> FEATURE:
<223> OTHER INFORMATION: Reverse primer - PCYT1

<400> SEQUENCE: 24
gggcttacta aagtcaactt caa                                           23

<210> SEQ ID NO 25
<211> LENGTH: 20
<212> TYPE: DNA
<213> ORGANISM: Artificial Sequence
<220> FEATURE:
<223> OTHER INFORMATION: Forward primer - PSS2

<400> SEQUENCE: 25
gagtggctgt ccctgaagac                                               20

<210> SEQ ID NO 26
<211> LENGTH: 20
<212> TYPE: DNA
<213> ORGANISM: Artificial Sequence
<220> FEATURE:
<223> OTHER INFORMATION: Reverse primer - PSS2

<400> SEQUENCE: 26
tcgtagatct cacgcatggc                                               20

<210> SEQ ID NO 27
<211> LENGTH: 245
<212> TYPE: PRT
<213> ORGANISM: Prunus avium

<400> SEQUENCE: 27
```

```
Met Met Lys Thr Leu Val Val Leu Ser Leu Ser Leu Thr Ile Leu
1               5                   10                  15

Ser Phe Gly Gly Ala His Ala Ala Thr Ile Ser Phe Lys Asn Asn Cys
                20                  25                  30

Pro Tyr Met Val Trp Pro Gly Thr Leu Thr Ser Asp Gln Lys Pro Gln
            35                  40                  45

Leu Ser Thr Thr Gly Phe Glu Leu Ala Ser Gln Ala Ser Phe Gln Leu
    50                  55                  60

Asp Thr Pro Val Pro Trp Asn Gly Arg Phe Trp Ala Arg Thr Gly Cys
65                  70                  75                  80

Ser Thr Asp Ala Ser Gly Lys Phe Val Cys Ala Thr Ala Asp Cys Ala
                85                  90                  95

Ser Gly Gln Val Met Cys Asn Gly Asn Gly Ala Ile Pro Pro Ala Thr
            100                 105                 110

Leu Ala Glu Phe Asn Ile Pro Ala Gly Gly Gln Asp Phe Tyr Asp
        115                 120                 125

Val Ser Leu Val Asp Gly Phe Asn Leu Pro Met Ser Val Thr Pro Gln
    130                 135                 140

Gly Gly Thr Gly Asp Cys Lys Thr Ala Ser Cys Pro Ala Asn Val Asn
145                 150                 155                 160

Ala Val Cys Pro Ser Glu Leu Gln Lys Lys Gly Ser Asp Gly Ser Val
                165                 170                 175

Val Ala Cys Leu Ser Ala Cys Val Lys Phe Gly Thr Pro Gln Tyr Cys
            180                 185                 190

Cys Thr Pro Pro Gln Asn Thr Pro Glu Thr Cys Pro Pro Thr Asn Tyr
        195                 200                 205

Ser Glu Ile Phe His Asn Ala Cys Pro Asp Ala Tyr Ser Tyr Ala Tyr
    210                 215                 220

Asp Asp Lys Arg Gly Thr Phe Thr Cys Asn Gly Gly Pro Asn Tyr Ala
225                 230                 235                 240

Ile Thr Phe Cys Pro
                245

<210> SEQ ID NO 28
<211> LENGTH: 160
<212> TYPE: PRT
<213> ORGANISM: Prunus avium

<400> SEQUENCE: 28

Met Gly Val Phe Thr Tyr Glu Ser Glu Phe Thr Ser Glu Ile Pro Pro
1               5                   10                  15

Pro Arg Leu Phe Lys Ala Phe Val Leu Asp Ala Asp Asn Leu Val Pro
                20                  25                  30

Lys Ile Ala Pro Gln Ala Ile His Ser Glu Ile Leu Glu Gly Asp
            35                  40                  45

Gly Gly Pro Gly Thr Ile Lys Lys Ile Thr Phe Gly Glu Gly Ser Gln
    50                  55                  60

Tyr Gly Tyr Val Lys His Lys Ile Asp Ser Ile Asp Lys Glu Asn Tyr
65                  70                  75                  80

Ser Tyr Ser Tyr Thr Leu Ile Glu Gly Asp Ala Leu Gly Asp Thr Leu
                85                  90                  95

Glu Lys Ile Ser Tyr Glu Thr Lys Leu Val Ala Ser Pro Ser Gly Gly
            100                 105                 110

Ser Ile Ile Lys Ser Thr Ser His Tyr His Thr Lys Gly Asn Val Glu
        115                 120                 125
```

```
Ile Lys Glu Glu His Val Lys Ala Gly Lys Glu Lys Ala Ser Asn Leu
    130                 135             140
Phe Lys Leu Ile Glu Thr Tyr Leu Lys Gly His Pro Asp Ala Tyr Asn
145                 150             155                 160
```